United States Patent
Zhu et al.

(10) Patent No.: US 10,407,484 B2
(45) Date of Patent: Sep. 10, 2019

(54) COMPOSITIONS AND METHODS FOR MODULATING T-CELL MEDIATED IMMUNE RESPONSE

(71) Applicant: The Regents of the University of Colorado, a body corporate, Denver, CO (US)

(72) Inventors: Yuwen Zhu, Parker, CO (US); Barish H. Edil, Castle Rock, CO (US); Richard D. Schulick, Cherry Hills Village, CO (US); Alessandro Paniccia, Denver, CO (US); Michelle Koenig, Denver, CO (US); Alexander C. Schulick, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 158 days.

(21) Appl. No.: 15/256,152

(22) Filed: Sep. 2, 2016

(65) Prior Publication Data
US 2017/0240613 A1   Aug. 24, 2017

Related U.S. Application Data

(60) Provisional application No. 62/370,512, filed on Aug. 3, 2016, provisional application No. 62/213,305, filed on Sep. 2, 2015.

(51) Int. Cl.
| | |
|---|---|
| C07K 16/00 | (2006.01) |
| C12P 21/08 | (2006.01) |
| C07K 14/705 | (2006.01) |
| C07K 16/28 | (2006.01) |
| A61K 39/395 | (2006.01) |
| A61K 45/06 | (2006.01) |
| C07K 14/725 | (2006.01) |
| A61K 47/68 | (2017.01) |
| A61K 47/69 | (2017.01) |

(52) U.S. Cl.
CPC .... *C07K 14/70503* (2013.01); *A61K 39/3955* (2013.01); *A61K 45/06* (2013.01); *A61K 47/68* (2017.08); *A61K 47/6937* (2017.08); *C07K 14/7051* (2013.01); *C07K 14/70517* (2013.01); *C07K 14/70521* (2013.01); *C07K 16/28* (2013.01); *C07K 16/2803* (2013.01); *C07K 2317/24* (2013.01); *C07K 2317/31* (2013.01); *C07K 2317/34* (2013.01); *C07K 2317/51* (2013.01); *C07K 2317/515* (2013.01); *C07K 2317/565* (2013.01); *C07K 2317/622* (2013.01); *C07K 2317/76* (2013.01); *C07K 2319/03* (2013.01); *C07K 2319/30* (2013.01); *C07K 2319/74* (2013.01)

(58) Field of Classification Search
None
See application file for complete search history.

(56) References Cited

U.S. PATENT DOCUMENTS

| | | | |
|---|---|---|---|
| 2015/0056655 A1* | 2/2015 | Aebischer-Gumy | ............................. C07K 16/32 435/69.6 |
| 2016/0244521 A1* | 8/2016 | White | ................ C07K 16/2803 |

FOREIGN PATENT DOCUMENTS

| | | |
|---|---|---|
| WO | 2013184912 A2 | 12/2013 |
| WO | 2016134335 A2 | 8/2016 |

OTHER PUBLICATIONS

Scott et al., 2012, Nat Reviews. vol. 12: 278-287.*
He et al., 2017, vol. 8: 67129-67139.*
Zhu,Y. et al., "Identification of CD112R as a Novel Checkpoint for Human T Cells," J Exper Med, vol. 213, No. 2, 2016, pp. 167-176.
International Search Report and Written Opinion dated Nov. 14, 2016, for International Application No. PCT/US2016/050219.

* cited by examiner

*Primary Examiner* — Amy E Juedes
(74) *Attorney, Agent, or Firm* — Saul Ewing Arnstein & Lehr LLP; Kathryn Doyle; Debora Plehn-Dujowich

(57) ABSTRACT

The present disclosure relates to compositions and methods for modulating T-cell mediated immune response in a subject in need thereof. The method includes administering to the subject an effective amount of a CD112R protein, a fusion polypeptide, a complex including CD112R and a second protein, or an anti-CD112R antibody of the present disclosure.

6 Claims, 55 Drawing Sheets
Specification includes a Sequence Listing.

FIG. 1A

MRTEAQVPALQPPEPGLEGAMGHRTLVLPWVLLTLCVTAGTPEVWVQVRMEATE

LSSFTIRCGFLGSGSISLVTVSWGGPNGAGGTTLAVLHPERGIRQWAPARQARW

ETQSSISLILEGSGASSPCANTTFCCKFASFPEGSWEACGSLPPSSDPGLSAPPTP

APILRADLAGILGVSGVLLFGCVYLLHLLRRHKHRPAPRLQPSRTSPQAPRARAWA

PSQASQAALHVPYATINTSCRPATLDTAHPHGGPSWWASLPTHAAHRPQGPAA

WASTPIPARGSFVSVENGLYAQAGERPPHTGPGLTLFPDPRGPRAMEGPLGVR (SEQ ID NO: 1)

FIG. 1B 55-150aa

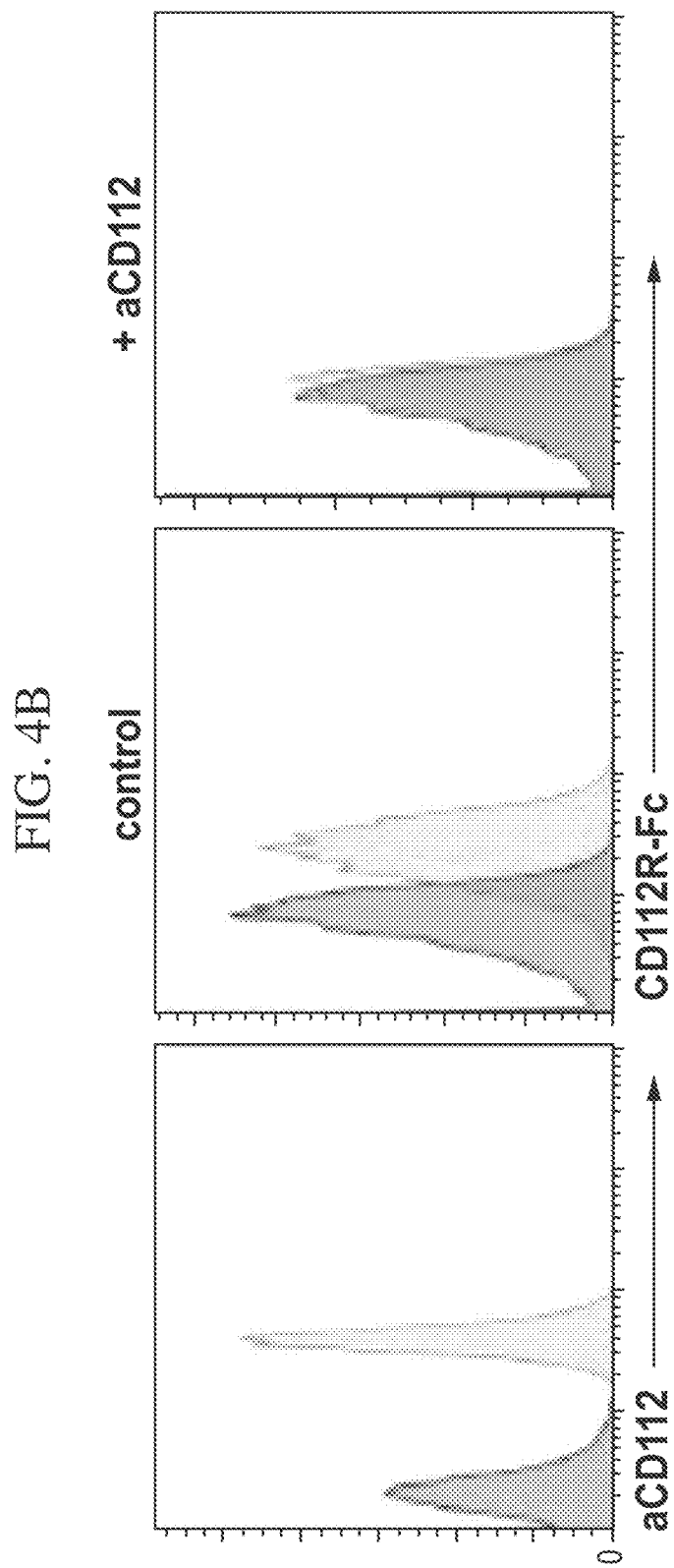

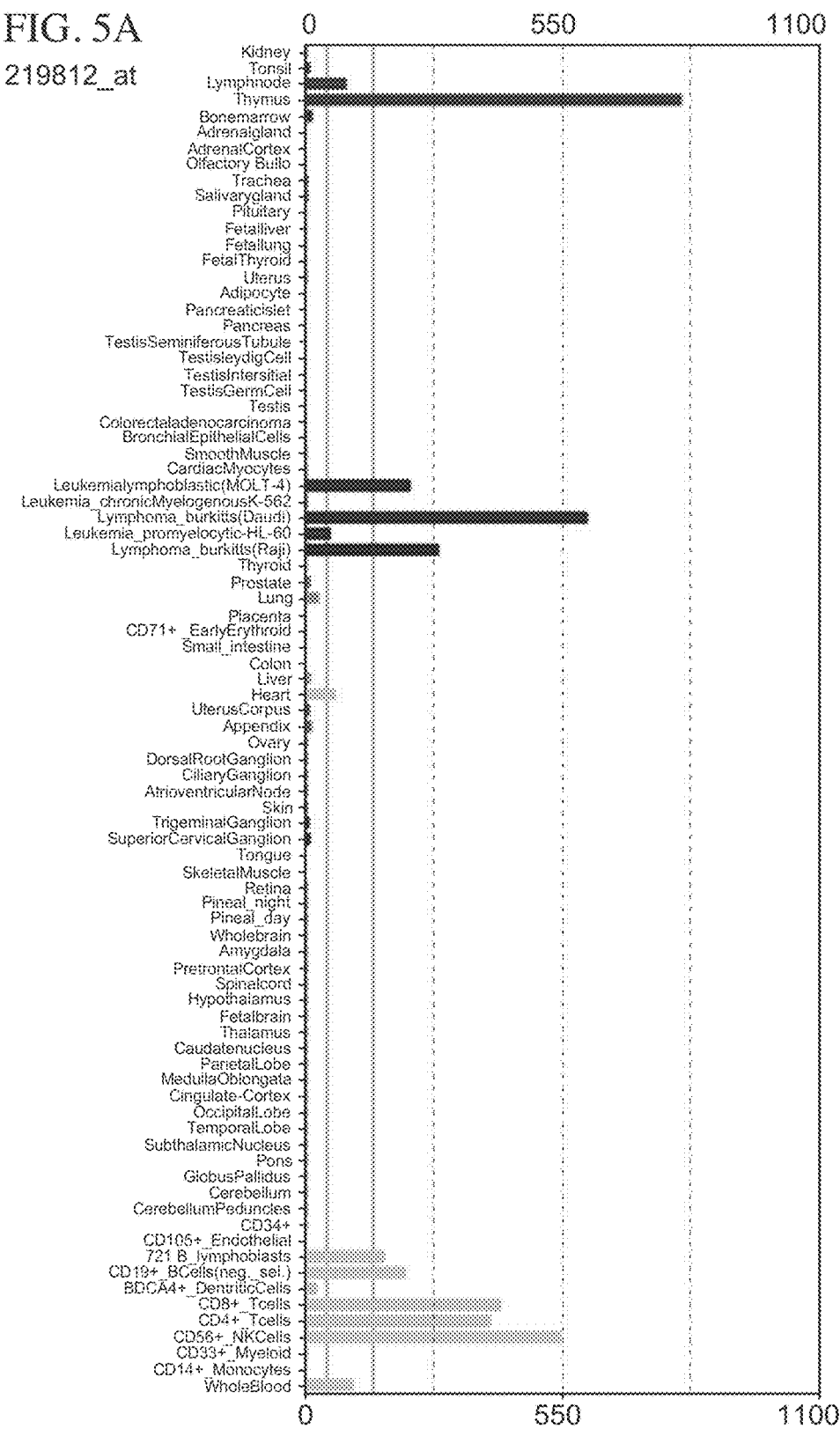

aCD112R

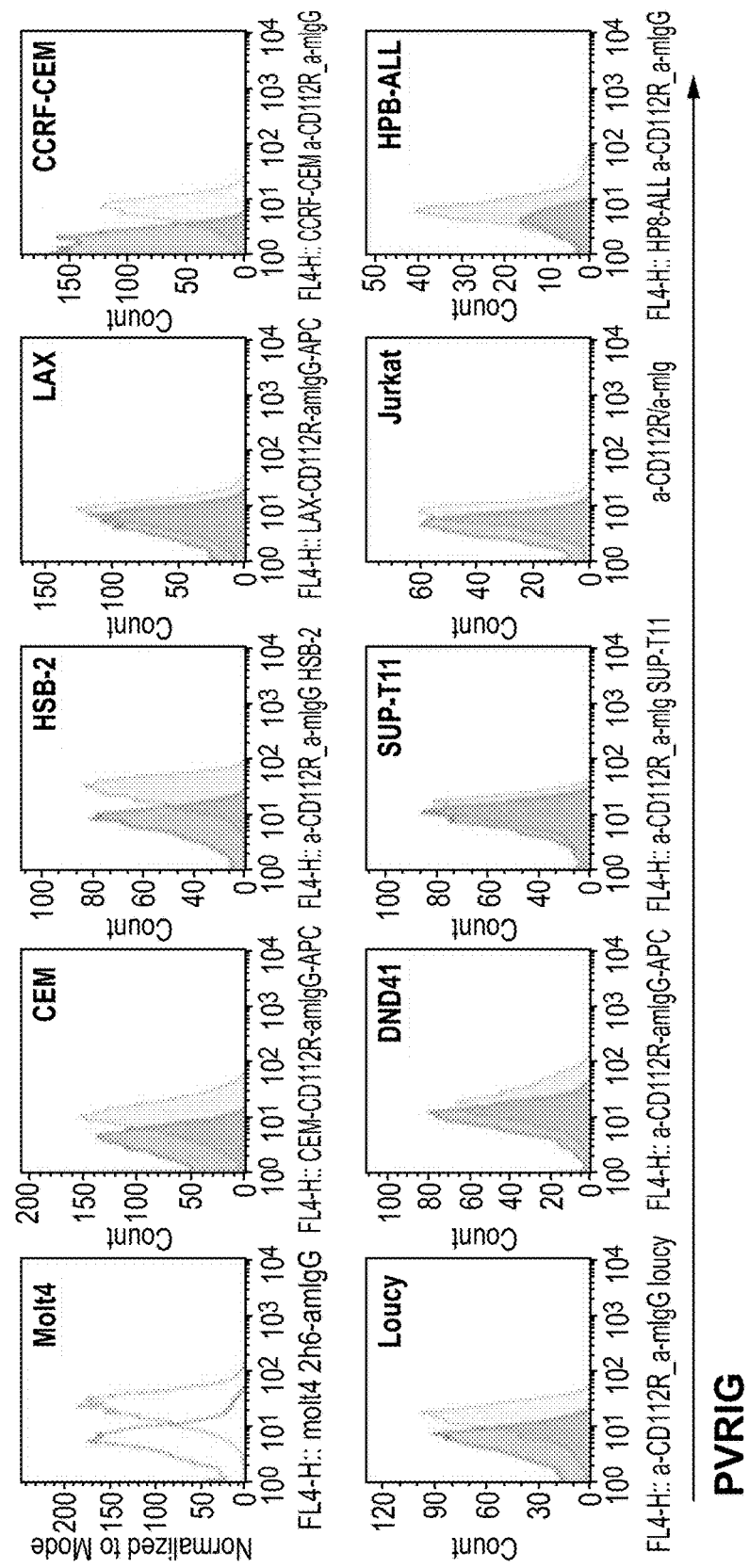

Melanoma
Positive: 9/9

PDAC
Positive: 7/9

SEQUENCE LISTING

<160> NUMBER OF SEQ ID NOS: 122

<210> SEQ ID NO 1
<211> LENGTH: 326
<212> TYPE: PRT
<213> ORGANISM: Artificial Sequence
<220> FEATURE:
<223> OTHER INFORMATION: Fusion Protein

<400> SEQUENCE: 1

Met Arg Thr Glu Ala Gln Val Pro Ala Leu Gln Pro Pro Glu Pro Gly
1               5                   10                  15

Leu Glu Gly Ala Met Gly His Arg Thr Leu Val Leu Pro Trp Val Leu
            20                  25                  30

Leu Thr Leu Cys Val Thr Ala Gly Thr Pro Glu Val Trp Val Gln Val
        35                  40                  45

Arg Met Glu Ala Thr Glu Leu Ser Ser Phe Thr Ile Arg Cys Gly Phe
    50                  55                  60

Leu Gly Ser Gly Ser Ile Ser Leu Val Thr Val Ser Trp Gly Gly Pro
65                  70                  75                  80

Asn Gly Ala Gly Gly Thr Thr Leu Ala Val Leu His Pro Glu Arg Gly
                85                  90                  95

Ile Arg Gln Trp Ala Pro Ala Arg Gln Ala Arg Trp Glu Thr Gln Ser
            100                 105                 110

Ser Ile Ser Leu Ile Leu Glu Gly Ser Gly Ala Ser Ser Pro Cys Ala
        115                 120                 125

Asn Thr Thr Phe Cys Cys Lys Phe Ala Ser Phe Pro Glu Gly Ser Trp
    130                 135                 140

Glu Ala Cys Gly Ser Leu Pro Pro Ser Ser Asp Pro Gly Leu Ser Ala
145                 150                 155                 160

Pro Pro Thr Pro Ala Pro Ile Leu Arg Ala Asp Leu Ala Gly Ile Leu
                165                 170                 175

Gly Val Ser Gly Val Leu Leu Phe Gly Cys Val Tyr Leu Leu His Leu
            180                 185                 190

Leu Arg Arg His Lys His Arg Pro Ala Pro Arg Leu Gln Pro Ser Arg
        195                 200                 205

Thr Ser Pro Gln Ala Pro Arg Ala Arg Ala Trp Ala Pro Ser Gln Ala
    210                 215                 220

Ser Gln Ala Ala Leu His Val Pro Tyr Ala Thr Ile Asn Thr Ser Cys
225                 230                 235                 240

Arg Pro Ala Thr Leu Asp Thr Ala His Pro His Gly Gly Pro Ser Trp
                245                 250                 255

Trp Ala Ser Leu Pro Thr His Ala Ala His Arg Pro Gln Gly Pro Ala
            260                 265                 270

Ala Trp Ala Ser Thr Pro Ile Pro Ala Arg Gly Ser Phe Val Ser Val
        275                 280                 285

Glu Asn Gly Leu Tyr Ala Gln Ala Gly Glu Arg Pro Pro His Thr Gly
    290                 295                 300

Pro Gly Leu Thr Leu Phe Pro Asp Pro Arg Gly Pro Arg Ala Met Glu
305                 310                 315                 320

Gly Pro Leu Gly Val Arg
                325

<210> SEQ ID NO 2
<211> LENGTH: 1164
<212> TYPE: DNA

<213> ORGANISM: Artificial Sequence
<220> FEATURE:
<223> OTHER INFORMATION: humanized antibody

<400> SEQUENCE: 2

```
gatcgactta gggcgattga tttagcggcc gcgaattcgc ccttctgcaa ccggtgtaca      60
ttccgacatc gtgatcacac agtctctgca accggtgtac attccgacat tgagatgaca    120
cagtctccag ccaccctgtc tgtgactcca ggagatagag tctctctttc ctgcagggcc    180
agccagagta ttagagacta cttacactgg tatcaacaaa aatcacatga gtctccaagg    240
cttctcatca aatatgtttc ccaatccatt tctgggatcc cctccaggtt cagtggcagt    300
ggatcagggt cagagttcac tctcagtatc aacagtgtgg aacctgaaga tgttggagta    360
tattactgtc aaaatggtca cagccttcct ctcacgttcg gctcggggac aaagttggaa    420
ataaaacgta cggtggcaag ggcgaattcg tttaaacctg caggactagt cccttagtg    480
agggttaatt ctgagcttgg cgtaatcatg gtcatagctg tttcctgtgt gaaattgtta    540
tccgctcaca attccacaca acatacgagc cggaagcata agtgtaaag cctggggtgc    600
ctaatgagtg agctaactca cattaattgc gttgcgctca ctgcccgctt tccagtcggg    660
aaacctgtcg tgccagctgc attaatgaat cggccaacgc gcgggagag gcggtttgcg    720
tattgggcgc tcttccgctt cctcgctcac tgactcgctg cgctcggtcg ttcggctgcg    780
gcgagcggta tcagctcact caaaggcggt aatacggtta ccacagaat caggggataa    840
cgcaggaaag aacatgtgag caaaaggcca gcaaaaggcc aggaaccgta aaaaggccgc    900
gttgctggcg ttttccata ggctccgccc cctgacgag catcacaaaa atcgacgctc    960
aagtcagagg tggcgaaacc cgacaggact ataaagatac caggcgtttc ccctgtaaa   1020
gctccctcgt gcgctctcct gtttccgacc ctgcccgctt taccgggata ccctgtccgc   1080
cctttttctc ccttcgggga agcgtgcgc tttctcatag ctcaacgctg gtagattaat   1140
ctctcaggtt ccggggttgt gtta                                          1164
```

<210> SEQ ID NO 3
<211> LENGTH: 110
<212> TYPE: PRT
<213> ORGANISM: Artificial Sequence
<220> FEATURE:
<223> OTHER INFORMATION: humanized antibody

<400> SEQUENCE: 3

```
Asp Ile Glu Met Thr Gln Ser Pro Ala Thr Leu Ser Val Thr Pro Gly
 1               5                  10                  15

Asp Arg Val Ser Leu Ser Cys Arg Ala Ser Gln Ser Ile Arg Asp Tyr
            20                  25                  30

Leu His Trp Tyr Gln Gln Lys Ser His Glu Ser Pro Arg Leu Leu Ile
        35                  40                  45

Lys Tyr Val Ser Gln Ser Ile Ser Gly Ile Pro Ser Arg Phe Ser Gly
    50                  55                  60

Ser Gly Ser Gly Ser Glu Phe Thr Leu Ser Ile Asn Ser Val Glu Pro
65                  70                  75                  80

Glu Asp Val Gly Val Tyr Tyr Cys Gln Asn Gly His Ser Leu Pro Leu
                85                  90                  95

Thr Phe Gly Ser Gly Thr Lys Leu Glu Ile Lys Arg Thr Val
           100                 105                 110
```

<210> SEQ ID NO 4

<211> LENGTH: 383
<212> TYPE: DNA
<213> ORGANISM: Artificial Sequence
<220> FEATURE:
<223> OTHER INFORMATION: Humanized antibody

<400> SEQUENCE: 4

```
gcaaccggtg tacattccga ggtgcaactg cagcagtcag gggctgaact ggtgaggtct    60
ggggcctcag tgaagatgtc ctgcaaggtt aatgactaca catttaccaa ttacaatatg   120
cactggttaa ggcagacacc tggccagggc ctggaatgga ttggatatat ttatcctgga   180
aatggcgata ctaactacaa tcagaaattc aagggcaagg ccacattgac tgcagacaca   240
tcctccagca cagcctacat gcagatcatc agcctgacat ctgaagaccc tgcggtctat   300
ttctgtgcaa gacagggaat tcattactat tacatcgatg tctggggcgc agggaccacg   360
gtcaccgtct cctcagggtc gac                                           383
```

<210> SEQ ID NO 5
<211> LENGTH: 120
<212> TYPE: PRT
<213> ORGANISM: Artificial Sequence
<220> FEATURE:
<223> OTHER INFORMATION: Humanized antibody

<400> SEQUENCE: 5

```
Glu Val Gln Leu Gln Gln Ser Gly Ala Glu Leu Val Arg Ser Gly Ala
1               5                   10                  15
Ser Val Lys Met Ser Cys Lys Val Asn Asp Tyr Thr Phe Thr Asn Tyr
            20                  25                  30
Asn Met His Trp Leu Arg Gln Thr Pro Gly Gln Gly Leu Glu Trp Ile
        35                  40                  45
Gly Tyr Ile Tyr Pro Gly Asn Gly Asp Thr Asn Tyr Asn Gln Lys Phe
    50                  55                  60
Lys Gly Lys Ala Thr Leu Thr Ala Asp Thr Ser Ser Thr Ala Tyr
65                  70                  75                  80
Met Gln Ile Ile Ser Leu Thr Ser Glu Asp Pro Ala Val Tyr Phe Cys
                85                  90                  95
Ala Arg Gln Gly Ile His Tyr Tyr Tyr Ile Asp Val Trp Gly Ala Gly
            100                 105                 110
Thr Thr Val Thr Val Ser Ser Gly
        115                 120
```

<210> SEQ ID NO 6
<211> LENGTH: 10
<212> TYPE: PRT
<213> ORGANISM: Artificial Sequence
<220> FEATURE:
<223> OTHER INFORMATION: Humanized antibody

<400> SEQUENCE: 6

```
Asp Tyr Thr Phe Thr Asn Tyr Asn Met His
1               5                   10
```

<210> SEQ ID NO 7
<211> LENGTH: 13
<212> TYPE: PRT
<213> ORGANISM: Artificial Sequence
<220> FEATURE:
<223> OTHER INFORMATION: Humanized antibody

<400> SEQUENCE: 7

Tyr Ile Tyr Pro Gly Asn Gly Asp Thr Asn Tyr Asn Gln
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Humanized antibody

<400> SEQUENCE: 8

Gln Gly Ile His Tyr Tyr Tyr Ile Asp Val
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Humanized antibody

<400> SEQUENCE: 9

Arg Ala Ser Gln Ser Ile Arg Asp Tyr Leu His
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Humanized antibody

<400> SEQUENCE: 10

Tyr Val Ser Gln Ser Ile Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Humanized antibody

<400> SEQUENCE: 11

Gln Asn Gly His Ser Leu Pro Leu Thr
1               5

<210> SEQ ID NO 12
<211> LENGTH: 15
<212> TYPE: PRT
<213> ORGANISM: Artificial Sequence
<220> FEATURE:
<223> OTHER INFORMATION: Synthetic tag

<400> SEQUENCE: 12

Gly Leu Asn Asp Ile Phe Glu Ala Gln Lys Ile Glu Trp His Glu
1               5                   10                  15

<210> SEQ ID NO 13
<211> LENGTH: 26
<212> TYPE: PRT
<213> ORGANISM: Artificial Sequence
<220> FEATURE:
<223> OTHER INFORMATION: Synthetic tag

<400> SEQUENCE: 13

Lys Arg Arg Trp Lys Lys Asn Phe Ile Ala Val Ser Ala Ala Asn Arg

```
                1               5                   10                  15
Phe Lys Lys Ile Ser Ser Ser Gly Ala Leu
                20                  25
```

<210> SEQ ID NO 14
<211> LENGTH: 6
<212> TYPE: PRT
<213> ORGANISM: Artificial Sequence
<220> FEATURE:
<223> OTHER INFORMATION: synthetic tag

<400> SEQUENCE: 14

```
Glu Glu Glu Glu Glu Glu
1               5
```

<210> SEQ ID NO 15
<211> LENGTH: 13
<212> TYPE: PRT
<213> ORGANISM: Artificial Sequence
<220> FEATURE:
<223> OTHER INFORMATION: Synthetic tag

<400> SEQUENCE: 15

```
Gly Ala Pro Val Pro Tyr Pro Asp Pro Leu Glu Pro Arg
1               5                   10
```

<210> SEQ ID NO 16
<211> LENGTH: 8
<212> TYPE: PRT
<213> ORGANISM: Artificial Sequence
<220> FEATURE:
<223> OTHER INFORMATION: synthetic tag

<400> SEQUENCE: 16

```
Asp Tyr Lys Asp Asp Asp Asp Lys
1               5
```

<210> SEQ ID NO 17
<211> LENGTH: 9
<212> TYPE: PRT
<213> ORGANISM: Artificial Sequence
<220> FEATURE:
<223> OTHER INFORMATION: Synthetic tag

<400> SEQUENCE: 17

```
Tyr Pro Tyr Asp Val Pro Asp Tyr Ala
1               5
```

<210> SEQ ID NO 18
<211> LENGTH: 6
<212> TYPE: PRT
<213> ORGANISM: Artificial Sequence
<220> FEATURE:
<223> OTHER INFORMATION: Synthetic tag

<400> SEQUENCE: 18

```
His His His His His His
1               5
```

<210> SEQ ID NO 19
<211> LENGTH: 10
<212> TYPE: PRT
<213> ORGANISM: Artificial Sequence
<220> FEATURE:
<223> OTHER INFORMATION: Synthetic tag

<400> SEQUENCE: 19

```
Glu Gln Lys Leu Ile Ser Glu Asp Leu
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Synthetic tag

<400> SEQUENCE: 20

Lys Glu Thr Ala Ala Ala Lys Phe Glu Arg Gln His Met Asp Ser
1               5                   10                  15

<210> SEQ ID NO 21
<211> LENGTH: 38
<212> TYPE: PRT
<213> ORGANISM: Artificial Sequence
<220> FEATURE:
<223> OTHER INFORMATION: Synthetic tag

<400> SEQUENCE: 21

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
                20                  25                  30

Gln Gly Gln Arg Glu Pro
        35

<210> SEQ ID NO 22
<211> LENGTH: 13
<212> TYPE: PRT
<213> ORGANISM: Artificial Sequence
<220> FEATURE:
<223> OTHER INFORMATION: Synthetic tag

<400> SEQUENCE: 22

Ser Leu Ala Glu Leu Leu Asn Ala Gly Leu Gly Gly Ser
1               5                   10

<210> SEQ ID NO 23
<211> LENGTH: 8
<212> TYPE: PRT
<213> ORGANISM: Artificial Sequence
<220> FEATURE:
<223> OTHER INFORMATION: Synthetic tag

<400> SEQUENCE: 23

Thr Gln Asp Pro Ser Arg Val Gly
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic tag

<400> SEQUENCE: 24

Trp Ser His Pro Gln Phe Glu Lys
1               5

<210> SEQ ID NO 25
<211> LENGTH: 6
<212> TYPE: PRT
```

```
<213> ORGANISM: Artificial Sequence
<220> FEATURE:
<223> OTHER INFORMATION: Synthetic tag

<400> SEQUENCE: 25

Cys Cys Pro Gly Cys Cys
1               5

<210> SEQ ID NO 26
<211> LENGTH: 14
<212> TYPE: PRT
<213> ORGANISM: Artificial Sequence
<220> FEATURE:
<223> OTHER INFORMATION: Synthetic tag

<400> SEQUENCE: 26

Gly Lys Pro Ile Pro Asn Pro Leu Leu Gly Leu Asp Ser Thr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic tag

<400> SEQUENCE: 27

Tyr Thr Asp Ile Glu Met Asn Arg Leu Gly Lys
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Synthetic tag

<400> SEQUENCE: 28

Asp Leu Tyr Asp Asp Asp Asp Lys
1               5

<210> SEQ ID NO 29
<211> LENGTH: 16
<212> TYPE: PRT
<213> ORGANISM: Artificial Sequence
<220> FEATURE:
<223> OTHER INFORMATION: Synthetic tag

<400> SEQUENCE: 29

Thr Asp Lys Asp Met Thr Ile Thr Phe Thr Asn Lys Lys Asp Ala Glu
1               5                   10                  15

<210> SEQ ID NO 30
<211> LENGTH: 13
<212> TYPE: PRT
<213> ORGANISM: Artificial Sequence
<220> FEATURE:
<223> OTHER INFORMATION: Synthetic tag

<400> SEQUENCE: 30

Ala His Ile Val Met Val Asp Ala Tyr Lys Pro Thr Lys
1               5                   10

<210> SEQ ID NO 31
<211> LENGTH: 25
<212> TYPE: DNA
<213> ORGANISM: Artificial Sequence
```

```
<220> FEATURE:
<223> OTHER INFORMATION: Recombinant sequence

<400> SEQUENCE: 31
tgcacgtggc agctttgtct ctgtt                                               25

<210> SEQ ID NO 32
<211> LENGTH: 118
<212> TYPE: PRT
<213> ORGANISM: Artificial Sequence
<220> FEATURE:
<223> OTHER INFORMATION: Humanized antibody

<400> SEQUENCE: 32
```

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Asp
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95

Ala Arg Gly Ser Ser Gly Ser Trp Phe Ala Tyr Trp Gly Gln Gly Thr
            100                 105                 110

Leu Val Thr Val Ser Ala
        115

```
<210> SEQ ID NO 33
<211> LENGTH: 111
<212> TYPE: PRT
<213> ORGANISM: Artificial Sequence
<220> FEATURE:
<223> OTHER INFORMATION: Humanized antibody

<400> SEQUENCE: 33
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110

```
<210> SEQ ID NO 34
<211> LENGTH: 5
<212> TYPE: PRT
<213> ORGANISM: Artificial Sequence
<220> FEATURE:
<223> OTHER INFORMATION: Humanzed antibody
```

```
<400> SEQUENCE: 34

Ser Asp Trp Met His
1               5

<210> SEQ ID NO 35
<211> LENGTH: 17
<212> TYPE: PRT
<213> ORGANISM: Artificial Sequence
<220> FEATURE:
<223> OTHER INFORMATION: Humanized antibody

<400> SEQUENCE: 35

Tyr Ile Asn Pro Ser Thr Gly Tyr Thr Glu Tyr Asn Gln Lys Phe Lys
1               5                   10                  15
Asp

<210> SEQ ID NO 36
<211> LENGTH: 9
<212> TYPE: PRT
<213> ORGANISM: Artificial Sequence
<220> FEATURE:
<223> OTHER INFORMATION: Humanized antibody

<400> SEQUENCE: 36

Gly Ser Ser Gly Ser Trp Phe Ala Tyr
1               5

<210> SEQ ID NO 37
<211> LENGTH: 15
<212> TYPE: PRT
<213> ORGANISM: Artificial Sequence
<220> FEATURE:
<223> OTHER INFORMATION: Humanized antibody

<400> SEQUENCE: 37

Arg Ala Ser Gln Ser Val Ser Thr Ser Ser Tyr Ser Tyr Met His
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: Humanized antibody

<400> SEQUENCE: 38

Tyr Ala Ser Asn Leu Glu Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Humanized antibody

<400> SEQUENCE: 39

Gln His Ser Trp Glu Ile Pro Tyr Thr
1               5

<210> SEQ ID NO 40
<211> LENGTH: 112
<212> TYPE: PRT
<213> ORGANISM: Artificial Sequence
<220> FEATURE:
```

<223> OTHER INFORMATION: Humanized antibody

<400> SEQUENCE: 40

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asn Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
            100                 105                 110

<210> SEQ ID NO 41
<211> LENGTH: 16
<212> TYPE: PRT
<213> ORGANISM: Artificial Sequence
<220> FEATURE:
<223> OTHER INFORMATION: Humanized antibody

<400> SEQUENCE: 41

Lys Ser Ser Gln Ser Leu Leu Asn Ser Asp Gly Lys Thr Tyr Leu Asn
1               5                   10                  15

<210> SEQ ID NO 42
<211> LENGTH: 7
<212> TYPE: PRT
<213> ORGANISM: Artificial Sequence
<220> FEATURE:
<223> OTHER INFORMATION: Humanized antibody

<400> SEQUENCE: 42

Leu Val Ser Lys Leu Asp Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Humanized antibody

<400> SEQUENCE: 43

Trp Gln Gly Thr His Phe Pro Arg Thr
1               5

<210> SEQ ID NO 44
<211> LENGTH: 96
<212> TYPE: PRT
<213> ORGANISM: Artificial Sequence
<220> FEATURE:
<223> OTHER INFORMATION: Fusion protein

<400> SEQUENCE: 44

Glu Ala Thr Glu Leu Ser Ser Phe Thr Ile Arg Cys Gly Phe Leu Gly
1               5                   10                  15

Ser Gly Ser Ile Ser Leu Val Thr Val Ser Trp Gly Gly Pro Asn Gly
            20                  25                  30

```
Ala Gly Gly Thr Thr Leu Ala Val Leu His Pro Glu Arg Gly Ile Arg
        35                  40                  45

Gln Trp Ala Pro Ala Arg Gln Ala Arg Trp Glu Thr Gln Ser Ser Ile
    50                  55                  60

Ser Leu Ile Leu Glu Gly Ser Gly Ala Ser Ser Pro Cys Ala Asn Thr
65                  70                  75                  80

Thr Phe Cys Cys Lys Phe Ala Ser Phe Pro Glu Gly Ser Trp Glu Ala
                85                  90                  95

<210> SEQ ID NO 45
<211> LENGTH: 160
<212> TYPE: PRT
<213> ORGANISM: Artificial Sequence
<220> FEATURE:
<223> OTHER INFORMATION: Fusion protein

<400> SEQUENCE: 45

Met Arg Thr Glu Ala Gln Val Pro Ala Leu Gln Pro Pro Glu Pro Gly
1               5                   10                  15

Leu Glu Gly Ala Met Gly His Arg Thr Leu Val Leu Pro Trp Val Leu
            20                  25                  30

Leu Thr Leu Cys Val Thr Ala Gly Thr Pro Glu Val Trp Val Gln Val
        35                  40                  45

Arg Met Glu Ala Thr Glu Leu Ser Ser Phe Thr Ile Arg Cys Gly Phe
    50                  55                  60

Leu Gly Ser Gly Ser Ile Ser Leu Val Thr Val Ser Trp Gly Gly Pro
65                  70                  75                  80

Asn Gly Ala Gly Gly Thr Thr Leu Ala Val Leu His Pro Glu Arg Gly
                85                  90                  95

Ile Arg Gln Trp Ala Pro Ala Arg Gln Ala Arg Trp Glu Thr Gln Ser
            100                 105                 110

Ser Ile Ser Leu Ile Leu Glu Gly Ser Gly Ala Ser Ser Pro Cys Ala
        115                 120                 125

Asn Thr Thr Phe Cys Cys Lys Phe Ala Ser Phe Pro Glu Gly Ser Trp
    130                 135                 140

Glu Ala Cys Gly Ser Leu Pro Pro Ser Asp Pro Gly Leu Ser Ala
145                 150                 155                 160

<210> SEQ ID NO 46
<211> LENGTH: 217
<212> TYPE: PRT
<213> ORGANISM: Artificial Sequence
<220> FEATURE:
<223> OTHER INFORMATION: Fusion Protein

<400> SEQUENCE: 46

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
```

```
                        85                  90                  95
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
            115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
            195                 200                 205

Lys Ser Leu Ser Leu Ser Pro Gly Lys
    210                 215

<210> SEQ ID NO 47
<211> LENGTH: 216
<212> TYPE: PRT
<213> ORGANISM: Artificial Sequence
<220> FEATURE:
<223> OTHER INFORMATION: Fusion protein

<400> SEQUENCE: 47

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
            115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
            195                 200                 205

Ser Leu Ser Leu Ser Pro Gly Lys
    210                 215
```

```
<210> SEQ ID NO 48
<211> LENGTH: 217
<212> TYPE: PRT
<213> ORGANISM: Artificial Sequence
<220> FEATURE:
<223> OTHER INFORMATION: Fusion protein

<400> SEQUENCE: 48

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215

<210> SEQ ID NO 49
<211> LENGTH: 217
<212> TYPE: PRT
<213> ORGANISM: Artificial Sequence
<220> FEATURE:
<223> OTHER INFORMATION: Fusion protein

<400> SEQUENCE: 49

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95
```

```
Gly Leu Pro Ser Ser Ile Glu Lys Thr Ile Ser Lys Ala Lys Gly Gln
                100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215
```

<210> SEQ ID NO 50
<211> LENGTH: 218
<212> TYPE: PRT
<213> ORGANISM: Artificial Sequence
<220> FEATURE:
<223> OTHER INFORMATION: Fusion protein

<400> SEQUENCE: 50

```
Ile Ala Glu Leu Pro Pro Lys Val Ser Val Phe Val Pro Pro Arg Asp
1               5                   10                  15

Gly Phe Phe Gly Asn Pro Arg Lys Ser Lys Leu Ile Cys Gln Ala Thr
            20                  25                  30

Gly Phe Ser Pro Arg Gln Ile Gln Val Ser Trp Leu Arg Glu Gly Lys
        35                  40                  45

Gln Val Gly Ser Gly Val Thr Thr Asp Gln Val Gln Ala Glu Ala Lys
    50                  55                  60

Glu Ser Gly Pro Thr Thr Tyr Lys Val Thr Ser Thr Leu Thr Ile Lys
65                  70                  75                  80

Glu Ser Asp Trp Leu Gly Gln Ser Met Phe Thr Cys Arg Val Asp His
                85                  90                  95

Arg Gly Leu Thr Phe Gln Gln Asn Ala Ser Ser Met Cys Val Pro Asp
            100                 105                 110

Gln Asp Thr Ala Ile Arg Val Phe Ala Ile Pro Pro Ser Phe Ala Ser
        115                 120                 125

Ile Phe Leu Thr Lys Ser Thr Lys Leu Thr Cys Leu Val Thr Asp Leu
130                 135                 140

Thr Thr Tyr Asp Ser Val Thr Ile Ser Trp Thr Arg Gln Asn Gly Glu
145                 150                 155                 160

Ala Val Lys Thr His Thr Asn Ile Ser Glu Ser His Pro Asn Ala Thr
                165                 170                 175

Phe Ser Ala Val Gly Glu Ala Ser Ile Cys Glu Asp Asp Trp Asn Ser
            180                 185                 190

Gly Glu Arg Phe Thr Cys Thr Val Thr His Thr Asp Leu Pro Ser Pro
        195                 200                 205

Leu Lys Gln Thr Ile Ser Arg Pro Lys Gly
    210                 215
```

<210> SEQ ID NO 51
<211> LENGTH: 1467

<212> TYPE: DNA
<213> ORGANISM: Artificial Sequence
<220> FEATURE:
<223> OTHER INFORMATION: Recombinant sequence

<400> SEQUENCE: 51

```
gccaccatgg gatggagctg tatcatcctc ttcttggtag caacagctac aggtgtccac    60
gaggtgcaac tgcagcagtc aggggctgaa ctggtgaggt ctggggcctc agtgaagatg   120
tcctgcaagg ttaatgacta cacatttacc aattacaata tgcactggtt aaggcagaca   180
cctggccagg gcctggaatg gattggatat atttatcctg gaaatggcga tactaactac   240
aatcagaaat tcaagggcaa ggccacattg actgcagaca catcctccag cacagcctac   300
atgcagatca tcagcctgac atctgaagac cctgcggtct atttctgtgc aagacaggga   360
attcattact attacatcga tgtctggggc gcagggacca cggtcaccgt ctcctcaggg   420
ggtggtggtg gttctggtgg tggtggttct ggtggtggtg gttctgacat tgagatgaca   480
cagtctccag ccaccctgtc tgtgactcca ggagatagag tctctctttc ctgcagggcc   540
agccagagta ttagagacta cttacactgg tatcaacaaa aatcacatga gtctccaagg   600
cttctcatca aatatgtttc caatccatt tctggcatcc cctccaggtt cagtggcagt   660
ggatcagggt cagagttcac tctcagtatc aacagtgtgg aacctgaaga tgttggagta   720
tattactgtc aaaatggtca cagccttcct ctcacgttcg gctcggggac aaagttggaa   780
ataaaacgta cggtgaccac gacgccagcg ccgcgaccac caacaccggc gcccaccatc   840
gcgtcgcagc cctgtccct gcgcccagag cgtgccggc cagcggcggg gggcgcagtg   900
cacacgaggg ggctggactt cgcctgtgat atctacatct gggcgccctt ggccgggact   960
tgtgggggtcc ttctcctgtc actggttatc accaggagta agaggagcag gctcctgcac  1020
agtgactaca tgaacatgac tccccgccgc cccgggccca cccgcaagca ttaccagccc  1080
tatgccccac cacgcgactt cgcagcctat cgctccagag tgaagttcag caggagcgca  1140
gacgccccg cgtaccagca gggccagaac cagctctata cgagctcaa tctaggacga  1200
agagaggagt acgatgtttt ggacaagaga cgtggccggg accctgagat gggggggaaag  1260
ccgcagagaa ggaagaaccc tcaggaaggc ctgtacaatg aactgcagaa agataagatg  1320
gcggaggcct acagtgagat tgggatgaaa ggcgagcgcc ggaggggcaa ggggcacgat  1380
ggcctttacc agggtctcag tacagccacc aaggacacct cgacgcccct tcacatgcag  1440
gccctgcccc ctcgcaaacc ggtttaa                                      1467
```

<210> SEQ ID NO 52
<211> LENGTH: 394
<212> TYPE: PRT
<213> ORGANISM: Artificial Sequence
<220> FEATURE:
<223> OTHER INFORMATION: fusion protein

<400> SEQUENCE: 52

```
Met Arg Thr Glu Ala Gln Val Pro Ala Leu Gln Pro Pro Glu Pro Gly
  1               5                  10                  15

Leu Glu Gly Ala Met Gly His Arg Thr Leu Val Leu Pro Trp Val Leu
             20                  25                  30

Leu Thr Leu Cys Val Thr Ala Gly Thr Pro Glu Val Trp Val Gln Val
         35                  40                  45

Arg Met Glu Ala Thr Glu Leu Ser Ser Phe Thr Ile Arg Cys Gly Phe
     50                  55                  60
```

```
Leu Gly Ser Gly Ser Ile Ser Leu Val Thr Val Ser Trp Gly Gly Pro
 65                  70                  75                  80

Asn Gly Ala Gly Gly Thr Thr Leu Ala Val Leu His Pro Glu Arg Gly
                 85                  90                  95

Ile Arg Gln Trp Ala Pro Ala Arg Gln Ala Arg Trp Glu Thr Gln Ser
            100                 105                 110

Ser Ile Ser Leu Ile Leu Glu Gly Ser Gly Ala Ser Ser Pro Cys Ala
        115                 120                 125

Asn Thr Thr Phe Cys Cys Lys Phe Ala Ser Phe Pro Glu Gly Ser Trp
130                 135                 140

Glu Ala Cys Gly Ser Leu Pro Pro Ser Asp Pro Gly Leu Ser Ala
145                 150                 155                 160

Arg Ser Pro Arg Gly Pro Thr Ile Lys Pro Cys Pro Pro Cys Lys Cys
                165                 170                 175

Pro Ala Pro Asn Leu Leu Gly Gly Pro Ser Val Phe Ile Phe Pro Pro
            180                 185                 190

Lys Ile Lys Asp Val Leu Met Ile Ser Leu Ser Pro Ile Val Thr Cys
        195                 200                 205

Val Val Val Asp Val Ser Glu Asp Asp Pro Asp Val Gln Ile Ser Trp
210                 215                 220

Phe Val Asn Asn Val Glu Val His Thr Ala Gln Thr Gln Thr His Arg
225                 230                 235                 240

Glu Asp Tyr Asn Ser Thr Leu Arg Val Val Ser Ala Leu Pro Ile Gln
                245                 250                 255

His Gln Asp Trp Met Ser Gly Lys Glu Phe Lys Cys Lys Val Asn Asn
            260                 265                 270

Lys Asp Leu Pro Ala Pro Ile Glu Arg Thr Ile Ser Lys Pro Lys Gly
        275                 280                 285

Ser Val Arg Ala Pro Gln Val Tyr Val Leu Pro Pro Pro Glu Glu Glu
290                 295                 300

Met Thr Lys Lys Gln Val Thr Leu Thr Cys Met Val Thr Asp Phe Met
305                 310                 315                 320

Pro Glu Asp Ile Tyr Val Glu Trp Thr Asn Asn Gly Lys Thr Glu Leu
                325                 330                 335

Asn Tyr Lys Asn Thr Glu Pro Val Leu Asp Ser Asp Gly Ser Tyr Phe
            340                 345                 350

Met Tyr Ser Lys Leu Arg Val Glu Lys Lys Asn Trp Val Glu Arg Asn
        355                 360                 365

Ser Tyr Ser Cys Ser Val Val His Glu Gly Leu His Asn His His Thr
370                 375                 380

Thr Lys Ser Phe Ser Arg Thr Pro Gly Lys
385                 390

<210> SEQ ID NO 53
<211> LENGTH: 17
<212> TYPE: PRT
<213> ORGANISM: Homo sapiens

<400> SEQUENCE: 53

Ala Val Leu His Pro Glu Arg Gly Ile Arg Gln Trp Ala Pro Ala Arg
 1               5                  10                  15

Gln

<210> SEQ ID NO 54
<211> LENGTH: 20
```

```
<212> TYPE: PRT
<213> ORGANISM: Homo sapiens

<400> SEQUENCE: 54

Ala Val Leu His Pro Glu Arg Gly Ile Arg Gln Trp Ala Pro Ala Arg
1               5                   10                  15

Gln Ala Arg Trp
            20

<210> SEQ ID NO 55
<211> LENGTH: 25
<212> TYPE: PRT
<213> ORGANISM: Homo sapiens

<400> SEQUENCE: 55

Ala Val Leu His Pro Glu Arg Gly Ile Arg Gln Trp Ala Pro Ala Arg
1               5                   10                  15

Gln Ala Arg Trp Glu Thr Gln Ser Ser
            20                  25

<210> SEQ ID NO 56
<211> LENGTH: 27
<212> TYPE: PRT
<213> ORGANISM: Homo sapiens

<400> SEQUENCE: 56

Ala Val Leu His Pro Glu Arg Gly Ile Arg Gln Trp Ala Pro Ala Arg
1               5                   10                  15

Gln Ala Arg Trp Glu Thr Gln Ser Ser Ile Ser
            20                  25

<210> SEQ ID NO 57
<211> LENGTH: 28
<212> TYPE: PRT
<213> ORGANISM: Homo sapiens

<400> SEQUENCE: 57

Ala Val Leu His Pro Glu Arg Gly Ile Arg Gln Trp Ala Pro Ala Arg
1               5                   10                  15

Gln Ala Arg Trp Glu Thr Gln Ser Ser Ile Ser Leu
            20                  25

<210> SEQ ID NO 58
<211> LENGTH: 25
<212> TYPE: DNA
<213> ORGANISM: Artificial Sequence
<220> FEATURE:
<223> OTHER INFORMATION: Recombinant sequence

<400> SEQUENCE: 58
acgtggcagc tttgtctctg ttgag                                    25

<210> SEQ ID NO 59
<211> LENGTH: 25
<212> TYPE: DNA
<213> ORGANISM: Artificial Sequence
<220> FEATURE:
<223> OTHER INFORMATION: Recombinant Sequence

<400> SEQUENCE: 59
tggcagcttt gtctctgttg agaat                                    25

<210> SEQ ID NO 60
```

```
<211> LENGTH: 25
<212> TYPE: DNA
<213> ORGANISM: Artificial Sequence
<220> FEATURE:
<223> OTHER INFORMATION: recombinant sequence

<400> SEQUENCE: 60
gctttgtctc tgttgagaat ggact                                        25

<210> SEQ ID NO 61
<211> LENGTH: 100
<212> TYPE: PRT
<213> ORGANISM: Homo sapiens

<400> SEQUENCE: 61
```

Val Gln Val Arg Met Glu Ala Thr Glu Leu Ser Ser Phe Thr Ile Arg
1               5                   10                  15

Cys Gly Phe Leu Gly Ser Gly Ser Ile Ser Leu Val Thr Val Ser Trp
            20                  25                  30

Gly Gly Pro Asn Gly Ala Gly Gly Thr Thr Leu Ala Val Leu His Pro
        35                  40                  45

Glu Arg Gly Ile Arg Gln Trp Ala Pro Ala Arg Gln Ala Arg Trp Glu
    50                  55                  60

Thr Gln Ser Ser Ile Ser Leu Ile Leu Glu Gly Ser Gly Ala Ser Ser
65                  70                  75                  80

Pro Cys Ala Asn Thr Thr Phe Cys Cys Lys Phe Ala Ser Phe Pro Glu
                85                  90                  95

Gly Ser Trp Glu
        100

```
<210> SEQ ID NO 62
<211> LENGTH: 116
<212> TYPE: PRT
<213> ORGANISM: Homo sapiens

<400> SEQUENCE: 62
```

Val Gln Val Leu Pro Glu Val Arg Gly Gln Leu Gly Gly Thr Val Glu
1               5                   10                  15

Leu Pro Cys His Leu Leu Pro Pro Val Pro Gly Leu Tyr Ile Ser Leu
            20                  25                  30

Val Thr Trp Gln Arg Pro Asp Ala Pro Ala Asn His Gln Asn Val Ala
        35                  40                  45

Ala Phe His Pro Lys Met Gly Pro Ser Phe Pro Ser Pro Lys Pro Gly
    50                  55                  60

Ser Glu Arg Leu Ser Phe Val Ser Ala Lys Gln Ser Thr Gly Gln Asp
65                  70                  75                  80

Thr Glu Ala Glu Leu Gln Asp Ala Thr Leu Ala Leu His Gly Leu Thr
                85                  90                  95

Val Glu Asp Glu Gly Asn Tyr Thr Cys Glu Phe Ala Thr Phe Pro Lys
            100                 105                 110

Gly Ser Val Arg
        115

```
<210> SEQ ID NO 63
<211> LENGTH: 105
<212> TYPE: PRT
<213> ORGANISM: Homo sapiens

<400> SEQUENCE: 63
```

-continued

Val Gln Ala Pro Thr Gln Val Pro Gly Phe Leu Gly Asp Ser Val Thr
1               5                   10                  15

Leu Pro Cys Tyr Leu Gln Val Pro Asn Met Glu Val Thr His Val Ser
            20                  25                  30

Gln Leu Thr Trp Ala Arg His Gly Glu Ser Gly Ser Met Ala Val Phe
        35                  40                  45

His Gln Thr Gln Gly Pro Ser Tyr Ser Glu Ser Lys Lys Arg Leu Glu
    50                  55                  60

Phe Val Ala Ala Arg Leu Gly Ala Glu Leu Arg Asn Ala Ser Leu Arg
65                  70                  75                  80

Met Phe Gly Leu Arg Val Glu Asp Glu Gly Asn Tyr Thr Cys Leu Phe
                85                  90                  95

Val Thr Phe Pro Gln Gly Ser Arg Ser
            100                 105

<210> SEQ ID NO 64
<211> LENGTH: 93
<212> TYPE: PRT
<213> ORGANISM: Homo sapiens

<400> SEQUENCE: 64

Ile Glu Thr Thr Gly Asn Ile Ser Ala Glu Lys Gly Gly Ser Ile Ile
1               5                   10                  15

Leu Gln Cys His Leu Ser Ser Thr Thr Ala Gln Val Thr Gln Val Asn
            20                  25                  30

Trp Glu Gln Gln Asp Gln Leu Leu Ala Ile Cys Asn Ala Asp Leu Gly
        35                  40                  45

Trp His Ile Ser Pro Ser Phe Lys Asp Arg Val Ala Pro Gly Pro Gly
    50                  55                  60

Leu Gly Leu Thr Leu Gln Ser Leu Thr Val Asn Asp Thr Gly Glu Tyr
65                  70                  75                  80

Phe Cys Ile Tyr His Thr Tyr Pro Asp Gly Thr Tyr Thr
                85                  90

<210> SEQ ID NO 65
<211> LENGTH: 103
<212> TYPE: PRT
<213> ORGANISM: Homo sapiens

<400> SEQUENCE: 65

Val Asn Thr Glu Glu Asn Val Tyr Ala Thr Leu Gly Ser Asp Val Asn
1               5                   10                  15

Leu Thr Cys Gln Thr Gln Thr Val Gly Phe Phe Val Gln Met Gln Trp
            20                  25                  30

Ser Lys Val Thr Asn Lys Ile Asp Leu Ile Ala Val Tyr His Pro Gln
        35                  40                  45

Tyr Gly Phe Tyr Cys Ala Thr Gly Arg Pro Cys Glu Ser Leu Val Thr
    50                  55                  60

Phe Thr Glu Thr Pro Glu Asn Gly Ser Lys Trp Thr Leu His Leu Arg
65                  70                  75                  80

Asn Met Ser Cys Ser Val Ser Gly Arg Tyr Glu Cys Met Leu Val Leu
                85                  90                  95

Tyr Pro Glu Gly Ile Gln Thr
            100

<210> SEQ ID NO 66
<211> LENGTH: 103

<212> TYPE: PRT
<213> ORGANISM: Homo sapiens

<400> SEQUENCE: 66

```
Val Gln Val Asn Asp Ser Met Tyr Gly Phe Ile Gly Thr Asp Val Val
1               5                   10                  15

Leu His Cys Ser Phe Ala Asn Pro Leu Pro Ser Val Lys Ile Thr Gln
            20                  25                  30

Val Thr Trp Gln Lys Ser Thr Asn Gly Ser Lys Gln Asn Val Ala Ile
        35                  40                  45

Tyr Asn Pro Ser Met Gly Val Ser Val Leu Ala Pro Tyr Arg Glu Arg
    50                  55                  60

Val Glu Phe Leu Arg Pro Ser Phe Thr Asp Gly Thr Ile Arg Leu Ser
65                  70                  75                  80

Arg Leu Glu Leu Glu Asp Glu Gly Val Tyr Ile Cys Glu Phe Ala Thr
                85                  90                  95

Phe Pro Thr Gly Asn Arg Glu
            100
```

<210> SEQ ID NO 67
<211> LENGTH: 100
<212> TYPE: PRT
<213> ORGANISM: Homo sapiens

<400> SEQUENCE: 67

```
Ile Ile Val Glu Pro His Val Thr Ala Val Trp Gly Lys Asn Val Ser
1               5                   10                  15

Leu Lys Cys Leu Ile Glu Val Asn Glu Thr Ile Thr Gln Ile Ser Trp
            20                  25                  30

Glu Lys Ile His Gly Lys Ser Ser Gln Thr Val Ala Val His His Pro
        35                  40                  45

Gln Tyr Gly Phe Ser Val Gln Gly Glu Tyr Gln Gly Arg Val Leu Phe
    50                  55                  60

Lys Asn Tyr Ser Leu Asn Asp Ala Thr Ile Thr Leu His Asn Ile Gly
65                  70                  75                  80

Phe Ser Asp Ser Gly Lys Tyr Ile Cys Lys Ala Val Thr Phe Pro Leu
                85                  90                  95

Gly Asn Ala Gln
            100
```

<210> SEQ ID NO 68
<211> LENGTH: 105
<212> TYPE: PRT
<213> ORGANISM: Homo sapiens

<400> SEQUENCE: 68

```
Leu Glu Thr Ser Asp Val Val Thr Val Val Leu Gly Gln Asp Ala Lys
1               5                   10                  15

Leu Pro Cys Phe Tyr Arg Gly Asp Ser Gly Glu Gln Val Gly Gln Val
            20                  25                  30

Ala Trp Ala Arg Val Asp Ala Gly Glu Gly Ala Gln Glu Leu Ala Leu
        35                  40                  45

Leu His Ser Lys Tyr Gly Leu His Val Ser Pro Ala Tyr Glu Gly Arg
    50                  55                  60

Val Glu Gln Pro Pro Pro Arg Asn Pro Leu Asp Gly Ser Val Leu
65                  70                  75                  80

Leu Arg Asn Ala Val Gln Ala Asp Glu Gly Glu Tyr Glu Cys Arg Val
```

```
                        85                  90                  95

Ser Thr Phe Pro Ala Gly Ser Phe Gln
                100                 105

<210> SEQ ID NO 69
<211> LENGTH: 102
<212> TYPE: PRT
<213> ORGANISM: Homo sapiens

<400> SEQUENCE: 69

Glu Glu Val Leu Trp His Thr Ser Val Pro Phe Ala Glu Asn Met Ser
1               5                   10                  15

Leu Glu Cys Val Tyr Pro Ser Met Gly Ile Leu Thr Gln Val Glu Trp
            20                  25                  30

Phe Lys Ile Gly Thr Gln Gln Asp Ser Ile Ala Ile Phe Ser Pro Thr
        35                  40                  45

His Gly Met Val Ile Arg Lys Pro Tyr Ala Glu Arg Val Tyr Phe Leu
    50                  55                  60

Asn Ser Thr Met Ala Ser Asn Asn Met Thr Leu Phe Phe Arg Asn Ala
65                  70                  75                  80

Ser Glu Asp Asp Val Gly Tyr Tyr Ser Cys Ser Leu Tyr Thr Thr Tyr
                85                  90                  95

Pro Gln Gly Thr Trp Gln
            100

<210> SEQ ID NO 70
<211> LENGTH: 10
<212> TYPE: PRT
<213> ORGANISM: Homo sapiens

<400> SEQUENCE: 70

Glu Ala Gln Val Pro Ala Leu Gln Pro Pro
1               5                   10

<210> SEQ ID NO 71
<211> LENGTH: 26
<212> TYPE: PRT
<213> ORGANISM: Homo sapiens

<400> SEQUENCE: 71

Val Leu Pro Trp Val Leu Leu Thr Leu Cys Val Thr Ala Gly Thr Pro
1               5                   10                  15

Glu Val Trp Val Gln Val Arg Met Glu Ala
            20                  25

<210> SEQ ID NO 72
<211> LENGTH: 32
<212> TYPE: PRT
<213> ORGANISM: Homo sapiens

<400> SEQUENCE: 72

Pro Trp Val Leu Leu Thr Leu Cys Val Thr Ala Gly Thr Pro Glu Val
1               5                   10                  15

Trp Gln Val Arg Met Glu Ala Thr Glu Leu Ser Ser Phe Thr Ile Arg
            20                  25                  30

<210> SEQ ID NO 73
<211> LENGTH: 7
<212> TYPE: PRT
<213> ORGANISM: Homo sapiens
```

```
<400> SEQUENCE: 73

Leu Cys Val Thr Ala Gly Thr
1               5

<210> SEQ ID NO 74
<211> LENGTH: 10
<212> TYPE: PRT
<213> ORGANISM: Homo sapiens

<400> SEQUENCE: 74

Val Thr Val Ser Trp Gly Gly Pro Asn Gly
1               5                   10

<210> SEQ ID NO 75
<211> LENGTH: 17
<212> TYPE: PRT
<213> ORGANISM: Homo sapiens

<400> SEQUENCE: 75

Ala Val Leu His Pro Glu Arg Gly Ile Arg Gln Trp Ala Pro Ala Arg
1               5                   10                  15

Gln

<210> SEQ ID NO 76
<211> LENGTH: 20
<212> TYPE: PRT
<213> ORGANISM: Homo sapiens

<400> SEQUENCE: 76

Ala Val Leu His Pro Glu Arg Gly Ile Arg Gln Trp Ala Pro Ala Arg
1               5                   10                  15

Gln Ala Arg Trp
            20

<210> SEQ ID NO 77
<211> LENGTH: 25
<212> TYPE: PRT
<213> ORGANISM: Homo sapiens

<400> SEQUENCE: 77

Ala Val Leu His Pro Glu Arg Gly Ile Arg Gln Trp Ala Pro Ala Arg
1               5                   10                  15

Gln Ala Arg Trp Glu Thr Gln Ser Ser
            20                  25

<210> SEQ ID NO 78
<211> LENGTH: 27
<212> TYPE: PRT
<213> ORGANISM: Homo sapiens

<400> SEQUENCE: 78

Ala Val Leu His Pro Glu Arg Gly Ile Arg Gln Trp Ala Pro Ala Arg
1               5                   10                  15

Gln Ala Arg Trp Glu Thr Gln Ser Ser Ile Ser
            20                  25

<210> SEQ ID NO 79
<211> LENGTH: 28
<212> TYPE: PRT
<213> ORGANISM: Homo sapiens

<400> SEQUENCE: 79
```

Ala Val Leu His Pro Glu Arg Gly Ile Arg Gln Trp Ala Pro Ala Arg
1               5                   10                  15

Gln Ala Arg Trp Glu Thr Gln Ser Ser Ile Ser Leu
            20                  25

<210> SEQ ID NO 80
<211> LENGTH: 9
<212> TYPE: PRT
<213> ORGANISM: Homo sapiens

<400> SEQUENCE: 80

Leu Ser Ala Arg Ser Pro Arg Gly Pro
1               5

<210> SEQ ID NO 81
<211> LENGTH: 11
<212> TYPE: PRT
<213> ORGANISM: Homo sapiens

<400> SEQUENCE: 81

Cys Lys Cys Pro Ala Pro Asn Leu Leu Gly Gly
1               5                   10

<210> SEQ ID NO 82
<211> LENGTH: 10
<212> TYPE: PRT
<213> ORGANISM: Homo sapiens

<400> SEQUENCE: 82

Val Phe Ile Phe Pro Pro Lys Ile Lys Asp
1               5                   10

<210> SEQ ID NO 83
<211> LENGTH: 12
<212> TYPE: PRT
<213> ORGANISM: Homo sapiens

<400> SEQUENCE: 83

Val Phe Ile Phe Pro Pro Lys Ile Lys Asp Val Leu
1               5                   10

<210> SEQ ID NO 84
<211> LENGTH: 9
<212> TYPE: PRT
<213> ORGANISM: Homo sapiens

<400> SEQUENCE: 84

Phe Ile Phe Pro Pro Lys Ile Lys Asp
1               5

<210> SEQ ID NO 85
<211> LENGTH: 11
<212> TYPE: PRT
<213> ORGANISM: Homo sapiens

<400> SEQUENCE: 85

Phe Ile Phe Pro Pro Lys Ile Lys Asp Val Leu
1               5                   10

<210> SEQ ID NO 86
<211> LENGTH: 12
<212> TYPE: PRT
<213> ORGANISM: Homo sapiens

<400> SEQUENCE: 86

Phe Ile Phe Pro Pro Lys Ile Lys Asp Val Leu Met
1               5                   10

<210> SEQ ID NO 87
<211> LENGTH: 8
<212> TYPE: PRT
<213> ORGANISM: Homo sapiens

<400> SEQUENCE: 87

Ile Phe Pro Pro Lys Ile Lys Asp
1               5

<210> SEQ ID NO 88
<211> LENGTH: 7
<212> TYPE: PRT
<213> ORGANISM: Homo sapiens

<400> SEQUENCE: 88

Phe Pro Pro Lys Ile Lys Asp
1               5

<210> SEQ ID NO 89
<211> LENGTH: 10
<212> TYPE: PRT
<213> ORGANISM: Homo sapiens

<400> SEQUENCE: 89

Phe Pro Pro Lys Ile Lys Asp Val Leu Met
1               5                   10

<210> SEQ ID NO 90
<211> LENGTH: 9
<212> TYPE: PRT
<213> ORGANISM: Homo sapiens

<400> SEQUENCE: 90

Pro Pro Lys Ile Lys Asp Val Leu Met
1               5

<210> SEQ ID NO 91
<211> LENGTH: 7
<212> TYPE: PRT
<213> ORGANISM: Homo sapiens

<400> SEQUENCE: 91

Pro Lys Ile Lys Asp Val Leu
1               5

<210> SEQ ID NO 92
<211> LENGTH: 8
<212> TYPE: PRT
<213> ORGANISM: Homo sapiens

<400> SEQUENCE: 92

Met Ile Ser Leu Ser Pro Val Thr
1               5

<210> SEQ ID NO 93
<211> LENGTH: 8
<212> TYPE: PRT
<213> ORGANISM: Homo sapiens

<400> SEQUENCE: 93

Ile Ser Leu Ser Pro Ile Val Thr

```
1               5

<210> SEQ ID NO 94
<211> LENGTH: 9
<212> TYPE: PRT
<213> ORGANISM: Homo sapiens

<400> SEQUENCE: 94

Val Ser Glu Asp Asp Pro Asp Val Gln
1               5

<210> SEQ ID NO 95
<211> LENGTH: 14
<212> TYPE: PRT
<213> ORGANISM: Homo sapiens

<400> SEQUENCE: 95

Phe Val Asn Asn Val Glu Val His Thr Ala Gln Thr Gln Thr
1               5                   10

<210> SEQ ID NO 96
<211> LENGTH: 23
<212> TYPE: PRT
<213> ORGANISM: Homo sapiens

<400> SEQUENCE: 96

Leu Arg Val Val Ser Ala Leu Pro Ile Gln His Gln Asp Trp Met Ser
1               5                   10                  15

Gly Lys Glu Phe Lys Cys Lys
            20

<210> SEQ ID NO 97
<211> LENGTH: 13
<212> TYPE: PRT
<213> ORGANISM: Homo sapiens

<400> SEQUENCE: 97

Arg Val Val Ser Ala Leu Pro Ile Gln His Gln Asp Trp
1               5                   10

<210> SEQ ID NO 98
<211> LENGTH: 18
<212> TYPE: PRT
<213> ORGANISM: Homo sapiens

<400> SEQUENCE: 98

Arg Val Val Ser Ala Leu Pro Ile Gln His Gln Asp Trp Met Ser Gly
1               5                   10                  15

Lys Glu

<210> SEQ ID NO 99
<211> LENGTH: 11
<212> TYPE: PRT
<213> ORGANISM: Homo sapiens

<400> SEQUENCE: 99

Val Ser Ala Leu Pro Ile Gln His Gln Asp Trp
1               5                   10

<210> SEQ ID NO 100
<211> LENGTH: 7
<212> TYPE: PRT
<213> ORGANISM: Homo sapiens
```

```
<400> SEQUENCE: 100

Pro Ile Gln His Gln Asp Trp
1               5

<210> SEQ ID NO 101
<211> LENGTH: 12
<212> TYPE: PRT
<213> ORGANISM: Homo sapiens

<400> SEQUENCE: 101

Pro Ile Gln His Gln Asp Trp Met Ser Gly Lys Glu
1               5                   10

<210> SEQ ID NO 102
<211> LENGTH: 15
<212> TYPE: PRT
<213> ORGANISM: Homo sapiens

<400> SEQUENCE: 102

Phe Lys Cys Lys Val Asn Asn Lys Asp Leu Pro Ala Pro Ile Glu
1               5                   10                  15

<210> SEQ ID NO 103
<211> LENGTH: 14
<212> TYPE: PRT
<213> ORGANISM: Homo sapiens

<400> SEQUENCE: 103

Leu Pro Ala Pro Ile Glu Arg Thr Ile Ser Lys Pro Lys Gly
1               5                   10

<210> SEQ ID NO 104
<211> LENGTH: 15
<212> TYPE: PRT
<213> ORGANISM: Homo sapiens

<400> SEQUENCE: 104

Arg Thr Ile Ser Lys Pro Lys Gly Ser Val Arg Ala Pro Gln Val
1               5                   10                  15

<210> SEQ ID NO 105
<211> LENGTH: 24
<212> TYPE: PRT
<213> ORGANISM: Homo sapiens

<400> SEQUENCE: 105

Gly Ser Val Arg Ala Pro Gln Val Tyr Val Leu Pro Pro Pro Glu Glu
1               5                   10                  15

Glu Met Thr Lys Lys Gln Val Thr
            20

<210> SEQ ID NO 106
<211> LENGTH: 8
<212> TYPE: PRT
<213> ORGANISM: Homo sapiens

<400> SEQUENCE: 106

Tyr Val Leu Pro Pro Pro Glu Glu
1               5

<210> SEQ ID NO 107
<211> LENGTH: 8
<212> TYPE: PRT
<213> ORGANISM: Homo sapiens
```

<400> SEQUENCE: 107

Lys Lys Gln Val Thr Leu Thr Cys
1               5

<210> SEQ ID NO 108
<211> LENGTH: 9
<212> TYPE: PRT
<213> ORGANISM: Homo sapiens

<400> SEQUENCE: 108

Val Thr Asp Phe Met Pro Glu Asp Ile
1               5

<210> SEQ ID NO 109
<211> LENGTH: 10
<212> TYPE: PRT
<213> ORGANISM: Homo sapiens

<400> SEQUENCE: 109

Val Thr Asp Phe Met Pro Glu Asp Ile Tyr
1               5                   10

<210> SEQ ID NO 110
<211> LENGTH: 8
<212> TYPE: PRT
<213> ORGANISM: Homo sapiens

<400> SEQUENCE: 110

Asp Phe Met Pro Glu Asp Ile Tyr
1               5

<210> SEQ ID NO 111
<211> LENGTH: 10
<212> TYPE: PRT
<213> ORGANISM: Homo sapiens

<400> SEQUENCE: 111

Phe Met Pro Glu Asp Ile Tyr Val Glu Trp
1               5                   10

<210> SEQ ID NO 112
<211> LENGTH: 13
<212> TYPE: PRT
<213> ORGANISM: Homo sapiens

<400> SEQUENCE: 112

Ile Tyr Val Glu Trp Thr Asn Asn Gly Lys Thr Glu Leu
1               5                   10

<210> SEQ ID NO 113
<211> LENGTH: 12
<212> TYPE: PRT
<213> ORGANISM: Homo sapiens

<400> SEQUENCE: 113

Tyr Val Glu Trp Thr Asn Asn Gly Lys Thr Glu Leu
1               5                   10

<210> SEQ ID NO 114
<211> LENGTH: 11
<212> TYPE: PRT
<213> ORGANISM: Homo sapiens

<400> SEQUENCE: 114

```
Val Glu Trp Thr Asn Asn Gly Lys Thr Glu Leu
1               5                   10
```

<210> SEQ ID NO 115
<211> LENGTH: 10
<212> TYPE: PRT
<213> ORGANISM: Homo sapiens

<400> SEQUENCE: 115

```
Glu Trp Thr Asn Asn Gly Lys Thr Glu Leu
1               5                   10
```

<210> SEQ ID NO 116
<211> LENGTH: 9
<212> TYPE: PRT
<213> ORGANISM: Homo sapiens

<400> SEQUENCE: 116

```
Asn Tyr Lys Asn Thr Glu Pro Val Leu
1               5
```

<210> SEQ ID NO 117
<211> LENGTH: 7
<212> TYPE: PRT
<213> ORGANISM: Homo sapiens

<400> SEQUENCE: 117

```
Lys Asn Thr Glu Pro Val Leu
1               5
```

<210> SEQ ID NO 118
<211> LENGTH: 20
<212> TYPE: PRT
<213> ORGANISM: Homo sapiens

<400> SEQUENCE: 118

```
Thr Glu Pro Val Leu Asp Ser Asp Gly Ser Tyr Phe Met Tyr Ser Lys
1               5                   10                  15

Leu Arg Val Glu
            20
```

<210> SEQ ID NO 119
<211> LENGTH: 7
<212> TYPE: PRT
<213> ORGANISM: Homo sapiens

<400> SEQUENCE: 119

```
Asp Ser Asp Gly Ser Tyr Phe
1               5
```

<210> SEQ ID NO 120
<211> LENGTH: 16
<212> TYPE: PRT
<213> ORGANISM: Homo sapiens

<400> SEQUENCE: 120

```
Arg Val Glu Lys Lys Asn Trp Val Glu Arg Asn Ser Tyr Ser Cys Ser
1               5                   10                  15
```

<210> SEQ ID NO 121
<211> LENGTH: 8
<212> TYPE: PRT
<213> ORGANISM: Homo sapiens

```
<400> SEQUENCE: 121

Ser Val Val His Glu Gly Leu His
1               5

<210> SEQ ID NO 122
<211> LENGTH: 25
<212> TYPE: DNA
<213> ORGANISM: Artificial Sequence
<220> FEATURE:
<223> OTHER INFORMATION: recombinant sequence

<400> SEQUENCE: 122
tgcacgtggc agctttgtct ctgtt                                          25
```

COMPOSITIONS AND METHODS FOR MODULATING T-CELL MEDIATED IMMUNE RESPONSE

RELATED APPLICATIONS

This application claims the benefit of U.S. Provisional Application No. 62/213,305, filed Sep. 2, 2015 and U.S. Provisional Application No. 62/370,512, filed Aug. 3, 2016, the contents of each of which are incorporated herein by reference in their entirety.

INCORPORATION OF SEQUENCE LISTING

The contents of the text file named "UNCO002001US_SeqList.txt," which was created on Sep. 2, 2016 and is 55.1 KB in size, are hereby incorporated by reference in their entirety.

FIELD OF THE DISCLOSURE

The present disclosure relates to compositions and methods for modulating T-cell mediated immune response in a subject in need thereof. The method includes administering to the subject an effective amount of a CD112R protein, a fusion polypeptide, a complex including CD112R and a second protein, or an anti-CD112R antibody of the present disclosure.

BACKGROUND OF THE DISCLOSURE

T cell activation is orchestrated by a cosignaling network, which is involved in all stages of the T cell response. The B7/CD28 family of immunoglobulin superfamilies (IGSFs) and several members of tumor necrosis factor receptor (TNFR) superfamily are the major groups of T cell cosignaling molecules. The importance of these cosignaling pathways has been emphasized in a variety of human diseases, including graft versus host disease (GVHD), autoimmunity, infection, and cancer. Poliovirus receptor (PVR)-like proteins are a newly emerging group of IGSFs with T cell costimulatory functions. This group of molecules shares PVR-signature motif in the first immunoglobulin variable-like (IgV) domain, and are originally known to mediate epithelial cell-cell contacts. The two ligands, CD155 (PVR/Nec1-5) and CD112 (PVRL2/nectin-2), interact with CD226 (DNAM1) to costimulate T cells, and they also inhibit T cell response through another coinhibitory receptor, T cell immunoglobulin and immunoreceptor tyrosine-based inhibitory motif [ITIM] domain (TIGIT). CD155 seems to be the predominant ligand in this ligand/receptor network because the interaction between CD112 and TIGIT is very weak. Adding to the complexity of this network CD155, but not CD112, interacts with CD96, another PVR-like protein present on T cells and natural killer (NK) cells, though the function of this interaction is still unclear. In addition, to its intrinsic inhibitory function, TIGIT exerts its T cell inhibitory effects through ligating CD155 on dendritic cells (DCs) to increase IL-10 secretion, or competes with the costimulatory receptor CD226 for ligand interaction.

Though the molecular and functional relationship between CD226 and TIGIT is still unclear, this novel cosignaling pathway represents important immunomodulators of T cell responses, as well as valuable targets for future immunotherapy. For instance, high TIGIT expression on CD8+ tumor-infiltrating lymphocytes (TILs) was observed in human tumor samples, and the ligands CD155 and CD122 were upregulated by the majority of APCs and cancer cells in the tumor microenvironment. TIGIT blockade synergized with PD-1 blockade to enhance CD8+ TIL activities both in mice and humans, and therefore rejected tumors in a transplanted mouse tumor model. Similarly, blockade of TIGIT and PD-L1 synergistically promoted anti-viral CD8+T cell response and therefore enhanced viral clearance in a inoculation of a soluble TIGIT fusion protein attenuated T cell-mediated response in a series of autoimmunity mouse models including, delayed-type hypersensitivity reactions (DTH), experimental autoimmune encephalomyelitis (EAE) and collagen-induced arthritis (CIA).

The current disclosure relates to CD112R as a new coinhibitory receptor for human T cells. The present disclosure identifies CD112 as the ligand for CD112R.

BRIEF SUMMARY OF THE DISCLOSURE

The current disclosure provides, inter alia, compositions and methods for modulating T-cell mediated immune response in a subject in need thereof. The method includes administering to the subject an effective amount of a CD112R protein, a fusion polypeptide, a complex including CD112R and a second protein, or an anti-CD112R antibody of the present disclosure, which are collectively referred to herein as "CD112R targeting molecules" or "anti-CD112R binding molecules").

In an aspect the present disclosure provides a fusion polypeptide including CD112R protein and a second protein. In embodiments, CD112R is a polypeptide capable of binding to CD112 and having at least 90% sequence identity to at least a 10 amino acid consecutive sequence to SEQ ID NO: 1. In embodiments, CD112R is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1.

In embodiments, the fusion polypeptide binds an epitope on human CD112R comprising at least the amino acid sequence AVLHPERGIRQWAPARQ (SEQ ID NO: 53). In embodiments, the fusion polypeptide binds an epitope on human CD112R comprising at least the amino acid sequence AVLHPERGIRQWAPARQARW (SEQ ID NO: 54). In embodiments, the fusion polypeptide binds an epitope on human CD112R comprising at least the amino acid sequence AVLHPERGIRQWAPARQARWETQSS (SEQ ID NO: 55). In embodiments, the fusion polypeptide binds an epitope on human CD112R comprising at least the amino acid sequence AVLHPERGIRQWAPARQARWETQSSIS (SEQ ID NO: 56). In embodiments, the fusion polypeptide binds an epitope on human CD112R comprising at least the amino acid sequence AVLHPERGIRQWAPARQARWETQSSISL (SEQ ID NO: 57).

In some embodiments, the CD112R is the minimal function region of the extracellular domain of CD112R comprising the amino acid sequence of SEQ ID NO: 44. In some embodiments, the CD112R is the extracellular domain of CD112R comprising the amino acid sequence of SEQ ID NO: 45.

In embodiments, the second protein is an Fc protein, and the resultant fusion protein is referred to herein as a CD112R-Fc fusion protein. In some embodiments, the CD112R-Fc fusion protein includes the minimal function region of the extracellular domain of CD112R comprising the amino acid sequence of SEQ ID NO: 44. In some embodiments, the CD112R-Fc fusion protein includes the extracellular domain of CD112R comprising the amino acid sequence of SEQ ID NO: 45. In embodiments, the CD112R-Fc fusion protein includes an Fc polypeptide sequence comprising an amino acid sequence selected from the group consisting of SEQ ID NO: 46-50.

In embodiments, the CD112R-Fc fusion protein includes the minimal function region of the extracellular domain of CD112R comprising the amino acid sequence of SEQ ID NO: 44 and a Fc polypeptide sequence comprising an amino acid sequence selected from the group consisting of SEQ ID NO: 46-50.

In embodiments, the CD112R-Fc fusion protein includes the extracellular domain of CD112R comprising the amino acid sequence of SEQ ID NO: 45 and a Fc polypeptide sequence comprising an amino acid sequence selected from the group consisting of SEQ ID NO: 46-50.

In embodiments, the CD112R-Fc fusion protein includes the minimal function region of the extracellular domain of CD112R comprising the amino acid sequence of SEQ ID NO: 44 and an Fc polypeptide sequence comprising the amino acid sequence of SEQ ID NO: 46.

In embodiments, the CD112R-Fc fusion protein includes the extracellular domain of CD112R comprising the amino acid sequence of SEQ ID NO: 45 and an Fc polypeptide sequence comprising the amino acid sequence of SEQ ID NO: 46.

The individualized elements of the CD112R fusion protein can be linked in any of a variety of ways, including for example, direct attachment, the use of an intermediate or a spacer peptide, the use of a hinge region, the use of a linker region, such as, by way of non-limiting example, one or more linker peptides, or any combination thereof. For example, the linker peptide includes anywhere from zero to 40 amino acids, e.g., from zero to 35 amino acids, from zero to 30 amino acids, from zero to 25 amino acids, from zero to 20 amino acids, from zero to 10 amino acids, or from zero to 5 amino acids. In embodiments, the linker is a flexible linker, such as for, example, a glycine-serine linker or glycine-serine based linker.

The CD112R-Fc fusion proteins of the disclosure are useful in partially or completely modulating, blocking, inhibiting, reducing, antagonizing, neutralizing or otherwise interfering with at least one biological activity of CD112R. For example, the CD112R-Fc fusion proteins of the disclosure are useful in partially or completely modulating, blocking, inhibiting, reducing, antagonizing, neutralizing or otherwise interfering with the interaction between CD112R and CD112. For example, the fusion proteins of the disclosure are also useful in partially or completely modulating, blocking, inhibiting, reducing, antagonizing, neutralizing or otherwise interfering with the interaction between CD112 and CD226. For example, the CD112R-Fc fusion proteins of the disclosure are useful in partially or completely modulating, blocking, inhibiting, reducing, antagonizing, neutralizing or otherwise interfering with TT-specific T cell response upon administration of a CD112R-Fc fusion protein of the disclosure.

The CD112R-Fc fusion proteins are considered to completely modulate, block, inhibit, reduce, antagonize, neutralize or otherwise interfere with CD112R functional activity when the level of CD112R functional activity in the presence of the CD112R-Fc fusion protein is decreased by at least 95%, e.g., by 96%, 97%, 98%, 99% or 100% as compared to the level of CD112R functional activity in the absence of binding with a CD112R-Fc fusion protein described herein. The CD112R-Fc fusion proteins are considered to partially modulate, block, inhibit, reduce, antagonize, neutralize or otherwise interfere with CD112R functional activity when the level of CD112R activity in the presence of the CD112R-Fc fusion protein is decreased by less than 95%, e.g., 10%, 20%, 25%, 30%, 40%, 50%, 60%, 75%, 80%, 85% or 90% as compared to the level of CD112R activity in the absence of binding with a CD112R-Fc fusion protein described herein.

In embodiments, the CD112R-binding fusion polypeptides described herein are used in conjunction with one or more additional agents or a combination of additional agents. Suitable additional agents include any suitable, known pharmaceutical and/or surgical therapies for an intended application, such as, for example, cancer, autoimmune diseases, inflammatory disorders, and/or infectious diseases. For example, the CD112R-binding fusion polypeptides can be used in conjunction with an additional chemotherapeutic or anti-neoplastic agent.

In embodiments, the at least one additional agent is a molecule that interacts with a target on an immune receptor, such as for example, an immune receptor on a T cell, a natural killer (NK) cell, or combinations thereof. In embodiments, the at least one additional agent can also be a chemical or molecule that modulates immune responses, for example, an agent that targets indoleamine-pyrrole 2,3-dioxygenase (IDO) or mechanistic Target Of Rapamycin (mTOR). In embodiments, the at least one additional agent is a molecule that targets TIGIT, PD-1, PD-L1, TIM-3, LAG-3, BTLA, CD226, CD160, CD137, CD96, CD70, CD47, CD40, NKG2D, VISTA, ICOS, B7-HE, GITR, OX40, KIR, SLAM7, CTLA-4, and combinations thereof.

In embodiments, one or more anti-CD112R-binding molecules of the disclosure are used in combination with one or more molecularly-targeted therapy. In embodiments, one or more anti-CD112R-binding molecules of the disclosure are used in combination with one or more vaccine. In embodiments, one or more anti-CD112R-binding molecules of the disclosure are used in combination with one or more chemotherapeutic agents and/or regimens. In embodiments, one or more anti-CD112R-binding molecules of the disclosure are used in combination with radiation or other radiation-based therapy. In embodiments, one or more anti-CD112R-binding molecules of the disclosure are used in combination with a surgical procedure, such as, by way of non-limiting example, surgical resection.

In embodiments, one or more anti-CD112R-binding molecules of the disclosure are used in combination with one or more bispecific T-cell engagers, one or more cancer vaccines, Freund's Adjuvant, one or more CAR-T cell therapies, one or more stem cell therapies, and/or one or more scFv therapies.

In embodiments, one or more anti-CD112R-binding molecules of the disclosure are used in combination with one or more commercially available anti-cancer agents. Suitable commercially available anti-cancer agents include, by way of non-limiting example, nivolumab, ipilimumab, IL-2, atezolizumab, elotuzumab, daratumumab, talimogene laherparepvec, pembrolizumab, ipilimumab, blinatumomab, ramucirumab, brentuximab, brentuximab vedotin, peginterferon alfa-2bj, sipuleucel-T, ofatumumab, denosumab, and combinations thereof.

In embodiments, one or more anti-CD112R-binding molecules of the disclosure are used in combination with one or more anti-cancer agents in clinical trials and/or undergoing regulatory review. An example of such an anti-cancer agent includes, by way of non-limiting example, tremelimumab.

In embodiments, the CD112R-binding fusion polypeptide and additional agent(s) are formulated into a single therapeutic composition, and the CD112R-binding fusion polypeptide and additional agent(s) are administered simultaneously. In embodiments, the CD112R-binding fusion polypeptide and additional agent(s) are separate from each other, e.g., each is formulated into a separate therapeutic composition, and the CD112R-binding fusion polypeptide and additional agent(s) are administered simultaneously, or the CD112R-binding fusion polypeptide and additional agent(s) are administered at different times during a treatment regimen. For example, the CD112R-binding fusion polypeptide is administered prior to the administration of the additional agent(s), the CD112R-binding fusion polypeptide is administered subsequent to the administration of the additional agent(s), or the CD112R-binding fusion polypeptide and additional agent(s) are administered in an alternating fashion. As described herein, the CD112R-binding fusion polypeptide and additional agent(s) are administered in single doses or in multiple doses.

In another aspect, the present disclosure provides a complex including a CD112R protein bound to an antibody, a detectable moiety, a therapeutic moiety, a solid support, or any combination thereof. In embodiments, the solid support is a bead or nanoparticle. In embodiment, the complex includes CD112R and an antibody including sequence of SEQ ID NO: 3 and/or SEQ ID NO: 5.

In another aspect, the present disclosure provides an in vitro complex of a CD112R protein bound to a CD112 protein. In embodiments, the in vitro complex includes CD112R protein or CD112 protein bound to an antibody, a detectable moiety, a therapeutic moiety, or a solid support. In embodiments, the in vitro complex includes a solid support bound to CD112R, and the solid support is, for example, a bead or nanoparticle. In embodiment, the in vitro complex includes CD 112R and an antibody including sequence of SEQ ID NO: 3 and/or SEQ ID NO: 5.

In another aspect, the present disclosure provides a purified antibody that binds specifically to CD112R protein. In embodiments the purified antibody binds to CD112R, which is a protein of SEQ ID NO: 1. In embodiments, the antibody binds to CD112R, which is a polypeptide capable of binding to CD112 and having at least 90% sequence identity to at least a 10 amino acid consecutive sequence to SEQ ID NO: 1. In embodiments, the antibody binds to CD112R, which is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1. In embodiments, the purified antibody is a humanized antibody that binds to CD112R, which is a polypeptide capable of binding to CD112 and having at least 90%, 91%, 92%, 93%, 94%, 95%, 96%, 97%, 98%, 99%, or 100% sequence identity to at least a 10 amino acid consecutive sequence of SEQ ID NO: 1.

In embodiments, the antibody or antigen binding fragment thereof binds an epitope on human CD112R comprising at least the amino acid sequence AVLHPERGIRQWAPARQ (SEQ ID NO: 53). In embodiments, the antibody or antigen binding fragment thereof binds an epitope on human CD112R comprising at least the amino acid sequence AVLHPERGIRQWAPARQARW (SEQ ID NO: 54). In embodiments, the antibody or antigen binding fragment thereof binds an epitope on human CD112R comprising at least the amino acid sequence AVLHPERGIRQWAPARQARWETQSS (SEQ ID NO: 55). In embodiments, the antibody or antigen binding fragment thereof binds an epitope on human CD112R comprising at least the amino acid sequence AVLHPERGIRQWAPARQARWETQSSIS (SEQ ID NO: 56). In embodiments, the antibody or antigen binding fragment thereof binds an epitope on human CD112R comprising at least the amino acid sequence AVLHPERGIRQWAPARQARWETQSSISL (SEQ ID NO: 57).

In embodiments, the antibody which binds to CD112R has a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the antibody which binds to CD112R has a heavy chain including SEQ ID NO: 5, and a light chain including SEQ ID NO: 3. This antibody is referred to herein as the 2H6 CD112R monoclonal antibody.

In embodiments, the antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the antibody which binds to CD112R has a heavy chain including SEQ ID NO: 32, and a light chain including SEQ ID NO: 33. This antibody is referred to herein as the CD112R monoclonal antibody mAb 4-4.

In embodiments, the antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the antibody which binds to CD112R has a heavy chain including SEQ ID NO: 32, and a light chain including SEQ ID NO: 40. This antibody is referred to herein as the CD112R monoclonal antibody mAb 4-5.

Suitable antibodies of the disclosure also include an antibody or antigen binding fragment thereof that cross-competes for binding to human CD112R to an anti-CD112R antibody comprising a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

Suitable antibodies of the disclosure also include an antibody or antigen binding fragment thereof that cross-competes for binding to human CD112R to an anti-CD112R antibody comprising a heavy chain including SEQ ID NO: 5, and a light chain including SEQ ID NO: 3.

Suitable antibodies of the disclosure also include an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

Suitable antibodies of the disclosure also include an antibody or antigen binding fragment thereof that cross-competes for binding to human CD112R to an anti-CD112R antibody comprising a heavy chain including SEQ ID NO: 32, and a light chain including SEQ ID NO: 33.

Suitable antibodies of the disclosure also include an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

Suitable antibodies of the disclosure also include an antibody or antigen binding fragment thereof that cross-competes for binding to human CD112R to an anti-CD112R antibody comprising a heavy chain including SEQ ID NO: 32, and a light chain including SEQ ID NO: 40.

In embodiments, the anti-CD112R antibody or antigen binding fragment also includes an agent conjugated to the antibody or antigen binding fragment. In embodiments, the agent is a therapeutic agent. In embodiments, the agent is a detectable moiety. In embodiments, the detectable moiety is a diagnostic agent. In embodiments, the agent is conjugated to the antibody or antigen binding fragment via a linker. In embodiments, the linker is a cleavable linker. In embodiments, the linker is a non-cleavable linker.

In embodiments, the anti-CD112R antibody or antigen binding fragments described herein are used in conjunction with one or more additional agents or a combination of additional agents. Suitable additional agents include any suitable, known pharmaceutical and/or surgical therapies for an intended application, such as, for example, cancer, autoimmune diseases, inflammatory disorders, and/or infectious diseases. For example, the anti-CD112R antibody or antigen binding fragments can be used in conjunction with an additional chemotherapeutic or anti-neoplastic agent.

In embodiments, the at least one additional agent is a molecule that interacts with a target on an immune receptor, such as for example, an immune receptor on a T cell, a natural killer (NK) cell, or combinations thereof. In embodiments, the at least one additional agent can also be a chemical or molecule that modulates immune responses, for example, an agent that targets indoleamine-pyrrole 2,3-dioxygenase (IDO) or mechanistic Target Of Rapamycin (mTOR). In embodiments, the at least one additional agent is a molecule that targets TIGIT, PD-1, PD-L1, TIM-3, LAG-3, BTLA, CD226, CD160, CD137, CD96, CD70, CD47, CD40, NKG2D, VISTA, ICOS, B7-HE, GITR, OX40, KIR, SLAM7, CTLA-4, and combinations thereof.

In embodiments, one or more anti-CD112R-binding molecules of the disclosure are used in combination with one or more molecularly-targeted therapy. In embodiments, one or more anti-CD112R-binding molecules of the disclosure are used in combination with one or more vaccine. In embodiments, one or more anti-CD112R-binding molecules of the disclosure are used in combination with one or more chemotherapeutic agents and/or regimens. In embodiments, one or more anti-CD112R-binding molecules of the disclosure are used in combination with radiation or other radiation-based therapy. In embodiments, one or more anti-CD112R-binding molecules of the disclosure are used in combination with a surgical procedure, such as, by way of non-limiting example, surgical resection.

In embodiments, one or more anti-CD112R-binding molecules of the disclosure are used in combination with one or more bispecific T-cell engagers, one or more cancer vaccines, Freund's Adjuvant, one or more CAR-T cell therapies, one or more stem cell therapies, and/or one or more scFv therapies.

In embodiments, one or more anti-CD112R-binding molecules of the disclosure are used in combination with one or more commercially available anti-cancer agents. Suitable commercially available anti-cancer agents include, by way of non-limiting example, nivolumab, ipilimumab, IL-2, atezolizumab, elotuzumab, daratumumab, talimogene laherparepvec, pembrolizumab, ipilimumab, blinatumomab, ramucirumab, brentuximab, brentuximab vedotin, peginterferon alfa-2bj, sipuleucel-T, ofatumumab, denosumab, and combinations thereof.

In embodiments, one or more anti-CD112R-binding molecules of the disclosure are used in combination with one or more anti-cancer agents in clinical trials and/or undergoing regulatory review. An example of such an anti-cancer agent includes, by way of non-limiting example, tremelimumab.

In embodiments, the anti-CD112R antibody or antigen binding fragment and additional agent(s) are formulated into a single therapeutic composition, and the anti-CD112R antibody or antigen binding fragment and additional agent(s) are administered simultaneously. In embodiments, the anti-CD112R antibody or antigen binding fragment and additional agent(s) are separate from each other, e.g., each is formulated into a separate therapeutic composition, and the anti-CD112R antibody or antigen binding fragment and additional agent(s) are administered simultaneously, or the anti-CD112R antibody or antigen binding fragment and additional agent(s) are administered at different times during a treatment regimen. For example, the anti-CD112R antibody or antigen binding fragment is administered prior to the administration of the additional agent(s), the anti-CD112R antibody or antigen binding fragment is administered subsequent to the administration of the additional agent(s), or the anti-CD112R antibody or antigen binding fragment and additional agent(s) are administered in an alternating fashion. As described herein, the anti-CD112R antibody or antigen binding fragment and additional agent(s) are administered in single doses or in multiple doses.

In another aspect, the present disclosure provides multispecific antibodies and antigen binding fragments thereof that bind CD112R and at least a second target. In embodiments, the multispecific antibody binds to CD112R, which is a protein of SEQ ID NO: 1, and at least a second target. In embodiments, the antibody binds to CD112R, which is a polypeptide capable of binding to CD112 and having at least 90% sequence identity to at least a 10 amino acid consecutive sequence to SEQ ID NO: 1, and at least a second target. In embodiments, the multispecific antibody binds to CD112R, which is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1, and at least a second target. In embodiments, the multispecific antibody is a humanized antibody that binds to CD112R, which is a polypeptide capable of binding to CD112 and having at least 90%, 91%, 92%, 93%, 94%, 95%, 96%, 97%, 98%, 99%, or 100% sequence identity to at least a 10 amino acid consecutive sequence of SEQ ID NO: 1, and at least a second target.

In embodiments, the multispecific antibody or antigen binding fragment thereof binds an epitope on human CD112R comprising at least the amino acid sequence AVLHPERGIRQWAPARQ (SEQ ID NO: 53) and binds to at least a second target. In embodiments, the multispecific antibody or antigen binding fragment thereof binds an epitope on human CD112R comprising at least the amino acid sequence AVLHPERGIRQWAPARQARW (SEQ ID NO: 54) and binds to at least a second target. In embodiments, the multispecific antibody or antigen binding fragment thereof binds an epitope on human CD112R comprising at least the amino acid sequence AVLHPERGIRQWAPARQARWETQSS (SEQ ID NO: 55) and binds to at least a second target. In embodiments, the multispecific antibody or antigen binding fragment thereof binds an epitope on human CD112R comprising at least the amino acid sequence AVLHPERGIRQWAPARQAR-WETQSSIS (SEQ ID NO: 56) and binds to at least a second target. In embodiments, the multispecific antibody or antigen binding fragment thereof binds an epitope on human CD112R comprising at least the amino acid sequence AVLHPERGIRQWAPARQARWETQSSISL (SEQ ID NO: 57) and binds to at least a second target.

In embodiments, the multispecific antibody which binds to CD112R and at least a second target has a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the multispecific antibody which binds to CD112R and at least a second target has a heavy chain including SEQ ID NO: 5, and a light chain including SEQ ID NO: 3. This antibody is referred to herein as the 2H6 CD112R monoclonal antibody.

In embodiments, the multispecific antibody which binds to CD112R and at least a second target has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the multispecific antibody which binds to CD112R and at least a second target has a heavy chain including SEQ ID NO: 32, and a light chain including SEQ ID NO: 33. This antibody is referred to herein as the CD112R monoclonal antibody mAb 4-4.

In embodiments, the multispecific antibody which binds to CD112R and at least a second target has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the multispecific antibody which binds to CD112R and at least a second target has a heavy chain including SEQ ID NO: 32, and a light chain including SEQ ID NO: 40. This antibody is referred to herein as the CD112R monoclonal antibody mAb 4-5.

Suitable multispecific antibodies of the disclosure also include a multispecific antibody or antigen binding fragment thereof that cross-competes for binding to human CD112R to an anti-CD112R antibody comprising a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

Suitable multispecific antibodies of the disclosure also include a multispecific antibody or antigen binding fragment thereof that cross-competes for binding to human CD112R to an anti-CD112R antibody comprising a heavy chain including SEQ ID NO: 5, and a light chain including SEQ ID NO: 3.

Suitable multispecific antibodies of the disclosure also include a multispecific antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

Suitable multispecific antibodies of the disclosure also include a multispecific antibody or antigen binding fragment thereof that cross-competes for binding to human CD112R to an anti-CD112R antibody comprising a heavy chain including SEQ ID NO: 32, and a light chain including SEQ ID NO: 33.

Suitable multispecific antibodies of the disclosure also include a multispecific antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

Suitable multispecific antibodies of the disclosure also include a multispecific antibody or antigen binding fragment thereof that cross-competes for binding to human CD112R to an anti-CD112R antibody comprising a heavy chain including SEQ ID NO: 32, and a light chain including SEQ ID NO: 40.

In embodiments, the at least one additional target is a target on an immune receptor, such as for example, an immune receptor on a T cell, a natural killer (NK) cell, or combinations thereof. In embodiments, the at least one additional agent can also be a chemical or molecule that modulates immune responses, for example, an agent that targets indoleamine-pyrrole 2,3-dioxygenase (IDO) or mechanistic Target Of Rapamycin (mTOR). In embodiments, the at least one additional target is TIGIT, PD-1, PD-L1, TIM-3, LAG-3, BTLA, CD226, CD160, CD137, CD96, CD70, CD47, CD40, NKG2D, VISTA, ICOS, B7-HE, GITR, OX40, KIR, SLAM7, CTLA-4, and combinations thereof.

In embodiments, the multispecific anti-CD112R antibody or antigen binding fragments described herein are used in conjunction with one or more additional agents or a combination of additional agents. Suitable additional agents include any suitable, known pharmaceutical and/or surgical therapies for an intended application, such as, for example, cancer, autoimmune diseases, inflammatory disorders, and/or infectious diseases. For example, the multispecific anti-CD112R antibody or antigen binding fragments can be used in conjunction with an additional chemotherapeutic or antineoplastic agent.

In embodiments, the at least one additional agent is a molecule that interacts with a target on an immune receptor, such as for example, an immune receptor on a T cell, a natural killer (NK) cell, or combinations thereof. In embodiments, the at least one additional agent can also be a chemical or molecule that modulates immune responses, for example, an agent that targets indoleamine-pyrrole 2,3-dioxygenase (IDO) or mechanistic Target Of Rapamycin (mTOR). In embodiments, the at least one additional agent is a molecule that targets TIGIT, PD-1, PD-L1, TIM-3, LAG-3, BTLA, CD226, CD160, CD137, CD96, CD70, CD47, CD40, NKG2D, VISTA, ICOS, B7-HE, GITR, OX40, KIR, SLAM7, CTLA-4, and combinations thereof.

In embodiments, one or more anti-CD112R-binding molecules of the disclosure are used in combination with one or more molecularly-targeted therapy. In embodiments, one or more anti-CD112R-binding molecules of the disclosure are used in combination with one or more vaccine. In embodiments, one or more anti-CD112R-binding molecules of the disclosure are used in combination with one or more chemotherapeutic agents and/or regimens. In embodiments, one or more anti-CD112R-binding molecules of the disclosure are used in combination with radiation or other radiation-based therapy. In embodiments, one or more anti-CD112R-binding molecules of the disclosure are used in combination with a surgical procedure, such as, by way of non-limiting example, surgical resection.

In embodiments, one or more anti-CD112R-binding molecules of the disclosure are used in combination with one or more bispecific T-cell engagers, one or more cancer vaccines, Freund's Adjuvant, one or more CAR-T cell therapies, one or more stem cell therapies, and/or one or more scFv therapies.

In embodiments, one or more anti-CD112R-binding molecules of the disclosure are used in combination with one or more commercially available anti-cancer agents. Suitable commercially available anti-cancer agents include, by way of non-limiting example, nivolumab, ipilimumab, IL-2, atezolizumab, elotuzumab, daratumumab, talimogene laherparepvec, pembrolizumab, ipilimumab, blinatumomab, ramucirumab, brentuximab, brentuximab vedotin, peginterferon alfa-2bj, sipuleucel-T, ofatumumab, denosumab, and combinations thereof.

In embodiments, one or more anti-CD112R-binding molecules of the disclosure are used in combination with one or more anti-cancer agents in clinical trials and/or undergoing regulatory review. An example of such an anti-cancer agent includes, by way of non-limiting example, tremelimumab.

In embodiments, the multispecific anti-CD112R antibody or antigen binding fragment and additional agent(s) are formulated into a single therapeutic composition, and the multispecific anti-CD112R antibody or antigen binding fragment and additional agent(s) are administered simultaneously. In embodiments, the multispecific anti-CD112R antibody or antigen binding fragment and additional agent(s) are separate from each other, e.g., each is formulated into a separate therapeutic composition, and the multispecific anti-CD112R antibody or antigen binding fragment and additional agent(s) are administered simultaneously, or the multispecific anti-CD112R antibody or antigen binding fragment and additional agent(s) are administered at different times during a treatment regimen. For example, the multispecific anti-CD112R antibody or antigen binding fragment is administered prior to the administration of the additional agent(s), the multispecific anti-CD112R antibody or antigen binding fragment is administered subsequent to the administration of the additional agent(s), or the multispecific anti-CD112R antibody or antigen binding fragment and additional agent(s) are administered in an alternating fashion. As described herein, the multispecific anti-CD112R antibody or antigen binding fragment and additional agent(s) are administered in single doses or in multiple doses.

In another aspect, the present disclosure provides bispecific antibodies and antigen binding fragments thereof that bind CD112R and a second target. In embodiments, the bispecific antibody binds to CD112R, which is a protein of SEQ ID NO: 1, and a second target. In embodiments, the antibody binds to CD112R, which is a polypeptide capable of binding to CD112 and having at least 90% sequence identity to at least a 10 amino acid consecutive sequence to SEQ ID NO: 1, and a second target. In embodiments, the bispecific antibody binds to CD112R, which is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1, and a second target. In embodiments, the bispecific antibody is a humanized antibody that binds to CD112R, which is a polypeptide capable of binding to CD112 and having at least 90%, 91%, 92%, 93%, 94%, 95%, 96%, 97%, 98%, 99%, or 100% sequence identity to at least a 10 amino acid consecutive sequence of SEQ ID NO: 1, and a second target.

In embodiments, the bispecific antibody or antigen binding fragment thereof binds an epitope on human CD112R comprising at least the amino acid sequence AVLHPERGIRQWAPARQ (SEQ ID NO: 53) and binds to a second target. In embodiments, the bispecific antibody or antigen binding fragment thereof binds an epitope on human CD112R comprising at least the amino acid sequence AVLHPERGIRQWAPARQARW (SEQ ID NO: 54) and binds to a second target. In embodiments, the bispecific antibody or antigen binding fragment thereof binds an epitope on human CD112R comprising at least the amino acid sequence AVLHPERGIRQWAPARQARWETQSS (SEQ ID NO: 55) and binds to a second target. In embodiments, the bispecific antibody or antigen binding fragment thereof binds an epitope on human CD112R comprising at least the amino acid sequence AVLHPERGIRQWAPARQARWETQSSIS (SEQ ID NO: 56) and binds to a second target. In embodiments, the bispecific antibody or antigen binding fragment thereof binds an epitope on human CD112R comprising at least the amino acid sequence AVLHPERGIRQWAPARQARWETQSSISL (SEQ ID NO: 57) and binds to a second target.

In embodiments, the bispecific antibody which binds to CD112R and a second target has a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the bispecific antibody which binds to CD112R and a second target has a heavy chain including SEQ ID NO: 5, and a light chain including SEQ ID NO: 3. This antibody is referred to herein as the 2H6 CD112R monoclonal antibody.

In embodiments, the bispecific antibody which binds to CD112R and a second target has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the bispecific antibody which binds to CD112R and a second target has a heavy chain including SEQ ID NO: 32, and a light chain including SEQ ID NO: 33. This antibody is referred to herein as the CD112R monoclonal antibody mAb 4-4.

In embodiments, the bispecific antibody which binds to CD112R and a second target has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the bispecific antibody which binds to CD112R and a second target has a heavy chain including SEQ ID NO: 32, and a light chain including SEQ ID NO: 40. This antibody is referred to herein as the CD112R monoclonal antibody mAb 4-5.

Suitable bispecific antibodies of the disclosure also include a bispecific antibody or antigen binding fragment thereof that cross-competes for binding to human CD112R to an anti-CD112R antibody comprising a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

Suitable bispecific antibodies of the disclosure also include a bispecific antibody or antigen binding fragment thereof that cross-competes for binding to human CD112R to an anti-CD112R antibody comprising a heavy chain including SEQ ID NO: 5, and a light chain including SEQ ID NO: 3.

Suitable bispecific antibodies of the disclosure also include a bispecific antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

Suitable bispecific antibodies of the disclosure also include a bispecific antibody or antigen binding fragment thereof that cross-competes for binding to human CD112R to an anti-CD112R antibody comprising a heavy chain including SEQ ID NO: 32, and a light chain including SEQ ID NO: 33.

Suitable bispecific antibodies of the disclosure also include a bispecific antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

Suitable bispecific antibodies of the disclosure also include a bispecific antibody or antigen binding fragment thereof that cross-competes for binding to human CD112R to an anti-CD112R antibody comprising a heavy chain including SEQ ID NO: 32, and a light chain including SEQ ID NO: 40.

In embodiments, the second target is a target on an immune receptor, such as for example, an immune receptor on a T cell, a natural killer (NK) cell, or combinations thereof. In embodiments, the at least one additional agent can also be a chemical or molecule that modulates immune responses, for example, an agent that targets indoleamine-pyrrole 2,3-dioxygenase (IDO) or mechanistic Target Of Rapamycin (mTOR). In embodiments, the second target is TIGIT, PD-1, PD-L1, TIM-3, LAG-3, BTLA, CD226, CD160, CD137, CD96, CD70, CD47, CD40, NKG2D, VISTA, ICOS, B7-HE, GITR, OX40, KIR, SLAM7, CTLA-4, and combinations thereof.

In embodiments, the bispecific anti-CD112R antibody or antigen binding fragments described herein are used in conjunction with one or more additional agents or a combination of additional agents. Suitable additional agents include any suitable, known pharmaceutical and/or surgical therapies for an intended application, such as, for example, cancer, autoimmune diseases, inflammatory disorders, and/or infectious diseases. For example, the bispecific anti-CD112R antibody or antigen binding fragments can be used in conjunction with an additional chemotherapeutic or antineoplastic agent.

In embodiments, the at least one additional agent is a molecule that interacts with a target on an immune receptor, such as for example, an immune receptor on a T cell, a natural killer (NK) cell, or combinations thereof. In embodiments, the at least one additional agent can also be a chemical or molecule that modulates immune responses, for example, an agent that targets indoleamine-pyrrole 2,3-dioxygenase (IDO) or mechanistic Target Of Rapamycin (mTOR). In embodiments, the at least one additional agent is a molecule that targets TIGIT, PD-1, PD-L1, TIM-3, LAG-3, BTLA, CD226, CD160, CD137, CD96, CD70, CD47, CD40, NKG2D, VISTA, ICOS, B7-HE, GITR, OX40, KIR, SLAM7, CTLA-4, and combinations thereof.

In embodiments, one or more anti-CD112R-binding molecules of the disclosure are used in combination with one or more molecularly-targeted therapy. In embodiments, one or more anti-CD112R-binding molecules of the disclosure are used in combination with one or more vaccine. In embodiments, one or more anti-CD112R-binding molecules of the disclosure are used in combination with one or more chemotherapeutic agents and/or regimens. In embodiments, one or more anti-CD112R-binding molecules of the disclosure are used in combination with radiation or other radiation-based therapy. In embodiments, one or more anti-CD112R-binding molecules of the disclosure are used in combination with a surgical procedure, such as, by way of non-limiting example, surgical resection.

In embodiments, one or more anti-CD112R-binding molecules of the disclosure are used in combination with one or more bispecific T-cell engagers, one or more cancer vaccines, Freund's Adjuvant, one or more CAR-T cell therapies, one or more stem cell therapies, and/or one or more scFv therapies.

In embodiments, one or more anti-CD112R-binding molecules of the disclosure are used in combination with one or more commercially available anti-cancer agents. Suitable commercially available anti-cancer agents include, by way of non-limiting example, nivolumab, ipilimumab, IL-2, atezolizumab, elotuzumab, daratumumab, talimogene laherparepvec, pembrolizumab, ipilimumab, blinatumomab, ramucirumab, brentuximab, brentuximab vedotin, peginterferon alfa-2bj, sipuleucel-T, ofatumumab, denosumab, and combinations thereof.

In embodiments, one or more anti-CD112R-binding molecules of the disclosure are used in combination with one or more anti-cancer agents in clinical trials and/or undergoing regulatory review. An example of such an anti-cancer agent includes, by way of non-limiting example, tremelimumab.

In embodiments, the bispecific anti-CD112R antibody or antigen binding fragment and additional agent(s) are formulated into a single therapeutic composition, and the bispecific anti-CD112R antibody or antigen binding fragment and additional agent(s) are administered simultaneously. In embodiments, the bispecific anti-CD112R antibody or antigen binding fragment and additional agent(s) are separate from each other, e.g., each is formulated into a separate therapeutic composition, and the bispecific anti-CD112R antibody or antigen binding fragment and additional agent(s) are administered simultaneously, or the bispecific anti-CD112R antibody or antigen binding fragment and additional agent(s) are administered at different times during a treatment regimen. For example, the bispecific anti-CD112R antibody or antigen binding fragment is administered prior to the administration of the additional agent(s), the bispecific anti-CD112R antibody or antigen binding fragment is administered subsequent to the administration of the additional agent(s), or the bispecific anti-CD112R antibody or antigen binding fragment and additional agent(s) are administered in an alternating fashion. As described herein, the bispecific anti-CD112R antibody or antigen binding fragment and additional agent(s) are administered in single doses or in multiple doses.

In another aspect, the present disclosure provides a purified single chain antibody that binds specifically to CD112R protein. In embodiments, a single chain antibody specific for binding CD112R, referred to herein as an "anti-CD112R single chain antibody," is fused to an Fc polypeptide. In embodiments, the Fc polypeptide is an Fc region of an IgG immunoglobulin, such as, an IgG immunoglobulin selected from the group consisting of IgG1 isotype, IgG2 isotype, IgG3 isotype, IgG4 isotype, and IgM isotype. In embodiments, the Fc polypeptide comprises an amino acid sequence selected from the group consisting of SEQ ID NO: 46-50.

In embodiments, the single chain antibody binds an epitope on human CD112R comprising at least the amino acid sequence AVLHPERGIRQWAPARQ (SEQ ID NO: 53). In embodiments, the single chain antibody binds an epitope on human CD112R comprising at least the amino acid sequence AVLHPERGIRQWAPARQARW (SEQ ID NO: 54). In embodiments, the single chain antibody binds an epitope on human CD112R comprising at least the amino acid sequence AVLHPERGIRQWAPARQARWETQSS (SEQ ID NO: 55). In embodiments, the single chain antibody binds an epitope on human CD112R comprising at least the amino acid sequence AVLHPERGIRQWAPARQARWETQSSIS (SEQ ID NO: 56). In embodiments, the single chain antibody binds an epitope on human CD112R comprising at least the amino acid sequence AVLHPERGIRQWAPARQARWETQSSISL (SEQ ID NO: 57).

In embodiments, the anti-CD112R single chain antibody is fused to the carboxy terminus of the Fc polypeptide. In embodiments, the anti-CD112R single chain antibody is fused to the amino terminus of the Fc polypeptide. The fusions are constructed as a single genetic construct and expressed in cells in culture.

In embodiments, the anti-CD112R single chain antibody binds to CD112R, which is a polypeptide capable of binding to CD112 and having at least 90% sequence identity to at least a 10 amino acid consecutive sequence to SEQ ID NO: 1. In embodiments, the anti-CD112R single chain antibody binds to CD112R, which is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1. In embodiments, the anti-CD112R single chain antibody binds to CD112R, which is a polypeptide capable of binding to CD112 and having at least 90%, 91%, 92%, 93%, 94%, 95%, 96%, 97%, 98%, 99%, or 100% sequence identity to at least a 10 amino acid consecutive sequence of SEQ ID NO: 1.

In embodiments, the anti-CD112R single chain antibody which binds to CD112R has a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the anti-CD112R single chain antibody which binds to CD112R has a heavy chain including SEQ ID NO: 5, and a light chain including SEQ ID NO: 3.

In embodiments, the anti-CD112R single chain antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the anti-CD112R single chain antibody which binds to CD112R has a heavy chain including SEQ ID NO: 32, and a light chain including SEQ ID NO: 33.

In embodiments, the anti-CD112R single chain antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the anti-CD112R single chain antibody which binds to CD112R has a heavy chain including SEQ ID NO: 32, and a light chain including SEQ ID NO: 40.

In embodiments, the anti-CD112R single chain antibody is an antibody or antigen binding fragment thereof that cross-competes for binding to human CD112R to an anti-CD112R antibody comprising a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the anti-CD112R single chain antibody is an antibody or antigen binding fragment thereof that cross-competes for binding to human CD112R to an anti-CD112R antibody comprising a heavy chain including SEQ ID NO: 5, and a light chain including SEQ ID NO: 3.

In embodiments, the anti-CD112R single chain antibody is an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the anti-CD112R single chain antibody is an antibody or antigen binding fragment thereof that cross-competes for binding to human CD112R to an anti-CD112R antibody comprising a heavy chain including SEQ ID NO: 32, and a light chain including SEQ ID NO: 33.

In embodiments, the anti-CD112R single chain antibody is an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the anti-CD112R single chain antibody is an antibody or antigen binding fragment thereof that cross-competes for binding to human CD112R to an anti-CD112R antibody comprising a heavy chain including SEQ ID NO: 32, and a light chain including SEQ ID NO: 40.

The anti-CD112R single chain antibodies or antigen binding fragment thereof are useful in therapeutic indications. In embodiments, the anti-CD112R single chain antibodies or antigen binding fragments thereof are administered in at a level that is sufficient to trigger antibody-dependent cell-mediated cytotoxicity (ADCC) in a subject in need thereof. For example, the anti-CD112R single chain antibodies or antigen binding fragments thereof are used to trigger antibody-dependent cell-mediated cytotoxicity (ADCC) in a subject who is suffering from or is at risk of developing cancer.

In embodiments, the anti-CD112R single chain antibody also includes an agent conjugated to the single chain antibody or antigen binding fragment. In embodiments, the agent is a therapeutic agent. In embodiments, the agent is a detectable moiety. In embodiments, the detectable moiety is a diagnostic agent. In embodiments, the agent is conjugated to the single chain antibody or antigen binding fragment via a linker. In embodiments, the linker is a cleavable linker. In embodiments, the linker is a non-cleavable linker.

In embodiments, the anti-CD112R single chain antibodies described herein are used in conjunction with one or more additional agents or a combination of additional agents. Suitable additional agents include any suitable, known pharmaceutical and/or surgical therapies for an intended application, such as, for example, cancer, autoimmune diseases, inflammatory disorders, and/or infectious diseases. For example, the anti-CD112R single chain antibody can be used in conjunction with an additional chemotherapeutic or anti-neoplastic agent.

In embodiments, the at least one additional agent is a molecule that interacts with a target on an immune receptor, such as for example, an immune receptor on a T cell, a natural killer (NK) cell, or combinations thereof. In embodiments, the at least one additional agent can also be a chemical or molecule that modulates immune responses, for example, an agent that targets indoleamine-pyrrole 2,3-dioxygenase (IDO) or mechanistic Target Of Rapamycin (mTOR). In embodiments, the at least one additional agent is a molecule that targets TIGIT, PD-1, PD-L1, TIM-3, LAG-3, BTLA, CD226, CD160, CD137, CD96, CD70, CD47, CD40, NKG2D, VISTA, ICOS, B7-HE, GITR, OX40, KIR, SLAM7, CTLA-4, and combinations thereof.

In embodiments, one or more anti-CD112R-binding molecules of the disclosure are used in combination with one or more molecularly-targeted therapy. In embodiments, one or more anti-CD112R-binding molecules of the disclosure are used in combination with one or more vaccine. In embodiments, one or more anti-CD112R-binding molecules of the disclosure are used in combination with one or more chemotherapeutic agents and/or regimens. In embodiments, one or more anti-CD112R-binding molecules of the disclosure are used in combination with radiation or other radiation-based therapy. In embodiments, one or more anti-CD112R-binding molecules of the disclosure are used in combination with a surgical procedure, such as, by way of non-limiting example, surgical resection.

In embodiments, one or more anti-CD112R-binding molecules of the disclosure are used in combination with one or more bispecific T-cell engagers, one or more cancer vaccines, Freund's Adjuvant, one or more CAR-T cell therapies, one or more stem cell therapies, and/or one or more scFv therapies.

In embodiments, one or more anti-CD112R-binding molecules of the disclosure are used in combination with one or more commercially available anti-cancer agents. Suitable commercially available anti-cancer agents include, by way of non-limiting example, nivolumab, ipilimumab, IL-2, atezolizumab, elotuzumab, daratumumab, talimogene laherparepvec, pembrolizumab, ipilimumab, blinatumomab, ramucirumab, brentuximab, brentuximab vedotin, peginterferon alfa-2bj, sipuleucel-T, ofatumumab, denosumab, and combinations thereof.

In embodiments, one or more anti-CD112R-binding molecules of the disclosure are used in combination with one or more anti-cancer agents in clinical trials and/or undergoing regulatory review. An example of such an anti-cancer agent includes, by way of non-limiting example, tremelimumab.

In embodiments, the anti-CD112R single chain antibody or antigen binding fragment and additional agent(s) are formulated into a single therapeutic composition, and the anti-CD112R single chain antibody or antigen binding fragment and additional agent(s) are administered simultaneously. In embodiments, the anti-CD112R single chain antibody or antigen binding fragment and additional agent(s) are separate from each other, e.g., each is formulated into a separate therapeutic composition, and the anti-CD112R single chain antibody or antigen binding fragment and additional agent(s) are administered simultaneously, or the anti-CD112R single chain antibody or antigen binding fragment and additional agent(s) are administered at different times during a treatment regimen. For example, the anti-CD112R single chain antibody or antigen binding fragment is administered prior to the administration of the additional agent(s), the anti-CD112R single chain antibody or antigen binding fragment is administered subsequent to the administration of the additional agent(s), or the anti-CD112R single chain antibody or antigen binding fragment and additional agent(s) are administered in an alternating fashion. As described herein, the anti-CD112R single chain antibody or antigen binding fragment and additional agent(s) are administered in single doses or in multiple doses.

In an aspect, the disclosure provides chimeric antigen receptor (CAR) constructs that include a domain that binds specifically to CD112R protein, referred to herein as the anti-CD112R binding domain of the CAR construct. In the embodiments presented herein, the CAR construct is used to graft an anti-CD112 binding domain onto a T cell. In embodiments, the CAR construct provided herein is a fusion of an anti-CD112R single chain antibody, e.g., and anti-CD112R single-chain variable fragment (scFv) derived from an anti-CD112 monoclonal antibody of the disclosure, fused to CD3-zeta transmembrane and endodomain.

In embodiments, the CAR constructs provided herein include an ectodomain, which consists of a signal peptide, an antibody recognition region comprising the scFv, and a spacer region that links the antigen binding domain to the transmembrane domain.

In embodiments, the antigen recognition region is an anti-CD112R binding domain. In embodiments, the anti-CD112R binding domain is a scFv. In embodiments, the anti-CD112R scFv of the CAR construct binds to CD112R, which is a polypeptide capable of binding to CD112 and having at least 90% sequence identity to at least a 10 amino acid consecutive sequence to SEQ ID NO: 1. In embodiments, the anti-CD112R scFv of the CAR construct binds to CD112R, which is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1. In embodiments, the anti-CD112R single chain antibody binds to CD112R, which is a polypeptide capable of binding to CD112 and having at least 90%, 91%, 92%, 93%, 94%, 95%, 96%, 97%, 98%, 99%, or 100% sequence identity to at least a 10 amino acid consecutive sequence of SEQ ID NO: 1.

In embodiments, the anti-CD112R scFv of the CAR construct binds an epitope on human CD112R comprising at least the amino acid sequence AVLHPERGIRQWAPARQ (SEQ ID NO: 53). In embodiments, the anti-CD112R scFv of the CAR construct binds an epitope on human CD112R comprising at least the amino acid sequence AVLHPER- GIRQWAPARQARW (SEQ ID NO: 54). In embodiments, the anti-CD112R scFv of the CAR construct binds an epitope on human CD112R comprising at least the amino acid sequence AVLHPERGIRQWAPARQARWETQSS (SEQ ID NO: 55). In embodiments, the anti-CD112R scFv of the CAR construct binds an epitope on human CD112R comprising at least the amino acid sequence AVLHPERGIRQWAPARQARWETQSSIS (SEQ ID NO: 56). In embodiments, the anti-CD112R scFv of the CAR construct binds an epitope on human CD112R comprising at least the amino acid sequence AVLHPERGIRQWAPARQARWETQSSISL (SEQ ID NO: 57).

In embodiments, the anti-CD112R scFv of the CAR construct binds to CD112R has a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the anti-CD112R scFv of the CAR construct binds to CD112R has a heavy chain including SEQ ID NO: 5, and a light chain including SEQ ID NO: 3.

In embodiments, the anti-CD112R single chain antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the anti-CD112R scFv of the CAR construct binds to CD112R has a heavy chain including SEQ ID NO: 32, and a light chain including SEQ ID NO: 33.

In embodiments, the anti-CD112R scFv of the CAR construct binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the anti-CD112R scFv of the CAR construct binds to CD112R has a heavy chain including SEQ ID NO: 32, and a light chain including SEQ ID NO: 40.

In embodiments, the anti-CD112R scFv of the CAR construct is an antibody or antigen binding fragment thereof that cross-competes for binding to human CD112R to an anti-CD112R antibody comprising a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the anti-CD112R scFv of the CAR construct is an antibody or antigen binding fragment thereof that cross-competes for binding to human CD112R to an anti-CD112R antibody comprising a heavy chain including SEQ ID NO: 5, and a light chain including SEQ ID NO: 3.

In embodiments, the anti-CD112R scFv of the CAR construct is an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the anti-CD112R scFv of the CAR construct is an antibody or antigen binding fragment thereof that cross-competes for binding to human CD112R to an anti-CD112R antibody comprising a heavy chain including SEQ ID NO: 32, and a light chain including SEQ ID NO: 33.

In embodiments, the anti-CD112R scFv of the CAR construct is an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the anti-CD112R scFv of the CAR construct is an antibody or antigen binding fragment thereof that cross-competes for binding to human CD112R to an anti-CD112R antibody comprising a heavy chain including SEQ ID NO: 32, and a light chain including SEQ ID NO: 40.

In embodiments, the spacer region is flexible enough to allow the anti-CD112R binding domain to orient in different directions to facilitate antigen recognition. In embodiments, the spacer is the hinge region from IgG1. In embodiments, the spacer includes the CH2CH3 region of immunoglobulin and portions of CD3.

The transmembrane domain is a hydrophobic alpha helix that spans the membrane. In embodiments, the transmembrane domain from the most membrane proximal component of the endodomain is used.

In embodiments, the endodomain component includes CD3-zeta which contains the immunoreceptor tyrosine-based activation motifs (ITAMs), which transmit an activation signal to the T cell after CD112R is bound.

In embodiments, the CAR construct has the following structural arrangement from N-terminus to C-terminus: anti-CD112R binding domain+hinge+transmembrane region (TM)+endodomain. In embodiments, the CAR construct has the following structural arrangement from N-terminus to C-terminus: anti-CD112R binding domain+hinge region+TM+costimulatory domain+CD3-zeta domain. In embodiments, the CAR construct has the following structural arrangement from N-terminus to C-terminus: anti-CD112R binding domain+CD8a hinge region+TM+CD28a (amino acids 180-219) costimulatory+CD3-zeta domain. In embodiments, the CAR construct has the following structural arrangement from N-terminus to C-terminus: (VH-linker-VL)–CD8a hinge+TM+CD28 (180-219aa) costimulatory domain+CD3-zeta (intracytoplasmic domain). In embodiments, the CAR construct has the structural arrangement shown in FIG. 15.

In embodiments, the CAR construct comprises the sequence of SEQ ID NO: 51.

In any of the embodiments described herein, the anti-CD112 binding molecules may be modified to alter one or more properties of the anti-CD112 binding molecule. In embodiments, it can be desirable to modify an anti-CD112 binding molecule of the disclosure with respect to effector function, so as to enhance or reduce such function to improve the effectiveness of the anti-CD112 binding molecule in treating diseases and disorders. In embodiments, the anti-CD112 binding molecule can modified to include one or more post-translational modifications, such as, for example, glycosylation to achieve the desired therapeutic efficacy. In embodiments where the anti-CD112 binding molecule includes an Fc region, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an anti-CD112 of the disclosure antibody can be engineered that has dual Fc regions and can thereby have enhanced complement lysis and ADCC capabilities. (See e.g., Stevenson et al., Anti-Cancer Drug Design, 3: 219-230 (1989)). In some embodiments, Fc mutations are made to remove glycosylation sites, thereby reducing Fc function. In embodiments, an anti-CD112 binding molecule is further modified through the use of Fc mutations in the FcRn binding site (Petkova, S. B. et al., Intl. Immunol. 18, 1759-1769 (2006)); Deng, R. et al., mAbs 4, 101-109 (2012)); Olafson, T Methods Mol. Biol. 907, 537-556 (2012)). In embodiments where the anti-CD112R binding molecule includes an Fc domain, the anti-CD112 binding molecule can include mutations in the Fc domain, such as an N297A mutation (Lund, J. et al., Mol. Immunol. 29, 53-39 (1992)) that reduces IgG effector functions (ADCC and CDC) in order to reduce off-target toxicities.

In another aspect, the present disclosure includes a method of modulating immune response in a subject in need thereof, including administering to the subject a CD112R protein, the fusion polypeptide, the complex, or the antibody of the present disclosure, respectively. The method of modulating immune response of the present disclosure induces tumor suppression or regression in the subject. The method of modulating immune response of the present disclosure modulates T-cell response in said subject.

In another aspect, the present disclosure includes a method of treating, preventing, delaying the progression of or otherwise ameliorating a symptom of one or more pathologies or alleviating a symptom associated with such pathologies, by administering an CD112R protein, a fusion polypeptide, a complex including CD112R and a second protein, or an anti-CD112R antibody of the disclosure (collectively referred to herein as "anti-CD112R binding molecules") to a subject in which such treatment or prevention is desired. The subject to be treated is, e.g., human or other mammal. In embodiments, the subject is a non-human mammal, such as a non-human primate, companion animal (e.g., cat, dog, horse), farm animal, work animal, or zoo animal. In embodiments, the subject is a rodent.

An anti-CD112R binding molecule of the disclosure used in any of the embodiments of these methods and uses can be administered either alone or in combination with one or more additional agents, including small molecule inhibitors, other antibody-based therapies, polypeptide or peptide-based therapies, nucleic acid-based therapies and/or other biologics. In embodiments, an anti-CD112R binding molecule is administered in combination with one or more additional agents such as, by way of non-limiting example, a chemotherapeutic agent, such as an alkylating agent, an anti-metabolite, an anti-microtubule agent, a topoisomerase inhibitor, a cytotoxic antibiotic, and any other nucleic acid damaging agent. In embodiments, the additional agent is a targeted agent, such as another antibody, e.g., a monoclonal antibody (e.g., bevacizumab), a bispecific antibody, or a multispecific antibody. In embodiments, the additional agent is a proteosome inhibitor, such as bortezomib or carfilzomib. In embodiments, the additional agent is an immune modulating agent, such as lenolidominde or IL-2. In embodiments, the additional agent is radiation. In embodiments, the additional agent is an agent considered standard of care by those skilled in the art. In embodiments, the additional agent is a chemotherapeutic agent well known to those skilled in the art. In embodiments, the additional agent(s) is a checkpoint inhibitor, a kinase inhibitor, an agent targeting inhibitors in the tumor microenvironment, and/or a T cell or NK agonist.

In embodiments, the anti-CD112R-binding molecule is administered during and/or after treatment in combination with one or more additional agents such as, for example, a chemotherapeutic agent, an anti-inflammatory agent, and/or a an immunosuppressive agent. In embodiments, the anti-CD112R-binding molecules and the additional agent(s) are formulated into a single therapeutic composition, and the anti-CD112R-binding molecules and additional agent(s) are administered simultaneously. Alternatively, the anti-CD112R-binding molecules and additional agent(s) are separate from each other, e.g., each is formulated into a separate therapeutic composition, and the anti-CD112R-binding molecules and the additional agent(s) are administered simultaneously, or the anti-CD112R-binding molecules and the additional agent(s) are administered at different times during a treatment regimen. For example, the anti-CD112R-binding molecule is administered prior to the administration of the additional agent, the anti-CD112R-binding molecule is administered subsequent to the administration of the additional agent, or the anti-CD112R-binding molecules and the additional agent(s) are administered in an alternating fashion. As described herein, the anti-CD112R-binding molecules and additional agent(s) are administered in single doses or in multiple doses.

In embodiments, the CD112R protein, a fusion polypeptide, a complex including CD112R and a second protein, or an anti-CD112R-binding molecule and the additional agent(s) are administered simultaneously. For example, the anti-CD112R-binding molecules and the additional agent(s) can be formulated in a single composition or administered as two or more separate compositions. In embodiments, the anti-CD112R-binding molecules and the additional agent(s) are administered sequentially, or the anti-CD112R-binding molecules and the additional agent(s) are administered at different times during a treatment regimen.

In an aspect is provided a method of treating cancer by administering an effective amount of a composition including a toxin and an anti-CD112R antibody to a subject in need thereof.

In an aspect is provided a drug delivery vehicle including a toxin and anti-CD112R antibodies. The drug delivery device includes a toxin. In embodiments, the toxin is an inhibitor of DNA topoisomerase I or topoisomerase II.

BRIEF DESCRIPTION OF THE DRAWINGS

Figure 1B:
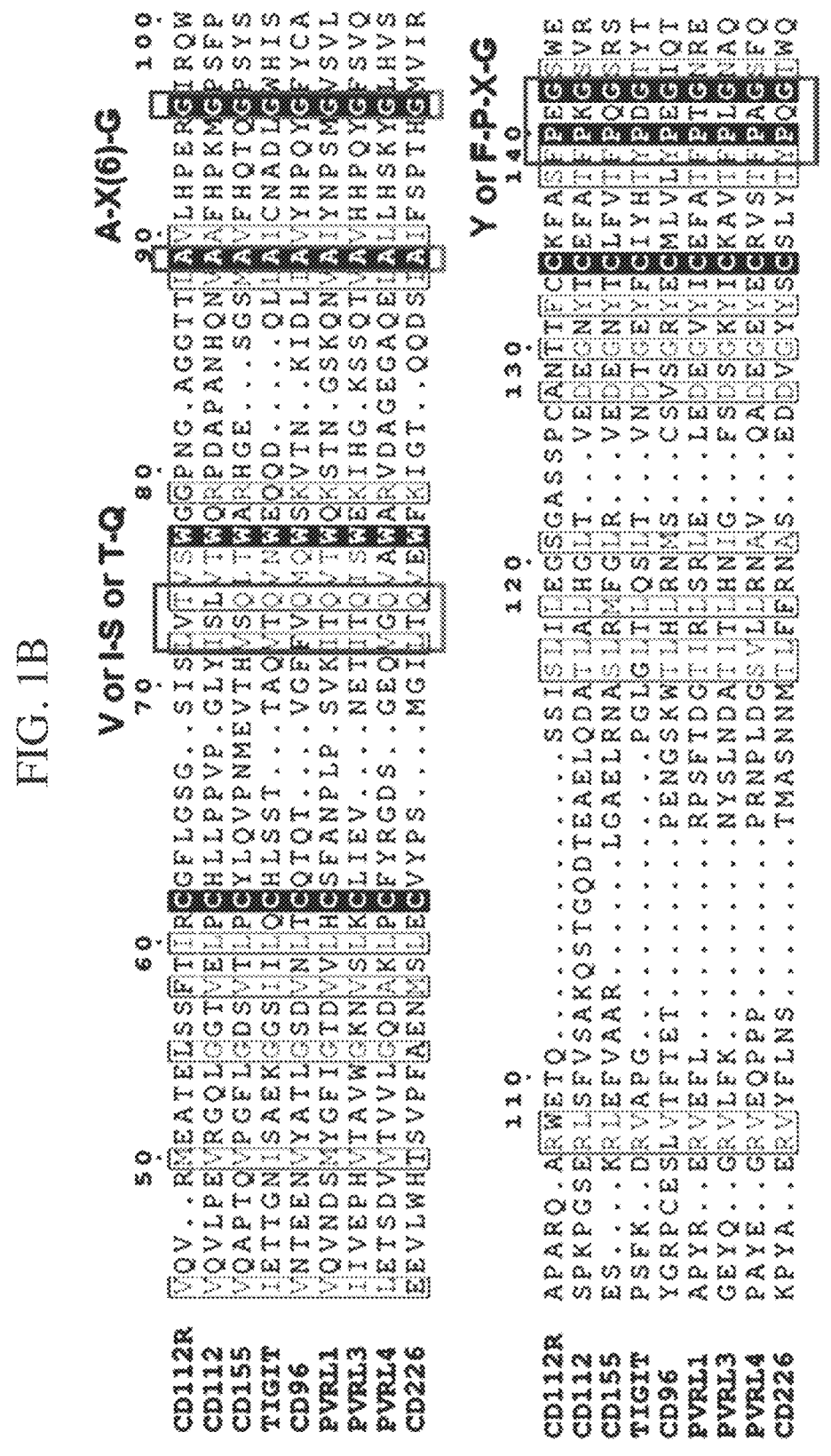

FIG. 1A is a sequence encoded by the human CD112R gene. Predicted extracellular IgV-like and transmembrane domains are highlighted in blue and red respectively. Two tyrosines in the cytoplasmic domain are underlined, with one within a possible ITIM motif underlined.

FIG. 1B is a multiple sequence alignment showing the amino acid sequence of CD112R to other known PVR family members, indicating that the IgV domain of CD112R contains residues conserved among the PVR family. Similar and identical residues are shaded in red and the PVR-signature motifs are outlined in green frame. Sequence identifiers are assigned to each sequence in the alignment as follows: CD112R (SEQ ID NO: 61), CD112 (SEQ ID NO: 62), CD155 (SEQ ID NO: 63), TIGIT (SEQ ID NO: 64), CD96 (SEQ ID NO: 65), PVRL1 (SEQ ID NO: 66), PVRL3 (SEQ ID NO: 67), PVRL4 (SEQ ID NO: 68), and CD226 (SEQ ID NO: 69).

FIG. 4B depicts graphs showing human pancreatic cell line PANC198 were stained for CD112 expression, they were preincubated with control or CD112 mAb (clone TX31) before being stained for CD112R fusion protein binding.

FIG. 5A is a graph showing that based on the mRNA expression data from BioGPS, CD112R gene is preferentially transcribed in lymphocytes, including T lymphocytes and NK cells.

FIG. 12C shows FACS of surface CD112R expression on cell lines of T-ALL.

FIG. 14A: is a series of graphs depicting the ability of a control, CD112-Fc, to bind human CD112R.

FIG. 14B: is a series of graphs depicting the ability of the anti-CD112R antibody, mAb 2H6, to bind human CD112R.

FIG. 14C: is a series of graphs depicting the ability of the anti-CD112R antibody, mAb 4-4, to bind human CD112R.

FIG. 14D: is a series of graphs depicting the ability of the anti-CD112R antibody, mAb 4-5, to bind human CD112R.

FIG. 16A: Expression of CD112 transcript in multiple human cancer specimens. >100 was deemed as positive.

FIG. 16B: Representatives of IHC staining of CD112 in human melanoma and PDAC tissues.

FIG. 16C: A representative of CD112R expression in CD8+ T cells of PBMC and TILs from PDAC patients. Cells were stained with CD3, CD8 and aCD112R. Data shown are gated on CD8+CD3+ cells.

FIG. 17A: HEK293T cells transfected with mCD112R plasmid (blue) or control vector (red) were stained with a rat anti-mCD112R mAb (Clone 6H11).

FIG. 17B: RMA-S/mCD112 stable cell line (blue) or RMA-S control cell (red) was stained for CD112R-Fc interaction, with (right) or without (left) the presence of amCD112R mAb (clone 6H11).

FIG. 17C: Immune cell subsets in naïve mice spleen were detected by surface markers, and stained for CD112R expression: B cell (CD19+CD3−), T cell (CD3+CD19−), Monocyte (CD11b+Ly6C+), and DC (CD11c+IAb+).

FIG. 17D: Spleen NK cells from mice injected with PBS or 100 µg poly IC overnight were stained for surface CD112R expression.

FIG. 17E: Expression of CD112R on mouse T cells activated by CD3/CD28 mAbs Beads.

FIG. 17F: CD112R is upregulated on OT-1 transgenic T cells in response to peptide stimulation.

FIG. 18A: CD112 expression on mouse tumor cell lines.

FIG. 18B: NK cells in TILs from transplanted B16F10 tumors were stained for surface CD112R.

FIG. 18C: T cells from dLNs and TILs were examined for CD112R expression.

FIG. 21A: Expression of CD112 and CD155 on human breast cancer cell lines.

FIG. 21B: Human NK cells were incubated with Herceptin-coated SK-BR3 cells for 15 hours, in the presence of different mAbs as indicated. The expression of intracellular IFN-γ on NK cells were detected by flow cytometry.

FIG. 21C: Human NK cells were incubated with Herceptin-coated SK-BR3 cells for 15 hours, in the presence of different mAbs as indicated. The expression of intracellular CD107a on NK cells were detected by flow cytometry.

DETAILED DESCRIPTION OF THE DISCLOSURE

Figure 1C:
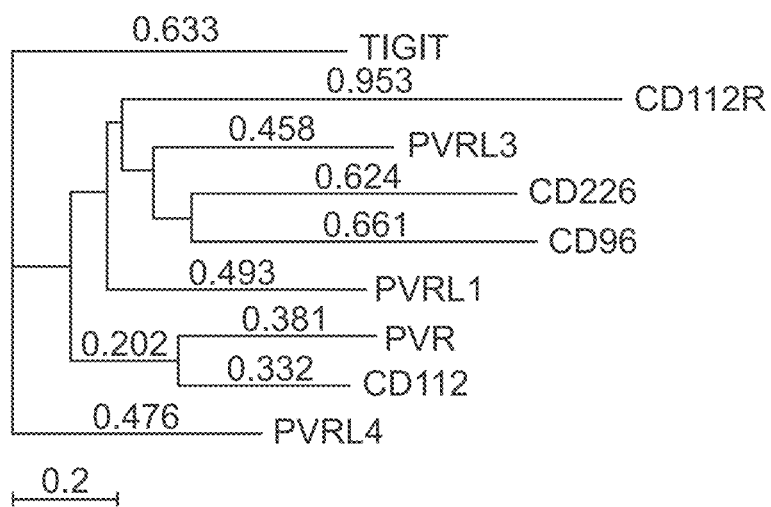
FIG. 1C is a phylogenic tree Guide showing analysis of human CD112R and the known PVR-like proteins via Clustal W program in MacVector 6.5.

Provided herein, inter alia, is compositions and methods for modulating T-cell mediated immune response in a subject in need thereof. The method includes administering to the subject an effective amount of a CD112R protein, a fusion polypeptide, a complex including CD112R and a second protein, or an anti-CD112R antibody of the present disclosure.

Definitions

The following definitions are included for the purpose of understanding the present subject matter and for constructing the appended patent claims. Abbreviations used herein have their conventional meaning within the chemical and biological arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this disclosure. The following definitions are provided to facilitate understanding of certain terms used frequently herein and are not meant to limit the scope of the present disclosure.

The terms "CD112R polypeptide", "CD112R protein" and "CD112R" are used interchangeably herein and refer to polypeptide sequences including homologues and embodiments thereof, capable of binding to a CD112 polypeptide. The CD112R described herein may be isolated from a variety of sources, such as from human or from a nonhuman organism, or prepared by recombinant or synthetic methods. CD112R is a polypeptide capable of binding to CD112 and having at least 90% sequence identity to at least a 10 amino acid consecutive sequence to SEQ ID NO: 1. In embodiments, CD112R is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1. All disclosures in this specification which refer to the "CD112R" refer to each of the polypeptides individually as well as jointly. For example, descriptions of the preparation of, purification of, derivation of, formation of antibodies to or against, administration of, compositions containing, treatment of a disease with, etc., pertain to each polypeptide of the disclosure individually. The terms "CD112R polypeptide", "CD112R protein" or "CD112R" also include variants of the CD112R disclosed herein or known in the art.

The CD112R "extracellular domain" or "ECD" refers to a form of the CD112R which is essentially free of the transmembrane and cytoplasmic domains. Ordinarily, a CD112R ECD will have less than 1% of such transmembrane and/or cytoplasmic domains. In embodiments, a CD112R ECD will have less than 0.5% of such domains. It will be understood that any transmembrane domains identified for a CD112R ECD of the present disclosure are identified pursuant to criteria routinely employed in the art for identifying that type of hydrophobic domain. The exact boundaries of a transmembrane domain may vary but most likely by no more than about 5 amino acids at either end of the domain as identified herein. Optionally, therefore, an extracellular domain of a CD112R may contain from about 5 or fewer amino acids on either side of the transmembrane domain/extracellular domain boundary and such polypeptides, with or without the associated signal peptide, and nucleic acid encoding them, are contemplated by the present disclosure.

"CD112R variant" means CD112R as defined above or below having at least about 80% amino acid sequence identity with a full-length native sequence CD112R peptide sequence as disclosed herein, an extracellular domain of a CD112R, as disclosed herein or any other fragment of a full-length CD112R sequence. Such CD112R variants include, for instance, CD112Rs in which one or more amino acid residues are added, or deleted, at the N- or C-terminus of the full-length native amino acid sequence. Ordinarily, a CD112R variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence CD112R sequence as disclosed herein, an extracellular domain of a CD112R, as disclosed herein or any other specifically defined fragment of a full-length CD112R sequence.

The human CD112R gene encodes a putative single transmembrane protein, which is composed of a single extracellular IgV domain, one transmembrane domain, and a long intracellular domain. The intracellular domain of CD112R contains two tyrosine residues, one within an ITIM-like motif that is a potential docking site for phosphatases. Alignment of the amino acid sequence of CD112R to other known PVR family members indicates that the IgV domain of CD112R contains residues conserved among the PVR family. These residues constitute at least three main motifs shared among the PVR family: Val or Ile-Ser or Thr-Gln at position 72-74aa of CD112R; Ala89-X6-Gly96; and Tyr139 or Phe139-Pro140-X-Gly142. Phylogenic tree analysis of the first IgV of PVR family further reveals that CD112R is close to all PVR-like proteins. Structural model of CD112R suggest that the protein adopts a V-set immunoglobulin fold consisting of a series of β-sheets.

"CD112" as used herein is a protein also known as PVRL2/nectin-2, which interacts with CD226 (DNAM1) to co-stimulate T cells. CD112 also inhibit T cell response through another co-inhibitory receptor, T cell immunoglobulin and immunoreceptor tyrosine-based inhibitory motif [ITIM] domain (TIGIT).

"Second protein," as used herein refers to a protein with biological activity (e.g., a binding activity). In embodiments, the second protein may be an antibody or an antibody fragment, any protein or polypeptide having biological or binding activity, or a detectable protein. The detectable protein may be a protein with a peptide tag, a covalent peptide tag, or a protein tag.

In embodiments, the peptide tags are: AviTag, a peptide allowing biotinylation by the enzyme BirA and so the protein can be isolated by streptavidin (GLNDIFEAQKIEWHE (SEQ ID NO: 12)), Calmodulin-tag, a peptide bound by the protein calmodulin (KRRWKKNFIAVSAANRFKKISSSGAL (SEQ ID NO: 13)), polyglutamate tag, a peptide binding efficiently to anion-exchange resin such as Mono-Q (EEEEEE (SEQ ID NO: 14)), E-tag, a peptide recognized by an antibody (GAPVPYPDPLEPR (SEQ ID NO: 15)), FLAG-tag, a peptide recognized by an antibody (DYKDDDDK (SEQ ID NO: 16)), HA-tag, a peptide recognized by an antibody (YPYDVPDYA (SEQ ID NO: 17)), His-tag, 5-10 histidines bound by a nickel or cobalt chelate (HHHHHH (SEQ ID NO: 18)), Myc-tag, a short peptide recognized by an antibody (EQKLISEEDL (SEQ ID NO: 19)), S-tag (KETAAAKFERQHMDS (SEQ ID NO: 20)), SBP-tag, a peptide which binds to streptavidin (MDEKTTGWRGGHVVEGLAGELEQLRARLEHHPQGQREP (SEQ ID NO: 21)), Softag 1, for mammalian expression (SLAELLNAGLGGS (SEQ ID NO: 22)), Softag 3, for prokaryotic expression (TQDPSRVG (SEQ ID NO: 23)), Strep-tag, a peptide which binds to streptavidin or the modified streptavidin called streptactin (Strep-tag II: WSHPQFEK (SEQ ID NO: 24)), TC tag, a tetracysteine tag that is recognized by FlAsH and ReAsH biarsenical compounds (CCPGCC (SEQ ID NO: 25)), V5 tag, a peptide recognized by an antibody (GKPIPNPLLGLDST (SEQ ID NO: 26)), VSV-tag, a peptide recognized by an antibody (YTDIEMNRLGK (SEQ ID NO: 27)), Xpress tag (DLYDDDDK (SEQ ID NO: 28)).

In embodiments, covalent peptide tags are: Isopeptag, a peptide which binds covalently to pilin-C protein (TDKDMTITFTNKKDAE (SEQ ID NO: 29)), SpyTag, a peptide which binds covalently to SpyCatcher protein (AHIVMVDAYKPTK (SEQ ID NO: 30)).

In embodiments, protein tags are: BCCP (Biotin Carboxyl Carrier Protein), a protein domain biotinylated by BirA enabling recognition by streptavidin, Glutathione-S-transferase-tag, a protein which binds to immobilized glutathione, Green fluorescent protein-tag, a protein which is spontaneously fluorescent and can be bound by nanobodies, Halo-tag, a mutated hydrolase that covalently attaches to the HaloLink™ Resin (Promega), Maltose binding protein-tag, a protein which binds to amylose agarose, Nus-tag, Thioredoxin-tag, Fc-tag, derived from immunoglobulin Fc domain, allow dimerization and solubilization.

"Detectable moiety" as used herein means poly-histidine (poly(His)), chitin binding protein, maltose binding protein, glutathione-S-transferase (GST), FLAG-tag, AviTag, Calmodulin-tag, polyglutamate tag, E-tag, HA-tag, Myc-tag, S-tag, SBP-tag, Softtag 1, Softtag 3, Strep-tag, TC tag, V5 tag, VSV tag, Xpress tag, Isopeptag, SpyTag, Biotin Carboxyl Carrier Protein (BCCP) tag, Halo-tag, thioredoxin-tag, or Fc-tag, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety.

"Therapeutic moiety" as used herein means anti-cancer agents, for example, chemotherapeutic agents, growth inhibitory agent; cytotoxic agents; immunogenic agent; immunomodulatory agents; agents that modulate T-cell activity; chemokines; an aptamer, small interfering RNAs (siRNAs); or short activating RNAs (saRNAs).

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

In embodiments, a toxin may be a topoisomerase inhibitor. Topoisomerase inhibitors are often divided according to which type of enzyme it inhibits. Topoisomerase I inhibitors: irinotecan, topotecan, camptothecin and lamellarin D all target type IB topoisomerases. Topoisomerase II inhibitors: etoposide (VP-16), teniposide, doxorubicin, daunorubicin, mitoxantrone, amsacrine, ellipticines, aurintricarboxylic acid, and HU-331, a quinolone synthesized from cannabidiol.

Human DNA topoisomerase I (Top1) is an essential enzyme that relaxes DNA supercoiling during replication and transcription. Top1 generates DNA single-strand breaks that allow rotation of the cleaved strand around the double helix axis. Top1 also re-ligates the cleaved strand to reestablish intact duplex DNA. The Top1-DNA intermediates, known as cleavage complexes, are transient and at low levels under normal circumstances. However, treatment with Top1 inhibitors, such as the camptothecins, stabilizes the cleavable complexes, prevent DNA re-ligation and induce lethal DNA strand breaks. Cancer cells are selectively sensitive to the generation of these DNA lesions.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhone-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce 01 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found, for example, in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995).

The term "cytokine" is a generic term for proteins released by one cell population which act on another cell as intercellular mediators. Certain examples of such cytokines are lymphokines, monokines, and traditional polypeptide hormones. Included among the cytokines are, e.g., growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor α and β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, β, and γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; a tumor necrosis factor such as TNF-α or TNF-β; and other polypeptide factors including LIP and kit ligand (KL). As used herein, the term cytokine includes proteins from natural sources or from recombinant cell culture and biologically active equivalents of the native sequence cytokines.

The term "aptamer" refers to a nucleic acid molecule that may be capable of binding to a target molecule, such as a polypeptide. For example, an aptamer of the disclosure can specifically bind to a CD112R, or to a molecule in a signaling pathway that modulates the expression of CD112R. The generation and therapeutic use of aptamers are well established in the art. See, e.g., U.S. Pat. No. 5,475,096.

An "immunogenic agent" or "immunogen" may be capable of inducing an immunological response against itself on administration to a mammal, optionally in conjunction with an adjuvant. Examples for an immunogen are fusion polypeptide including CD112R or a fragment thereof, conjugates as provided herein. Immunogenic agents can be linked to carriers by chemical crosslinking. Techniques for linking an immunogen to a carrier include the formation of disulfide linkages using N-succinimidyl-3-(2-pyridyl-thio)propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described by Immun. Rev. 62, 185 (1982). Other bifunctional coupling agents form a thioether rather than a disulfide linkage. Many of these thio-ether-forming agents are commercially available and include reactive esters of 6-maleimidocaproic acid, 2-bromoacetic acid, and 2-iodoacetic acid, 4-(N-maleimidomethyl)cyclohexane-1-carboxylic acid. The carboxyl groups can be activated by combining them with succinimide or 1-hydroxyl-2-nitro-4-sulfonic acid, sodium salt.

"Isolated," when used to describe the various polypeptides disclosed herein, means a polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In embodiments, the polypeptide may be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the polypeptide natural environment will not be present. In embodiments, isolated polypeptide may be prepared by at least one purification step.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H C_{H1}$ by a disulfide bond. The F(ab)'$_2$ may be reduced under mild conditions to break the disulfide linkage in the hinge region, thereby converting the F(ab)'$_2$ dimer into a Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

The term "agonistic antibody or agonist antibody" represents a class of antibodies designed to mimic the activity of endogenous ligands, thereby activating the downstream signaling pathways of targeted molecules. Many tumor necrosis factor receptor (TNFR) superfamily members such as CD40 and DR5 control key signaling pathways involved in immune and antitumor responses, and agonistic antibodies targeting these molecules have antitumor activities.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

For preparation of monoclonal or polyclonal antibodies, any technique known in the art can be used (see, e.g., Kohler & Milstein, Nature 256:495-497 (1975); Kozbor et al., Immunology Today 4:72 (1983); Cole et al., pp. 77-96 in Monoclonal Antibodies and Cancer Therapy (1985)). "Monoclonal" antibodies (mAb) refer to antibodies derived from a single clone. Techniques for the production of single chain antibodies (U.S. Pat. No. 4,946,778) can be adapted to produce antibodies to polypeptides of this disclosure. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348: 552-554 (1990); Marks et al., Biotechnology 10:779-783 (1992)).

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e., fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

Antibodies exist, for example, as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as use d herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the present disclosure and for use according to the disclosure, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be clone d from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this disclosure. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substitute d by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well-known procedures from a variety of human cells.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the disclosure include humanized and/or chimeric monoclonal antibodies.

A "therapeutic antibody" as provided herein refers to any antibody or functional fragment thereof that is used to treat cancer, autoimmune diseases, transplant rejection, cardiovascular disease or other diseases or conditions such as those described herein. Non-limiting examples of therapeutic antibodies include murine antibodies, murinized or humanized chimera antibodies or human antibodies including, but not limited to, Erbitux (cetuximab), ReoPro (abciximab), Simulect (basiliximab), Remicade (infliximab); Orthoclone OKT3 (muromonab-CD3); Rituxan (rituximab), Bexxar (tositumomab) Humira (adalimumab), Campath (alemtuzumab), Simulect (basiliximab), Avastin (bevacizumab), Cimzia (certolizumab pegol), Zenapax (daclizumab), Soliris (eculizumab), Raptiva (efalizumab), Mylotarg (gemtuzumab), Zevalin (ibritumomab tiuxetan), Tysabri (natalizumab), Xolair (omalizumab), Synagis (palivizumab), Vectibix (panitumumab), Lucentis (ranibizumab), and Herceptin (trastuzumab).

Techniques for conjugating therapeutic agents to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody. A "therapeutic agent" as referred to herein, is a composition useful in treating or preventing a disease such as cancer.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab)'$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the VH and VL domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93111161; and Hollinger et al., Proc. Natl. Acad. Sci. USA, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using a dye or stain such as, but not limited to, Coomassie blue or silver stain. Isolated antibody includes the antibody in situ within recombinant cells since at least one component of the antibody's natural environment will not be present. Ordinarily, however, isolated antibody will be prepared by at least one purification step.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies having a heavy chain only are functional and stable in the absence of light chain. See, e.g., Hamers-Casterman et al., Nature 363:446-448 (1993); Sheriff et al., Nature Struct. Biol. 3:733-736 (1996).

A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain.

The Kabat numbering system is generally used when referring to a residue in the variable domain (approximately residues 1-111 of the light chain and residues 1-114 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. Bio/Technology 10:779-783 (1992) describes affinity maturation by VH and VL domain shuffling. Random mutagenesis of HVR and/or framework residues is described by, for example, Barbas et al. Proc Nat. Acad. Sci. USA 91:3809-3813 (1994); Schier et al. Gen e169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen. An "agonist antibody," as used herein, is an antibody which partially or fully mimics at least one of the functional activities of a polypeptide of interest.

A "ligand" refers to an agent, e.g., a polypeptide or other molecule, capable of binding to a receptor.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
 1) Alanine (A), Glycine (G);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V);
 6) Phenylalanine (F), Tyrosine (Y), Tryptophan (W);
 7) Serine (S), Threonine (T); and
 8) Cysteine (C), Methionine (M)
(see, e.g., Creighton, Proteins (1984)).

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a DNA nucleic acid sequence (e.g., a gene) means the transcriptional and/or translational product of that sequence. The level of expression of a DNA molecule in a cell may be determined on the basis of either the amount of corresponding mRNA that is present within the cell or the amount of protein encoded by that DNA produced by the cell (Sambrook et al., 1989 Molecular Cloning: A Laboratory Manual, 18.1-18.88). When used in reference to polypeptides, expression includes any step involved in the production of a polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the disclosure or individual domains of the polypeptides of the disclosure), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, PASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

An example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http_www_ncbi_nlm_nih_gov/). This algorithm involves first identifying high scoring sequence pairs (HSPs) by identifying short words of length Win the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

An amino acid residue in an antibody "corresponds" to a given residue when it occupies the same essential structural position within the antibody as the given residue. For example, a selected residue in a comparison antibody corresponds to position 97 (according to the Kabat numbering system as described herein) in an antibody provided herein when the selected residue occupies the same essential spatial or structural relationship to Kabat position 97 as assessed using applicable methods in the art. For example, a comparison antibody may be aligned for maximum sequence homology with the antibody provided herein and the position in the aligned comparison antibody that aligns with Kabat position 97 may be determined to correspond to it. Alternatively, instead of (or in addition to) a primary sequence alignment as described above, a three dimensional structural alignment can also be used, e.g., where the structure of the comparison antibody is aligned for maximum correspondence with an antibody provided herein and the overall structures compared. In this case, an amino acid that occupies the same essential position as Kabat position 97 in the structural model may be said to correspond.

The term "epitope tagged" when used herein refers to a chimeric polypeptide comprising a polypeptide of interest (as one nonlimiting example, a CD112R) fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesion") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. In embodiments, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Active" or "activity" for the purposes herein refers to form(s) of a polypeptide (as a nonlimiting example, a CD112R) which retain a biological and/or an immunological activity of native or naturally-occurring form of that polypeptide (in the previous example, a CD112R activity), where "biological" activity refers to a biological function (either inhibitory or stimulatory) caused by a native or naturally-occurring polypeptide other than the ability to induce the production of an antibody against an antigenic epitope possessed by a native or naturally-occurring polypeptide and an "immunological" activity refers to the ability to induce the production of an antibody against an antigenic epitope possessed by a native or naturally-occurring polypeptide (in the previous example, a CD112R antigenic epitope).

The term "antagonist" is used in the broadest sense, and includes any molecule that partially or fully blocks, inhibits, or neutralizes a biological activity of a native polypeptide disclosed herein. In a similar manner, the term "agonist" is used in the broadest sense and includes any molecule that mimics a biological activity of a native polypeptide disclosed herein. Suitable agonist or antagonist molecules specifically include agonist or antagonist antibodies or antibody fragments, fragments or amino acid sequence variants of native polypeptides, peptides, antisense oligonucleotides, small organic molecules, etc. Methods for identifying agonists or antagonists of a polypeptide may comprise contacting a polypeptide with a candidate agonist or antagonist molecule and measuring a detectable change in one or more biological activities normally associated with the polypeptide.

The terms "CD112R antagonist" and "antagonist of CD112R activity or CD112R expression" are used interchangeably and refer to a compound or a biological agent that interferes with the normal functioning of CD112R, either by decreasing transcription or translation of CD112R-encoding nucleic acid, or by inhibiting or blocking CD112R activity, or both. Examples of CD112R antagonists include, but are not limited to, CD112-binding fragments of CD112R, antisense polynucleotides, interfering RNAs, catalytic RNAs, RNA-DNA chimeras, CD112R-specific aptamers, anti-CD112R antibodies, CD112R-binding fragments of anti-CD112R antibodies, CD112R-binding small molecules, CD112R-binding peptides, and other polypeptides that specifically bind CD112R (including, but not limited to, CD112R-binding fragments of one or more CD112R ligands, optionally fused to one or more additional domains). The CD112R antagonist reduces or inhibits CD112R activity or expression. It will be understood by one of ordinary skill in the art that in some instances, a CD112R antagonist may antagonize one CD112R activity without affecting another CD112R activity. For example, a desirable CD112R antagonist for use in certain of the methods herein is a CD112R antagonist that antagonizes CD112R activity in response to one of poliovirus receptor (PVR) interaction, e.g., without affecting or minimally affecting any of the other CD112R interactions.

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating a peptide or an antibody to the label may be employed, e.g., using methods described in Hermanson, Bioconjugate Techniques 1996, Academic Press, Inc., San Diego. The label may be detectable by itself (e.g., radioisotope labels or fluorescent labels) or, in the case of an enzymatic label, may catalyze chemical alteration of a substrate compound or composition which is detectable.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

By "solid phase" is meant a non-aqueous matrix to which the antibody of the present disclosure can adhere. Examples of solid phases encompassed herein include, but are not limited to, those formed partially or entirely of glass (e.g., controlled pore glass), polysaccharides (e.g., agarose), polyacrylamides, polystyrene, polyvinyl alcohol and silicones. In embodiments, depending on the context, the solid phase can include the well of an assay plate; in others it is a purification column (e.g., an affinity chromatography column).

A "liposome" is a small vesicle composed of various types of lipids, phospholipids and/or surfactant which is useful for delivery of a drug (such as a polypeptide described herein or antibody thereto) to a mammal. The components of the liposome are commonly arranged in a bilayer formation, similar to the lipid arrangement of biological membranes.

A "small molecule" is defined herein to have a molecular weight below about 500 Daltons.

A "siRNA," "small interfering RNA," "small RNA," or "RNAi" as provided herein refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In embodiments, a siRNA or RNAi refers to a nucleic acid that has substantial or complete identity to a target gene and forms a double stranded siRNA. In embodiments, the siRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded siRNA is 15-50 nucleotides in length, and the double stranded siRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length. Non-limiting examples of siRNAs include ribozymes, RNA decoys, short hairpin RNAs (shRNA), micro RNAs (miRNA) and small nucleolar RNAs (snoRNA). The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. Transgenic cells and plants are those that express a heterologous gene or coding sequence, typically as a result of recombinant methods.

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "immune-related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means an immune-related disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, which can be treated according to the disclosure include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disorder (IBD) (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections also may have immune and/or inflammatory components and/or etiology.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Patient," "subject," "patient in need thereof," and "subject in need thereof" are herein used interchangeably and refer to a living organism suffering from or prone to a disease or condition that can be treated by administration using the methods and compositions provided herein. Non-limiting examples include humans, other mammals, bovines, rats, mice, dogs, monkeys, goat, sheep, cows, deer, and other non-mammalian animals. In some embodiments, a patient is human. Tissues, cells and their progeny of a biological entity obtained in vitro or cultured in vitro are also contemplated.

"Disease" or "condition" refers to a state of being or health status of a patient or subject capable of being treated with the compounds or methods provided herein. In some instances, "disease" or "condition" refers to a "cancer".

As used herein, the term "cancer" refers to all types of cancer, neoplasm, malignant or benign tumors found in mammals, including leukemia, carcinomas and sarcomas. Exemplary cancers include breast cancer, ovarian cancer, colon cancer, liver cancer, kidney cancer and pancreatic cancer. Additional examples include leukemia (e.g., acute myeloid leukemia ("AML") or chronic myelogenous leukemia ("CML")), cancer of the brain, lung cancer, non-small cell lung cancer, melanoma, sarcomas, and prostate cancer, cervix cancers, stomach cancers, head & neck cancers, uterus cancers, mesothelioma, metastatic bone cancer, Medulloblastoma, Hodgkin's Disease, Non-Hodgkin's Lymphoma, multiple myeloma, neuroblastoma, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas.

As used herein, the term "T-ALL" or "T-ALLs" refer to T cell acute lymphoblastic leukemias, which are aggressive hematologic tumors resulting from the malignant transformation of T cell progenitors. T-ALL accounts for 10%-15% of pediatric and 25% of adult ALL cases. Clinically, T-ALL patients show diffuse infiltration of the bone marrow by immature T cell lymphoblasts, high white blood cell counts, mediastinal masses with pleural effusions, and frequent infiltration of the central nervous system at diagnosis.

As used herein, the term "infectious disease" refers to all types of diseases caused by pathogenic microorganisms, such as bacteria, viruses, parasites or fungi; the diseases can be spread, directly or indirectly, from one person to another. Zoonotic diseases are infectious diseases of animals that can cause disease when transmitted to humans. A disease is said to be linked or associated with an infectious pathogen when that pathogen is found more frequently in patients with the disease than in healthy controls.

The term "effective amount" is a concentration or amount of a polypeptide and/or agonist/antagonist which results in achieving a particular stated purpose. An "effective amount" of a polypeptide or agonist or antagonist thereof may be determined empirically. Furthermore, a "therapeutically effective amount" is a concentration or amount of a polypeptide and/or agonist/antagonist which is effective for achieving a stated therapeutic effect. This amount may also be determined empirically.

As used herein, the term "inflammatory cells" designates cells that enhance the inflammatory response such as mononuclear cells, eosinophils, macrophages, and polymorphonuclear neutrophils (PMN).

The terms "phenotype" and "phenotypic" as used herein refer to an organism's observable characteristics such as onset or progression of disease symptoms, biochemical properties, or physiological properties.

The terms "treat," "treating" or "treatment," and other grammatical equivalents as used herein, include alleviating, abating, ameliorating, or preventing a disease, condition or symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "prevent," "preventing," or "prevention," and other grammatical equivalents as used herein, include to keep from developing, occur, hinder or avert a disease or condition symptoms as well as to decrease the occurrence of symptoms. The prevention may be complete (i.e., no detectable symptoms) or partial, so that fewer symptoms are observed than would likely occur absent treatment. The terms further include a prophylactic benefit. For a disease or condition to be prevented, the compositions may be administered to a patient at risk of developing a particular disease, or to a patient reporting one or more of the physiological symptoms of a disease, even though a diagnosis of this disease may not have been made.

The term "inhibiting" also means reducing an effect (disease state or expression level of a gene/protein/mRNA) relative to the state in the absence of a compound or composition of the present disclosure.

The term "modulate", "modulating" as used herein means regulating or adjusting to a certain degree.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

Agents of the disclosure are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

The compositions can be administered for therapeutic or prophylactic treatments. In therapeutic applications, compositions are administered to a patient suffering from a disease (e.g., whooping cough) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present disclosure includes both humans and other animals, particularly mammals. Thus the methods are applicable to both human therapy and veterinary applications. In the preferred embodiment the patient is a mammal, preferably a primate, and in the most preferred embodiment the patient is human.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immuno stimulating agents (i.e., adjuvants).

As used herein, the term "Dendrimers" is used as in its common use. Dendrimers are synthetic polymeric macromolecules of nanometer dimensions that composed of multiple highly branched monomers that emerge radially from the central core. Their structure offers various advantages such as monodisperse and controllable size, modifiable surface, functionality, multivalency, water solubility, and an available internal cavity for drug delivery. The resultant spherical macromolecular structure has a size similar to albumin and hemoglobin, although it is smaller than multimers like the IgM antibody complex. The characteristic architecture of dendrimers and the flexibility in the modification of their structure has allowed a greater progress in the application of biocompatible dendrimers for targeted drug delivery. Regarding this, there are studies on the use of biocompatible dendrimers for cancer treatment to deliver chemotherapeutic drugs such as cisplatin and doxorubicin.

The compositions provided herein, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this disclosure, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administrations contemplates coadministration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing whopping cough for guidance.

Throughout the description and claims of this specification the word "comprise" and other forms of the word, such as "comprising" and "comprises," means including but not limited to, and is not intended to exclude, for example, other components.

Fusion Polypeptide

The present disclosure provides a fusion polypeptide including CD112R protein and a second protein. In embodiments, CD112R is a polypeptide capable of binding to CD112 and having at least 90% sequence identity to at least a 10 amino acid consecutive sequence to SEQ ID NO: 1. In embodiments, CD112R is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1.

(SEQ ID NO: 1)
MRTEAQVPALQPPEPGLEGAMGHRTLVLPWVLLTLCVTAGTPEVWVQVRM

EATELSSFTIRCGFLGSGSISLVTVSWGGPNGAGGTTLAVLHPERGIRQW

APARQARWETQSSISLILEGSGASSPCANTTFCCKFASFPEGSWEACGSL

PPSSDPGLSAPPTPAPILRADLAGILGVSGVLLFGCVYLLHLLRRHKHRP

APRLQPSRTSPQAPRARAWAPSQASQAALHVPYATINTSCRPATLDTAHP

HGGPSWWASLPTHAAHRPQGPAAWASTPIPARGSFVSVENGLYAQAGERP

PHTGPGLTLFPDPRGPRAMEGPLGVR.

In embodiments, the CD112R includes the minimal function region of the extracellular domain of CD112R comprising the amino acid sequence of SEQ ID NO: 44. In embodiments, CD112R is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 44.

(SEQ ID NO: 44)
EATELSSFTIRCGFLGSGSISLVTVSWGGPNGAGGTTLAVLHPERGIRQW

APARQARWETQSSISLILEGSGASSPCANTTFCCKFASFPEGSWEA.

In embodiments, the CD112R includes the extracellular domain of CD112R comprising the amino acid sequence of SEQ ID NO: 45. In embodiments, CD112R is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 45.

(SEQ ID NO: 45)
MRTEAQVPALQPPEPGLEGAMGHRTLVLPWVLLTLCVTAGTPEVWVQVRM

EATELSSFTIRCGFLGSGSISLVTVSWGGPNGAGGTTLAVLHPERGIRQW

APARQARWETQSSISLILEGSGASSPCANTTFCCKFASFPEGSWEACGSL

PPSSDPGLSA.

In embodiments, the fusion polypeptide binds an epitope on human CD112R comprising at least the amino acid sequence AVLHPERGIRQWAPARQ (SEQ ID NO: 53). In embodiments, the fusion polypeptide binds an epitope on human CD112R comprising at least the amino acid sequence AVLHPERGIRQWAPARQARW (SEQ ID NO: 54). In embodiments, the fusion polypeptide binds an epitope on human CD112R comprising at least the amino acid sequence AVLHPERGIRQWAPARQARWETQSS (SEQ ID NO: 55). In embodiments, the fusion polypeptide binds an epitope on human CD112R comprising at least the amino acid sequence AVLHPERGIRQWAPARQARWETQSSIS (SEQ ID NO: 56). In embodiments, the fusion polypeptide binds an epitope on human CD112R comprising at least the amino acid sequence AVLHPERGIRQWAPARQARWETQSSISL (SEQ ID NO: 57).

In embodiments, the second protein is an antibody or a fragment thereof, a binding protein or a fragment thereof, or a detectable protein, or a fragment thereof. In embodiments, the antibody fragment is the Fc region of an antibody. In embodiments, the binding protein or a fragment thereof is CD112R or a fragment thereof, respectively.

In embodiments, the second protein is a Fc region of an IgG immunoglobulin, such as, an IgG immunoglobulin selected from the group consisting of IgG1 isotype, IgG2 isotype, IgG3 isotype, IgG4 isotype, and IgM isotype.

In embodiments, the fusion protein includes a human IgG1 Fc polypeptide sequence having the amino acid sequence of SEQ ID NO: 46:

(SEQ ID NO: 46)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSRDELTKNQVSLTCLVKGFYPSDIAVE

WESNGQPENNYKTTPPVLDSDGSFFLYSKLTVDKSRWQQGNVFSCSVMHE

ALHNHYTQKSLSLSPGK

In embodiments, the fusion protein includes a human IgG1 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 46.

In embodiments, the fusion protein includes a human IgG2 Fc polypeptide sequence having the following amino acid sequence:

(SEQ ID NO: 47)
APPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAP

IEKTISKTKGQPREPQVYTLPPSREEMTKNQVSLTCLVKGFYPSDIAVEW

ESNGQPENNYKTTPPMLDSDGSFFLYSKLTVDKSRWQQGNVFSCSVMHEA

LHNHYTQKSLSLSPGK

In embodiments, the fusion protein includes a human IgG2 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 47.

In embodiments, the fusion protein includes a human IgG3 Fc polypeptide sequence having the following amino acid sequence:

(SEQ ID NO: 48)
APELLGGPSVFLFPPKPKDTLMISRTPEVTCVVVDVSHEDPEVQFKWYVD

GVEVHNAKTKPREEQYNSTFRVVSVLTVLHQDWLNGKEYKCKVSNKALPA

PIEKTISKTKGQPREPQVYTLPPSREEMTKNQVSLTCLVKGFYPSDIAVE

WESSGQPENNYNTTPPMLDSDGSFFLYSKLTVDKSRWQQGNIFSCSVMHE

ALHNRFTQKSLSLSPGK

In embodiments, the fusion protein includes a human IgG3 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 48.

In embodiments, the fusion protein includes a human IgG4 Fc polypeptide sequence having the following amino acid sequence:

(SEQ ID NO: 49)
APEFLGGPSVFLFPPKPKDTLMISRTPEVTCVVVDVSQEDPEVQFNWYVD

GVEVHNAKTKPREEQFNSTYRVVSVLTVLHQDWLNGKEYKCKVSNKGLPS

SIEKTISKAKGQPREPQVYTLPPSQEEMTKNQVSLTCLVKGFYPSDIAVE

WESNGQPENNYKTTPPVLDSDGSFFLYSRLTVDKSRWQEGNVFSCSVMHE

ALHNHYTQKSLSLSLGK

In embodiments, the fusion protein includes a human IgG4 Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 49.

In embodiments, the fusion protein includes a human IgM Fc polypeptide sequence having the following amino acid sequence:

(SEQ ID NO: 50)
IAELPPKVSVFVPPRDGFFGNPRKSKLICQATGFSPRQIQVSWLREGKQV

GSGVTTDQVQAEAKESGPTTYKVTSTLTIKESDWLGQSMFTCRVDHRGLT

FQQNASSMCVPDQDTAIRVFAIPPSFASIFLTKSTKLTCLVTDLTTYDSV

TISWTRQNGEAVKTHTNISESHPNATFSAVGEASICEDDWNSGERFTCTV

THTDLPSPLKQTISRPKG

In embodiments, the fusion protein includes a human IgM Fc polypeptide sequence that is at least 50%, 60%, 65%, 70%, 75%, 80%, 85%, 90%, 91%, 92%, 93%, 94%, 95%, 96%, 97%, 98% or 99% identical to the amino acid sequence of SEQ ID NO: 50.

In embodiments, the fusion protein includes a detectable protein, such as: a phosphorylated protein, a protein with a fluorescent marker, a protein with a radioactive agent, a glycosylated protein, a protein tagged with poly-histidine (poly(His)), a chitin binding protein, a maltose binding protein, a glutathione-S-transferase (GST), a FLAG-tagged protein, a protein with AviTag, a protein with Calmodulin-tag, a protein with polyglutamate tag, a protein with E-tag, a protein with HA-tag, a protein with Myc-tag, a protein with S-tag, a protein with SBP-tag, a protein with Softtag 1, a protein with Softtag 3, a protein with Strep-tag, a protein with TC tag, a protein with V5 tag, a protein with VSV tag, a protein with Xpress tag, a protein with Isopeptag, a protein with SpyTag, a protein with Biotin Carboxyl Carrier Protein (BCCP) tag, a protein with Halo-tag, a protein with thioredoxin-tag, or a protein with Fc-tag.

Complex

The present disclosure provides a complex including a CD112R protein bound to an antibody, a detectable moiety, a therapeutic moiety, a solid support, or any combination thereof. In embodiments, the solid support is a bead or nanoparticle. In embodiment, the complex includes CD112R and an antibody including sequence of SEQ ID NO: 3 and/or SEQ ID NO: 5. In embodiments, the CD112R and antibody sequence of SEQ ID NO: 3 and/or SEQ ID NO: 5 are in an in vitro complex.

In embodiments, the complex includes a detectable moiety bound to CD112R. In embodiments, the detectable moiety is poly-histidine (poly(His)), chitin binding protein, maltose binding protein, glutathione-S-transferase (GST), FLAG-tag, AviTag, Calmodulin-tag, polyglutamate tag, E-tag, HA-tag, Myc-tag, S-tag, SBP-tag, Softtag 1, Softtag 3, Strep-tag, TC tag, V5 tag, VSV tag, Xpress tag, Isopeptag, SpyTag, Biotin Carboxyl Carrier Protein (BCCP) tag, Halo-tag, thioredoxin-tag, or Fc-tag, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety.

In embodiments, the complex includes a therapeutic moiety bound to CD112R. In embodiments, a therapeutic agent may be anti-cancer agents, for example, chemotherapeutic agents, growth inhibitory agent; cytotoxic agents; immunogenic agent; immunomodulatory agents; agents that modulate T-cell activity; chemokines; an aptamer, small interfering RNAs (siRNAs); or short activating RNAs (saRNAs).

In Vitro Complex

The present disclosure provides an in vitro complex of a CD112R protein bound to a CD112 protein. In embodiments, the in vitro complex includes CD112R protein or CD112 protein bound to an antibody, a detectable moiety, a therapeutic moiety, or a solid support. In embodiments, the in vitro complex includes a solid support bound to CD112R, and the solid support is, for example, a bead or nanoparticle. In embodiment, the in vitro complex includes CD112R and an antibody including sequence of SEQ ID NO: 3 and/or SEQ ID NO: 5.

In embodiments, the in vitro complex includes a detectable moiety bound to CD112R. In embodiments, the detectable moiety is poly-histidine (poly(His)), chitin binding protein, maltose binding protein, glutathione-S-transferase (GST), FLAG-tag, AviTag, Calmodulin-tag, polyglutamate tag, E-tag, HA-tag, Myc-tag, S-tag, SBP-tag, Softtag 1, Softtag 3, Strep-tag, TC tag, V5 tag, VSV tag, Xpress tag, Isopeptag, SpyTag, Biotin Carboxyl Carrier Protein (BCCP) tag, Halo-tag, thioredoxin-tag, or Fc-tag, electron-dense reagent, enzyme, biotin, digoxigenin, paramagnetic molecule, paramagnetic nanoparticle, contrast agent, magnetic resonance contrast agent, X-ray contrast agent, Gadolinium, radioisotope, radionuclide, fluorodeoxyglucose, gamma ray emitting radionuclide, positron-emitting radionuclide, biocolloid, microbubble, iodinated contrast agent, barium sulfate, thorium dioxide, gold, gold nanoparticle, gold nanoparticle aggregate, fluorophore, two-photon fluorophore, hapten, protein, or fluorescent moiety.

In embodiments, the in vitro complex includes a therapeutic moiety bound to CD112R. In embodiments, a therapeutic agent may be anti-cancer agents, for example, chemotherapeutic agents, growth inhibitory agent; cytotoxic agents; immunogenic agent; immunomodulatory agents; agents that modulate T-cell activity; chemokines; an aptamer, small interfering RNAs (siRNAs); or short activating RNAs (saRNAs).

Antibodies

The present disclosure provides a purified antibody that binds specifically to CD112R protein.

In embodiments the purified antibody binds to CD112R, which is a protein of SEQ ID NO: 1. In embodiments, the antibody binds to CD112R, which is a polypeptide capable of binding to CD112 and having at least 90% sequence identity to at least a 10 amino acid consecutive sequence to SEQ ID NO: 1. In embodiments, the antibody binds to CD112R, which is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1. In embodiments, the purified antibody is a humanized antibody that binds to CD112R, which is a polypeptide capable of binding to CD112 and having at least 90%, 91%, 92%, 93%, 94%, 95%, 96%, 97%, 98%, 99%, or 100% sequence identity to at least a 10 amino acid consecutive sequence of SEQ ID NO: 1.

In embodiments, the antibody or antigen binding fragment thereof binds an epitope on human CD112R comprising at least the amino acid sequence AVLHPERGIRQWAPARQ (SEQ ID NO: 53). In embodiments, the antibody or antigen binding fragment thereof binds an epitope on human CD112R comprising at least the amino acid sequence AVLHPERGIRQWAPARQARW (SEQ ID NO: 54). In embodiments, the antibody or antigen binding fragment thereof binds an epitope on human CD112R comprising at least the amino acid sequence AVLHPERGIRQWAPARQARWETQSS (SEQ ID NO: 55). In embodiments, the antibody or antigen binding fragment thereof binds an epitope on human CD112R comprising at least the amino acid sequence AVLHPERGIRQWAPARQARWETQSSIS (SEQ ID NO: 56). In embodiments, the antibody or antigen binding fragment thereof binds an epitope on human CD112R comprising at least the amino acid sequence AVLHPERGIRQWAPARQARWETQSSISL (SEQ ID NO: 57).

In embodiments, the antibody which binds to CD112R has a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the antibody which binds to CD112R has a heavy chain including SEQ ID NO: 5, and a light chain including SEQ ID NO: 3. This antibody is referred to herein as the 2H6 CD112R monoclonal antibody.

Peptide sequence of the Kappa chain of the 2H6 CD112R monoclonal antibody:

(SEQ ID NO: 3)
DIEMTQSPATLSVTPGDRVSLSCRASQSIRDYLHWYQQKSHESPRLLIKY

VSQSISGIPSRFSGSGSGSEFTLSINSVEPEDVGVYYCQNGHSLPLTFGS

GTKLEIKRTV.

Peptide sequence of the heavy chain of the 2H6 CD112R monoclonal antibody:

(SEQ ID NO: 5)
EVQLQQSGAELVRSGASVKMSCKVNDYTFTNYNMHWLRQTPGQGLEWIGY

IYPGNGDTNYNQKFKGKATLTADTSSSTAYMQIISLTSEDPAVYFCARQG

IHYYYIDVWGAGTTVTVSSG.

TABLE 1A

CDR sequences of anti-CD112R monoclonal antibody

| CDR | Sequence | SEQ ID NO: |
|---|---|---|
| CDRH1 | DYTFTNYNMH | 6 |
| CDRH2 | YIYPGNGDTNYNQ | 7 |
| CDRH3 | QGIHYYYIDV | 8 |
| CDRL1 | RASQSIRDYLH | 9 |
| CDRL2 | YVSQSIS | 10 |
| CDRL3 | QNGHSLPLT | 11 |

In embodiments, the antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the antibody which binds to CD112R has a heavy chain including SEQ ID NO: 32, and a light chain including SEQ ID NO: 33. This antibody is referred to herein as the CD112R monoclonal antibody mAb 4-4.

Peptide sequence of the heavy chain of the CD112R monoclonal antibody mAb 4-4:

(SEQ ID NO: 32)
QVQLQQSGAELAKPGASVKMSCKASGYTFTSDWMHWVKQRPGQGLEWIG

YINPSTGYTEYNQKFKDKATLTADKSSSTAYMQLRSLTSEDSAVYYCAR

GSSGSWFAYWGQGTLVTVSA.

Peptide sequence of the Kappa chain of the CD112R monoclonal antibody mAb 4-4:

(SEQ ID NO: 33)
DIVLTQSPASLAVSLGQRATISCRASQSVSTSSYSYMHWYQQKPGQPPKL

LIKYASNLESGVPARFSGSGSGTDFTLNIHPVEEEDTATYYCQHSWEIPY

TFGGGTKLEIK.

TABLE 1B

CDR sequences of the anti-CD112R monoclonal antibody mAb 4-4:

| CDR | Sequence | SEQ ID NO: |
|---|---|---|
| CDRH1 | SDWMH | 34 |
| CDRH2 | YINPSTGYTEYNQKFKD | 35 |
| CDRH3 | GSSGSWFAY | 36 |
| CDRL1 | RASQSVSTSSYSYMH | 37 |
| CDRL2 | YASNLES | 38 |
| CDRL3 | QHSWEIPYT | 39 |

In embodiments, the antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the antibody which binds to CD112R has a heavy chain including SEQ ID NO: 32, and a light chain including SEQ ID NO: 40. This antibody is referred to herein as the CD112R monoclonal antibody mAb 4-5.

Peptide sequence of the heavy chain of the CD112R monoclonal antibody mAb 4-5:

(SEQ ID NO: 32)
QVQLQQSGAELAKPGASVKMSCKASGYTFTSDWMHWVKQRPGQGLEWIGY

INPSTGYTEYNQKFKDKATLTADKSSSTAYMQLRSLTSEDSAVYYCARGS

SGSWFAYWGQGTLVTVSA.

Peptide sequence of the Kappa chain of the CD112R monoclonal antibody mAb 4-5:

(SEQ ID NO: 40)
DVVMTQTPLTLSVTIGQPASISCKSSQSLLNSDGKTYLNWLLQRPGQSPK

RLIYLVSKLDSGVPDRFTGSGSGTDFTLKISRVEAEDLGVYYCWQGTHFP

RTFGGGTKLEIK.

TABLE 1C

CDR sequences of the anti-CD112R monoclonal antibody mAb 4-5:

| CDR | Sequence | SEQ ID NO: |
|---|---|---|
| CDRH1 | SDWMH | 34 |
| CDRH2 | YINPSTGYTEYNQKFKD | 35 |
| CDRH3 | GSSGSWFAY | 36 |

TABLE 1C-continued

CDR sequences of the anti-CD112R monoclonal antibody mAb 4-5:

| CDR | Sequence | SEQ ID NO: |
|---|---|---|
| CDRL1 | KSSQSLLNSDGKTYLN | 41 |
| CDRL2 | LVSKLDS | 42 |
| CDRL3 | WQGTHFPRT | 43 |

Suitable antibodies of the disclosure also include an antibody or antigen binding fragment thereof that cross-competes for binding to human CD112R to an anti-CD112R antibody comprising a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

Suitable antibodies of the disclosure also include an antibody or antigen binding fragment thereof that cross-competes for binding to human CD112R to an anti-CD112R antibody comprising a heavy chain including SEQ ID NO: 5, and a light chain including SEQ ID NO: 3.

Suitable antibodies of the disclosure also include an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

Suitable antibodies of the disclosure also include an antibody or antigen binding fragment thereof that cross-competes for binding to human CD112R to an anti-CD112R antibody comprising a heavy chain including SEQ ID NO: 32, and a light chain including SEQ ID NO: 33.

Suitable antibodies of the disclosure also include an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

Suitable antibodies of the disclosure also include an antibody or antigen binding fragment thereof that cross-competes for binding to human CD112R to an anti-CD112R antibody comprising a heavy chain including SEQ ID NO: 32, and a light chain including SEQ ID NO: 40.

In embodiments, the purified antibody of the present disclosure is an agonist antibody of CD112R. In embodiments, the purified antibody of the present disclosure blocks interaction between CD112R and CD112. Agonistic antibody may activate antigen presenting cells (APC) and promote T-cell responses and to foster cytotoxic myeloid cells with the potential to modulate immune response in the absence of T-cell immunity.

In embodiments, the antibody or antigen binding fragment thereof modulates, blocks, inhibits, reduces, antagonizes, neutralizes or otherwise interferes with the functional activity of CD112R. These antibodies or antigen binding fragments thereof are referred to herein as "neutralizing anti-CD112R antibodies" or "blocking anti-CD112R antibodies". Functional activities of CD112R include, by way of non-limiting example, interaction with CD112. For example, the anti-CD112R antibodies completely or partially inhibit CD112R activity by partially or completely modulating, blocking, inhibiting, reducing antagonizing, neutralizing, or otherwise interfering with the binding of CD112R to CD112. The anti-CD112R antibodies are considered to completely modulate, block, inhibit, reduce, antagonize, neutralize or otherwise interfere with CD112R functional activity when the level of CD112R functional activity in the presence of the anti-CD112R antibody is decreased by at least 95%, e.g., by 96%, 97%, 98%, 99% or 100% as compared to the level of CD112R functional activity in the absence of binding with an anti-CD112R antibody described herein. The anti-CD112R antibodies are considered to partially modulate, block, inhibit, reduce, antagonize, neutralize or otherwise interfere with CD112R functional activity when the level of CD112R activity in the presence of the anti-CD112R antibody is decreased by less than 95%, e.g., 10%, 20%, 25%, 30%, 40%, 50%, 60%, 75%, 80%, 85% or 90% as compared to the level of CD112R activity in the absence of binding with an anti-CD112R antibody described herein.

In embodiments, the neutralizing anti-CD112R antibody or antigen binding fragment thereof comprises a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the neutralizing anti-CD112R antibody or antigen binding fragment thereof comprises a heavy chain including SEQ ID NO: 5, and a light chain including SEQ ID NO: 3.

In embodiments, the neutralizing anti-CD112R antibody or antigen binding fragment thereof comprises an antibody or antigen binding fragment thereof that cross-competes for binding to human CD112R to an anti-CD112R antibody comprising a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the neutralizing anti-CD112R antibody or antigen binding fragment thereof comprises an antibody or antigen binding fragment thereof that cross-competes for binding to human CD112R to an anti-CD112R antibody comprising a heavy chain including SEQ ID NO: 5, and a light chain including SEQ ID NO: 3.

Single Chain Antibodies

The present disclosure provides a purified single chain antibody that binds specifically to CD112R protein.

In embodiments, a single chain antibody specific for binding CD112R, referred to herein as an "anti-CD112R single chain antibody," is fused to an Fc polypeptide. In embodiments, the Fc polypeptide is an Fc region of an IgG immunoglobulin, such as, an IgG immunoglobulin selected from the group consisting of IgG1 isotype, IgG2 isotype, IgG3 isotype, IgG4 isotype, and IgM isotype. In embodiments, the Fc polypeptide comprises an amino acid sequence selected from the group consisting of SEQ ID NO: 46-50.

In embodiments, the anti-CD112R single chain antibody is fused to the carboxy terminus of the Fc polypeptide. In embodiments, the anti-CD112R single chain antibody is fused to the amino terminus of the Fc polypeptide. The fusions are constructed as a single genetic construct and expressed in cells in culture.

In embodiments, the anti-CD112R single chain antibody binds to CD112R, which is a polypeptide capable of binding to CD112 and having at least 90% sequence identity to at least a 10 amino acid consecutive sequence to SEQ ID NO: 1. In embodiments, the anti-CD112R single chain antibody binds to CD112R, which is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1. In embodiments, the anti-CD112R single chain antibody binds to CD112R, which is a polypeptide capable of binding to CD112 and having at least 90%, 91%, 92%, 93%, 94%, 95%, 96%, 97%, 98%, 99%, or 100% sequence identity to at least a 10 amino acid consecutive sequence of SEQ ID NO: 1.

In embodiments, the single chain antibody binds an epitope on human CD112R comprising at least the amino acid sequence AVLHPERGIRQWAPARQ (SEQ ID NO: 53). In embodiments, the single chain antibody binds an epitope on human CD112R comprising at least the amino acid sequence AVLHPERGIRQWAPARQARW (SEQ ID NO: 54). In embodiments, the single chain antibody binds an epitope on human CD112R comprising at least the amino acid sequence AVLHPERGIRQWAPARQARWETQSS (SEQ ID NO: 55). In embodiments, the single chain antibody binds an epitope on human CD112R comprising at least the amino acid sequence AVLHPERGIRQWAPARQARWETQSSIS (SEQ ID NO: 56). In embodiments, the single chain antibody binds an epitope on human CD112R comprising at least the amino acid sequence AVLHPERGIRQWAPARQARWETQSSISL (SEQ ID NO: 57).

In embodiments, the anti-CD112R single chain antibody which binds to CD112R has a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the anti-CD112R single chain antibody which binds to CD112R has a heavy chain including SEQ ID NO: 5, and a light chain including SEQ ID NO: 3.

In embodiments, the anti-CD112R single chain antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the anti-CD112R single chain antibody which binds to CD112R has a heavy chain including SEQ ID NO: 32, and a light chain including SEQ ID NO: 33.

In embodiments, the anti-CD112R single chain antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the anti-CD112R single chain antibody which binds to CD112R has a heavy chain including SEQ ID NO: 32, and a light chain including SEQ ID NO: 40.

In embodiments, the anti-CD112R single chain antibody is an antibody or antigen binding fragment thereof that cross-competes for binding to human CD112R to an anti-CD112R antibody comprising a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the anti-CD112R single chain antibody is an antibody or antigen binding fragment thereof that cross-competes for binding to human CD112R to an anti-CD112R antibody comprising a heavy chain including SEQ ID NO: 5, and a light chain including SEQ ID NO: 3.

In embodiments, the anti-CD112R single chain antibody is an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the anti-CD112R single chain antibody is an antibody or antigen binding fragment thereof that cross-competes for binding to human CD112R to an anti-CD112R antibody comprising a heavy chain including SEQ ID NO: 32, and a light chain including SEQ ID NO: 33.

In embodiments, the anti-CD112R single chain antibody is an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the anti-CD112R single chain antibody is an antibody or antigen binding fragment thereof that cross-competes for binding to human CD112R to an anti-CD112R antibody comprising a heavy chain including SEQ ID NO: 32, and a light chain including SEQ ID NO: 40.

The anti-CD112R single chain antibodies or antigen binding fragment thereof are useful in therapeutic indications. In embodiments, the anti-CD112R single chain antibodies or antigen binding fragments thereof are administered in at a level that is sufficient to trigger antibody-dependent cell-mediated cytotoxicity (ADCC) in a subject in need thereof. For example, the anti-CD112R single chain antibodies or antigen binding fragments thereof are used to trigger antibody-dependent cell-mediated cytotoxicity (ADCC) in a subject who is suffering from or is at risk of developing cancer.

Chimeric Antigen Receptor (CAR) Constructs

The present disclosure provides chimeric antigen receptor (CAR) constructs that include a domain that binds specifically to CD112R protein, referred to herein as the anti-CD112R binding domain of the CAR construct.

Artificial T cell receptors, which are also known as chimeric T cell receptors, chimeric immunoreceptors, and/or chimeric antigen receptors (CARs), are engineered receptors, which graft an arbitrary specificity onto an immune effector cell. Typically, these receptors are used to graft the specificity of a monoclonal antibody onto a T cell; with transfer of their coding sequence facilitated by retroviral vectors. In the embodiments presented herein, the CAR construct is used to graft an anti-CD112 binding domain onto a T cell.

Artificial T cell receptors are under investigation as a therapy for cancer, using a technique called adoptive cell transfer. (See e.g., Pule, M; Finney H; Lawson A (2003). "Artificial T-cell receptors". Cytotherapy 5 (3): 211-26). Briefly, T cells are removed from a patient and modified so that they express receptors specific to the patient's particular cancer. The T cells, which can then recognize and kill the cancer cells, are reintroduced into the patient.

In embodiments, the CAR construct provided herein is a fusion of an anti-CD112R single chain antibody, e.g., and anti-CD112R single-chain variable fragment (scFv) derived from an anti-CD112 monoclonal antibody of the disclosure, fused to CD3-zeta transmembrane and endodomain.

In embodiments, the variable portions of an immunoglobulin heavy and light chain are fused by a flexible linker to form a scFv. This scFv is preceded by a signal peptide to direct the nascent protein to the endoplasmic reticulum and subsequent surface expression (cloven). A flexible spacer allows the scFv to orient in different directions to enable antigen binding. The transmembrane domain is a typical hydrophobic alpha helix derived from the original molecule of the signaling endodomain that protrudes into the cell and transmits the desired signal.

Type I proteins are in fact two protein domains linked by a transmembrane alpha helix. The cell membrane lipid bilayer, through which the transmembrane domain passes, isolates the inside portion (endodomain) from the external portion (ectodomain). Attaching an ectodomain from one protein to an endodomain of another protein makes a molecule that combines the recognition of the former to the signal of the latter.

ScFv/CD3-zeta hybrids result in the transmission of a zeta signal in response to recognition by the scFv of CD112R. When T cells express this molecule, e.g., by use of oncoretroviral vector transduction, they recognize and kill target cells that express CD112R.

The CAR constructs provided herein include an ectodomain, which consists of a signal peptide, an antibody recognition region comprising the scFv, and a spacer region that links the antigen binding domain to the transmembrane domain.

The signal peptide directs the nascent protein into the endoplasmic reticulum. Any eukaryotic signal peptide sequence can be used in the CAR constructs provided herein. In embodiments, the signal peptide natively attached to the amino-terminal component is used, for example, in a scFv with orientation light chain-linker-heavy chain, the native signal of the light-chain is used.

In embodiments, the antigen recognition region is an anti-CD112R binding domain. In embodiments, the anti-CD112R binding domain is a scFv. In embodiments, the anti-CD112R scFv of the CAR construct binds to CD112R, which is a polypeptide capable of binding to CD112 and having at least 90% sequence identity to at least a 10 amino acid consecutive sequence to SEQ ID NO: 1. In embodiments, the anti-CD112R scFv of the CAR construct binds to CD112R, which is a polypeptide capable of binding to CD112 and having at least 91%, 92%, 93%, 94%, 95%, 96%, 97%, 98%, 99%, or 100% sequence identity to at least a 10 amino acid consecutive sequence of SEQ ID NO: 1. In embodiments, the anti-CD112R single chain antibody binds to CD112R, which is a polypeptide capable of binding to CD112 and having at least 90%, 91%, 92%, 93%, 94%, 95%, 96%, 97%, 98%, 99%, or 100% sequence identity to at least a 10 amino acid consecutive sequence of SEQ ID NO: 1.

In embodiments, the anti-CD112R scFv of the CAR construct binds an epitope on human CD112R comprising at least the amino acid sequence AVLHPERGIRQWAPARQ (SEQ ID NO: 53). In embodiments, the anti-CD112R scFv of the CAR construct binds an epitope on human CD112R comprising at least the amino acid sequence AVLHPERGIRQWAPARQARW (SEQ ID NO: 54). In embodiments, the anti-CD112R scFv of the CAR construct binds an epitope on human CD112R comprising at least the amino acid sequence AVLHPERGIRQWAPARQARWETQSS (SEQ ID NO: 55). In embodiments, the anti-CD112R scFv of the CAR construct binds an epitope on human CD112R comprising at least the amino acid sequence AVLHPERGIRQWAPARQARWETQSSIS (SEQ ID NO: 56). In embodiments, the anti-CD112R scFv of the CAR construct binds an epitope on human CD112R comprising at least the amino acid sequence AVLHPERGIRQWAPARQARWETQSSISL (SEQ ID NO: 57).

In embodiments, the anti-CD112R scFv of the CAR construct binds to CD112R has a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the anti-CD112R scFv of the CAR construct binds to CD112R has a heavy chain including SEQ ID NO: 5, and a light chain including SEQ ID NO: 3.

In embodiments, the anti-CD112R single chain antibody which binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the anti-CD112R scFv of the CAR construct binds to CD112R has a heavy chain including SEQ ID NO: 32, and a light chain including SEQ ID NO: 33.

In embodiments, the anti-CD112R scFv of the CAR construct binds to CD112R has a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the anti-CD112R scFv of the CAR construct binds to CD112R has a heavy chain including SEQ ID NO: 32, and a light chain including SEQ ID NO: 40.

In embodiments, the anti-CD112R scFv of the CAR construct is an antibody or antigen binding fragment thereof that cross-competes for binding to human CD112R to an anti-CD112R antibody comprising a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

In embodiments, the anti-CD112R scFv of the CAR construct is an antibody or antigen binding fragment thereof that cross-competes for binding to human CD112R to an anti-CD112R antibody comprising a heavy chain including SEQ ID NO: 5, and a light chain including SEQ ID NO: 3.

In embodiments, the anti-CD112R scFv of the CAR construct is an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 37, a light chain CDR2 including SEQ ID NO: 38, and a light chain CDR3 including SEQ ID NO: 39.

In embodiments, the anti-CD112R scFv of the CAR construct is an antibody or antigen binding fragment thereof that cross-competes for binding to human CD112R to an anti-CD112R antibody comprising a heavy chain including SEQ ID NO: 32, and a light chain including SEQ ID NO: 33.

In embodiments, the anti-CD112R scFv of the CAR construct is an antibody or antigen binding fragment thereof that cross-competes for binding to human CD112R to an anti-CD112R antibody comprising a heavy chain CDR1 including SEQ ID NO: 34, a heavy chain CDR2 including SEQ ID NO: 35, a heavy chain CDR3 including SEQ ID NO: 36, a light chain CDR1 including SEQ ID NO: 41, a light chain CDR2 including SEQ ID NO: 42, and a light chain CDR3 including SEQ ID NO: 43.

In embodiments, the anti-CD112R scFv of the CAR construct is an antibody or antigen binding fragment thereof that cross-competes for binding to human CD112R to an anti-CD112R antibody comprising a heavy chain including SEQ ID NO: 32, and a light chain including SEQ ID NO: 40.

In embodiments, the spacer region is flexible enough to allow the anti-CD112R binding domain to orient in different directions to facilitate antigen recognition. In embodiments, the spacer is the hinge region from IgG1. In embodiments, the spacer includes the CH2CH3 region of immunoglobulin and portions of CD3.

The transmembrane domain is a hydrophobic alpha helix that spans the membrane. In embodiments, the transmembrane domain from the most membrane proximal component of the endodomain is used.

The endodomain is the functional end of the CAR construct. After CD112R recognition, receptors cluster and a signal is transmitted to the cell. In embodiments, the endodomain component is CD3-zeta which contains the immunoreceptor tyrosine-based activation motifs (ITAMs), which transmit an activation signal to the T cell after CD112R is bound. In embodiments, co-stimulatory signaling is used to provide a fully competent activation signal. In embodiments, chimeric CD28 and OX40 can be used with CD3-Zeta to transmit a proliferative/survival signal. In embodiments, CD28, OX40, and CD3-Zeta are used together.

Figure 15:
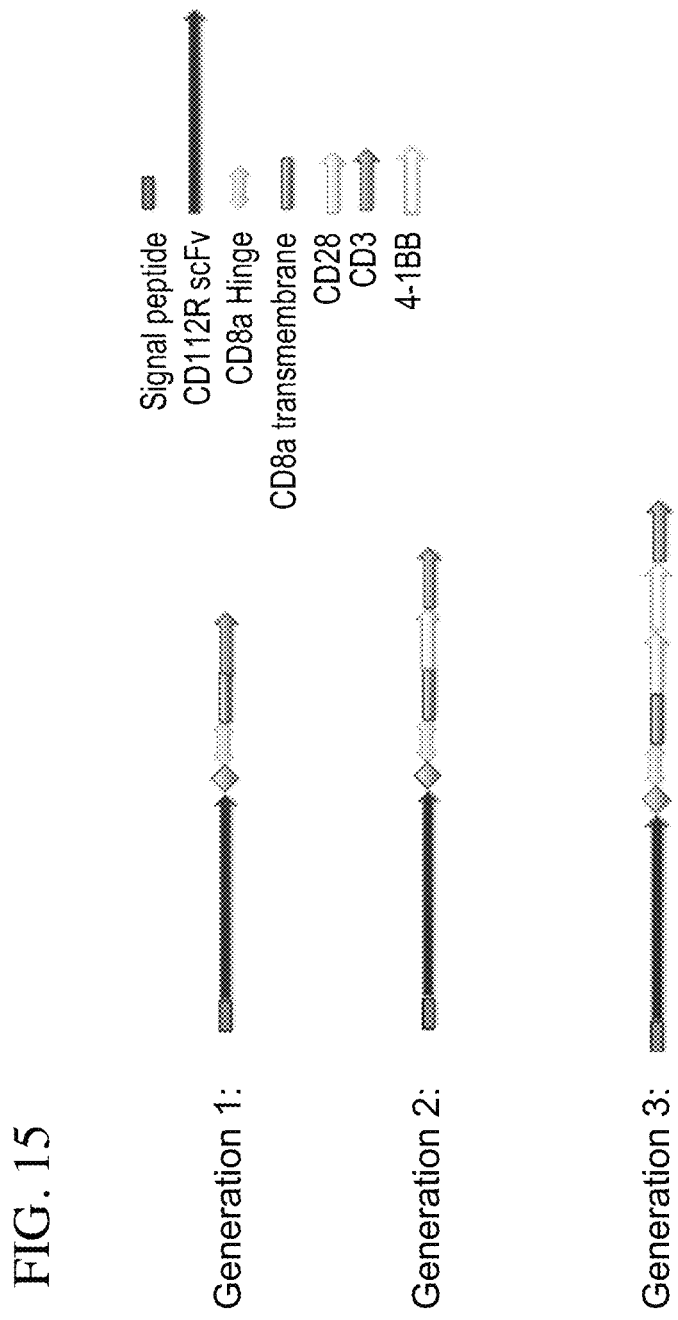
FIG. 15 is a schematic representation of three embodiments of CAR constructs of the disclosure which include a CD112R scFv.

In embodiments, the CAR construct has the following structural arrangement from N-terminus to C-terminus: anti-CD112R binding domain+hinge+transmembrane region (TM)+endodomain. In embodiments, the CAR construct has the following structural arrangement from N-terminus to C-terminus: anti-CD112R binding domain+hinge region+TM+costimulatory domain+CD3-zeta domain. In embodiments, the CAR construct has the following structural arrangement from N-terminus to C-terminus: anti-CD112R binding domain+CD8a hinge region+TM+CD28a (amino acids 180-219) costimulatory+CD3-zeta domain. In embodiments, the CAR construct has the following structural arrangement from N-terminus to C-terminus: (VH-linker-VL)–CD8a hinge+TM+CD28 (180-219aa) costimulatory domain+CD3-zeta (intracytoplasmic domain). In embodiments, the CAR construct has the structural arrangement shown in FIG. 15.

In embodiments, the CAR construct comprises the sequence of SEQ ID NO: 51:

(SEQ ID NO: 51)
GCCACCATGGGATGGAGCTGTATCATCCTCTTCTTGGTAGCAACAGCTAC

AGGTGTCCACGAGGTGCAACTGCAGCAGTCAGGGGCTGAACTGGTGAGGT

CTGGGGCCTCAGTGAAGATGTCCTGCAAGGTTAATGACTACACATTTACC

AATTACAATATGCACTGGTTAAGGCAGACACCTGGCCAGGGCCTGGAATG

GATTGGATATATTTATCCTGGAAATGGCGATACTAACTACAATCAGAAAT

TCAAGGGCAAGGCCACATTGACTGCAGACACATCCTCCAGCACAGCCTAC

ATGCAGATCATCAGCCTGACATCTGAAGACCCTGCGGTCTATTTCTGTGC

AAGACAGGGAATTCATTACTATTACATCGATGTCTGGGGCGCAGGGACCA

CGGTCACCGTCTCCTCAGGGGGTGGTGGTGGTTCTGGTGGTGGTGGTTCT

GGTGGTGGTGGTTCTGACATTGAGATGACACAGTCTCCAGCCACCCTGTC

TGTGACTCCAGGAGATAGAGTCTCTCTTTCCTGCAGGGCCAGCCAGAGTA

TTAGAGACTACTTACACTGGTATCAACAAAAATCACATGAGTCTCCAAGG

CTTCTCATCAAATATGTTTCCCAATCCATTTCTGGCATCCCCTCCAGGTT

CAGTGGCAGTGGATCAGGGTCAGAGTTCACTCTCAGTATCAACAGTGTGG

AACCTGAAGATGTTGGAGTATATTACTGTCAAAATGGTCACAGCCTTCCT

CTCACGTTCGGCTCGGGGACAAAGTTGGAAATAAAACGTACGGTGACCAC

GACGCCAGCGCCGCGACCACCAACACCGGCGCCCACCATCGCGTCGCAGC

CCCTGTCCCTGCGCCCAGAGGCGTGCCGGCCAGCGGCGGGGGCGCAGTG

CACACGAGGGGCTGGACTTCGCCTGTGATATCTACATCTGGGCGCCCTT

GGCCGGGACTTGTGGGGTCCTTCTCCTGTCACTGGTTATCACCAGGAGTA

AGAGGAGCAGGCTCCTGCACAGTGACTACATGAACATGACTCCCCGCCGC

CCCGGGCCCACCCGCAAGCATTACCAGCCCTATGCCCCACCACGCGACTT

CGCAGCCTATCGCTCCAGAGTGAAGTTCAGCAGGAGCGCAGACGCCCCCG

CGTACCAGCAGGGCCAGAACCAGCTCTATAACGAGCTCAATCTAGGACGA

AGAGAGGAGTACGATGTTTTGGACAAGAGACGTGGCCGGGACCCTGAGAT

GGGGGGAAAGCCGCAGAGAAGGAAGAACCCTCAGGAAGGCCTGTACAATG

AACTGCAGAAAGATAAGATGGCGGAGGCCTACAGTGAGATTGGGATGAAA

GGCGAGCGCCGGAGGGGCAAGGGGCACGATGGCCTTTACCAGGGTCTCAG

TACAGCCACCAAGGACACCTACGACGCCCTTCACATGCAGGCCCTGCCCC

CTCGCAAACCGGTTTAA.

The CAR constructs are useful to target CD112R-expressing tumors and malignancy, including NHL and T-ALL. In embodiments, the CAR constructs are useful to transduce human T cells and to direct the anti-tumor effect of the transduced human T cells against NHL and T-ALL.

Nucleic Acids, Polypeptides

An isolated nucleic acid encoding a humanized antibody capable of binding CD112R is provided. The antibody includes a humanized heavy chain and a humanize d light chain. The humanized antibodies encoded by the isolated nucleic acids are described in detail through this application (including the description above and in the examples section). Thus, the humanized antibodies encoded by the isolated nucleic acids include all of the embodiments described herein. For example, the nucleic acid may encode at least one CDR; residues involved in binding the epitope, including homologues or conserved variations, and embodiments thereof; or binding framework residues including homologues or conserved variations, and embodiments thereof.

Nucleotide sequence of the Kappa chain of the 2H6 CD112R monoclonal antibody:

(SEQ ID NO: 2)
GATCGACTTAGGGCGATTGATTTAGCGGCCGCGAATTC<u>GCCCTTC</u>TGCAA

CCGGTGTACATTCCGACATCGTGATCACACAGTCTCTGCA<u>ACCGGT</u>GTAC

ATTCC<u>GACATTGAG</u><u>ATGACACAGTCTCCAGCCACCCTGTCTGTGACTCCA</u>

<u>GGAGATAGAGTCTCTCTTTCCTGCAGGGCCAGCCAGAGTATTAGAGACTA</u>

<u>CTTACACTGGTATCAACAAAAATCACATGAGTCTCCAAGGCTTCTCATCA</u>

<u>AATATGTTTCCCAATCCATTTCTGGGATCCCCTCCAGGTTCAGTGGCAGT</u>

<u>GGATCAGGGTCAGAGTTCACTCTCAGTATCAACAGTGTGGAACCTGAAGA</u>

<u>TGTTGGAGTATATTACTGTCAAAATGGTCACAGCCTTCCTCTCACGTTCG</u>

<u>GCTCGGGGACAAAGTTGGAAATAAAA</u>CGTACGGTGGCAAGGGCGAATTCG

TTTAAACCTGCAGGACTAGTCCCTTTAGTGAGGGTTAATTCTGAGCTTGG

CGTAATCATGGTCATAGCTGTTTCCTGTGTGAAATTGTTATCCGCTCACA

ATTCCACACAACATACGAGCCGGAAGCATAAAGTGTAAAGCCTGGGGTGC

CTAATGAGTGAGCTAACTCACATTAATTGCGTTGCGCTCACTGCCCGCTT

TCCAGTCGGGAAACCTGTCGTGCCAGCTGCATTAATGAATCGGCCAACGC

GCGGGGAGAGGCGGTTTGCGTATTGGGCGCTCTTCCGCTTCCTCGCTCAC

TGACTCGCTGCGCTCGGTCGTTCGGCTGCGGCGAGCGGTATCAGCTCACT

CAAAGGCGGTAATACGGTTATCCACAGAATCAGGGGATAACGCAGGAAAG

AACATGTGAGCAAAAGGCCAGCAAAAGGCCAGGAACCGTAAAAAGGCCGC

GTTGCTGGCGTTTTTCCATAGGCTCCGCCCCCCTGACGAGCATCACAAAA

ATCGACGCTCAAGTCAGAGGTGGCGAAACCCGACAGGACTATAAAGATAC

CAGGCGTTTCCCCCTGTAAAGCTCCCTCGTGCGCTCTCCTGTTTCCGACC

CTGCCCGCTTTACCGGATACCCTGTCCGCCCTTTTTCTCCCTTCGGGGA

AAGCGTGCGCTTTCTCATAGCTCAACGCTGGTAGATTAATCTCTCAGGTT

CCGGGGTTGTGTTA.

Peptide sequence of the Kappa chain of the 2H6 CD112R monoclonal antibody:

(SEQ ID NO: 3)
L1 D L2 I L3 E L4 M L5 T L6 Q L7 S L8 P L9 A L10

T L11 L L12 S L13 V L14 T L15 P L16 G L17 D L18

R L19 V L20 S L21 L L22 S L23 C L24 R L25 A L26

S L27 Q L28 S L29 I L30 R L31 D L32 Y L33 L L34 H

L35 W L36 Y L37 Q L38 Q L39 K L40 S L41 H L42 E

L43 S L44 P L45 R L46 L L47 L L48 I L49 K L50 Y

L51 V L52 S L53 Q L54 S L55 I L56 S L57 G L58 I

L59 P L60 S L61 R L62 F L63 S L64 G L65 S L66 G

L67 S L68 G L69 S L70 E L71 F L72 T L73 L L74 S

L75 I L76 N L77 S L78 V L79 E L80 P L81 E L82 D

-continued

L83 V L84 G L85 V L86 Y L87 Y L88 C L89 Q L90 N

L91 G L92 H L93 S L94 L L95 P L96 L L97 T L98 F

L99 G L100 S L101 G L102 T L103 K L104 L L105 E

L106 I L107 K L108 R L110 T L111 V.

(SEQ ID NO: 3)
DIEMTQSPATLSVTPGDRVSLSCRASQSIRDYLHWYQQKSHES

PRLLIKYVSQSISGIPSRFSGSGSGSEFTLSINSVEPEDVGVYYC

QNGHSLPLTFGSGTKLEIKRTV.

Nucleotide sequence of the Heavy chain of the 2H6 CD112R monoclonal antibody:

(SEQ ID NO: 4)
GCAACCGGTGTACATTCCGAGGTGCAACTGCAGCAGTCAGGGGCTGAACT

GGTGAGGTCTGGGGCCTCAGTGAAGATGTCCTGCAAGGTTAATGACTACA

CATTTACCAATTACAATATGCACTGGTTAAGGCAGACACCTGGCCAGGGC

CTGGAATGGATTGGATATATTTATCCTGGAAATGGCGATACTAACTACAA

TCAGAAATTCAAGGGCAAGGCCACATTGACTGCAGACACATCCTCCAGCA

CAGCCTACATGCAGATCATCAGCCTGACATCTGAAGACCCTGCGGTCTAT

TTCTGTGCAAGACAGGGAATTCATTACTATTACATCGATGTCTGGGGCGC

AGGGACCACGGTCACCGTCTCCTCAGGGTCGAC.

Peptide sequence of the Heavy chain of the 2H6 CD112R monoclonal antibody:
H1 E H2 V H3 Q H4 L H5 Q H6 Q H7 S H8 G H9 A H10 E H11 L H12 V H13 R H14 S H15 G H16 A H17 S H18 V H19 K H20 M H21 S H22 C H23 K H24 V H25 N H26 D H27 Y H28 T H29 F H30 T H31 N H32 Y H33 N H34 M-H35 H H36 W H37 L H38 R H39 Q H40 T H41 P H42 G H43 Q H44 G H45 L H46 E H47 W H48 I H49 G H50 Y H51 I H52 Y H52A P H53 G H54 N H55 G H56 D H57 T H-58 N H59 Y H60 N H61 Q H62 K H63 F H64 K H65 G H66 K H67 A H68 T H69 L H70 T H71 A H72 D H73 T H74 S H75 S H76 S H77 T H78 A H79 Y H80 M H81 Q H82 I H82A I H82B S H82C L H83 T H84 S H85 E H86 D H87 P H88 A H89 V H90 Y H91 F H92 C H93 A H94 R H95 Q H96 G H97 I H98 H H99 Y H100 Y H100A Y H100B I H-101 D H102 V H103 W H104 G H105 A H106 G H107 T H108 T H109 V H110 T H111 V H112 S H113 S H114 G (SEQ ID NO: 5).

(SEQ ID NO: 5)
EVQLQQSGAELVRSGASVKMSCKVNDYTFTNYNMHWLRQTP

GQGLEWIGYIYPGNGDTNYNQKFKGKATLTADTSSSTAYMQII

SLTSEDPAVYFCARQGIHYYYIDVWGAGTTVTVSSG.

Humanized Antibodies

A humanized antibody is a genetically engineered antibody in which at least one CDR (or functional fragment thereof) from a mouse antibody ("donor antibody", which can also be rat, hamster or other non-human species) are grafted onto a human antibody ("acceptor antibody"). In embodiments, more than one mouse CDR is grafted (e.g., all six mouse CDRs are grafted). The sequence of the acceptor antibody can be, for example, a mature human antibody sequence (or fragment thereof), a consensus sequence of a human antibody sequence (or fragment thereof), or a germline region sequence (or fragment thereof). Thus, a humanized antibody may be an antibody having one or more CDRs from a donor antibody and variable region framework (FR). The FR may form part of a constant region within a human antibody. In addition, in order to retain high binding affinity, amino acids in the human acceptor sequence may be replaced by the corresponding amino acids from the donor sequence, for example where: (1) the amino acid is in a CDR; (2) the amino acid is in the human framework region (e.g., the amino acid is immediately adjacent to one of the CDR's). See, U.S. Pat. Nos. 5,530,101 and 5,585,089, incorporated herein by reference, which provide detailed instructions for construction of humanized antibodies. Although humanized antibodies often incorporate all six CDRs (e.g., as defined by Kabat, but often also including hypervariable loop H1 as defined by Chothia) from a mouse antibody, they can also be made with fewer mouse CDRs and/or less than the complete mouse CDR sequence (e.g., a functional fragment of a CDR) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

Thus, in embodiments it may be necessary to incorporate only part of the donor CDRs, namely the subset of CDR residues required for binding, termed the SDRs, into the humanize d antibody. Donor CDR residues not contacting antigen and not in the SDRs can be identified based on previous studies (for example residues H60-H65 (Kabat numbering system) in mouse CDR H2 are often not required), from regions of Kabat CDRs lying outside Chothia hypervariable loops (Chothia, J. Mol. Biol. 196: 901, 1987), by molecular modeling and/or empirically, or as described in Gonzales et al., Mol. Immunol. 41: 863, 2004. In such humanized antibodies at positions in which one or more donor CDR residues is absent, the amino acid occupying the position can be an amino acid occupying the corresponding position (by Kabat numbering) in the acceptor antibody sequence. The number of such substitutions of acceptor amino acids for donor amino acids in a donor CDR may reflect a balance of competing considerations.

Typically a humanized antibody as provided herein may include (i) a light chain comprising at least one CDR (often three CDRs) from a mouse antibody (also referred to herein as a mouse CDR) and a human variable region framework; and (ii) a heavy chain comprising at least one CDR (often three CDRs) from the mouse antibody and a human variable region framework (FR). The light and heavy chain variable region frameworks (FRs) may each be a mature human antibody variable region framework sequence (or fragment thereof), a germline variable region framework sequence (combined with a J region sequence) (or fragment thereof), or a consensus sequence of a human antibody variable region framework sequence (or fragment thereof). In embodiments, the humanized antibody includes a light chain as described in (i), a heavy chain as described in (ii) together with a light chain human constant region and a heavy chain constant region.

A chimeric antibody is an antibody in which the variable region of a mouse (or other rodent) antibody is combined with the constant region of a human antibody; their construction by means of genetic engineering is well-known. Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or using transgenic animals (Lonberg et al., WO93/12227; Kucherlapati WO91/10741, each of which is incorporated herein by reference).

Other approaches to design humanized antibodies may also be used to achieve the same result as the methods in U.S. Pat. Nos. 5,530,101 and 5,585,089 described above, for example, "superhumanization" (see Tan et al. J. Immunol. 169: 1119, 2002, and U.S. Pat. No. 6,881,557) or the method of Studnicak et al., Protein Eng. 7:805, 1994. Moreover, other approaches to produce genetically engineered, reduced-immunogenicity mAbs include "reshaping", "hyperchimerization" and veneering/resurfacing, as described, e.g., in Vaswami et al., Annals of Allergy, Asthma and Immunology 81:105, 1998; Roguska et al. Protein Eng. 9:895, 1996; and U.S. Pat. Nos. 6,072,035 and 5,639,641.

In an aspect a humanized antibody capable of binding CD112R is provided. The humanized antibody includes a humanized heavy chain and a humanized light chain. As described above the variable regions of the heavy chain and the light chain of an antibody include complementarity determining regions (CDRs). CDRs are defined as regions within an antibody that are directly involved in antigen binding. Proceeding from the amino-terminus, these regions are designated CDR H1, CDR H2 and CDR H3 for the heavy chain, and CDR L1, CDR L2, and CDR L3 for the light chain, respectively. The CDRs are held in place by more conserved framework regions (FRs). Proceeding from the amino-terminus, these regions are designated FR H1, FR H2, FR H3, and FR H4 for the heavy chain and FR L1, FR L2, FR L3, and FR L4, for the light chain, respectively. For humanized antibodies, one or more of the CDRs are derived from a donor antibody (also referred to herein as a donor CDR, such as a mouse CDR), whereas the FRs are of human origin. The locations of CDR and FR regions and a numbering system have been defined by, e.g., Kabat et al. (Kabat et al., Sequences of Proteins of Immunological Interest, Fifth Edition, U.S. Department of Health and Human Services, U.S. Government Printing Office (1991)).

The humanized antibodies provided herein include at least one mouse CDR or a functional fragment thereof. A functional fragment of a CDR is a portion of a complete CDR amino acid sequence that may be capable of binding to an antigen. Thus, a functional fragment of a CDR typically includes the amino acid residues required for CDR binding to the antigen. A "mouse CDR" is a complete CDR amino acid sequence or a functional fragment thereof derived from a mouse antibody that may be capable of binding CD112R or a fragment thereof. Thus, a functional fragment of a mouse CDR typically includes the amino acid residues required for CDR binding to CD112R or a fragment thereof. Where a humanized antibody includes at least one mouse CDR, the at least one mouse CDR or a functional fragment thereof is derived from a donor antibody. A person of skill in the art will immediately recognize that a humanized antibody including at least one mouse CDR is a humanized antibody with at least one mouse CDR derived from a donor antibody and additional CDRs derived from the acceptor antibody (e.g., where the light chain includes a total of three CDRs and the heavy chain includes a total of three CDRs).

In embodiments, the humanized heavy chain and the humanized light chain may include combined one mouse CDR or functional fragment of a mouse CDR. Thus, in embodiments, the humanized heavy chain and the humanized light chain include a combined 6 CDRs wherein at least one of the 6 CDRs is a mouse CDR. Where the humanized heavy chain and the humanized light chain include combined one mouse CDR, the humanized heavy chain or the humanized light chain include one mouse CDR. For example, a humanized antibody may include CDR H3 derived from the donor antibody (e.g., mouse, also referred to herein as a mouse CDR H3) and CDR H1, CDR H2, CDR L1, CDR L2, and CDR L3 derived from the acceptor antibody (i.e., human).

In embodiments, the humanized heavy chain and the humanized light chain may include combined two mouse CDRs. Where the humanized heavy chain and the humanized light chain include combined two mouse CDRs, the humanized heavy chain and the humanized light chain each include one mouse CDR (i), the humanized heavy chain includes two mouse CDRs (ii), or the humanized light chain includes two mouse CDRs (iii). For example, a humanize d antibody may include CDR H3 and CDR L3 derived from the donor antibody (also referred to herein as a mouse CDR H3, mouse CDR L3, and mouse CDR H2 respectively), such as a mouse CDR and CDR H1, CDR H2, CDR L1, and CDR L2 derived from the acceptor antibody (i.e., human).

In embodiments, the humanized heavy chain and the humanized light chain may include combined three mouse CDRs. Where the humanized heavy chain and the humanized light chain include combined three mouse CDRs, the humanized heavy chain may include one mouse CDR and the humanized light chain may include two mouse CDRs (i), the humanize d heavy chain includes two mouse CDRs and the humanized light chain includes one mouse CDR (ii), the humanized heavy chain includes three mouse CDRs (iii), or the humanized light chain includes three mouse CDRs (vi). For example, a humanized antibody may include CDR H3, CDR L3 and CDR H2 derived from the donor antibody (e.g., mouse, also referred to herein as a CDR H3, mouse CDR L3, and mouse CDR H2 respectively) and CDR H1, CDR L1, and CDR L2 derived from the acceptor antibody (i.e., human).

In embodiments, the humanized heavy chain and the humanized light chain may include combined four mouse CDRs. Where the humanized heavy chain and the humanized light chain include combined four mouse CDRs, the humanized heavy chain includes one mouse CDR and the humanized light chain includes three mouse CDRs (i), the humanized heavy chain includes three mouse CDRs and the humanized light chain includes one mouse CDR (ii), or the humanized heavy chain includes two mouse CDRs and the humanized light chain includes two mouse CDRs (iii). For example, a humanized antibody may include CDR H3, CDR L3, CDR H2 and CDR H1 derived from the donor antibody (e.g., mouse, also referred to herein as a mouse CDR H3, mouse CDR L3, mouse CDR H2 and mouse CDR H1 respectively) and CDR L1 and CDR L2 derived from the acceptor antibody (i.e., human).

In embodiments, the humanized heavy chain and the humanized light chain each may include at least one mouse CDR. Where the humanized heavy chain and the humanized light chain each include at least one mouse CDR, the humanized heavy chain includes at least one mouse CDR and the humanized light chain includes at least one mouse CDR. Thus, in embodiments, the humanized heavy chain includes mouse CDR H1 and the humanized light chain includes mouse CDR L1.

In embodiments, the presence of mouse CDR H3 and mouse CDR L3 may be sufficient for binding of a humanized antibody to a CD112R. Thus, in embodiments, the humanized antibody may not include mouse CDR H1, mouse CDR H2, CDR L1 or mouse CDR L2. Where the humanized antibody does not include mouse CDR H1, mouse CDR H2, mouse CDR L1 or mouse CDR L2, the humanized antibody includes CDR H1, CDR H2, CDR L1 or CDR L2 derived from the acceptor antibody (i.e., human). Thus, a humanized antibody that does not include mouse CDR H1, mouse CDR H2, mouse CDR L1 or mouse CDR L2, does not include CDR H1, CDR H2, CDR L1 or CDR L2 from a donor antibody (e.g., mouse, rat, rabbit), but includes CDR H1, CDR H2, CDR L1 or CDR L2 from the acceptor antibody (i.e., human). Thus, in embodiments the humanized heavy chain may not include mouse CDR H1 or mouse CDR H2 and the humanized light chain does not include mouse CDR L1 or mouse CDR L2. In embodiments, the humanized heavy chain may not include mouse CDR H1 and mouse CDR H2 and the humanized light chain does not include mouse CDR L1 and mouse CDR L2.

In embodiments, the humanized heavy chain may include mouse CDR H2 and mouse CDR H3 and the humanized light chain may include mouse CDR L2 and mouse CDR L3. In embodiments, the humanized heavy chain may include mouse CDR H1, mouse CDR H2 and mouse CDR H3 and the humanized light chain may include mouse CDR L1, mouse CDR L2 and mouse CDR L3.

As described above, it may be necessary to incorporate only functional fragments of CDRs into the humanized antibody. A functional fragment of a CDR may be a part of a CDR or a subset of on one or more CDR residues required for binding. Thus, the humanized heavy chain and humanized light chain may include only certain residues of a donor antibody CDR (e.g., a mouse CDR). Where the humanized heavy chain and the humanized light chain include only certain residues of a donor antibody CDR, these donor antibody CDR residues are part of a corresponding acceptor antibody CDR. For example, a CDR H3 of a humanized antibody may contain one or more residues derived from a donor antibody CDR H3 (e.g., mouse) residing within the acceptor antibody CDR H3. Therefore, the CDR H3 of this humanized antibody includes one or more mouse CDR H3 residues residing within an acceptor antibody CDR H3. The one or more mouse CDR residues required for binding of a humanized antibody may be part of a single CDR within the humanized antibody (e.g., CDR H3, CDR H2, CDR H1, CDR L3, CDR L2, CDR L1). For example, the one or more mouse CDR residues required for binding of a humanized antibody may be part of CDR H3 within the humanized antibody. Alternatively, the one or more mouse CDR residues required for binding of a humanized antibody may be part of multiple CDRs within the humanized antibody. For example, the one or more mouse CDR residues may reside within CDR H3 and CDR L3 within a humanized antibody.

The position of CDRs and FRs may be defined by the Kabat numbering system (Kabat et al., Sequences of Proteins of Immunological Interest, Fifth Edition, U.S. Department of Health and Human Services, U.S. Government Printing Office (1991)). Likewise, the positions occupied by individual residues within the heavy or the light chain of an antibody may be defined by the Kabat numbering system. Therefore, the location of residues required for binding within a humanized heavy chain and a humanized light chain of a humanized antibody may be defined by the position of the residue according to the Kabat numbering system as is well known in the art.

As described above, a humanized antibody may be an antibody having CDRs from a donor antibody (e.g., mouse) and variable region framework (FR) from a human antibody. The framework regions (FRs) are said to hold the CDRs in place in a humanized antibody. Proceeding from the amino-terminus, these regions are designated FR H1, FR H2, FR H3, and FR H4 for the heavy chain and FR L1, FR L2, FR L3, and FR L4, for the light chain, respectively. Surprisingly, the present disclosure provides for humanized antibodies that include one or more residues within the framework regions that are important for epitope binding of the humanized antibody. A framework region residue involved in (or important for) epitope binding (e.g., CD112R or a fragment thereof binding) is referred to herein as a binding framework region residue. The binding framework region residues may reside in the framework region of a humanized heavy chain (i.e., FR H1, FR H2, FR H3, FR H4) or they may reside in the framework of a humanized light chain (i.e., FR L1, FR L2, FR L3, FR L4). A binding framework residue residing in the FR L3 region of a humanized light chain is referred to herein as a FR L3 binding framework region residue. Thus, a binding framework region residue residing in the FR H3 region of a humanized heavy chain is referred to herein as a FR H3 binding framework region residue.

In embodiments, the humanized antibody may include at least one binding framework region residue. In embodiments, the humanized heavy chain may include at least one binding framework region residue. In embodiments, the humanized heavy chain may include one or more FR H3 binding framework region residues. In embodiments, the humanized heavy chain may include one or more FR H2 binding framework region residues. In embodiments, the humanized light chain may include at least one binding framework region residue. In embodiments, the humanized light chain may include one or more FR L3 binding framework region residues. In embodiments, the humanized light chain may include one or more FR L1 binding framework region residues.

In embodiments, the humanized heavy chain may include at least one binding framework region residue and the humanized light chain may include at least one binding framework region residue. In embodiments, the humanized light chain may include at least one FR H3 binding framework region residue and the humanized light chain may include at least one FR L3 binding framework region residue. In embodiments, the humanized light chain may include at least one FR H3 binding framework region residue and at least one FR H2 binding framework region residue, and the humanized light chain may include at least one FR L3 binding framework region residue and at least one FR L1 binding framework region residue. The position of a binding framework region residue within a humanized antibody may be defined by the Kabat numbering system similar to the positions CDR residues.

The humanized antibodies as provided herein may be Fab' fragments. Where the humanized antibodies are Fab' fragments, the humanized antibodies include a humanized heavy chain (e.g., including a constant and a variable region) and a humanized light chain (e.g., including a constant and a variable region). In embodiments, the humanized antibody is a Fab' fragment. In other embodiments, the humanized antibody includes a human constant region. In other embodiments, the humanized antibody is an IgG. In other embodiments, the humanized antibody is an IgA. In other embodiments, the humanized antibody is an IgM. In embodiments, the humanized antibody includes the amino acid sequence of SEQ ID NO: 1.

In embodiments, the humanized antibody may be a single chain antibody. A single chain antibody includes a variable light chain and a variable heavy chain. A person of skill in the art will immediately recognize that a single chain antibody includes a single light chain and a single heavy chain, in contrast to an immunoglobulin antibody, which includes two identical pairs of polypeptide chains, each pair having one light chain and one heavy chain. Each light chain and heavy chain in turn consists of two regions: a variable ("V") region (i.e., variable light chain and variable heavy chain) involved in binding the target antigen, and a constant ("C") region that interacts with other components of the immune system. The variable light chain and the variable heavy chain in a single chain antibody may be linked through a linker peptide. Examples for linker peptides of single chain antibodies are described in Bird, R. E., Hardman, K. D., Jacobson, J. W., Johnson, S., Kaufman, B. M., Lee, S. M., Lee, T., Pope, S. H., Riordan, G. S. and Whitlow, M. (1988). Methods of making scFv antibodies have been described. See, Huse et al., Science 246:1275-1281 (1989); Ward et al., Nature 341:544-546 (1989); and Vaughan et al., Nature Biotech. 14:309-314 (1996). Briefly, mRNA from B-cells from an immunized animal is isolated and cDNA is prepared. The cDNA is amplified using primers specific for the variable regions of heavy and light chains of immunoglobulins. The PCR products are purified and the nucleic acid sequences are joined. If a linker peptide is desired, nucleic acid sequences that encode the peptide are inserted between the heavy and light chain nucleic acid sequences. The nucleic acid which encodes the scFv is inserted into a vector and expressed in the appropriate host cell.

The ability of an antibody to bind a specific epitope can be described by the equilibrium dissociation constant ($K_D$). The equilibrium dissociation constant ($K_D$) as defined herein is the ratio of the dissociation rate (K-off) and the association rate (K-on) of a humanize d antibody to CD112R. It is described the following formula: $K_D$=K-off/K-on. In embodiments, the humanized antibody may be capable of binding CD112R with an equilibrium dissociation constant ($K_D$) of about 100 nM. In embodiments, the humanized antibody may be capable of binding CD112R with an equilibrium dissociation constant ($K_D$) of about 90 nM. In embodiments, the humanized antibody may be capable of binding CD112R with an equilibrium dissociation constant ($K_D$) of about 80 nM. In embodiments, the humanized antibody may be capable of binding CD112R with an equilibrium dissociation constant ($K_D$) of about 70 nM. In embodiments, the humanized antibody may be capable of binding CD112R with an equilibrium dissociation constant ($K_D$) of about 60 nM. In embodiments, the humanized antibody may be capable of binding CD112R with an equilibrium dissociation constant ($K_D$) of about 50 nM. In embodiments, the humanized antibody may be capable of binding CD112R with an equilibrium capable of binding CD112R with an equilibrium dissociation constant ($K_D$) of about 30 nM. In embodiments, the humanized antibody may be capable of binding CD112R with an equilibrium dissociation constant ($K_D$) of about 20 nM. In embodiments, the humanized antibody may be capable of binding CD112R with an equilibrium dissociation constant ($K_D$) of about 10 nM. In embodiments, the humanized antibody may be capable of binding CD112R with an equilibrium dissociation constant ($K_D$) of about 9.5 nM. In embodiments, the humanized antibody may be capable of binding CD112R with an equilibrium dissociation constant ($K_D$) of about 9 nM. In embodiments, the humanized antibody may be capable of binding CD112R with an equilibrium dissociation constant ($K_D$) of about 8.5 nM. In embodiments, the humanized antibody may be capable of binding CD112R with an equilibrium dissociation constant ($K_D$) of about 8 nM. In embodiments, the humanized antibody may be capable of binding CD112R with an equilibrium dissociation constant ($K_D$) of about 7.5 nM. In embodiments, the humanized antibody may be capable of binding CD112R with an equilibrium dissociation constant ($K_D$) of about 7 nM. In embodiments, the humanized antibody may be capable of binding CD112R with an equilibrium dissociation constant ($K_D$) of about 6.5 nM. In embodiments, the humanized antibody may be capable of binding CD112R with an equilibrium dissociation constant ($K_D$) of about 6 nM. In embodiments, the humanized antibody may be capable of binding CD112R with an equilibrium dissociation constant ($K_D$) of about 5.5 nM. In embodiments, the humanized antibody may be capable of binding CD112R with an equilibrium dissociation constant ($K_D$) of about 5 nM. In embodiments, the humanized antibody may be capable of binding CD112R with an equilibrium dissociation constant ($K_D$) of about 4.5 nM. In embodiments, the humanized antibody may be capable of binding CD112R with an equilibrium dissociation constant ($K_D$) of about 4 nM. In embodiments, the humanized antibody may be capable of binding CD112R with an equilibrium dissociation constant ($K_D$) of about 3.5 nM. In embodiments, the humanized antibody may be capable of binding CD112R with an equilibrium dissociation constant ($K_D$) of about 3 nM. In embodiments, the humanized antibody may be capable of binding CD112R with an equilibrium dissociation constant ($K_D$) of about 2.5 nM. In embodiments, the humanized antibody may be capable of binding CD112R with an equilibrium dissociation constant ($K_D$) of about 2 nM.

In embodiments, the humanized antibody may be capable of binding CD112R with an equilibrium dissociation constant ($K_D$) of less than 10 nM. In embodiments, the equilibrium dissociation constant ($K_D$) is less than 8 nM and more than 1 nM. In embodiments, the equilibrium dissociation constant ($K_D$) is less than 6 nM and more than 1.25 nM. In embodiments, the equilibrium dissociation constant ($K_D$) is less than 4 nM and more than 1.5 nM.

In embodiments, the humanized antibody provided herein binds to an extracellular domain or fragment of CD112R. In embodiments, the humanized antibody may be capable of binding CD112R conjugate with an equilibrium dissociation constant ($K_D$) of less than 10 nM. In embodiments, the equilibrium dissociation constant ($K_D$) is less than 8 nM and more than 1 nM. In embodiments, the equilibrium dissociation constant ($K_D$) is less than 6 nM and more than 1.25 nM. In embodiments, the equilibrium dissociation constant ($K_D$) is less than 4 nM and more than 1 nM. In embodiments, the equilibrium dissociation constant ($K_D$) is about 1.5 nM.

The ability of a particular antibody to recognize the same epitope as another antibody can be determined by the ability of one antibody to competitively inhibit binding of the second antibody to the antigen, e.g., to CD112R or a fragment thereof. Any of a number of competitive binding assays can be used to measure competition between two antibodies to the same antigen. An exemplary assay is a Biacore® assay. Briefly, in these assays, binding sites can be mapped in structural terms by testing the ability of interactants, e.g., different antibodies, to inhibit the binding of another. Injecting two consecutive antibody samples in sufficient concentration can identify pairs of competing antibodies for the same binding epitope.

Other conventional immunoassays known in the art can be used in the present disclosure. For example, antibodies can be differentiated by the epitope to which they bind using a sandwich ELISA assay. This is carried out by using a capture antibody (e.g., a mouse 1B7 antibody) to coat the surface of a well. A sub-saturating concentration of tagged-antigen is then added to the capture surface. This protein will be bound to the antibody through a specific antibody:epitope interaction. After washing a second antibody (e.g., a humanized antibody capable of binding CD112R), which has been covalently linked to a detectable moiety (e.g., HRP, with the labeled antibody being defined as the detection antibody) is added to the ELISA. If this antibody recognizes the same epitope as the capture antibody it will be unable to bind to the target protein as that particular epitope will no longer be available for binding. If however this second antibody recognizes a different epitope on the target protein it will be able to bind and this binding can be detected by quantifying the level of activity (and hence antibody bound) using a relevant substrate. The background is defined by using a single antibody as both capture and detection antibody, whereas the maximal signal can be established by capturing with an antigen specific antibody and detecting with an antibody to the tag on the antigen. By using the background and maximal signals as references, antibodies can be assessed in a pair-wise manner to determine epitope specificity.

In embodiments, the humanized antibody is an antibody which competes with an antibody that may be capable of binding CD112R including the amino acid sequence corresponding to amino acid residues 1 to 326 of SEQ ID NO: 1.

Method of Modulating Immune Response

In embodiments, the present disclosure includes a method of modulating immune response in a subject in need thereof, including administering to the subject a CD112R protein, the fusion polypeptide, the complex, or the antibody of the present disclosure, respectively. The method of modulating immune response of the present disclosure induces tumor suppression or regression in the subject. The method of modulating immune response of the present disclosure modulates T-cell response in said subject.

In embodiments, the method of modulating immune response of the present disclosure modulates immune-related and inflammatory diseases. In embodiments, the method of modulating immune response of the present disclosure modulates autoimmune disease, transplantation related disease or disorder, or an infectious disease.

Non-limiting examples of autoimmune disease include Rheumatoid arthritis, Type 1 diabetes (also known as insulin-dependent diabetes mellitus), multiple sclerosis, vasculitis, alopecia areata, lupus, polymyalgia rheumatica, ankylosing spondylitis, celiac disease, Sjogren's disease, temporal arteritis/giant cell arteritis, Acquired Immunodeficiency Syndrome (AIDS, which is a viral disease with an autoimmune component), antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigoid, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, juvenile chronic arthritis (Still's disease), juvenile rheumatoid arthritis, Meniere's disease, mixed connective tissue disease, myasthenia gravis, pernacious anemia, polyarteritis nodosa, polychondritis, polyglandular syndromes, polymyositis and dermatomyositis, primary agammaglobulinemia, primary biliary cirrhosis, psoriasis, psoriatic arthritis, Raynaud's phenomena, Reiter's syndrome, rheumatic fever, sarcoidosis, scleroderma (progressive systemic sclerosis (PSS), also known as systemic sclerosis (SS)), stiff-man syndrome, systemic lupus erythematosus, Takayasu arteritis, ulcerative colitis, uveitis, vitiligo and Wegener's granulomatosis.

Non-limiting inflammatory disorders include chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

Non-limiting transplantation related disease or disorder include post-transplant lymphoproliferative disorder (PTLD), blood disorders associated with renal transplantation, transplant-related thrombotic microangiopathy, hemophagocytic syndrome, and graft-versus-host disease. Post-transplant lymphoproliferative disorder (PTLD) is the name given to a B-cell proliferation due to therapeutic immunosuppression after organ transplantation. These patients may develop infectious mononucleosis-like lesions or polyclonal polymorphic B-cell hyperplasia.

Non-limiting examples of infectious diseases include viral infections such as HIV infection, hepatitis A, B, C, D, or E infection, herpes virus type 1 (HSV-1) or type 2 (HSV-2) infection, Epstein Barr virus, BK virus, cytomegalovirus, adenovirus, influenza virus, West Nile virus, Ebola virus, etc., bacterial infections, fungal infections, protozoan infections, and parasitic infections.

In embodiments, present disclosure includes administering to a subject by intravenous, parenteral, subcutaneous, intramuscular, transdermal, intraperitoneal, intranasal, aerosol, oral, or topical administration, a CD112R protein, the fusion polypeptide, the complex, or the antibody of the present disclosure. In embodiments, the treatment is dose-dependent of the CD112R protein, the fusion polypeptide, the complex, or the antibody of the present disclosure. In embodiments, about 0.001 mg/kg to about 100 mg/kg of the CD112R protein, the fusion polypeptide, the complex, or the antibody of the present disclosure is administered to the subject. All digits and various ranges within this range are also implied.

The present disclosure includes a method of stimulating an immune response in a subject in need thereof, the method including administering to the subject an effective amount of a CD112R protein, the fusion polypeptide, the complex, or the antibody of the present disclosure. In embodiments, the stimulation of immune response includes maturation, differentiation, or proliferation of T cells. In embodiments, the stimulation of immune response includes an increase in TH1-type immune response. In embodiments the stimulation of immune response may recruit dendritic cells and CD8+ T cells into an organ of the subject. In embodiments, the stimulation of immune response expands population of antigen-presenting cells in the subject. In embodiments, the stimulation of immune response suppresses proliferation of cancer cells in the subject. In embodiments, a CD112R protein, the fusion polypeptide, the complex, or the antibody of the present disclosure is administered to the subject by intravenous, parenteral, subcutaneous, intramuscular, transdermal, intraperitoneal, intranasal, aerosol, oral, or topical administration in order to stimulate immune response.

The present disclosure includes a method of suppressing an immune response in a subject in need thereof, the method including administering to the subject an effective amount of a CD112R protein, the fusion polypeptide, a complex, or an anti-CD112R antibody of the present disclosure.

Method of Treating Cancer

In an aspect is provided a method of treating cancer by administering an effective amount of a composition including a toxin and an anti-CD112R antibody to a subject in need thereof. In embodiments, the composition includes a drug delivery vehicle. In embodiments, the drug delivery vehicle includes a toxin and an anti-CD112R antibody. In embodiments, the method of treating cancer of the present disclosure involves administering a drug delivery vehicle including a toxin and anti-CD112R antibodies to the subject, in which the toxin may be a cytotoxic agent, e.g., an inhibitor of DNA topoisomerase I or topoisomerase II. In embodiments, the cytotoxic agent may be Bendamustine, Busulfan, Carmustine, Chlorambucil, Cyclophosphamide, Dacarbazine, Ifosfamide, Melphalan, Procarbazine, Streptozocin, Temozolomide, Asparaginase, Capecitabine, Cytarabine, 5-FluoroUracil, Fludarabine, Gemcitabine, Methotrexate, Pemetrexed, Raltitrexed. In embodiments, the toxin is may be irinotecan, topotecan, camptothecin (CPT), lamellarin D, etoposide (VP-16), teniposide, doxorubicin, daunorubicin, mitoxantrone, amsacrine, ellipticines, aurintricarboxylic acid, HU-331, or combination(s) thereof. In embodiments, the drug delivery vehicle may also include a second anti-cancer or anti-tumor agent, for example Actinomycin D/Dactinomycin, Bleomycin, Daunorubicin, Doxorubicin, Doxorubicin (pegylated liposomal), Epirubicin, Idarubicin, Mitomycin, or Mitoxantrone. In embodiments, the drug delivery vehicle may also include a plant alkaloid or microtubule inhibitors, for example, Etoposide, Docetaxel, Irinotecan, Paclitaxel, Topotecan, Vinblastine, Vincristine, or Vinorelbine. In embodiments, the drug delivery vehicle may include a DNA linking agent, for example, Carboplatin, Cisplatin, or Oxaliplatin. In embodiments, the drug delivery vehicle may also include a second anti-cancer or anti-tumor biological agent, for example, Alemtuzamab, BCG, Bevacizumab, Cetuximab, Denosumab, Erlotinib, Gefitinib, Imatinib, Interferon, Ipilimumab, Lapatinib, Panitumumab, Rituximab, Sunitinib, Sorafenib, Temsirolimus, or Trastuzumab.

In embodiments, the drug delivery vehicle is a nanoparticle. In embodiments, the nanoparticle is a poly(lactidecoglycolide) particle. In embodiments, the nanoparticle comprises a peripheral layer of anti-CD112R antibodies. In embodiments, the anti-CD112R antibodies are covalently conjugated to the nanoparticle.

In embodiments, the method of treating cancer of the present disclosure delivers a drug delivery vehicle including a toxin and anti-CD112R antibodies to cancerous cells of a subject in need thereof. In embodiments, the cancerous cells are T cell acute lymphoblastic leukemia (T-ALL) cells. In embodiments, the method is provided for treating non-Hodgkin's lymphoma, leukemia, or pancreatic cancer.

Small Interfering RNAs

In an aspect, the present disclosure includes compositions of one or more of anti-CD112R siRNAs. Non-limiting examples of CD112R siRNAs are listed in Table 2.

TABLE 2

| SEQ ID NO: | |
|---|---|
| 31 | TGCACGTGGCAGCTTTGTCTCTGTT |
| 122 | TGCACGTGGCAGCTTTGTCTCTGTT |
| 58 | ACGTGGCAGCTTTGTCTCTGTTGAG |
| 59 | TGGCAGCTTTGTCTCTGTTGAGAAT |
| 60 | GCTTTGTCTCTGTTGAGAATGGACT |

Drug Delivery Vehicle

In an aspect is provided a drug delivery vehicle including a toxin and anti-CD112R antibodies. The drug delivery device includes a toxin. The toxin may be a cytotoxic agent, e.g., an inhibitor of DNA topoisomerase I or topoisomerase II. In embodiments, the cytotoxic agent may be Bendamustine, Busulfan, Carmustine, Chlorambucil, Cyclophosphamide, Dacarbazine, Ifosfamide, Melphalan, Procarbazine, Streptozocin, Temozolomide, Asparaginase, Capecitabine, Cytarabine, 5-FluoroUracil, Fludarabine, Gemcitabine, Methotrexate, Pemetrexed, Raltitrexed. In embodiments, the toxin is may be irinotecan, topotecan, camptothecin (CPT), lamellarin D, etoposide (VP-16), teniposide, doxorubicin, daunorubicin, mitoxantrone, amsacrine, ellipticines, aurintricarboxylic acid, HU-331, or combination(s) thereof. In embodiments, the drug delivery vehicle may also include a second anti-cancer or anti-tumor agent, for example Actinomycin D/Dactinomycin, Bleomycin, Daunorubicin, Doxorubicin, Doxorubicin (pegylated liposomal), may also include a plant alkaloid or microtubule inhibitors, for example, Etoposide, Docetaxel, Irinotecan, Paclitaxel, Topotecan, Vinblastine, Vincristine, or Vinorelbine. In embodiments, the drug delivery vehicle may include a DNA linking agent, for example, Carboplatin, Cisplatin, or Oxaliplatin. In embodiments, the drug delivery vehicle may also include a second anti-cancer or anti-tumor biological agent, for example, Alemtuzamab, BCG, Bevacizumab, Cetuximab, Denosumab, Erlotinib, Gefitinib, Imatinib, Interferon, Ipilimumab, Lapatinib, Panitumumab, Rituximab, Sunitinib, Sorafenib, Temsirolimus, or Trastuzumab.

In embodiments, the drug delivery vehicle is a nanoparticle. In embodiments, the nanoparticle is a poly(lactidecoglycolide) particle. In embodiments, the nanoparticle comprises a peripheral layer of anti-CD112R antibodies. In embodiments, the anti-CD112R antibodies are covalently conjugated to the nanoparticle.

In embodiments, the nanoparticle includes a polymer (e.g., copolymer) described herein. Natural polymers and synthetic polymers for nanoparticles such as N-(2-hydroxypropyl)-methacrylamide, copolymer (HPMA), poly(ethylene glycol) (PEG), poly(lactic acid-glycolic acid) (PLGA), and poly(lactic acid) PLA may be used in embodiments of the present disclosure.

In embodiments, the nanoparticles of the present disclosure may be polymeric micelles. Micelles are biocompatible nanoparticles varying in size from 50 to 200 nm in which poorly soluble drugs can be encapsulated. Polymers are used in core-shell nanoparticles because they offer a wide range of applications from drug delivery to bioimaging. A polymeric core-shell nano structure comprises a polymeric core and/or a polymeric shell and can be dispersed in a matrix of any material class whose property is to be modified or enhanced. In drug delivery, polymeric-based micellar systems which contain a hydrophobic core surrounded by hydrophilic polymers are used as carriers for hydrophobic drugs.

In embodiments, the nanoparticles of the present disclosure may be biodegradable polymers or dendrimers.

In embodiments, the nanoparticle has a longest dimension (e.g., diameter) of between about 1 and about 1000 nm. In embodiments, the nanoparticle has a longest dimension (e.g., diameter) of between about 5 and about 100 nm. In embodiments, the nanoparticle has a longest dimension (e.g., diameter) of between about 10 and about 50 nm. In embodiments, the nanoparticle has a longest dimension (e.g., diameter) of between 1 and 1000 nm. In embodiments, the nanoparticle has a longest dimension (e.g., diameter) of between 5 and 100 nm. In embodiments, the nanoparticle has a longest dimension (e.g., diameter) of between 10 and 50 nm.

In embodiments, the nanoparticle has a longest dimension (e.g., diameter) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm.

In embodiments, the nanoparticle has a longest dimension (e.g., diameter) of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 5145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 10240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 15335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 20430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 25525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 30620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, or 1000 nm.

In embodiments, the nanoparticle longest dimension (e.g., diameter) is a hydrodynamic longest dimension (e.g., diameter). In embodiments, the longest dimension (e.g., diameter) is an average longest dimension (e.g., diameter) of a sample.

Combination Therapies

The present disclosure also provides methods of treating, preventing, delaying the progression of or otherwise ameliorating a symptom of one or more pathologies or alleviating a symptom associated with such pathologies, by administering a an CD112R protein, a fusion polypeptide, a complex including CD112R and a second protein, or an anti-CD112R antibody of the disclosure (collectively referred to herein as "anti-CD112R-binding molecules") to a subject in which such treatment or prevention is desired. The subject to be treated is, e.g., human or other mammal. In embodiments, the subject is a non-human mammal, such as a non-human primate, companion animal (e.g., cat, dog, horse), farm animal, work animal, or zoo animal. In embodiments, the subject is a rodent.

An anti-CD112R-binding molecules used in any of the embodiments of these methods and uses can be administered at any stage of the disease. For example, an anti-CD112R-binding molecule can be administered to a patient suffering cancer of any stage, from early to metastatic. The terms subject and patient are used interchangeably herein.

An anti-CD112R-binding molecules used in any of the embodiments of these methods and uses can be used in a treatment regimen comprising neoadjuvant therapy.

An anti-CD112R-binding molecules used in any of the embodiments of these methods and uses can be administered either alone or in combination with one or more additional agents, including small molecule inhibitors, other antibody-based therapies, polypeptide or peptide-based therapies, nucleic acid-based therapies and/or other biologics.

In embodiments, one or more anti-CD112R-binding molecules of the disclosure are used in combination with one or more immunotherapies. Suitable immunotherapies for use include, by way of non-limiting example, immunotherapies that target TIGIT, PD-1, PD-L1, TIM-3, LAG-3, BTLA, CD226, CD160, CD137, CD96, CD70, CD47, CD40, NKG2D, VISTA, ICOS, B7-HE, GITR, OX40, KIR, SLAM7, CTLA-4, and combinations thereof.

In embodiments, the at least one additional agent can also be a chemical or molecule that modulates immune responses, for example, an agent that targets indoleamine-pyrrole 2,3-dioxygenase (IDO) or mechanistic Target Of Rapamycin (mTOR).

In embodiments, one or more anti-CD112R-binding molecules of the disclosure are used in combination with one or more molecularly-targeted therapy.

In embodiments, one or more anti-CD112R-binding molecules of the disclosure are used in combination with one or more vaccine.

In embodiments, one or more anti-CD112R-binding molecules of the disclosure are used in combination with one or more chemotherapeutic agents and/or regimens.

In embodiments, one or more anti-CD112R-binding molecules of the disclosure are used in combination with radiation or other radiation-based therapy.

In embodiments, one or more anti-CD112R-binding molecules of the disclosure are used in combination with a surgical procedure, such as, by way of non-limiting example, surgical resection.

In embodiments, one or more anti-CD112R-binding molecules of the disclosure are used in combination with one or more bispecific T-cell engagers, one or more cancer vaccines, Freund's Adjuvant, one or more CAR-T cell therapies, one or more stem cell therapies, and/or one or more scFv therapies.

In embodiments, one or more anti-CD112R-binding molecules of the disclosure are used in combination with one or more commercially available anti-cancer agents. Suitable commercially available anti-cancer agents include, by way of non-limiting example, nivolumab, ipilimumab, IL-2, atezolizumab, elotuzumab, daratumumab, talimogene laherparepvec, pembrolizumab, ipilimumab, blinatumomab, ramucirumab, brentuximab, brentuximab vedotin, peginterferon alfa-2bj, sipuleucel-T, ofatumumab, denosumab, and combinations thereof.

In embodiments, one or more anti-CD112R-binding molecules of the disclosure are used in combination with one or more anti-cancer agents in clinical trials and/or undergoing regulatory review. An example of such an anti-cancer agent includes, by way of non-limiting example, tremelimumab.

In embodiments, an anti-CD112R-binding molecule is administered in combination with one or more additional agents such as, by way of non-limiting example, a chemotherapeutic agent, such as an alkylating agent, an anti-metabolite, an anti-microtubule agent, a topoisomerase inhibitor, a cytotoxic antibiotic, and any other nucleic acid damaging agent. In embodiments, the additional agent is a taxane, such as paclitaxel (e.g., Abraxane®). In embodiments, the additional agent is an anti-metabolite, such as gemcitabine. In embodiments, the additional agent is an alkylating agent, such as platinum-based chemotherapy, such as carboplatin or cisplatin. In embodiments, the additional agent is a targeted agent, such as a kinase inhibitor, e.g., sorafenib or erlotinib. In embodiments, the additional agent is a targeted agent, such as another antibody, e.g., a monoclonal antibody (e.g., bevacizumab), a bispecific antibody, or a multispecific antibody. In embodiments, the additional agent is a proteosome inhibitor, such as bortezomib or carfilzomib. In embodiments, the additional agent is an immune modulating agent, such as lenolidominde or IL-2. In embodiments, the additional agent is radiation. In embodiments, the additional agent is an agent considered standard of care by those skilled in the art. In embodiments, the additional agent is a chemotherapeutic agent well known to those skilled in the art. In embodiments, the anti-CD112R binding molecule and the additional agent(s) are formulated in a single composition. In embodiments, the anti-CD112R binding molecule and the additional agent(s) are administered as two or more separate compositions. In embodiments, the anti-CD112R binding molecule and the additional agent(s) are administered simultaneously. In embodiments, the anti-CD112R binding molecule and the additional agent(s) are administered sequentially.

In embodiments, the additional agent(s) is a chemotherapeutic agent, such as a chemotherapeutic agent selected from the group consisting of docetaxel, paclitaxel, abraxane (i.e., albumin-conjugated paclitaxel), doxorubicin, oxaliplatin, carboplatin, cisplatin, irinotecan, and gemcitabine.

In embodiments, the additional agent(s) is a checkpoint inhibitor, a kinase inhibitor, an agent targeting inhibitors in the tumor microenvironment, and/or a T cell or NK agonist. In embodiments, the additional agent(s) is radiation therapy, alone or in combination with another additional agent(s) such as a chemotherapeutic or anti-neoplastic agent. In embodiments, the additional agent(s) is a vaccine, an oncovirus, and/or a DC-activating agent such as, by way of non-limiting example, a toll-like receptor (TLR) agonist and/or α-CD40. In embodiments, the additional agent(s) is a tumor-targeted antibody designed to kill the tumor via ADCC or via direct conjugation to a toxin (e.g., an antibody drug conjugate (ADC).

In embodiments, the checkpoint inhibitor is an inhibitor of a target selected from the group consisting of CTLA-4, LAG-3, PD-1, PDL1, TIGIT, TIM-3, B7H4, and Vista. In embodiments, the kinase inhibitor is selected from the group consisting of B-RAFi, MEKi, and Btk inhibitors, such as ibrutinib. In embodiments, the kinase inhibitor is crizotinib. In embodiments, the tumor microenvironment inhibitor is selected from the group consisting of an IDO inhibitor, an α-CSF1R inhibitor, an α-CCR4 inhibitor, a TGF-beta, a myeloid-derived suppressor cell, or a T-regulatory cell. In embodiments, the agonist is selected from the group consisting of Ox40, GITR, CD137, ICOS, CD27, and HVEM. In embodiments, the checkpoint inhibitor is an antibody that binds a target selected from CTLA-4, PD-1, and/or PD-L1. In embodiments, the checkpoint inhibitor is an anti-CTLA4 antibody, an anti-PD-1 antibody, and an anti-PD-L1 antibody, and/or combinations thereof. In embodiments, the checkpoint inhibitor is an anti-CTLA4 antibody such as, e.g., Yervoy™. In embodiments, the checkpoint inhibitor is an anti-PD-1 antibody such as, e.g., Opdivo™ and/or Keytruda™.

In embodiments, the inhibitor is a CTLA-4 inhibitor. In embodiments, the inhibitor is a LAG-3 inhibitor. In embodiments, the inhibitor is a PD-1 inhibitor. In embodiments, the inhibitor is a PDL1 inhibitor. In embodiments, the inhibitor is a TIGIT inhibitor. In embodiments, the inhibitor is a TIM-3 inhibitor. In embodiments, the inhibitor is a B7H4 inhibitor. In embodiments, the inhibitor is a Vista inhibitor. In embodiments, the inhibitor is a B-RAFi inhibitor. In embodiments, the inhibitor is a MEKi inhibitor. In embodiments, the inhibitor is a Btk inhibitor. In embodiments, the inhibitor is ibrutinib. In embodiments, the inhibitor is crizotinib. In embodiments, the inhibitor is an IDO inhibitor. In embodiments, the inhibitor is an α-CSF1R inhibitor. In embodiments, the inhibitor is an α-CCR4 inhibitor. In embodiments, the inhibitor is a TGF-beta. In embodiments, the inhibitor is a myeloid-derived suppressor cell. In embodiments, the inhibitor is a T-regulatory cell.

In embodiments, the agonist is Ox40. In embodiments, the agonist is GITR. In embodiments, the agonist is CD137. In embodiments, the agonist is ICOS. In embodiments, the agonist is CD27. In embodiments, the agonist is HVEM.

In embodiments, the additional agent(s) is an antibody or antigen-binding fragment thereof or a conjugated antibody or antigen-binding fragment thereof. In embodiments, the additional agent(s) is an antibody or antigen-binding fragment thereof or a conjugated antibody or antigen-binding fragment thereof binds CD122R. In embodiments, the additional agent(s) is an antibody or antigen-binding fragment thereof or a conjugated antibody or antigen-binding fragment thereof against a target other than CD112R.

In embodiments, the anti-CD112R-binding molecule is administered during and/or after treatment in combination with one or more additional agents such as, for example, a chemotherapeutic agent, an anti-inflammatory agent, and/or a an immunosuppressive agent. In embodiments, the anti-CD112R-binding molecules and the additional agent(s) are formulated into a single therapeutic composition, and the anti-CD112R-binding molecules and additional agent(s) are administered simultaneously. Alternatively, the anti-CD112R-binding molecules and additional agent(s) are separate from each other, e.g., each is formulated into a separate therapeutic composition, and the anti-CD112R-binding molecules and the additional agent(s) are administered simultaneously, or the anti-CD112R-binding molecules and the additional agent(s) are administered at different times during a treatment regimen. For example, the anti-CD112R-binding molecule is administered prior to the administration of the additional agent, the anti-CD112R-binding molecule is administered subsequent to the administration of the additional agent, or the anti-CD112R-binding molecules and the additional agent(s) are administered in an alternating fashion. As described herein, the anti-CD112R-binding molecules and additional agent(s) are administered in single doses or in multiple doses.

In embodiments, the CD112R protein, a fusion polypeptide, a complex including CD112R and a second protein, or an anti-CD112R-binding molecule and the additional agent(s) are administered simultaneously. For example, the anti-CD112R-binding molecules and the additional agent(s) can be formulated in a single composition or administered as two or more separate compositions. In embodiments, the anti-CD112R-binding molecules and the additional agent(s)

are administered sequentially, or the anti-CD112R-binding molecules and the additional agent(s) are administered at different times during a treatment regimen.

EXAMPLES

Example 1: Characterization of CD112R as a New Receptor of PVR Family

An extensive genome-wide search was performed to identify genes that were both preferentially expressed on human T cells and that encoded transmembrane proteins with a single IgV extracellular domain. Through this search a candidate human gene was discovered, previously named as polio virus receptor related immunoglobulin domain containing (PVRIG) (gene ID 79037). It was renamed the receptor for CD112 (CD112R) to reflect its strong interaction with CD112 described herein.

Figure 1D:
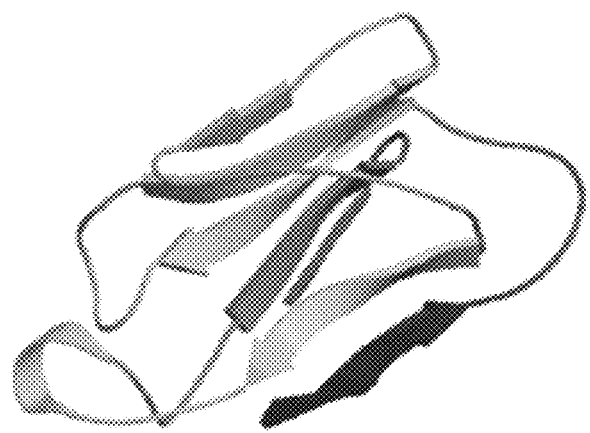
FIG. 1D is a predicted protein structure model of human CD112R IgV domain (55-150aa) using human PVRL4 (protein Data Bank accession no. 4JJH) as the template.

The CD112R gene encodes a putative single transmembrane protein (which is composed of a single extracellular IgV domain) one transmembrane domain, and a long intracellular domain (FIG. 1A). Notably, the intracellular domain of CD112R contains two tyrosine residues, one within an ITIM-like motif that is a potential docking site for phosphatases (Billadeau and Leibson, 2002). Alignment of the amino acid sequence of CD112R to other known PVR family members indicated that the IgV domain of CD112R contains residues conserved among the PVR family (FIG. 1B). These residues constitute at least three main motifs shared among the PVR family: Val or Ile-Ser or Thr-Gln at position 72-74aa of CD112R; Ala89-X6-Gly96; and Tyr139 or Phe139-Pro140-X-Gly142 (Yu et al., 2009). Phylogenic tree analysis of the first IgV of PVR family further revealed that CD112R was close to all PVR-like proteins (FIG. 1C). Using the first IgV domain of PVRL4 as a template, a structural model of CD112R was constructed. CD112R adapted a V-set immunoglobulin fold consisting of a series of β-sheets (FIG. 1D).

Figure 1E:
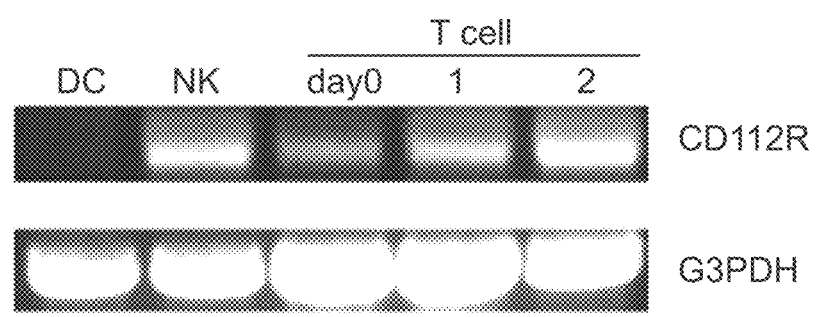
FIG. 1E is a blot showing PCR analysis of human CD112R transcript in human immune cells.
Figure 1F:
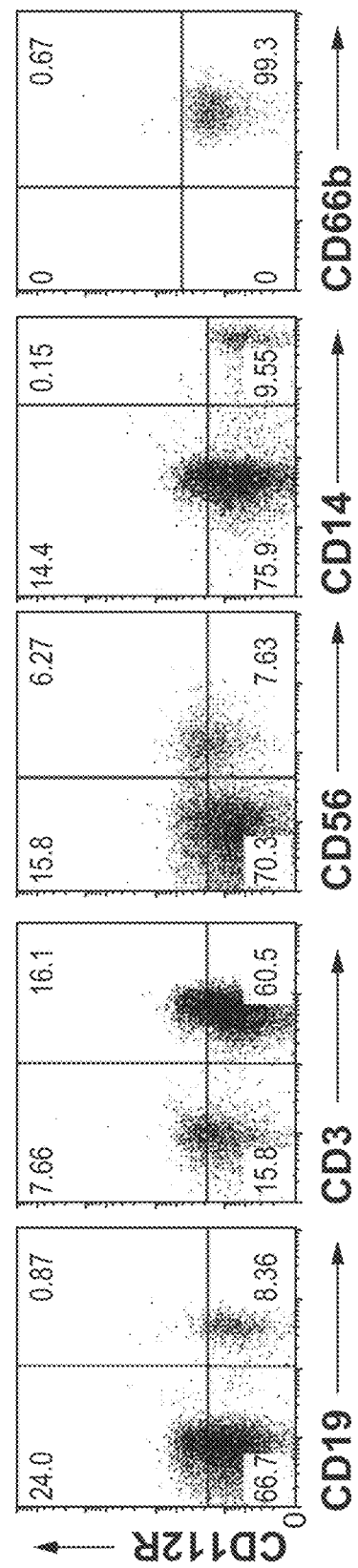
FIG. 1F depicts a graph showing FACS analysis of surface CD112R expression on naive or activated human T cells from PBMCs of healthy donors. A significant population of T (CD3+) and NK (CD56+) cells expressed low but detectable surface CD112R, although the percentage of CD112R-expressing T cells varied in different donors.
Figure 5B:
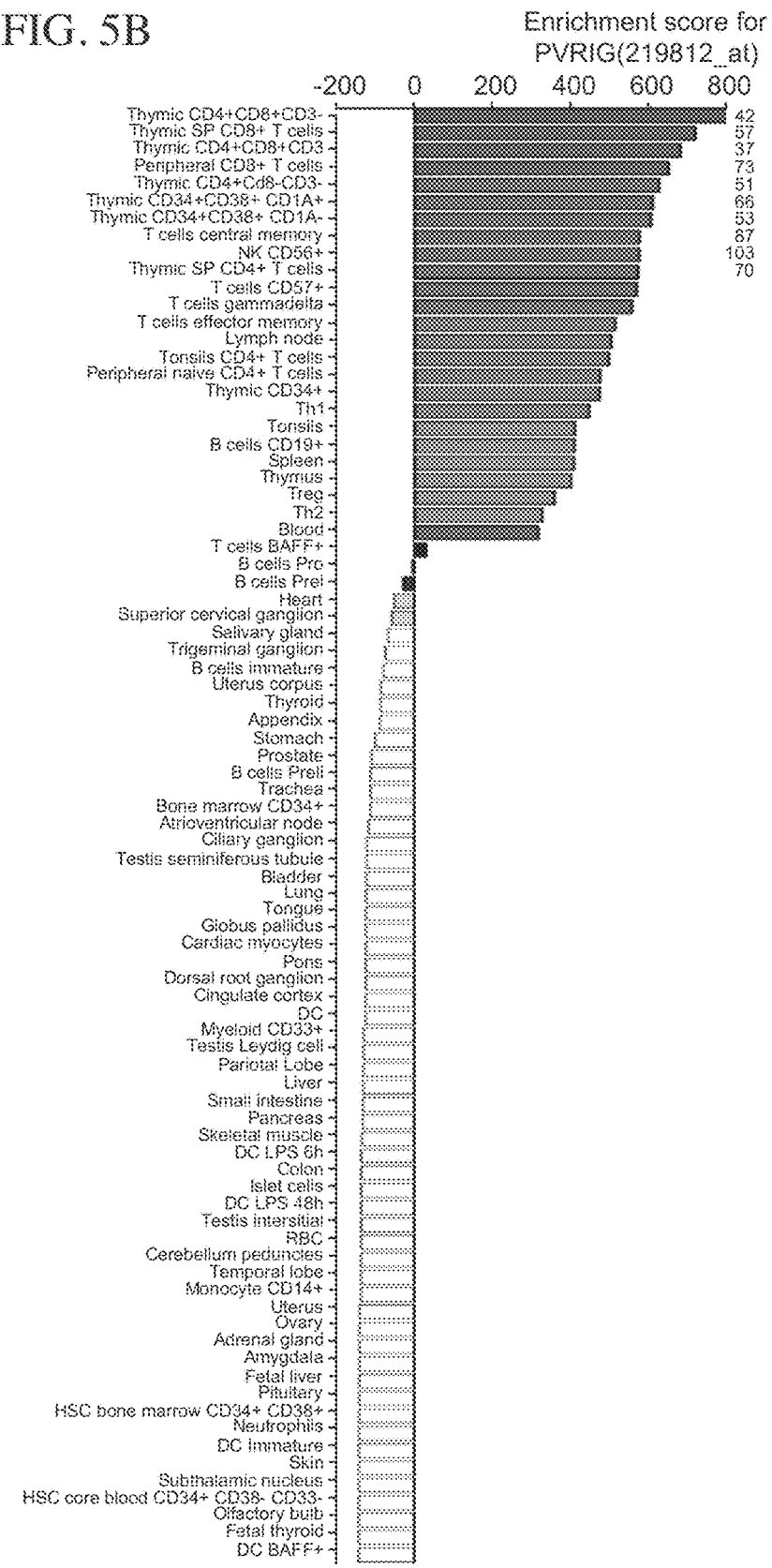
FIG. 5B is a graph showing that based on the mRNA expression data from Gene Enrichment Profile; the CD112R gene is one of the genes heavily enriched in T cell subsets and NK cells.
Figure 6A:
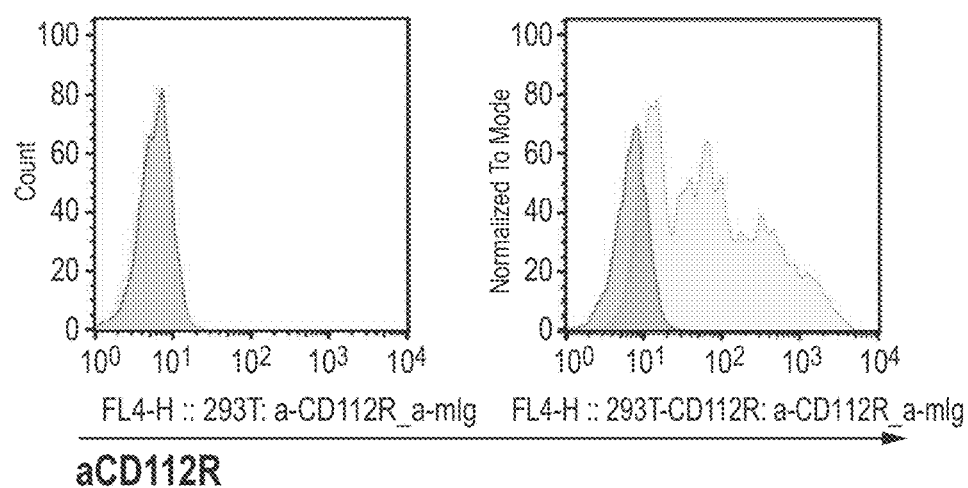
FIG. 6A depicts graphs showing the specificity of CD112R mAb by verifying its binding to CD112R transfectants by flow cytometry. HEK293T eels were transfected with control or CD112R gene and live cells were stained with control (red) or CD112R mAb (Clone 2H6) (blue) by flow cytometry.
Figure 6B:
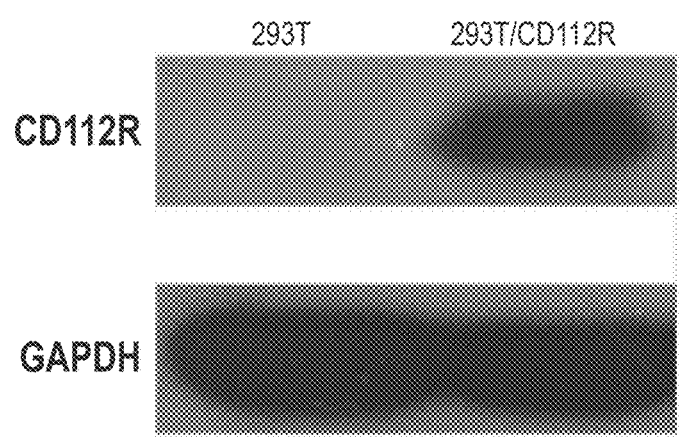
FIG. 6B depicts western blots showing CD112R by Clone 2H6 or GAPDH proteins. Cell lysates from CD112R transfectant or control HEK293T cells were used.
Figure 6C:
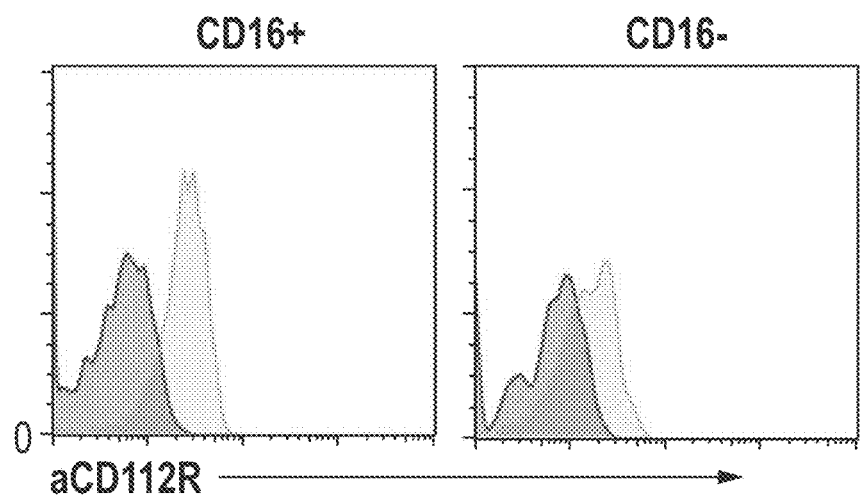
FIG. 6C depicts graphs showing CD112R expression on CD16+ and CD16− cells by flow cytometry.
Figure 12A:
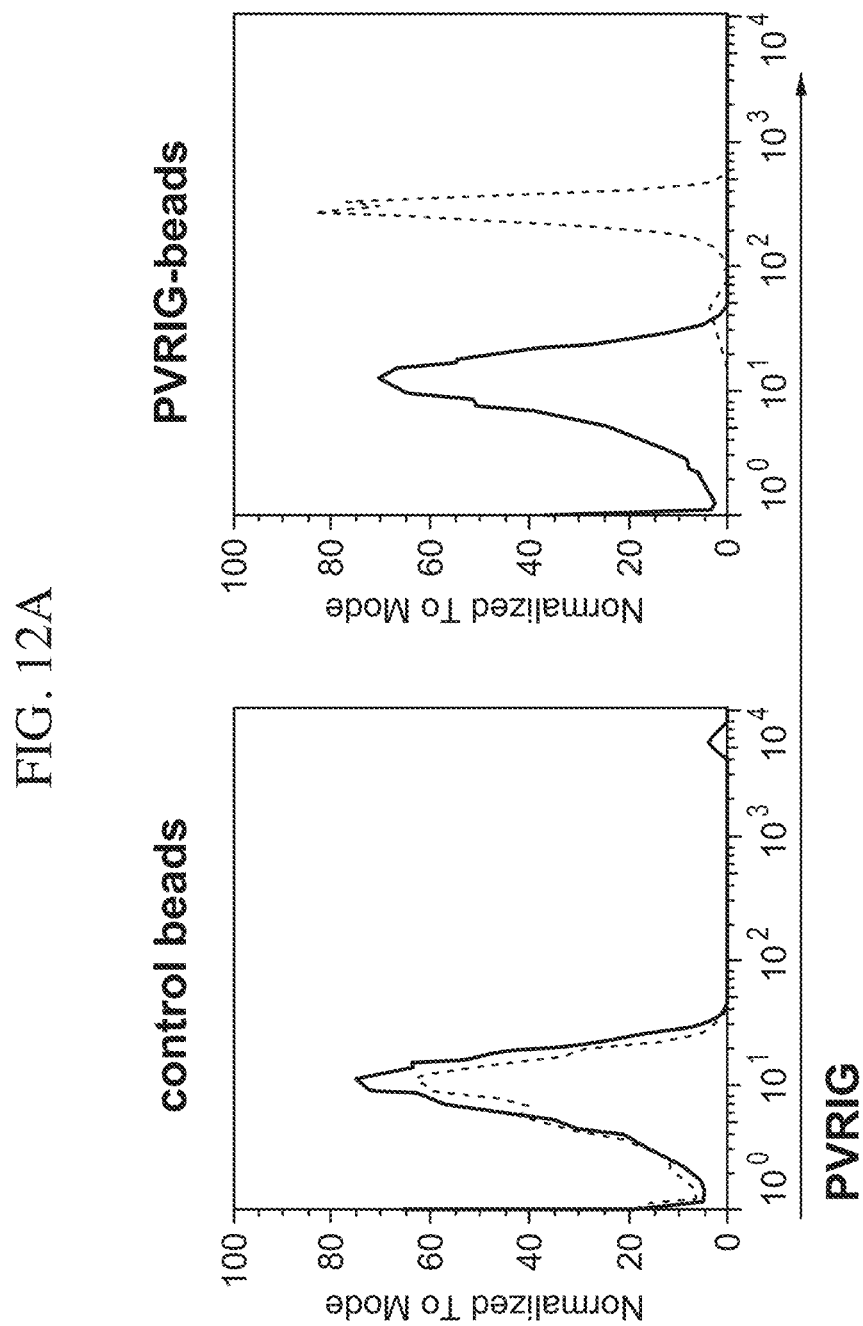
FIG. 12A shows FACS of beads coated with control or CD112R protein were stained with CD112R mAb (clone 2H6) (green line) or isotype control antibody (red line).
Figure 12B:
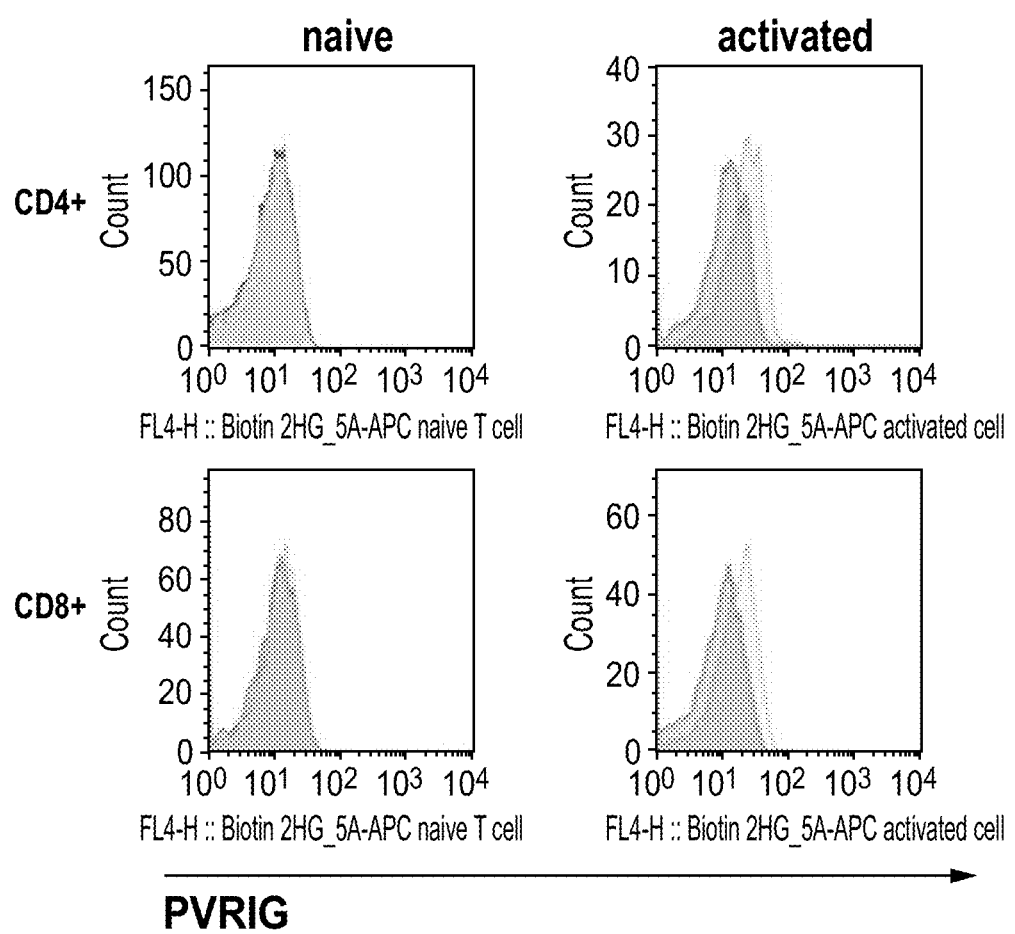
FIG. 12B shows FACS of freshly isolated and activated human T cells were stained for surface CD112R by CD112R mAb.

Using the mRNA expression data from BioGPS (www_biogps_org), CD112R gene was preferentially transcribed in lymphocytes, including T lymphocytes and NK cells (FIG. 5A). Consistently, the CD112R gene was one of the genes heavily enriched in T cell subsets, and NK cells (FIG. 5B), based on Gene Enrichment Profile. The CD112R expression in human immune cells was confirmed by reverse-transcript PCR (FIG. 1E). Human dendritic cells (DCs) derived from monocytes did not express CD112R, while both NK and T cells contained a substantial amount of CD112R transcript. The expression of CD112R was further upregulated in T cells upon activation. To further examine the expression of CD112R protein, a monoclonal antibody (mAb) (Clone 2H6) was generated against human CD112R by immunizing mice with purified CD112R-Ig recombinant protein. The specificity of CD112R mAb was verified by its binding to CD112R transfectants by flow cytometry and Western blot (FIGS. 6A and 6B). T cells freshly isolated from normal human peripheral blood mononuclear cells (PBMCs) did not express any detectable surface CD112R. Upon stimulation, CD112R was upregulated on activated T cells (FIG. 1F). Similarly, CD112R was not present on natural killer cells freshly-isolated from PBMCs of healthy donors, but it was induced in response to stimulation (FIG. 1F). CD112R transcript was also detected in human leukemia and lymphoma cell lines (FIG. 12B).

Figure 12D:
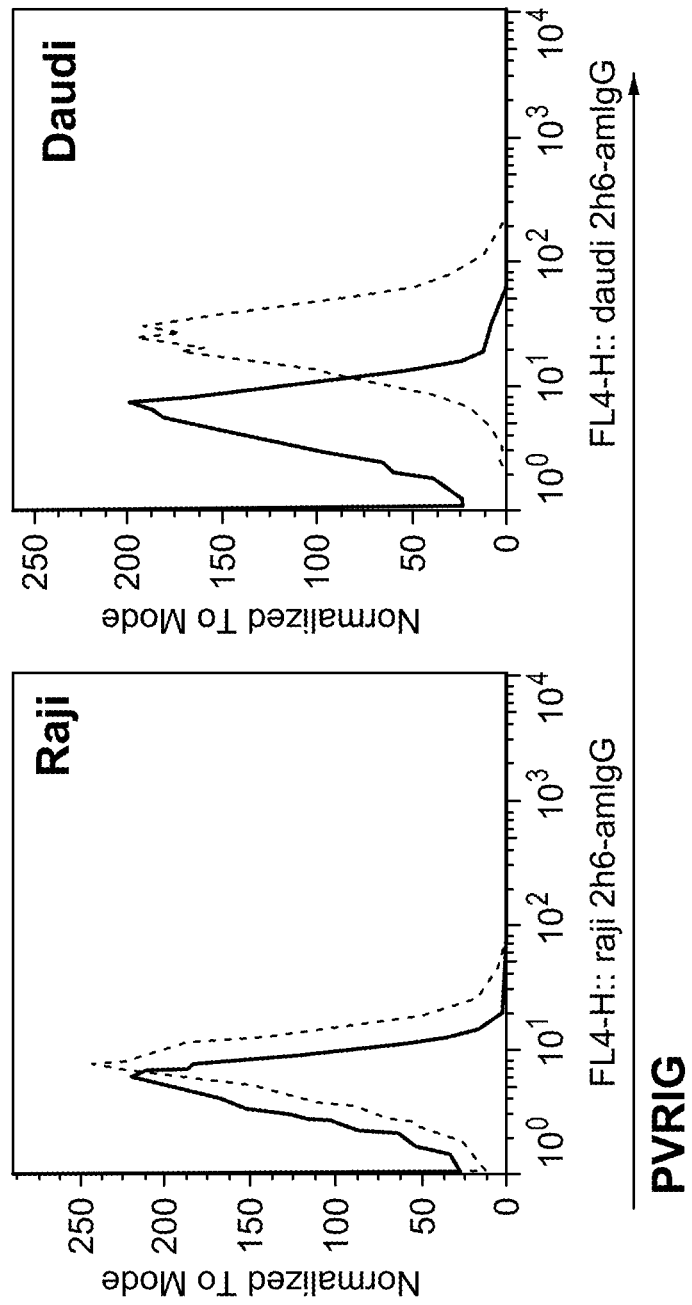
FIG. 12D shows FACS of surface CD112R expression on cell lines of NHL.
Figure 12E:
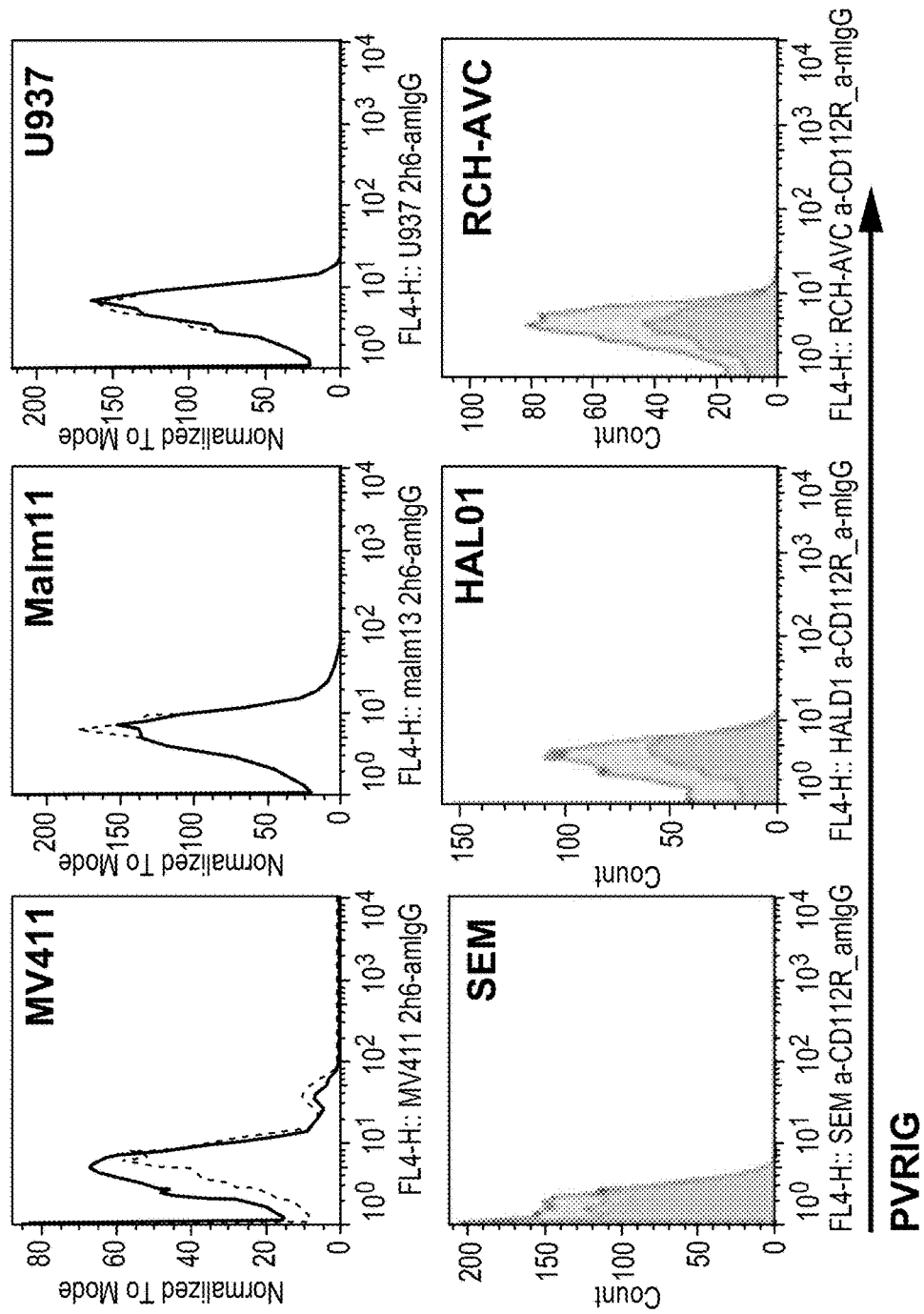
FIG. 12E shows FACS of surface CD112R expression on cell lines of lymphoma/leukemia.

CD112R gene expression in human cancer cell lines based on cell origin was examined. CD112R was found to be exclusively transcribed in cancer cells of leukemia/lymphoma origin (FIG. 12C). Further analyses of cell lines from leukemia/lymphoma origin indicate that T-ALLs and non-Hodgkin's lymphoma (NHL) cell lines predominately express abundant CD112R mRNAs (FIG. 12D). Therefore, CD112R gene is highly transcribed in human T-ALL and NHL.

Example 2: Signal Through CD112R Inhibited TCR-Mediated Signal

Plasmids and fusion proteins Human CD112R cDNA was cloned from human thymus tissue cDNAs (Clontech) by PCR. The full-length coding region was further put into a pcDNA3.1(−) expression vector by restricted enzyme digestion. Mouse CD112R cDNA was synthesized and purchased from Genscript. The extracellular domains of CD112R and other PVR-like molecules were cloned and fused into pMigV expression vectors containing the constant region of mouse IgG2a. Fusion proteins were expressed by transiently transfecting the freestyle 293-F cells using the polyethylenimine (PEI) transfection method, and fusion proteins were purified using a Protein A Sepharose column according to the manufacturer's instructions (GE Healthcare).

Antibodies

Mouse anti-human CD112R (clone 2H6) was generated from a hybridoma derived from the fusion of SP2 myeloma with B cells from a mouse immunized with human CD112R-Fc. Hybridomas were adapted and cultured in Hybridoma-SFM medium from Life Technologies. Antibodies in supernatant were purified by Hitrap protein G affinity column (GE Healthcare). Functional grade human CD112 mAb clone TX31 was purchased from Biolegend. Control hamster IgG (hamster anti-mouse TNP) and human TIGIT mAb were purchased from eBioscience. All other antibodies used in flow cytometry were purchased from BD Bioscience (San Jose, Calif.), eBioscience, RnDSystems or Biolegend.

Jurkat-Luc-NFAT Activation Assay

The mCD28/hCD28 and mCD28/hCD112R chimeras were generated by PCR and cloned into a pcDNA3.1(−) expression vector. Chimera genes were transduced into Jurkat cells stably expressing a luciferase reporter under the control of NFAT response element (Promega). Transfectants were selected with zeosin and further enriched by flow cytometry sorting. Transfected Jurkat cells were stimulated with coated human CD3 mAb (OKT3) for four hours with or without mouse CD28 mAb (clone 3751). Cells were lysed with ONE-Glo™ Luciferase Assay System (Promega) and measured for luminescent signal intensity.

T-Cell Proliferation Assay

Human PBMCs from healthy donors were purchased from the Bonfils Blood Center at Denver, Colo. OKT mAb (anti-human CD3) was precoated in the 96-well plates at the indicated concentrations. CD112-Fc or control Ig at 5 µg/mL were also immobilized in the wells. Human peripheral blood T cells were negatively selected and purified by a human pan-T-cell selection kit or naive human CD4 T-cell selection kit (Miltenyi Biotec, Auburn, Calif.). T cells were CFSE-labeled, and added into each well at $2.5-3 \times 10^5$ per well and cultured for 3 days. Cells were collected and stained with surface markers before flow cytometry analysis.

The studies indicated that CD112R and TIGIT share many similarities including protein structure and expression profile (Yu et al., 2009). Therefore CD112R was tested for its ability to provide a T cell co-receptor to regulate T cell response. Similar to TIGIT, the intracellular domain of human CD112R contains two tyrosines, one within an ITIM-like motif (Billadeau and Leibson, 2002) (FIG. 1A).

Figure 1G:
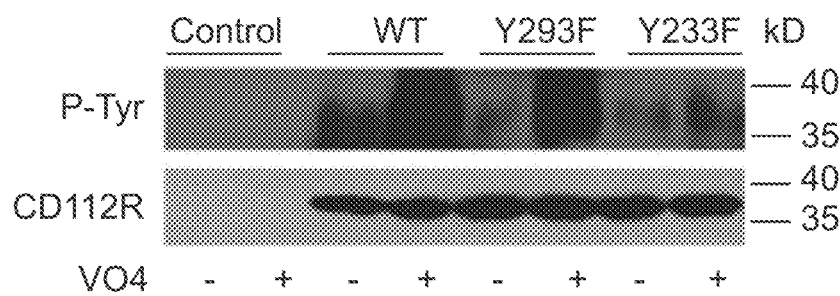
FIG. 1G depicts blots showing tyrosine phosphorylation of CD112R protein upon pervanadate treatment. HEK293T cells were transiently transfected with control or CD112R plasmid. Cells were incubated 10 minutes with or without pervanadate before analysis for tyrosine phosphorylation.

First it was examined whether these two tyrosines in the intracellular domain of CD112R can be phosphorylated to transduce a signal. HEK293T cells were transfected with CD112R gene and then treated with pervanadate. A significant amount of p-Tyr signal of the CD112R protein was observed, even without pervanadate treatment (FIG. 1G). This was interpreted by the finding of the presence of CD112R ligand on HEK293T cells (FIG. 3A), which may have triggered the tyrosine phosphorylation of CD112R protein. Pervanadate treatment further increased tyrosine phosphorylation of the CD112R protein (FIG. 1G), indicating that tyrosines in the CD112R intracellular domain were capable of being phosphorylated and therefore were able to mediate signal transduction.

Figure 1H:
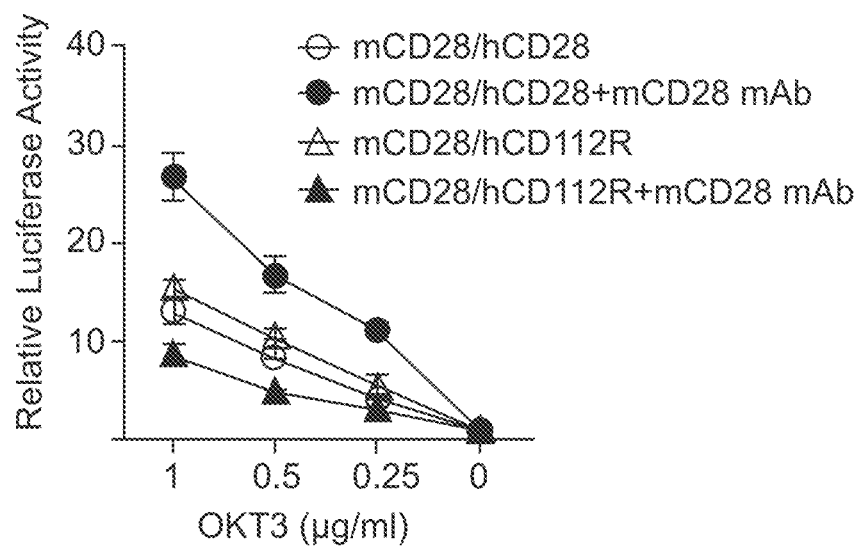
FIG. 1H depicts a graph showing the effect of chimera receptor stimulation on NFAT activity in a luciferase assay. Jurkat-NFAT-Luc cells transfected with different chimeras were stimulated with OKT3, in the presence or absence of a mouse CD28 agonistic mAb.
Figure 7:
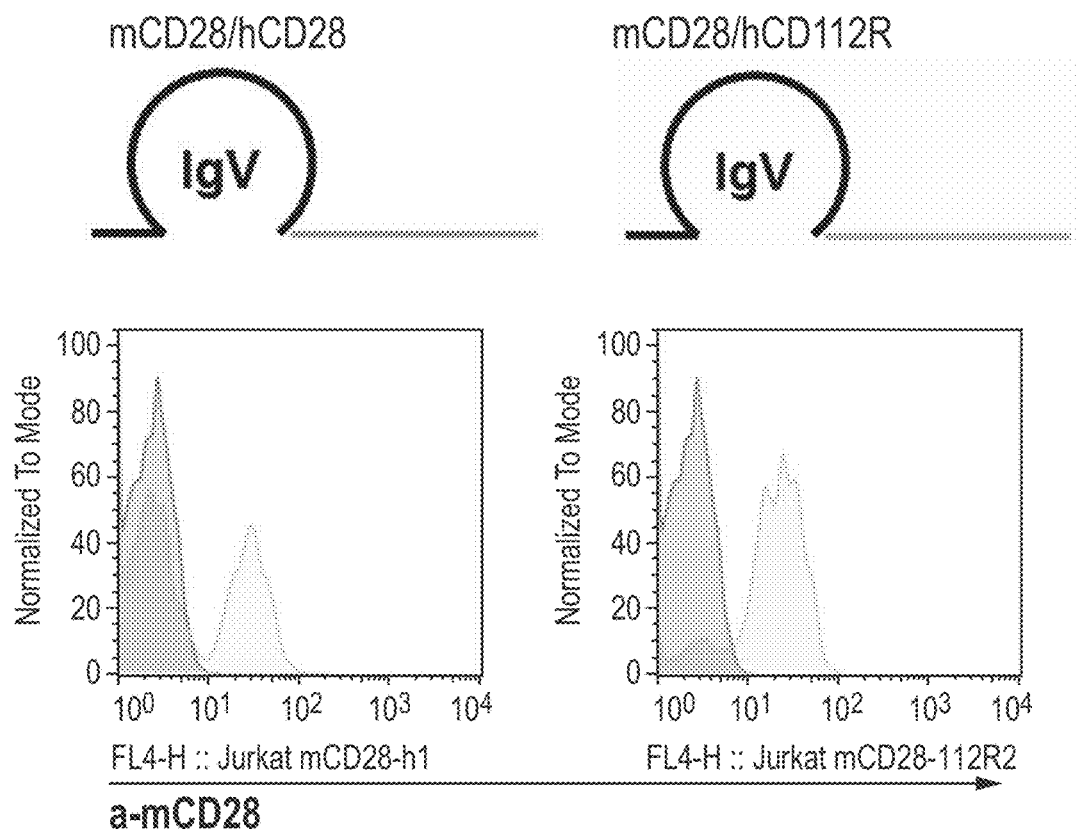
FIG. 7 depicts graphs showing transducing Jurkat-Luc-NFAT cells with mouse CD28 chimera genes. Jurkat-Luc-NFAT cells were transfected with mCD28/hCD28 or mCD28/hCD112R chimera genes. Cells were selected with zeocin, and stained with mouse CD28 mAb. Cells were further enriched by flow cytometry sorting for mouse CD28+ cells.

Secondly, regulation of T cell receptor (TCR)-mediated signals via CD112R was investigated. The nuclear factor of activated T cells (NFAT) pathway was examined, which was strongly induced upon T cell activation and regulated by costimulatory signals (Chen and Flies, 2013; Smith-Garvin et al., 2009). A Jurkat cell line (Jurkat-NFAT-Luc) stably transfected with a luciferase reporter under the control of the NFAT response element (Huang et al., 2008) was established. By taking advantage of the well-known characteristics of an agonistic mouse CD28 mAb (Clone 37.51) (Gross et al., 1992), two chimeric molecules were constructed: the mCD28/hCD28 chimera composed of the extracellular domain of mouse CD28, the transmembrane and intracellular domains of human CD28; and the mCD28/hCD112R chimera which contained mouse CD28 extracellular domain, the transmembrane and intracellular domains of human CD112R (FIG. 7). Jurkat-NFAT-Luc cells were transfected with these two chimeric molecules. Jurkat cells stably expressing surface mouse CD28 were next selected by flow cytometry sorting. These cell lines were stimulated with human CD3 mAb (OKT3) together with control antibody or mouse CD28 agonistic mAb. The addition of the mouse CD28 mAb cross-linked the chimera resulting in the amplification of the intracellular signal. The addition of mCD28 mAb to mCD28/hCD28 transfectant amplified human CD28 signal and increased NFAT activity upon TCR stimulation. However, inclusion of mCD28 mAb in mCD28/hCD112R-expressing cells significantly inhibited the luciferase activation, indicating that signaling through CD112R inhibits TCR-mediated NFAT activation (FIG. 1H). Thus, the results indicated that CD112R could be a new coinhibitory receptor that suppressed TCR signal.

Figure 2A:
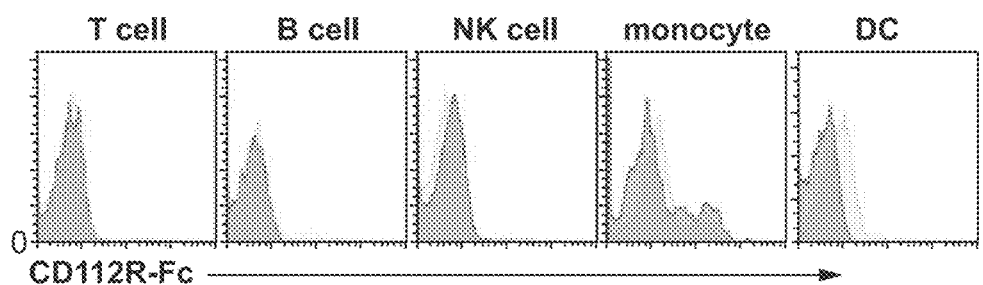
FIG. 2A depicts a graph showing human immune cells in PBMCs were stained for CD112R protein binding.
Figure 2B:
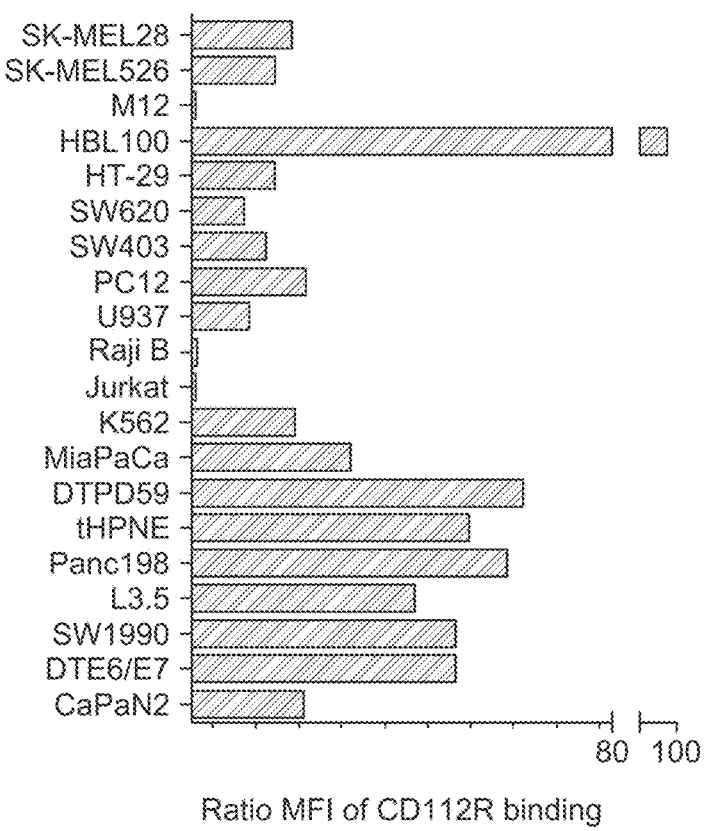
FIG. 2B depicts a bar graph showing cultured human tumor cell lines were stained for CD112R protein binding. Data shown is the median fluorescence intensity (MFI) ratio of CD112R binding to control protein binding.

Example 3: The Majority of Human Cancer Cell Lines Expressed a Putative Ligand for CD112R To identify the interacting partner for CD112R, a potential ligand on human cells was searched. Human peripheral blood mononuclear cells (PBMCs) were stained with CD112R fusion protein for binding by flow cytometry. CD112R protein did not interact with T, B, or natural killer (NK) cells. However, it showed slight binding with human monocytes, indicating the presence of a putative ligand for CD112R on human monocytes (FIG. 2A). This interaction became more obvious when human monocyte-derived dendritic cells were stained by CD112R protein (FIG. 2A). Human tumor cell lines were also stained with CD112R fusion protein for possible CD112R ligand. Interestingly, virtually all adherent tumor cell lines had a strong binding signal to CD112R protein, indicating a possible ligand on cancer cells for CD112R (FIG. 2B). In contrast, most tumors of hematopoietic origin did not interact with CD112R. The data implied that the putative ligand for CD112R on tumor cells could be a surface molecule mediating cellular adhesion.

Figure 2C:
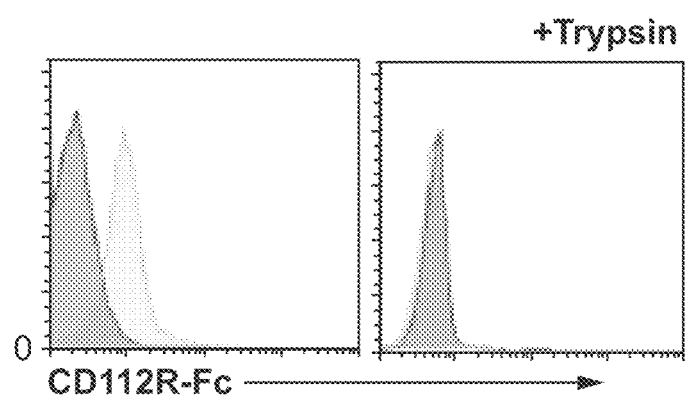
FIG. 2C depicts a graph showing tumor cell lines with or without trypsin treatment (10 minutes) were stained for CD112R protein binding.
Figure 2D:
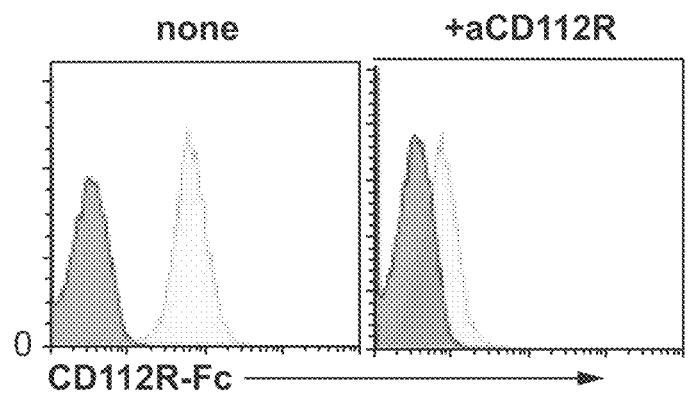
FIG. 2D depicts a graph showing blockade of CD112R binding by a CD112R mAb. HEK293T cells were stained for CD112R binding, with or without the presence of a CD112R mAb (clone 2H6).

This potential ligand was sensitive to trypsin cleavage, as when cancer cells were treated with trypsin for a long period of time (>10 minutes), the tumor cells completely lost the CD112R-binding capacity (FIG. 2C). CD112R protein bound to untransfected HEK293T cells, and inclusion of a CD112R mAb (clone 2H6) eliminated this interaction, further confirming the specificity of this interaction with CD112R protein (FIG. 2D). These results indicated that the presence of a putative surface ligand for CD112R was on the majority of tumor cells and DCs.

Example 4: CD112 is the Ligand for CD112R

Biacore Assay

All bio sensor experiments were run on a Biacore 3000 instrument (GE Healthcare, Piscataway, N.J., USA). PBS with 0.005% P20 buffer (Gibco) was used as the running buffer for both the immobilization and kinetics experiments. Amine-coupling chemistry was used to immobilize protein FLAG, CD112 and CD155 to a CM5 sensor chip surface at 2SOC. Kinetic experiments were carried out for three different ligands using three different concentration series: 4, 12, 36, 111, 333 nM of CD112R; 9000, 3000, 1000, 333, 111 nM TGIT; 9000, 3000, 1000, 333, 111 nM PVR L3. All samples were diluted in PBS buffer and were injected for 3 minutes across the surface at a flowrate of 20 flL/min and the dissociation of analyte from the surface-bound ligands was monitored for 5 minutes. All analyte concentrations were performed in duplicate and an unmodified reference flow cell was used to correct for instrument drift and/or noise. Buffer blanks were used to double-reference the obtained kinetic data. Raw sensogram data was processed and fit using the Scrubber software package (Version 2.0b, Bio-Logic Software, Campbell, Australia; http_www_biologic_com_au).

Figure 3A:
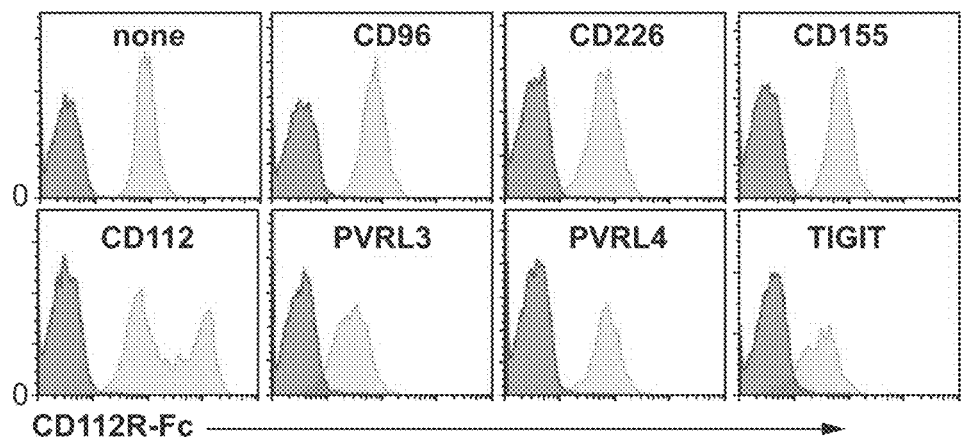
FIG. 3A depicts a graph showing that HEK293T cells were transiently transfected with different PVR-like genes as indicated, and stained for CD112R fusion protein binding.
Figure 3B:
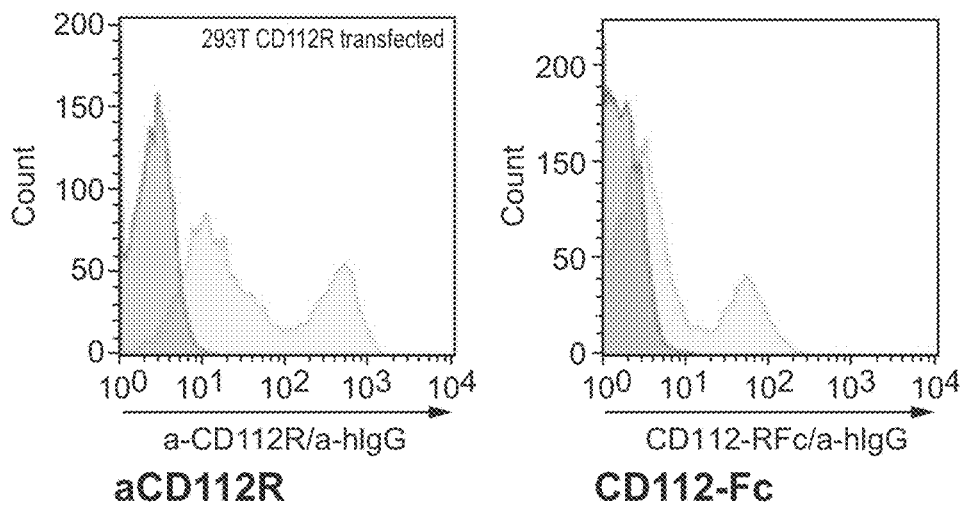
FIG. 3B depicts a graph showing that HEK293T cells were transfected with CD112R (blue) or control plasmid (red), and were stained with CD112R mAb (left) or CD112-Fc fusion protein (right).

The presence of a putative ligand for CD112R on cancer cells and its regulatory function on T cells led to the identification of this specific ligand. Immunoprecipitation assays were performed with CD112R fusion protein of cell lysate from HBL100, which strongly bound to CD112R protein by flow cytometry (FIG. 2B). Mass spectrometry of the sample had no success. Meanwhile, a few candidate genes for a possible CD112R ligand were tested. Because CD112R is an immunoglobulin-containing protein, it was predicted that the binding partner for CD112R should also be a member of immunoglobulin superfamily (IGSF). Several groups of IGSF genes were tested with known T cell modulatory functions, including the B7 family, butyrophilin-like molecules, T-cell immunoglobulin mucin (TIM) family and PVR-like molecules (Zhu et al., 2011). Genes were individually transfected on HEK293T cells, and stained for CD112R protein binding by flow cytometry. CD112R bound to untransfected HEK293T cells, indicating a putative ligand for CD112R on those cells. No member from the B7, butyrophilin-like, or TIM family bound to CD112R protein was identified. However, when PVR members were individually transduced on HEK293T cells an even stronger binding peak was detected when CD112 (also called as PVRL2, nectin2) was transfected onto HEK293T cells (FIG. 3A). This indicated that CD112 could be a binding partner for CD112R. This interaction was further verified through the production of an CD112-Ig fusion protein to stain CD112R-expressing cells. As CD112R was transduced on HEK293T cells, the surface expression of CD112R was verified by CD112R mAb staining (FIG. 3B left). CD112 fusion protein bound to CD112R transfectant but not control HEK293T cells (FIG. 3B).

Binding Affinities for the Interaction of CD112R with CD112

Figure 3C:
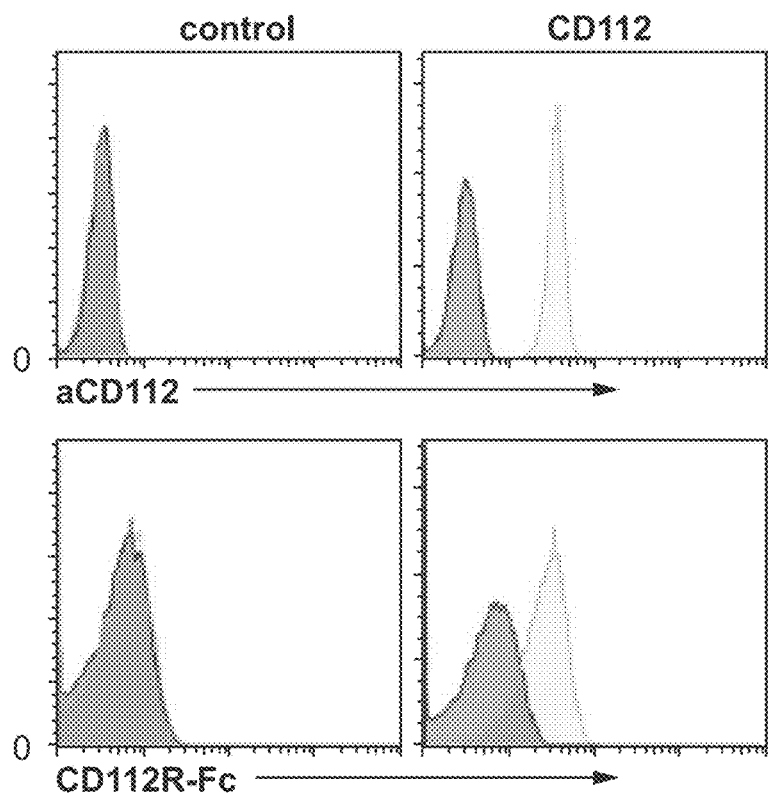
FIG. 3C depicts a graph showing that beads coated with CD112 (right) or control protein (left) were stained with CD112 mAb (blue) or isotype control (red) to confirm the presence of CD112 on beads. Beads were also incubated with CD112R fusion protein (blue) or control (red) for direct interaction.
Figure 3D:
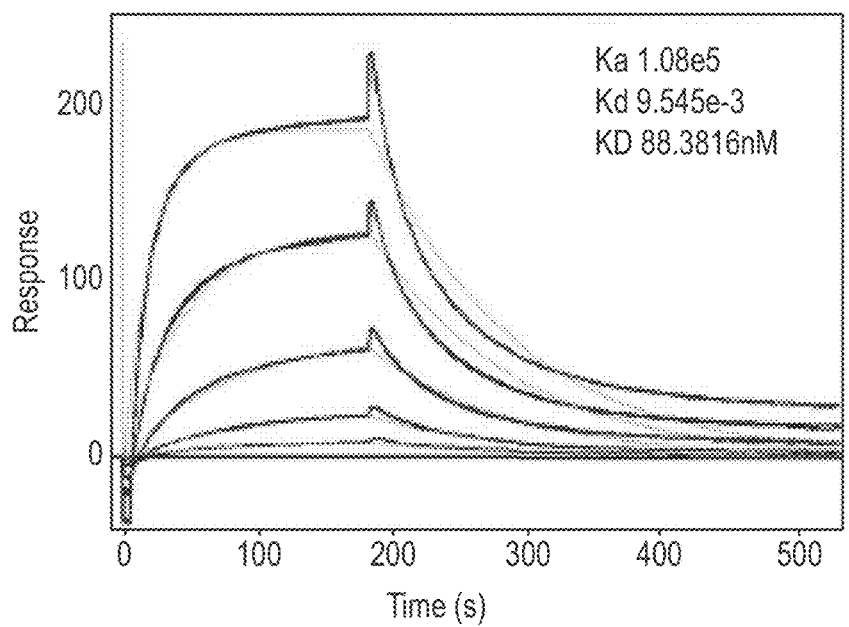
FIG. 3D depicts a graph showing BIAcore3000 analysis of CD112R binding to CD112. A series of concentrations of CD112R protein was used to measure the binding kinetics with immobilized CD112.

To determine the direct interaction of CD112R with interacts with CD112, beads were coated with CD112 or control protein. The presence of CD112 protein on coated beads was confirmed by CD112 mAb staining. CD112R protein bound to CD112 coated beads but not control beads, indicating that CD112R directly interacted with CD112 (FIG. 3C). Biacore measurement of this interaction revealed that the $K_D$ of the CD112-CD112R interaction was 0.088 fIM (FIG. 3D), which was higher than the interaction between CD112 and CD226 ($K_D$=8.97 μM or $K_D$=0.31 μM) with similar measurement method (Liu et al., 2012; Tahara-Hanaoka et al., 2004). The interaction between TIGIT and CD112 was too weak to determine the affinity by the Biacore experiment. Therefore, the results indicated that CD112R was a new receptor for CD112 with higher affinity than CD226.

Figure 3E:
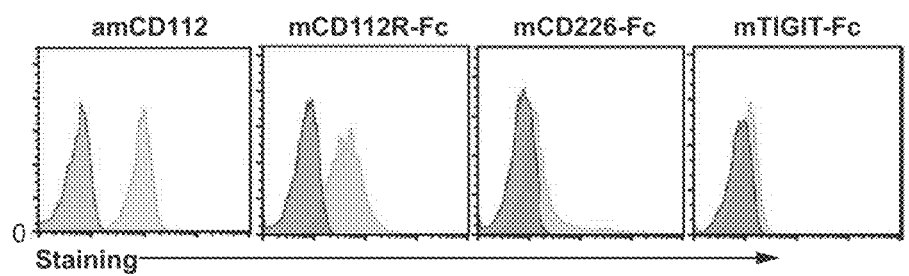
FIG. 3E depicts graphs showing that the CD112R/CD112 interaction was conserved in mice. RMA-S/mCD112 cells (blue), a mouse lymphoma cell line stably expressing mCD112, or control RMA-S cells (red) were stained with mouse CD112R-Fc, mouse CD226-Fc or mouse TIGIT-Fc respectively.

CD112R/CD112 interaction was conserved in mice The CD112R/CD112 interaction was also conserved in mice. RMA-S, a mouse lymphoma cell line, does not express CD112, and this cell line was transduced with mouse CD112 gene to generate a stable cell line expressing surface mouse CD112 (RMA-S/mCD112) (FIG. 3E, left). These cells were stained with several mouse PVR-like receptor fusion proteins for binding. As shown in FIG. 3E, mouse CD112R fusion protein bound strongly to RMA-S/mCD112 cells, but not mock RMA-S transfectant. Mouse CD226 fusion protein weakly interacted with RMA-S/mCD112 transfectant, while the interaction of TIGIT protein to RMA-S/mCD112 cells was negligible (FIG. 3E). Taken together, the studies indicate that CD112R is the receptor for CD112 with the highest affinity both in human and mouse.

Figure 3F:
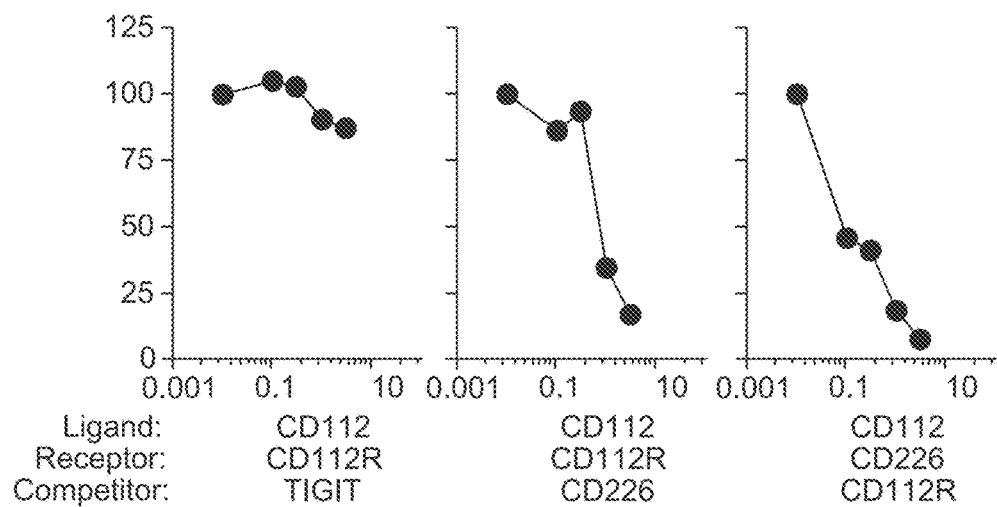
FIG. 3F depicts graphs showing the competitive binding assay for CD112 among CD112R, CD226, and TIGIT. Coated CD112 was stained by CD112R protein in the presence of different concentration of TIGIT or CD226 protein; on the other hand, coated CD112 were stained by CD226 protein, in the presence of different concentration of CD112R protein.
Figure 8:
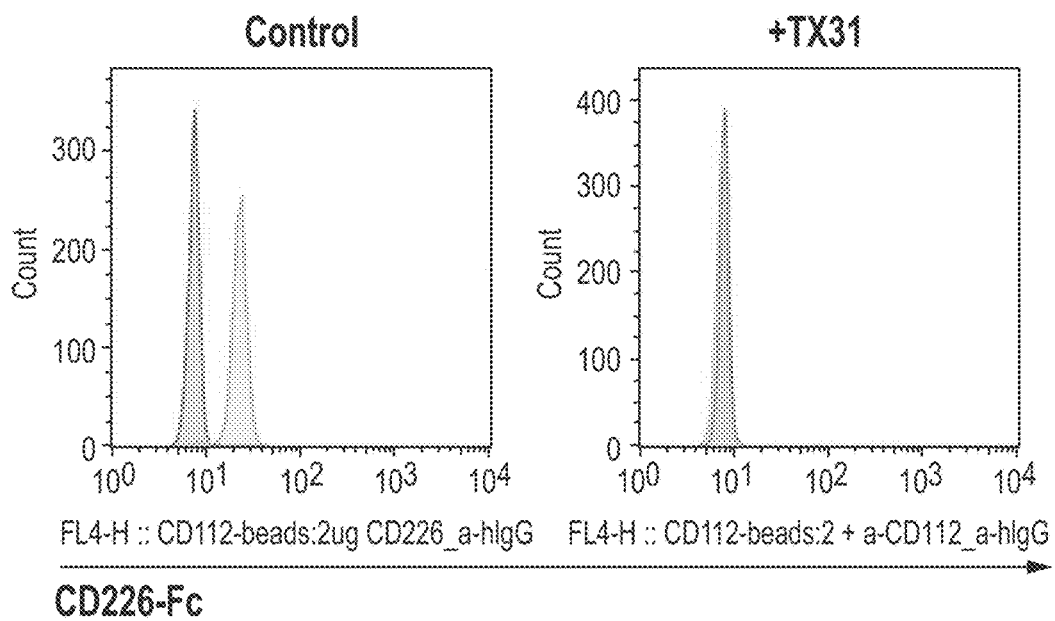
FIG. 8 depicts graphs showing that a CD112 mAb, clone TX31, blocks the CD112/CD226 interaction. CD112-coated beads were pre-incubated with control Ig (left) or CD112 mAb (right), and then were stained with CD226-Fc for binding.

Example 5: Competitive Analysis Between CD112R and Other PVR Member Interactions CD112 is known to interact with both CD226 and TIGIT, though the latter interaction is relatively weak (Bottino et al., 2003; Stanietsky et al., 2009; Yu et al., 2009). It was investigated whether these two counter receptors compete with CD112R for CD112 interaction. CD112 protein was coated on beads, and stained with CD112R protein in the presence of different concentration of TIGIT or CD226 protein. Inclusion of TIGIT had little effect on disrupting this interaction, while CD226 was a good inhibitor of the CD112-CD112R binding (FIG. 3F). This result was consistent with the relatively higher affinity between the CD112-CD226 pair than the CD112-TIGIT interaction (Martinet and Smyth, 2015; Yu et al., 2009). Conversely, when CD112R was used as a competitor, the CD112-CD226 interaction was significantly inhibited even in a relatively low concentration. Because of the weak interaction between CD112 and TIGIT, as well as limited coated CD112 protein on beads, binding between these two molecules by flow cytometry was not observed. Thus the competition studies indicated that CD112R and CD226 share a common binding site on CD112. This conclusion was further supported by the studies that a CD112 mAb, clone TX31, blocked the binding of CD112 to both CD112R and CD226 (FIG. 4B and FIG. 8).

Example 6: CD112 Mediated the CD112R-Binding to DCs and Tumor Cells

Figure 4A:
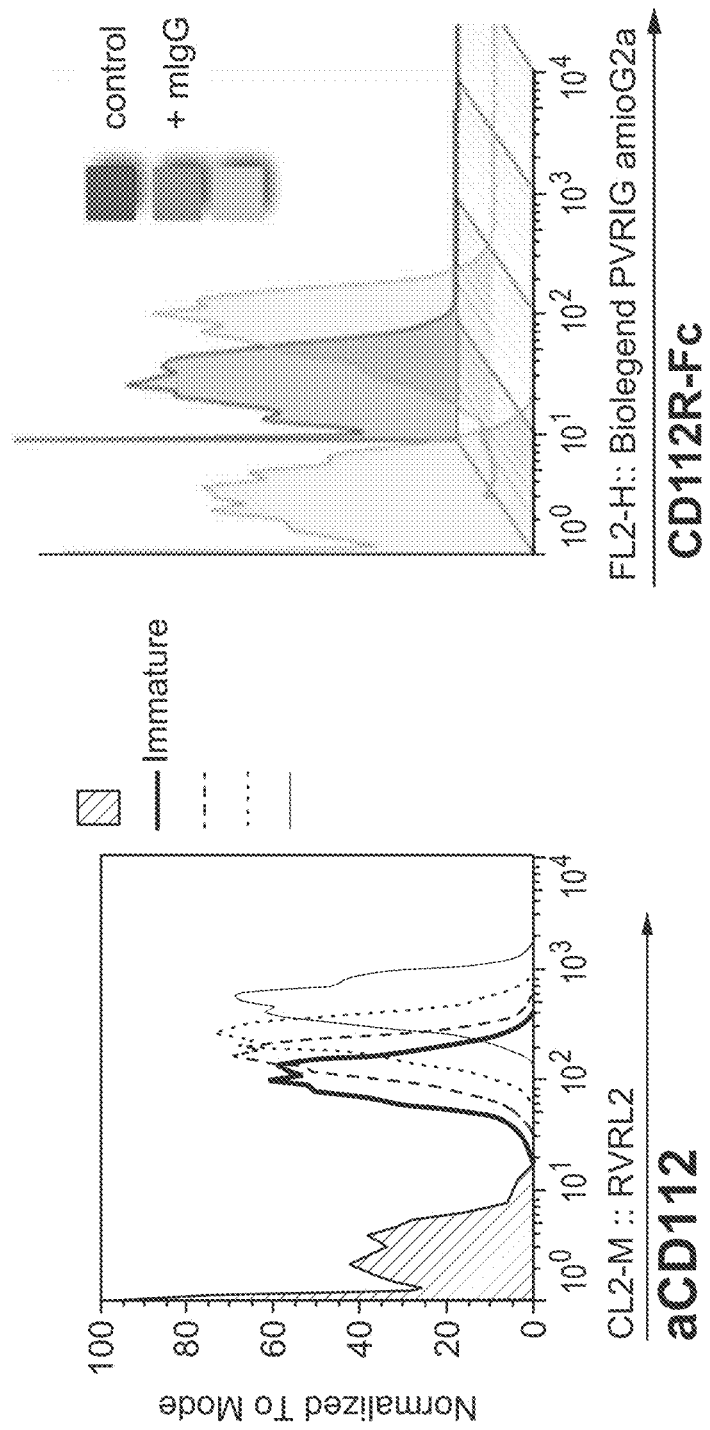
FIG. 4A depicts graphs showing that human monocyte-derived DCs were stimulated with TLR agonists overnight, and were stained for CD112 expression (left). They were preincubated with control or CD112 mAb (clone TX31) before stained for CD112R fusion protein binding (right).
Figure 9:
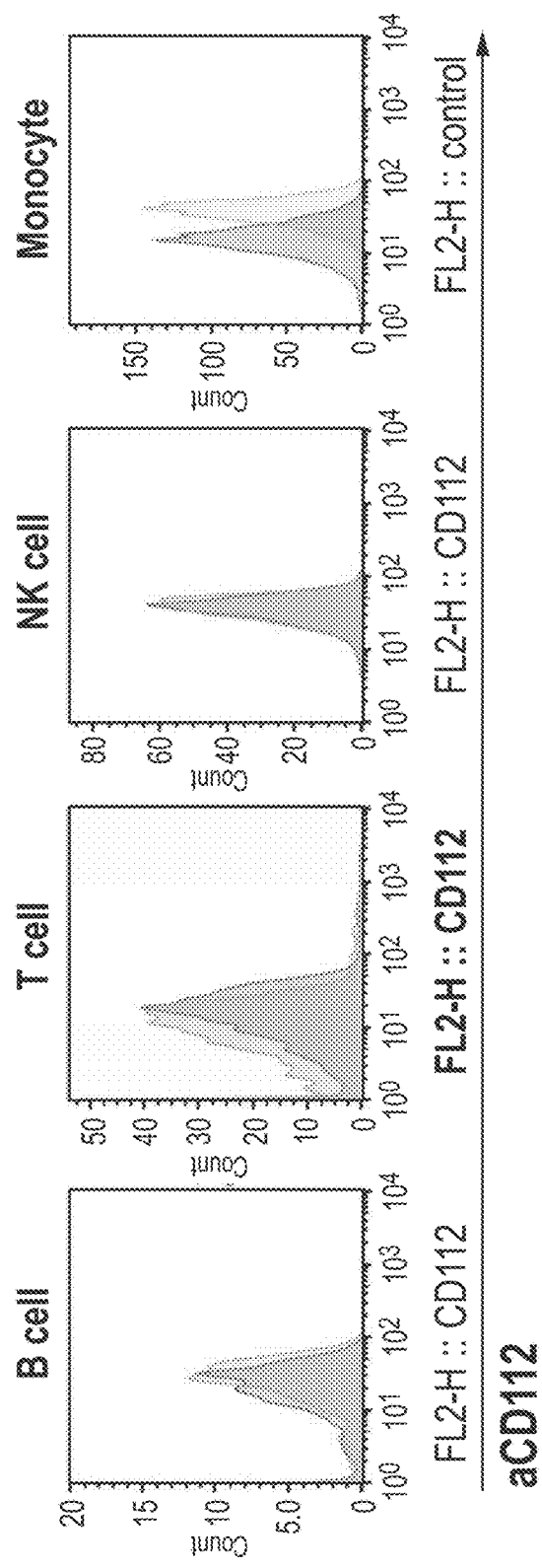
FIG. 9 depicts graphs showing that human T, B or NK cells did not express any detectable CD112 protein, while monocytes expressed a significant level of surface CD112. Cell subsets were identified from human PBMCs by surface markers, and CD112 expression on individual subset was revealed by flow cytometry.

Studies established CD112 as a ligand for CD112R. Because initial studies revealed that CD112R protein bound many cell types, including DCs and human cancer cells, it was further investigated whether CD112 was the surface molecule responsible for the CD112R interaction. Human T, B or NK cells did not express any detectable CD112 protein, while monocytes expressed a significant level of surface CD112 (FIG. 9). This is consistent with previous result showing that CD112R did not bind to these cells (FIG. 2A). Human monocyte-derived DCs expressed high level of CD112, and this expression was further upregulated by TLR agonists. The CD112R interaction with DCs was completely blocked when DCs were pre-incubated with a CD112 blocking mAb (Clone TX31), implying that CD112 on DC mediated the CD112R interaction (FIG. 4A). The majority of adherent tumor cells constitutively expressed high level of CD112, while most of tumor cells with hematopoietic origin were CD112-negative (Table 3). Therefore, the expression profile of CD112 on tumor cells was consistent with that of CD112R protein binding to tumor cells.

TABLE 3

CD112 expression on tumor cells correlates with CD112R binding

| Cell line | CD112 expression | CD112 binding | Cell line | CD112 expression | CD112 binding |
|---|---|---|---|---|---|
| SK-MEL-28 | ++ | +++ | HT29 | ++ | ++ |
| SK-MEL-526 | ++ | ++ | SW620 | ++ | ++ |
| MIA PaCa | + | + | HBL100 | +++ | +++ |
| DTPD59 | ++ | ++ | HEK293T | ++ | ++ |
| tHPNE | +++ | +++ | M12 | — | — |
| Panc 198 | ++ | ++ | Jurkat | +/− | — |
| CaPaN2 | ++ | ++ | Raji B | — | — |
| SW1990 | ++ | ++ | | | |

Tumor cells were pre-incubated with CD112 blocking mAb and stained with CD112R to confirm that CD112 was the ligand that mediated the interaction. As a representative result shown in FIG. 4B, inclusion of a CD112 mAb completely eliminated the CD112R binding to PANC198, a human pancreatic cancer cell line. In all the tumor cell lines tested, pre-incubating tumor cells with the CD112 blocking mAb completely prevented CD112R fusion protein from binding.

Figure 10:
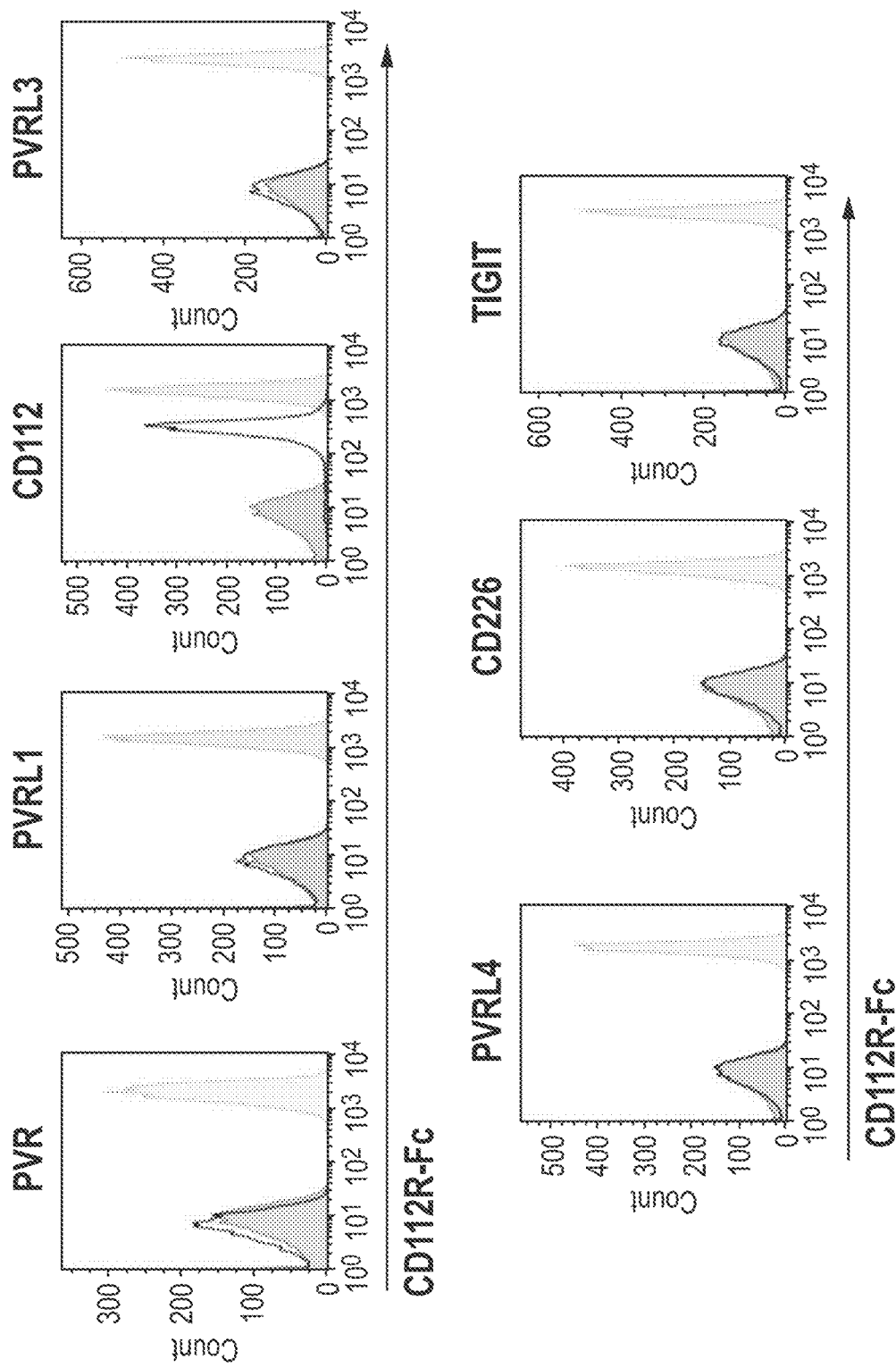
FIG. 10 depicts graphs showing that no known PVR-like protein except CD112 interacts with CD112R protein. Beads coated with individual PVR-like fusion proteins (Fc fragment of mouse IgG2a) were stained with control (red) or CD112R fusion protein (human IgG1 Fc) (open black) for binding. The presence of coated protein was confirmed by staining antibodies specific for mouse IgG2a Fc fragment (blue).
Figure 11A:
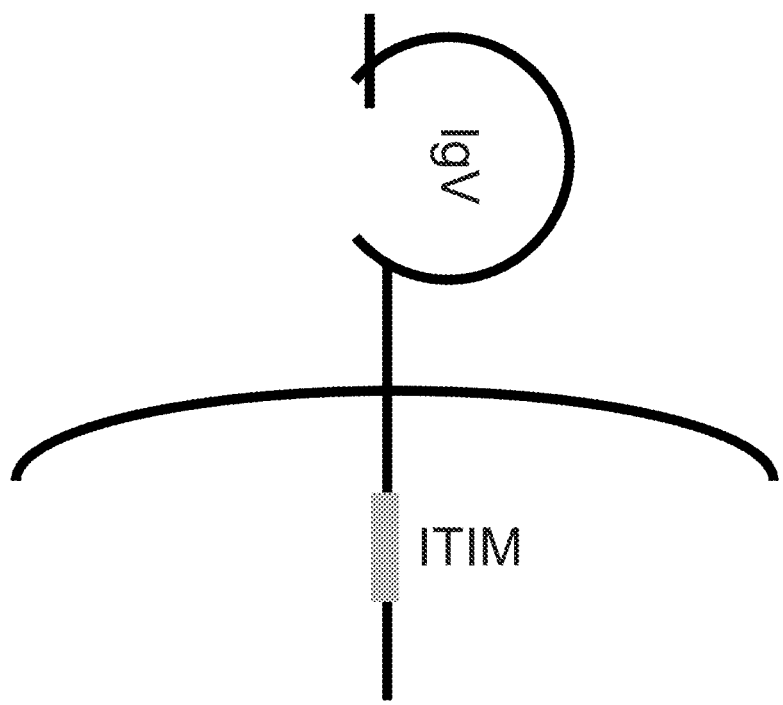
FIG. 11A shows a diagram of the predicted protein structure of human CD112R based on amino acid sequence.
Figure 11B:
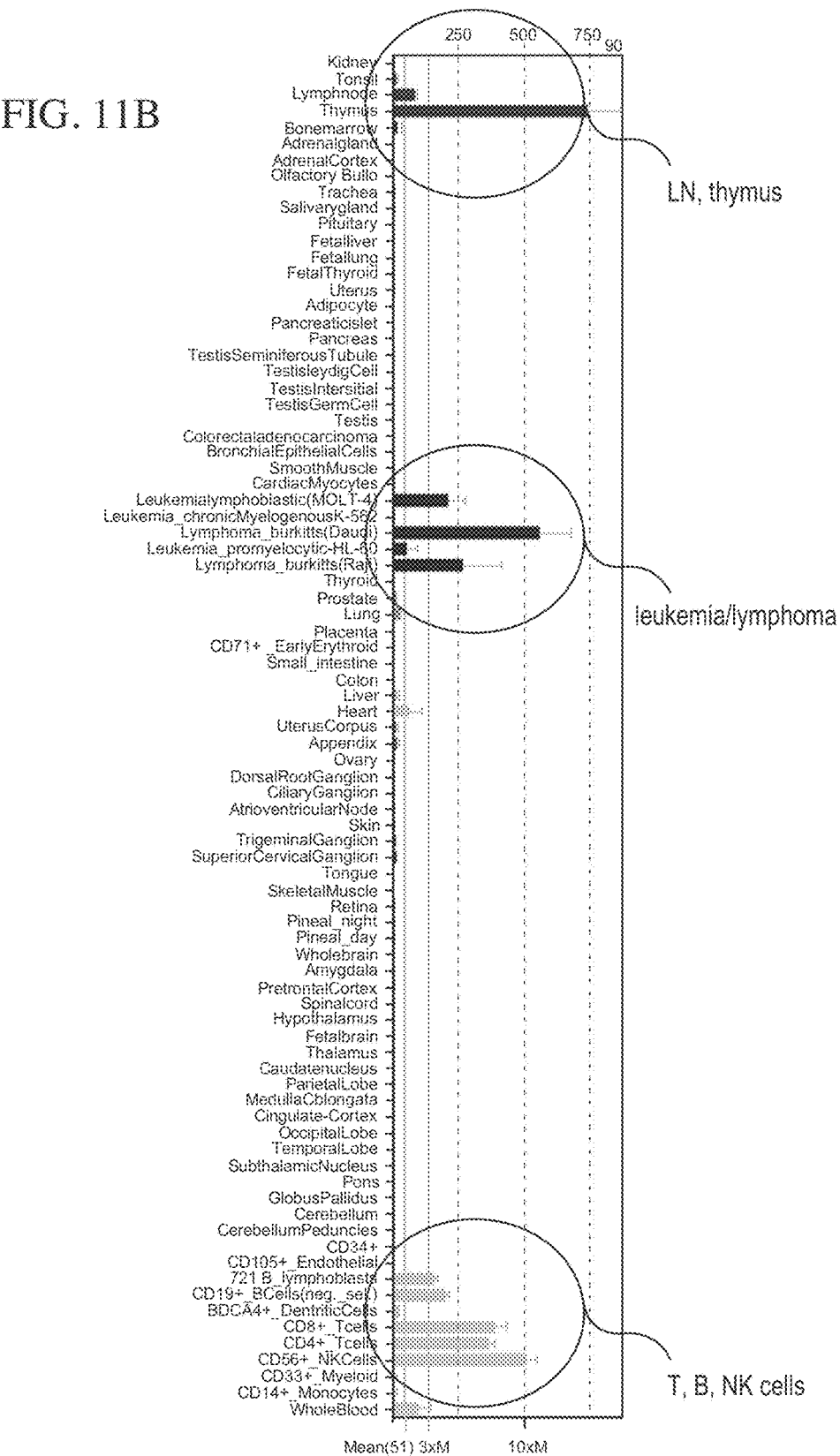
FIG. 11B is a bar graph representing CD112R expression profile of CD112R gene in different cell types and tissues.
Figure 11C:
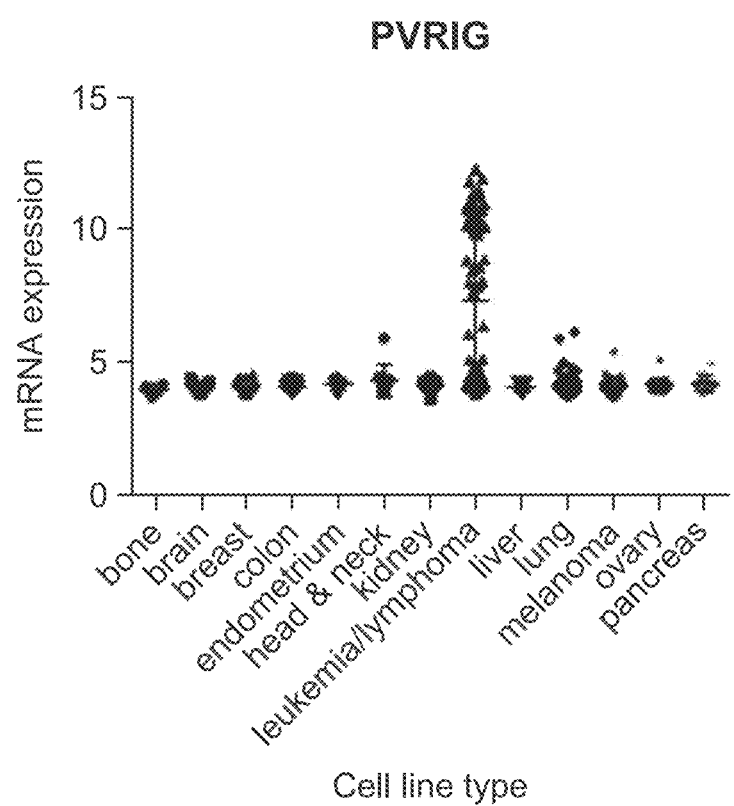
FIG. 11C shows scatter graph representing CD112R transcripts in tumor cell lines of different tissue origin.
Figure 11D:
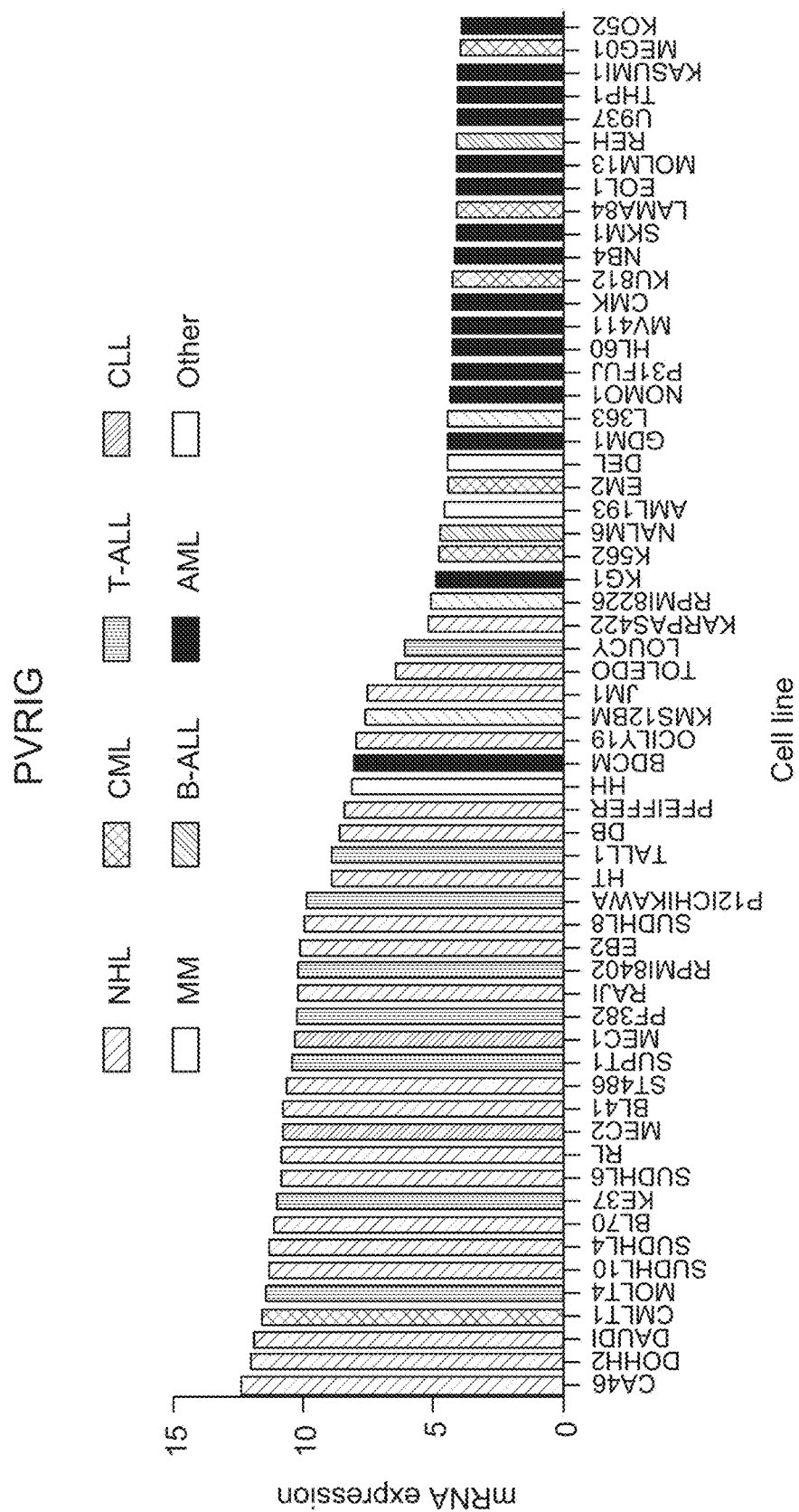
FIG. 11D is a line graph representing CD112R transcripts in different subtypes of lymphoma/leukemia cell lines.

Finally, PVR-like proteins are known to mediate hetero-interactions among members (Martinet and Smyth, 2015; Takai et al., 2008). The presence of high-affinity ligand CD112 on the majority of cell types could have hidden any possible weak binding between CD112R with other PVR members. Coated beads with individual PVR-like proteins and stained for CD112R protein binding were prepared. As shown in FIG. 10, no PVR-like protein except CD112 could interact with CD112R protein. Taken together, the studies indicate that CD112 is the main ligand, which mediates the interaction of CD112R to DCs and tumor cells.

Example 7: CD112 Interacts with CD112R to Suppress T Cell Response

Tetanus Toxoid (TT)-Specific Human T-Cell Response

For in vitro TT stimulation, autologous dendritic cells were co-cultured with CFSE-labeled purified human T cells at different ratios in the presence of 50 ng/mL TT (List Biological Laboratories) for 10-14 days. Antibodies or fusion proteins were added from the beginning of culture. Cell division of human CD4+ T cells was examined by fluorescence-activated cell sorting for CFSE dilution, as described (Zhu et al., 2013)

Figure 4C:
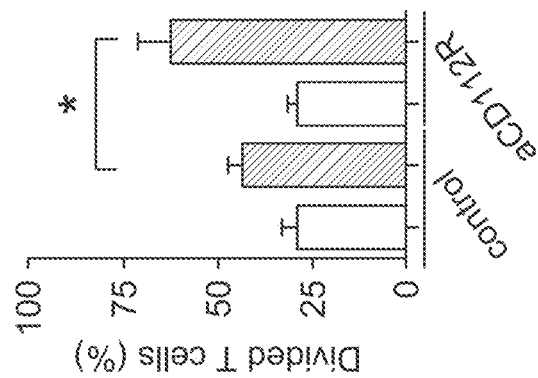
FIG. 4C depicts graphs showing purified human T cells were CFSE-labeled, and stimulated with OKT3 together with coated CD112 or control protein. Control or CD112R mAb was added during cell culture. The CFSE diluted cells indicated were counted as divided T cells.
Figure 4C:
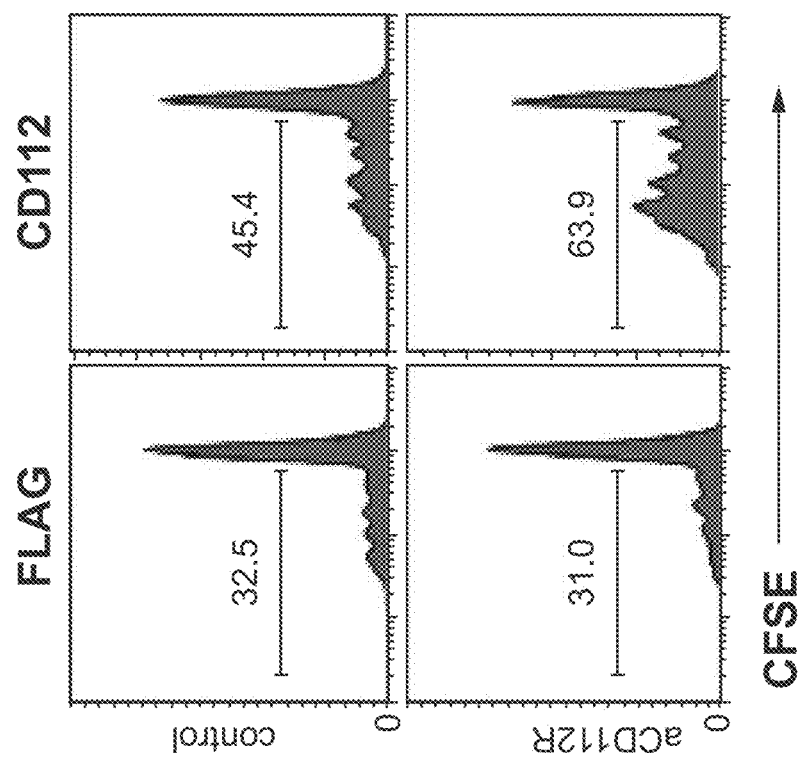

The studies indicated that CD112R, rather than TIGIT, was the dominant inhibitory receptor for CD112. To test the potential function of the CD112/CD112R interaction on T-cell response, purified human T cells were labeled with CFSE, and stimulated with plate-coated CD112-Ig in the presence of human CD3 mAb (FIG. 4C). Immobilized CD112-Ig modestly increased human T-cell division, as revealed by dilution of CFSE dye. This costimulatory effect of CD112 on T cell response was mediated through CD226, a known T cell costimulatory receptor for CD112 (Shibuya et al., 2003; Tahara-Hanaoka et al., 2004). Inclusion of a CD112R neutralizing mAb (clone 2H6, FIG. 2D) further enhanced the costimulatory effect of CD112 (FIG. 4C), indicating that CD112 interacted with CD112R to inhibit T cell proliferation.

Figure 4D:
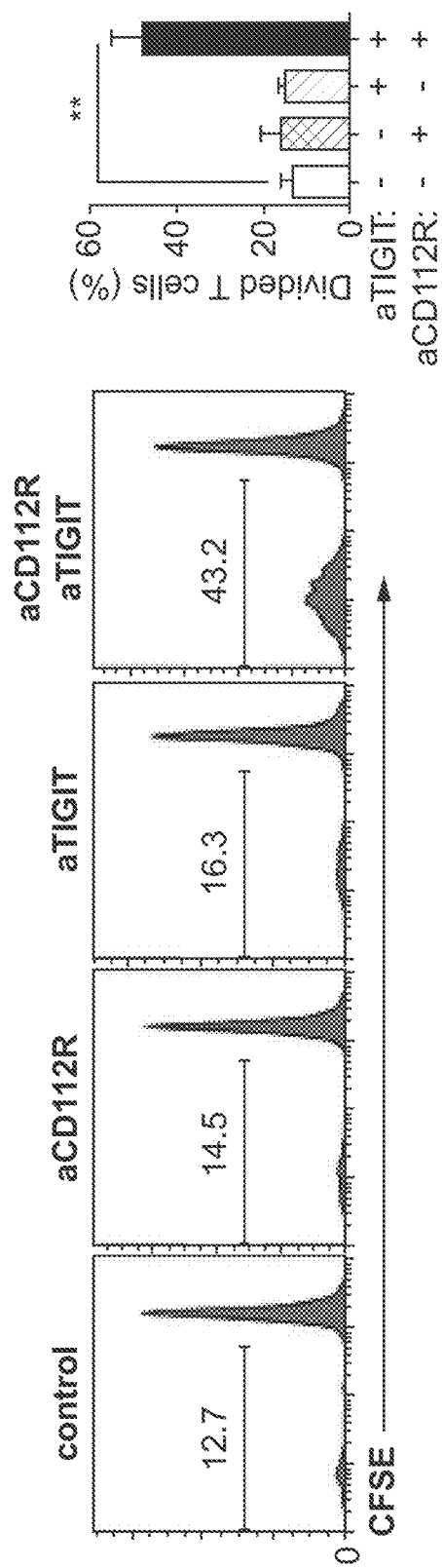
FIG. 4D depicts graphs showing that purified human T cells were labelled with CFSE, and were co-cultured with autologous dendritic cells in the presence of TT. Control, CD112R mAb or TIGIT (tyrosine-based inhibitory motif [ITIM] domain) mAb was included at the beginning of culture. The proliferation of TT-specific CD4+ T cells was determined by CFSE dilution of the human CD3 and CD4 double-positive cells.
Figure 4E:
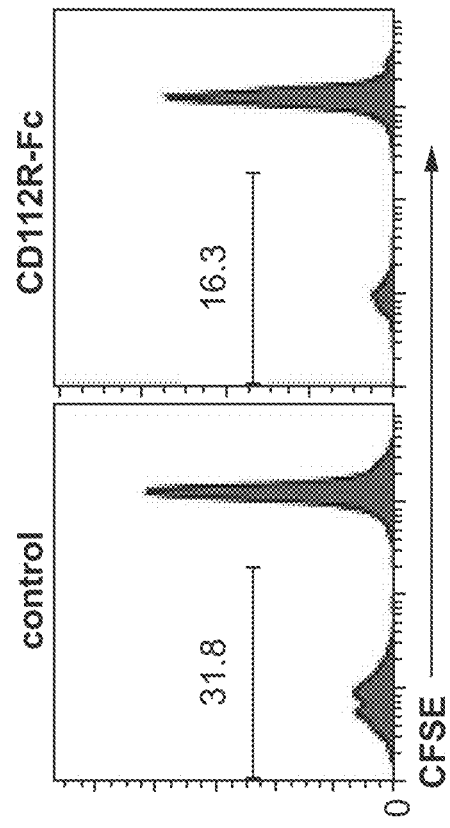
FIG. 4E depicts graphs showing that the addition of CD112R-Fc fusion protein modestly inhibited T cell proliferation.
Figure 4F:
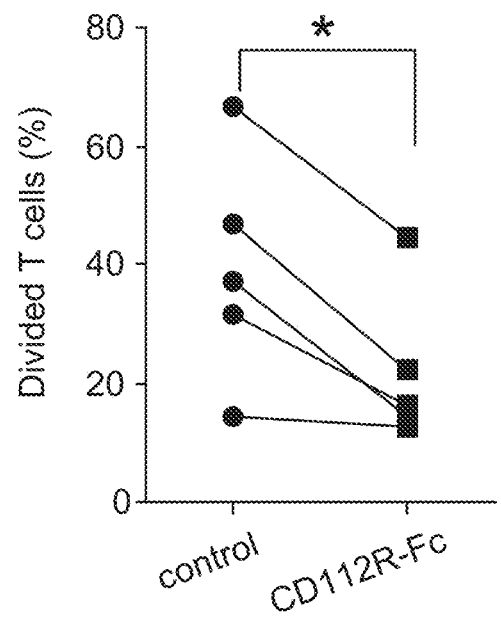
FIG. 4F is a graph depicting the decrease in TT-specific T cell response using CD112R-Fc fusion protein.
Figure 4G:
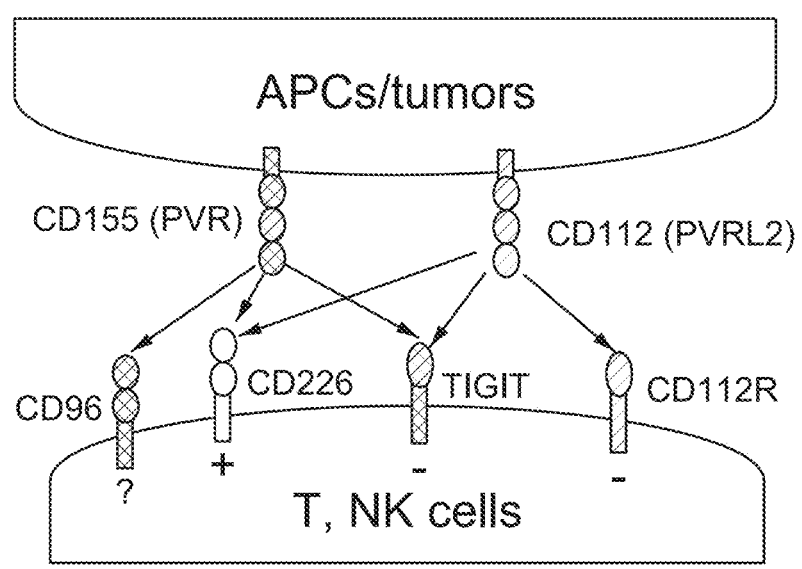
FIG. 4G is a cartoon showing a model of the new CD112/CD155 molecular network. The ligands CD112 and CD155 are abundantly expressed on antigen-presenting cells and tumor cells. They both interact with a costimulatory receptor CD226 on T cell and NK cell to increase their activities, and suppress T cell and NK cell-mediated responses through TIGIT. In addition, CD155 can bind to CD96 though the effect on lymphocytes is unclear, while CD112 interacts with CD112R to inhibit immune response.

To further evaluate the function of endogenous CD112/CD112R interaction on the T-cell response, the effect of this pathway in an antigen-specific T-cell response was examined. Purified human T cells were labelled with CFSE, and cultured with autologous monocyte-derived dendritic cells in the presence of tetanus toxoid (TT). The inclusion of CD112R or TIGIT blocking mAb alone had a minor effect on TT-specific T-cell proliferation. However, the combination of CD112R and TIGIT mAbs were able to significantly augment T cell proliferation (FIG. 4D), demonstrating a synergistic effect of these two inhibitory receptors on T cell response. On the other hand, the addition of CD112R-Fc fusion protein modestly inhibited T cell proliferation in the same model (FIG. 4E). Since all three receptors for CD112 share a similar binding site on CD112, inclusion of a CD112R-Fc fusion protein eliminated all the CD112 interactions by its receptors. These data are consistent with the overall positive effect of CD112 on T cells (FIG. 4C) (Tahara-Hanaoka et al., 2006; Tahara-Hanaoka et al., 2004).

CD112R, a new T cell co-inhibitor, is a receptor for CD112 with high affinity. CD112 interacts weakly with TIGIT and CD226, and was believed to play a minor role in the TIGIT/CD226 network, compared to CD155 (Guillerey et al., 2015; Lozano et al., 2012; Yu et al., 2009). The results indicate that CD112R, also a PVR-like molecule, is a main co-inhibitory receptor for CD112.

TIGIT is involved in T cell checkpoint for cancer immunotherapy (Chauvin et al., 2015; Pauken and Wherry, 2014). TIGIT and its ligands are highly expressed and contribute to the suppressive microenvironment of cancer, and disrupting this pathway together with PD-1 blockade improves anti-tumor immune response. Consistently, the present example indicated that CD112 is highly expressed on the majority of cancer cell lines (FIG. 2B) and cancer tissues. TIGIT and CD112R share a same ligand in CD112, and both could compete with costimulatory receptor CD226 for ligand interaction. Consistently, blockade of CD112R together with TIGIT blockade displayed a great synergy to enhance T cell response in vitro.

Example 8: Cancer Immunotherapy

For subcutaneous mouse tumor model, a half million CT26 cells are implanted into the right flank of wild type (WT) Balb/c mice. Tumor-bearing mice are treated with 200 µg per mouse control rat IgG, mCD112R mAb at day 1 and 5 after tumor inoculation. Tumor size is measured in two dimensions using a caliper. In some experiments, mice are sacrificed to examine TILs, including the number, cytokine secretion, such as IL-2, IFN-gamma and TNF-alpha. Given the discovery here that CD112R is an inhibitory receptor for CD112, blockage of the CD112R/CD112 interaction is expected to promote anti-tumor response. As a result, inoculation of CD112R blocking mAb inhibits tumor growth. Co-blockade of CD112R and TIGIT results in significant suppression of cancer and tumor size and growth, and exceeds that seen with blockade of CD112R or TIGIT alone.

In a B16 melanoma lung metastasis model, $1\times10^5$ melanoma cells suspended in 100 µl saline are injected in the tail vein of WT C57BL/6 mice. Mice are separated into two groups, and treated with control rat IgG, mCD112R mAb respectively. The survival of mice will be monitored every day after 10 days of tumor inoculation. In some experiments, mice will be sacrificed on day 14 after tumor inoculation to examine tumors in the lung. Given the discovery here that CD112R is an inhibitory receptor for CD112, blockage of the CD112R/CD112 interaction is expected to promote anti-tumor response. As a result, inoculation of CD112R blocking mAb inhibits tumor progression so as to extend survival of tumor-bearing mice. Co-blockade of CD112R and TIGIT results in significant suppression of cancer metastasis, and promotes survival of mice with tumor challenge, which will exceed than that seen with blockade of CD112R or TIGIT alone.

Example 9: Experimental Autoimmune Encephalomyelitis (EAE)

WT C57BL/6 mice are immunized with an emulsion of $MOG_{35-55}$ in complete Freund's adjuvant (CFA), followed by administration of pertussis toxin (PTX) in PBS, on the first day of immunization and then again the following day. Immunized mice are treated with 300 µg control mouse IgG1 or mCD112R-mFc on day 1, 4 and 7 after immunization. Mice are monitored daily for the development of disease, which is scored according to the following scale: 0, no clinical signs; 1, loss of tail tone; 2, hindlimb weakness; 3, hindlimb paralysis; 4, forelimb paralysis; and 5, moribund or dead. EAE symptoms are generally attenuated by agents that inhibit T cell response. Because CD112R competes with CD226 for CD112 binding, administration of CD112R-Fc will reduce EAE symptoms or disease markers. In view of CD112R as a new checkpoint for T cells, agents like agonistic antibody to amplify CD112R signal will also help to suppress pathological T cell responses, and therefore reduce EAE symptoms or disease markers.

Example 10: Graft Versus Host Disease

Graft versus host disease (GVHD) usually occurs after a stem cell or bone marrow transplant, in which the donor's immune cells mistakenly attack the patient's normal cells. In the nonirradiated parent-to-F1 GVHD model, $5\times10^7$ spleen cells isolated from wild-type (WT) B6 mice are transferred intravenously into BDF1 recipients on day 0. In some experiments, donor spleen cells are labeled with 5 µM carboxyfluorescein diacetate succinimidyl ester (CFSE) prior to transfer. On days 0, 3, and 6 after cell transfer, 300 µg mCD112R-mFc or control FLAG-mFc is administered intraperitoneally. The recipient mice are sacrificed on day 7, and the spleen cells are analyzed by flow cytometry and chromium 51 (51Cr)-release assay. In the model employing 2C T cells, $1\times10^7$ spleen cells from 2C TCR-transgenic mice are mixed with $3\times10^7$ B6 spleen cells and then transferred intravenously into the BDF1 host on day 0. Recipient mice are subsequently administered 300 µg mCD112R-mFc or control FLAG-mFc intraperitoneally on days 0 and 4. On day 7, recipient spleen cells are harvested and assessed for the presence of 2C T cells by flow cytometric analysis using 1B2 clonotypic mAb and anti-CD8 mAb. Because mCD112R competes with CD226 for CD112 binding, we expect to see administration of CD112R protein will inhibit GVHD responses.

In addition, two survival models of GVHD induced by allogeneic bone marrow transplantation are employed. First, BDF1 recipient mice, which are preconditioned with lethal irradiation (12 Gy), are injected intravenously with T cell-depleted B6 BM cells (5×10⁶ cells) with or without WT B6 T cells (2-3×10⁶ cells). T-cell depletion from BM cells and T-cell isolation from spleen cells is performed by MACS systems using anti-Thy1.2 mAb-conjugate d microbeads and pan-T cell isolation kits, respectively. Mice are intraperitoneally administered 300 µg mCD112R-mFc or control FLAG-mFc on days 0, 3, and 6. The survival of recipient mice is monitored daily. In the second model, BALB/c mice are exposed to lethal irradiation (10 Gy) followed by intravenous transfer of T cell-depleted B6 BM cells (5×10⁶ cells) with or without WT B6 T cells (1×10⁶ cells). Mice are intraperitoneally administered 300 µg mCD112R-mFc or control FLAG-mFc on days 0, 3, and 6. In this fully major histocompatibility complex (MHC)-mismatched GVHD model, the survival and body weight change of recipient mice are monitored regularly. Because mCD112R competes with CD226 for CD112 binding, we are expecting to see administration of CD112R protein will inhibit GVHD responses and promote survival of mice with GVHD Similarly, in view of CD112R as a checkpoint for T cells, agents like antibody to amplify CD112R signal will help to suppress GVHD responses, and therefore elongate survival of mice with GVHD.

Example 11: Ovalbumin (OVA)-Induced Allergic Asthma

WT C57BL/6, male at 8-10 weeks old are sensitized via i.p. injection of 20 µg OVA protein (Sigma-Aldrich) adsorbed to 4 mg aluminum hydroxide Gel (Sigma-Aldrich) on days 0 and 5. Mice are intraperitoneally administered 300 µg mCD112R-mFc or control FLAG-mFc on days 0, 3, and 6. Then, mice are challenged with aerosolized 1% OVA in PBS using a nebulizer (Proneb Ultra II) for 60 minutes on days 12-14. Mice are sacrificed the next day for analysis. Blood is collected and serum is separated for OVA-specific IgE determination. Supernatant from bronchoalveolar lavage fluids (BALF) is collected to determine cytokine IL-5 and IL-13 levels. Cell pellets are counted, spun onto microscope slides and stained with Hema3 to determine different cell types. For histopathology analysis of lung inflammation, peribronchial and perivascular inflammation is evaluated on a scale of 0-4, for no inflammation (0), few inflammatory cells present (1), a few loci of inflammation (2), multiple loci of inflammation (3), inflammatory cells throughout the lung (4). The scores are presented as mean±SEM. For mucus-secreting cells in the airways, mucous scores of 0-3 are evaluated for: no positive cells present (0), a few positive cells (1), many positive cells (2), and extensive staining of mucus-secreting cells (3) Similarly, because asthma symptoms are generally reduced by agents that inhibit T cell response, administration of CD112R-Fc reduces asthma symptoms or disease markers.

Example 12: Collagen-Induced Arthritis (CIA)

Chicken Collagen II (CII, Sigma-Aldrich) is dissolved in 10 mM acetic acid at 4 mg/ml and emulsified with an equal volume of CPA (Difco). WT male DBA/1 J mice at the age of 8-10 week old are immunized s.c. at both flanks with 100 µl of emulsion and a boosted with the same concentration of CII 16 or 18 days after the primary immunization. Immunized mice are treated with 300 µg control mouse IgG1 or mCD112R-mFc on day 1, 4 and 7 after immunization.

Animals are evaluated by visual inspection for arthritis incidence; severity was scored individually on a 0-4 scale. Scores from all four paws are added to give the total for each animal. Arthritis symptoms are generally reduced by agents that inhibit T cell response, and administration of CD112R-Fc, therefore, reduces CIA symptoms or disease markers. Similarly, in view of CD112R as a checkpoint for T cells, agents like antibody to amplify CD112R signal will help to reduce CIA symptoms.

Example 13: CD112R Surface Protein is Constitutively Expressed in T-ALL

To look at the protein expression of CD112R gene, a mAb against human CD112R protein was generated. The specificity of CD112R mAb was verified by its binding to CD112R transfectants, but not control HEK293T transfectants (FIG. 12A). CD112R expression in the peripheral blood mononuclear cells (PBMCs) of healthy human donors was analyzed using flow cytometry. No detectable surface CD112R was found on freshly isolated human T cells from multiple healthy donors. However, upon stimulated by CD3 and CD28 mAb, a large portion of CD3+ T cells from the PBMCs of the healthy donors expressed surface CD112R (FIG. 12B).

CD112R expression in human cell lines from hematologic malignancies was further evaluated by flow cytometry. The results showed that all T-ALL cell lines (10110) tested constitutively expressed CD112R, though in different extent. NHLs, such as Raji and Daudi, constitutively expression surface CD112R protein (FIG. 2D). No CD112R protein was detected on other subtypes of human lymphoma/leukemia, such as pre-BALL or Acute myeloid leukemia (AML) (FIG. 2E).

Example 14: CD112R Expression in Human Patients with T-ALLs and NHL

The studies presented here demonstrated that CD112R protein is constitutively expressed on certain types of lymphoma/leukemia, including T-ALL, but not normal human PBMCs. Therefore, CD112R is targeted for the therapy of human T-ALLs. First, CD112R protein expression on primary cancer cells directly from T-ALL patients is confirmed. Second, antibodies to target CD112R for the treatment of human T-ALL are developed.

CD112R protein expression from hPBMCs of patients with hematologic malignancies was examined. hPBMCs from five patients with T-ALLs, seven with pre-BALLs and four with AMLs, were analyzed. No surface CD112R was detected from PBMCs of patients with pre-B ALLs or AMLs. However, in 5 out of 6 T-ALL patients, CD112R was constitutively expressed on tumor cells (Table 4).

TABLE 4

Surface CD112R expression in human leukemia patients

| Leukemia type | Source | Surface CD112R expression |
| --- | --- | --- |
| Pre-BALL | Peripheral blood | 0/7 |
| T-ALL | Peripheral blood, bone marrow | 4/5 |
| AML | Peripheral blood | 0/4 |

CD112R protein expression in patients with T-ALLs and NHL from established tissue bank at Children's Hospital are analyzed. CD112R is overexpressed and serves as a good diagnostic marker for T-ALL disease. In addition, other well-defined molecular signatures defining human T-ALLs, such as CD1a, CD4, CD5 and CD3, are compared according to the expression of CD112R by flow cytometry. Common genetic alterations in human T-ALLs, like NOTCH signaling network, PTEN, FBXW7, and LEF1, are examined to see if any of these pathways contributes to CD112R expression on T-ALLs.

Example 15: Using CD112R as a Target for the Treatment of Human T-ALL and NHL

Figure 13A:
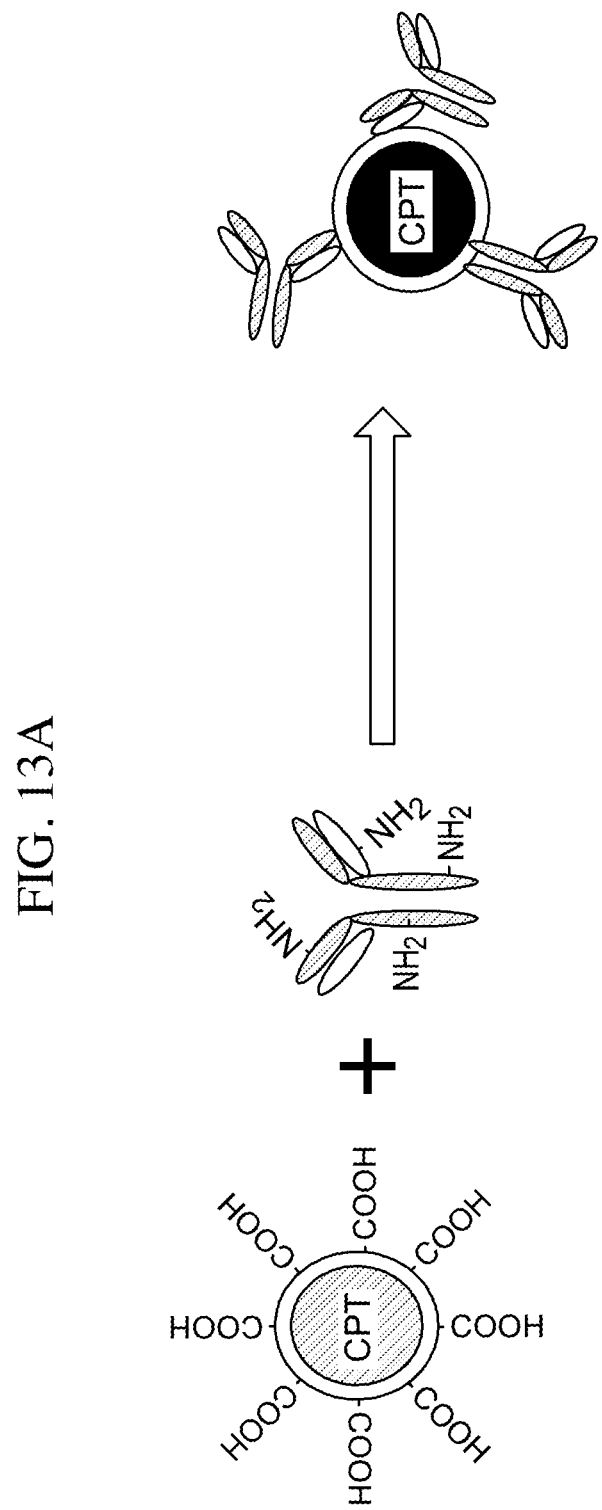
FIG. 13A shows a schematic diagram of nanoparticle comprised a layer of peripheral antibodies targeting CD112R covalently attached to poly(lactideco-glycolide) nanoparticles (NP) loaded with camptothecin.
Figure 13B:
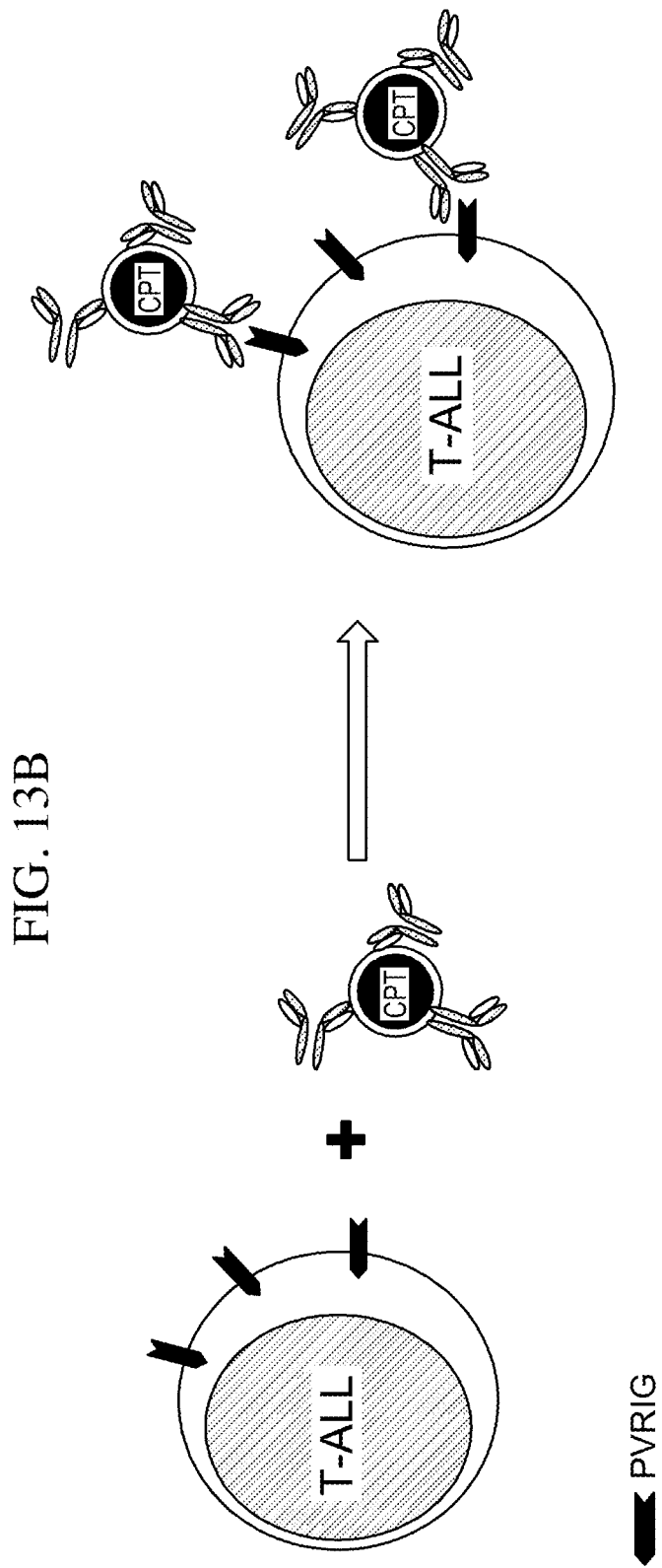
FIG. 13B shows a schematic diagram of nanoparticles coupled with non-specific isotype antibody will be used as control. Fluorescence visualization can be used to study internalization of nanoconstructs into T-ALL cell line, like Molt4.
Figure 14A:
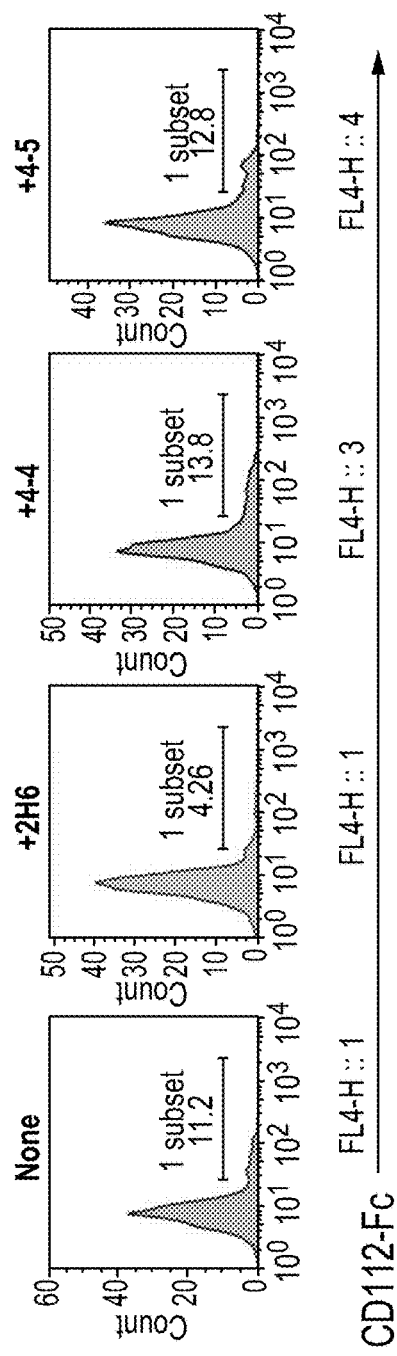
FIGS. 14A, 14B, 14C, 14D are a series of graphs depicting the ability of three anti-CD112R antibodies of the disclosure, mAb 2H6, mAb 4-4, and mAb 4-5, to bind human CD112R.
Figure 14B:
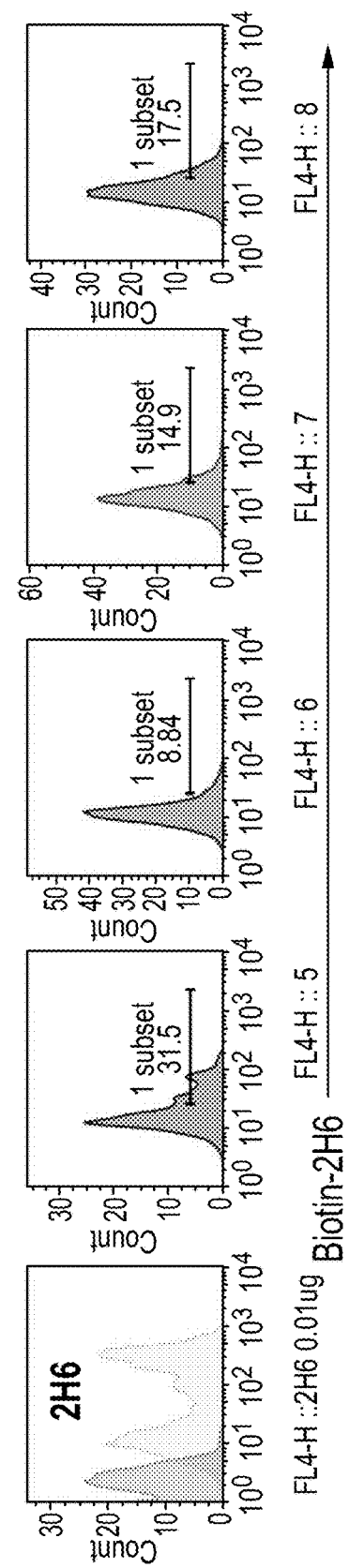
Figure 14C:
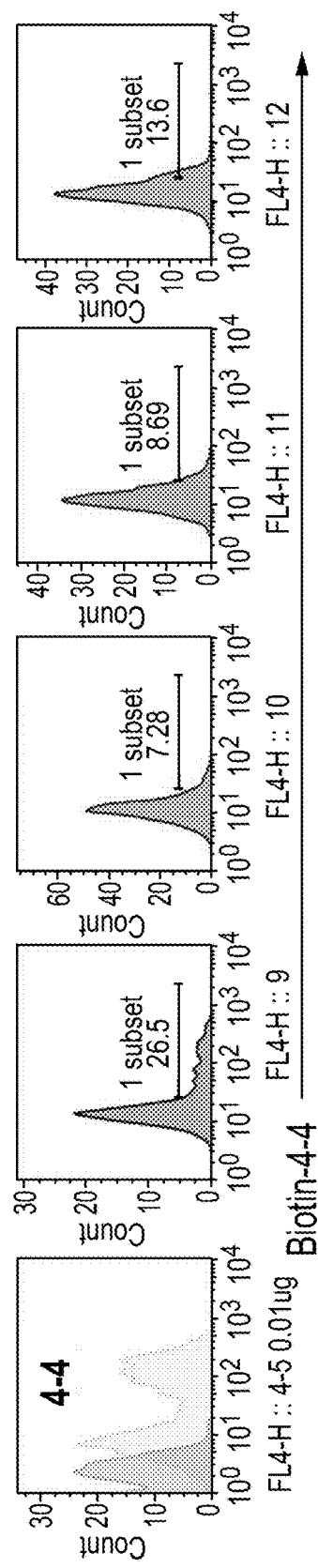
Figure 14D:
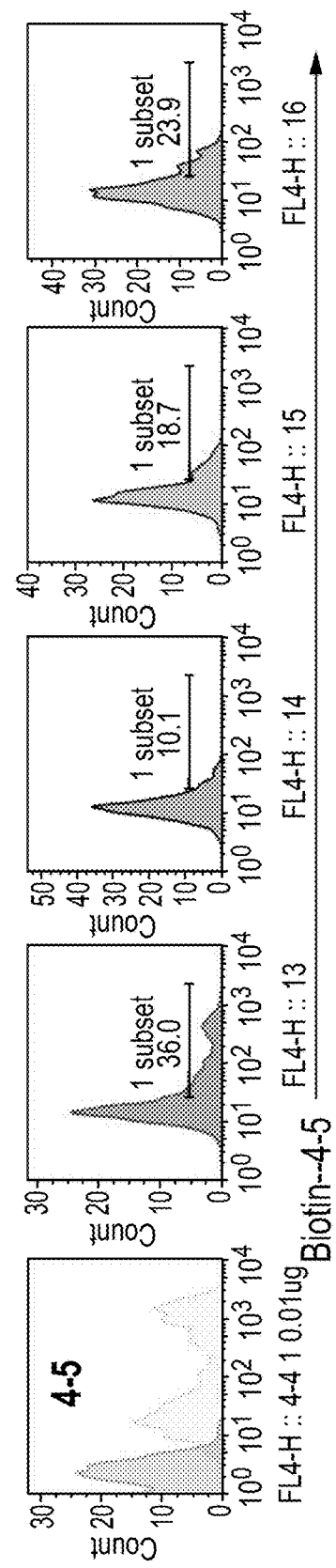

Targeting CD112R using nanoparticle for T-ALL treatment: a mAb (clone 2H6) against human CD112R with high affinity (FIG. 12A) was generated. This antibody is used as a vehicle to deliver nanoparticles loaded with camptothecin (CPT) to T-ALL (FIG. 13A). CPT, originally isolated from the bark and stem of Camptotheca acuminata (Camptotheca, Happy tree), is a cytotoxic quinoline alkaloid which inhibits the DNA enzyme topoisomerase I. Nanoparticle including a layer of peripheral antibodies targeting CD112R covalently attached to poly(lactideco-glycolide) nanoparticles (NP) loaded with camptothecin were generated (FIG. 13A). Nanoparticles coupled with non-specific isotype antibody are used as control. Fluorescence visualization are used to study internalization of nanoconstructs into T-ALL cell line, like Molt4 (FIG. 13B).

Example 16: Strategy of Targeting T-ALL by Nanoparticles Coated with CD112R mAb

Cytotoxicity studies against Molt4 as an example are carried out in vitro culturing with nanoparticles. By doing this, a novel immuno-nanoparticle with improved therapeutic effect against human T-ALL is developed.

Example 17: Targeting T-ALL Using CD112R mAb to Trigger Antibody-Dependent Cellular Cytotoxicity (ADCC)

First, a construct for a chimera antibody, 2H6-hFcl, is generated by PCR, which contains the binding sequence from 2H6 mAb and a Fc fragment from human IgG1, which is known to induce ADCC to kill target cells. 2H6-hFcl protein is produced by transiently transducing 293F cells with 2H6-hFcl plasmid using 293FECTIN™. The binding of 2H6-hFcl is confirmed by flow cytometry. To test whether this chimera mAb triggers ADCC, peripheral blood monocytes (PBMCs) are isolated from human whole blood obtained from healthy donors using a Lymphocyte Separation Medium (MP BioMedicals, Solon, Ohio). Isolated PBMCs are incubated with Molt4 cells with or without 2H6-hFcl at an effector-to-target ratio of 100:1, 50:1 or 25:1 for 4 hours at 37° C. After the 4-hour incubation period, the cell supernatant is transferred to a 96-well plate to determine the amount of lactate dehydrogenase (LDH) released using a colorimetric assay (Promega, Madison, Wis.). Percent cytotoxicity is calculated as follows: percent cytotoxicity= (experimental-effector spontaneous-target spontaneous)/ (target maximum-target spontaneous)×100, where "experimental" corresponds to the signal measured in a treated sample, "effector spontaneous" corresponds to the signal measured in the presence of PBMCs alone, "target spontaneous" corresponds to the signal measured in the presence of tumor cells alone, and "target maximum" corresponds to the signal measured in the presence of detergent lysed tumor cells. Additional studies using purified NK cells will be tested in the LDH release assays.

To test the anti-tumor effect of the 2H6-hFcl in vivo, purified fresh hPBMCs is transferred into the immune-deficient mice NOD scid gamma (NSG) mice. Mice is injected intravenously with human T-ALL cell line Molt4 with fluoresce, and then treated with CD112R mAb or control antibody. Tumor burden is revealed by imaging every two days, and results of mouse survival are recorded.

Example 18: Epitope Analysis of Anti-CD112R Antibodies

In the studies presented herein, the ability of three anti-CD112R antibodies of the disclosure, mAb 2H6, mAb 4-4, and mAb 4-5, to bind human CD112R was analyzed. The results of these studies are shown in FIG. 14.

It was determined that mAb 2H6 is a blocking antibody, while the antibodies mAb 4-4 and mAb 4-5 are not. All three antibodies tested, mAb 2H6, mAb 4-4, and mAb 4-5 were found to compete with each other for binding to human CD112R, which suggests that each of the epitopes of CD112R to which each of these antibodies binds at least partially overlap.

Example 19. The Role of the CD112R Pathway in Tumor Studies

Expression of the CD112R/CD112 Pathway in Human Cancers.

Figure 16A:
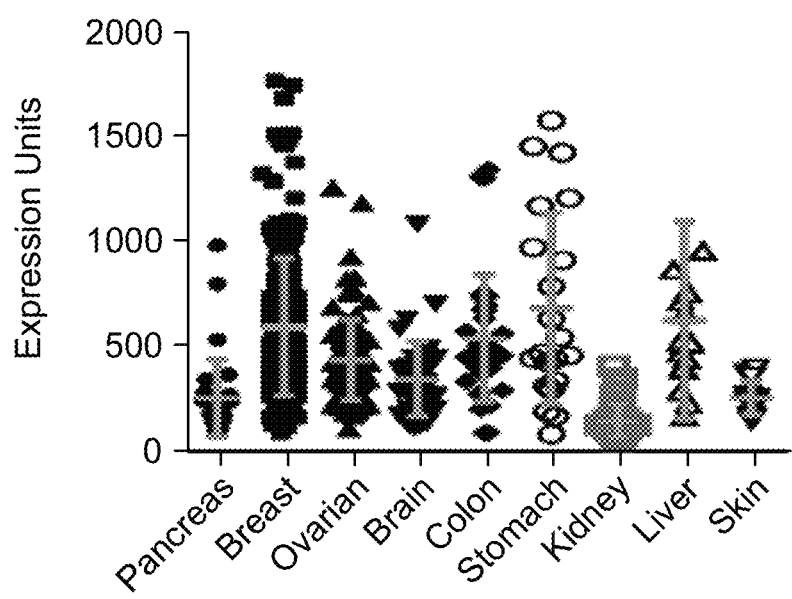
FIGS. 16A, 16B, and 16C are a series of graphs depicting expression of the CD112R pathway in human cancers.
Figure 16B:
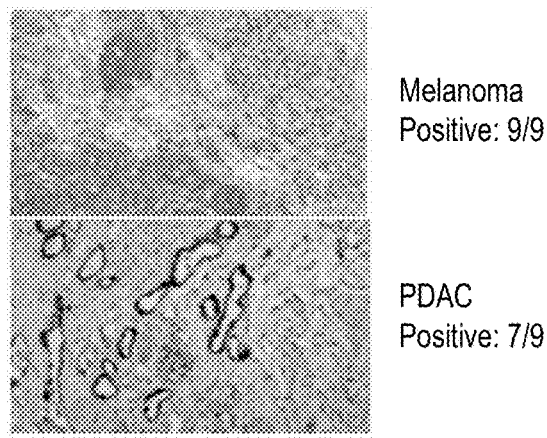
Figure 16C:
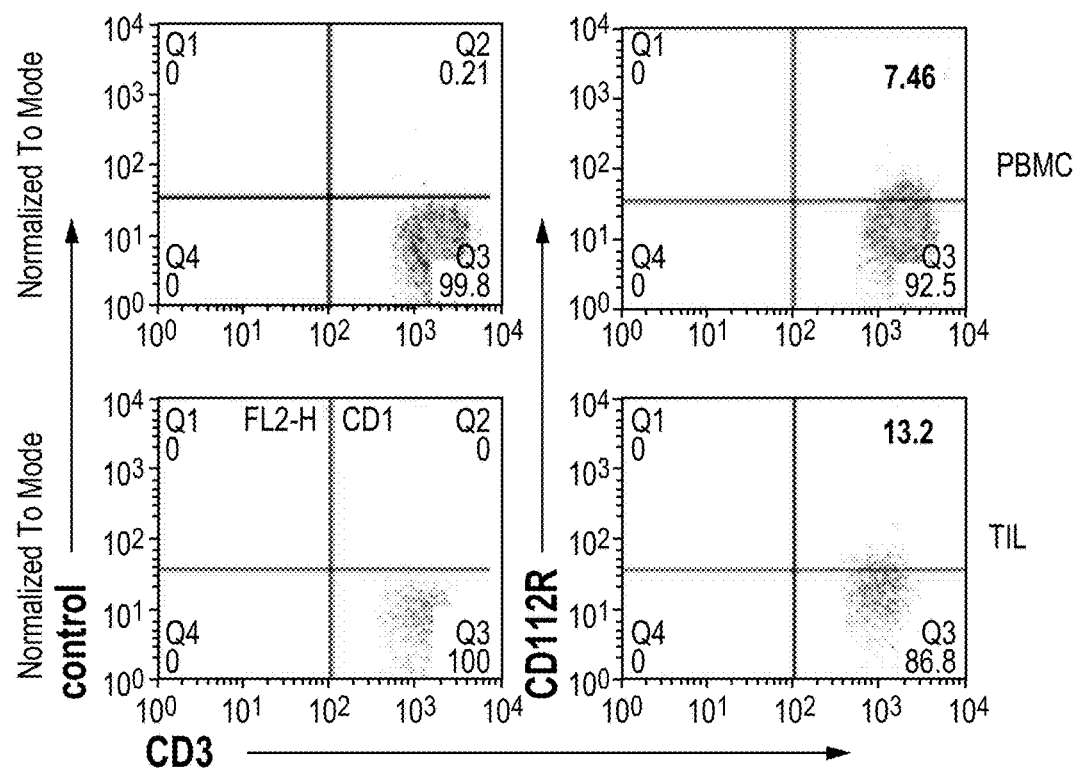

CD112 is known to be highly expressed in human cancers. Earlier studies found that the majority of adherent human cancer cell lines express CD112. The array data from human cancers indicated that CD112 is highly transcribed in multiple human cancer types (FIG. 16A). Immunohistochemistry also demonstrated that the majority of melanomas and human pancreatic adenocarcinomas (PDAC) express high levels of surface CD112 (FIG. 16B). Furthermore, there were significantly more CD112R+ T cells in TILs than those in PBMCs from PDAC patients (FIG. 16C).

Characterization of CD112R Expression in Mice.

Figure 17A:
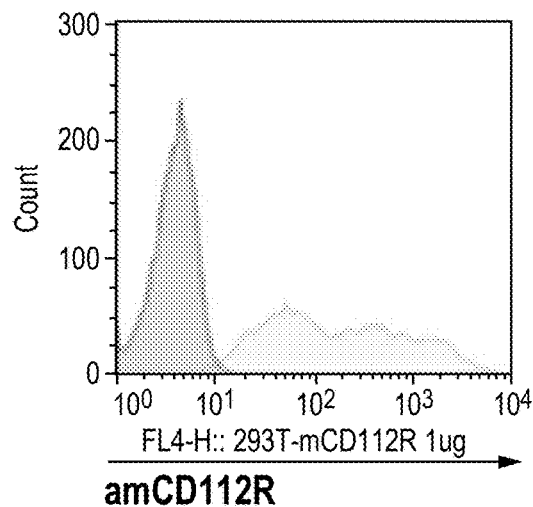
FIGS. 17A, 17B, 17C, 17D, 17E, and 17F are a series of graphs depicting that CD112R is upregulated on mouse lymphocytes upon activation.
Figure 17B:
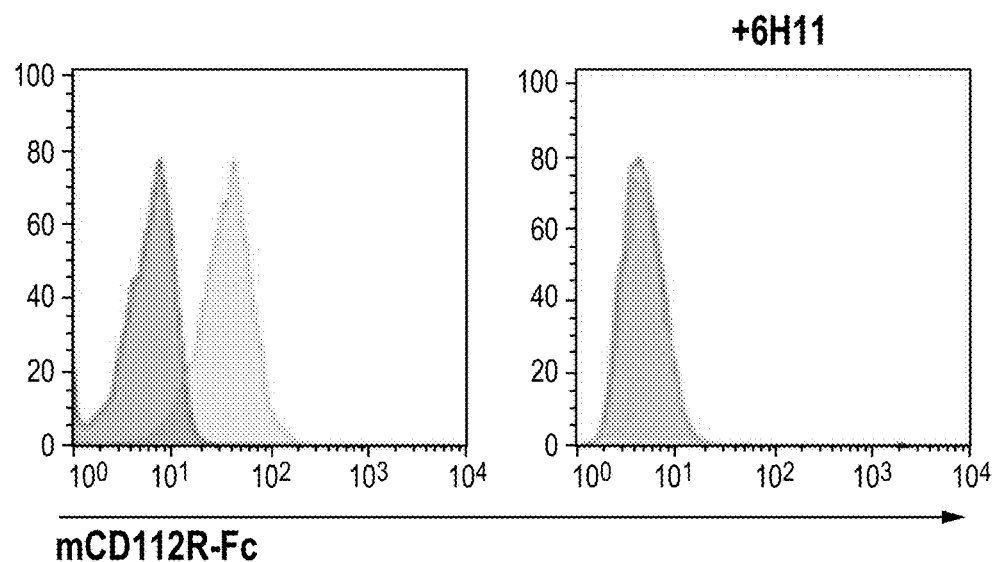
Figure 17C:
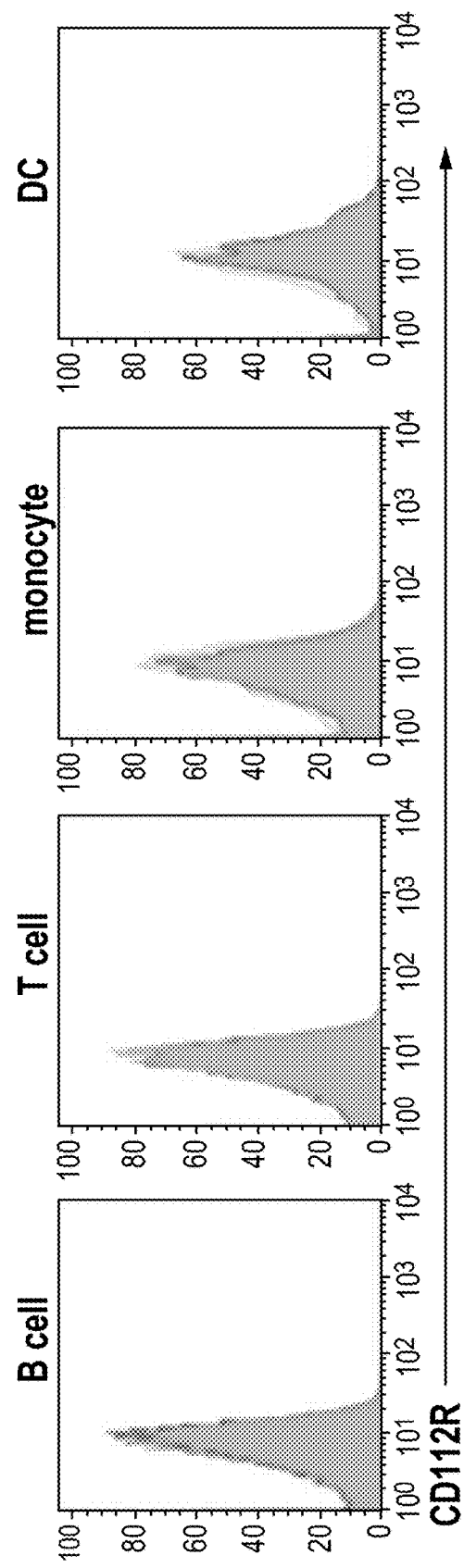
Figure 17D:
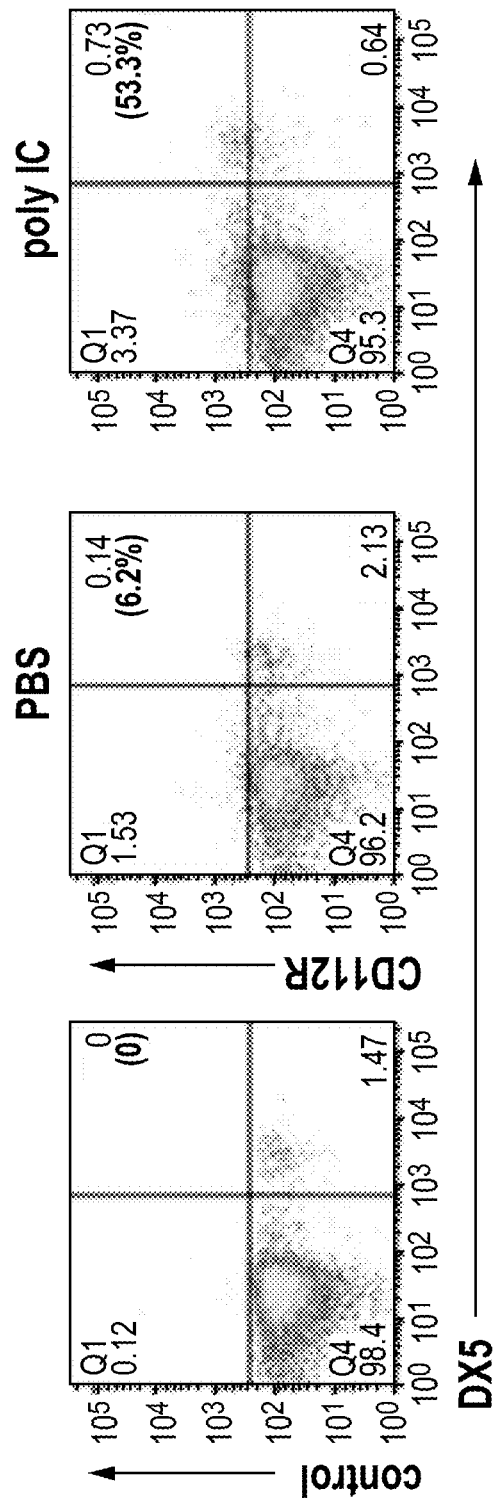
Figure 17E:
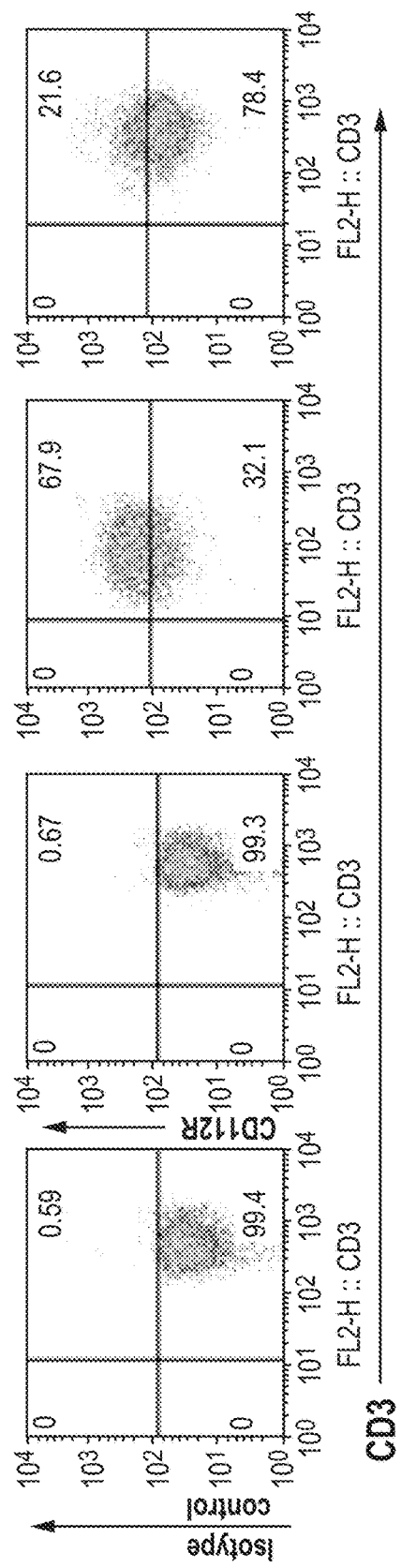
Figure 17F:
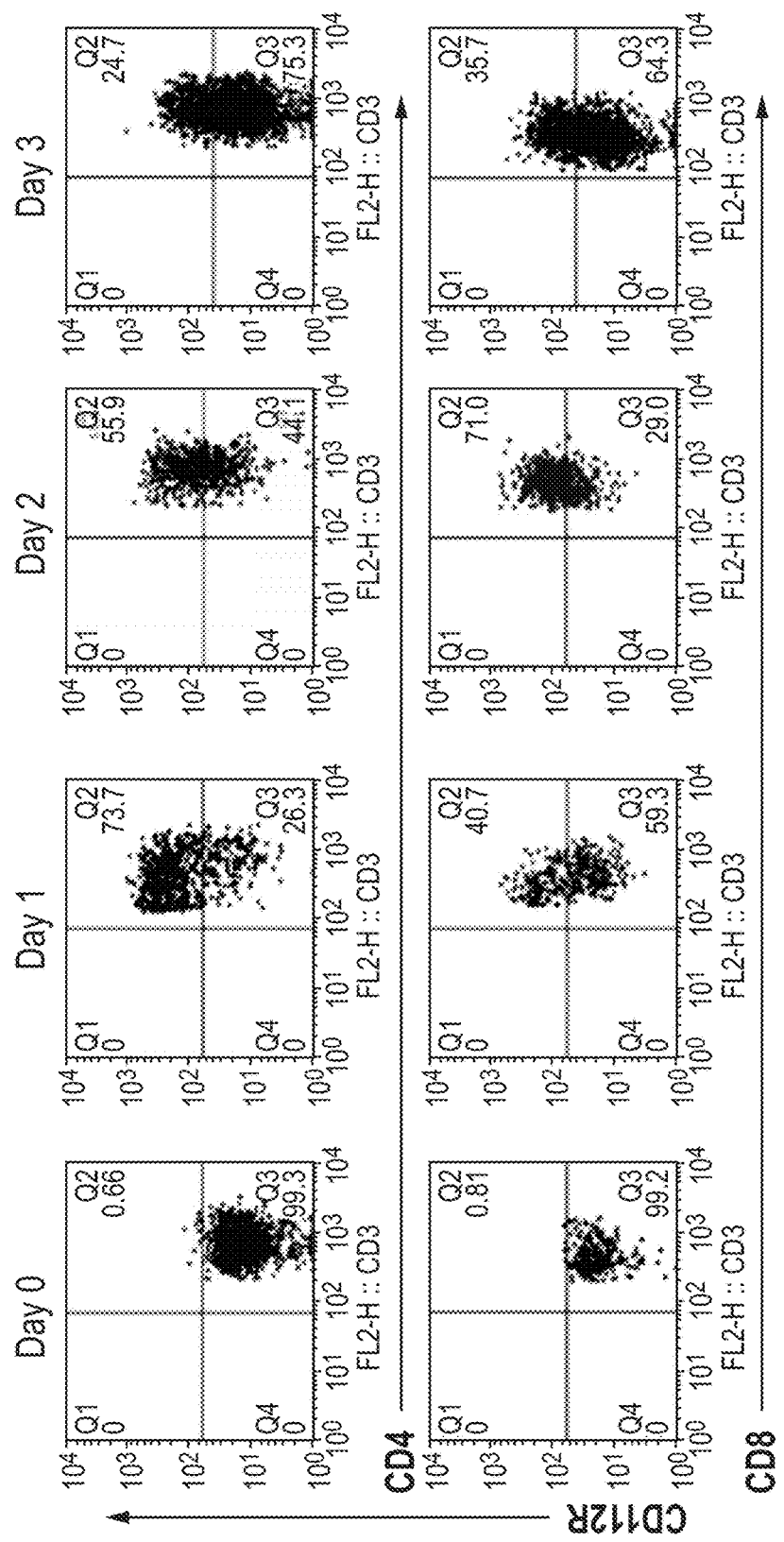

To examine CD112R expression in mice, a rat monoclonal antibody against mouse CD112R (Clone 6H11) was generated. The specificity of this mAb was validated through its specific binding to mCD112R/HEK293T transfectants, but not to HEK293T control cells (FIG. 17A). Clone 6H11 mAb completely eliminated the binding of mCD112R-Fc protein to mCD112 transfectants, indicating it is a blocking mAb for the CD112R/CD112 interaction in mouse (FIG. 17B). Surface CD112R expression on immune cells from naïve mouse spleen was not detected, other than by a small percentage of NK cells (FIGS. 17C and 17D). Upon activation in vivo by poly IC injection, many NK cells (53.3%) upregulated surface expression of CD112R (FIG. 17D). Naïve OT-1 T cells do not express CD112R; however, upon activation by OVA peptide in vitro, OT-1 substantially upregulated surface CD112R (FIG. 17E). Similarly, both CD4+ and CD8+ T cells from wild type (WT) B6 mice upregulated CD112R in response to stimulation by CD3 plus CD28 mAbs (FIG. 17F). Thus, the expression of CD112R in mouse was enriched in activated T and NK cells, similar to findings in humans.

The CD112R/CD112 Pathway is Highly Expressed at Mouse Tumor Sites.

Figure 18A:
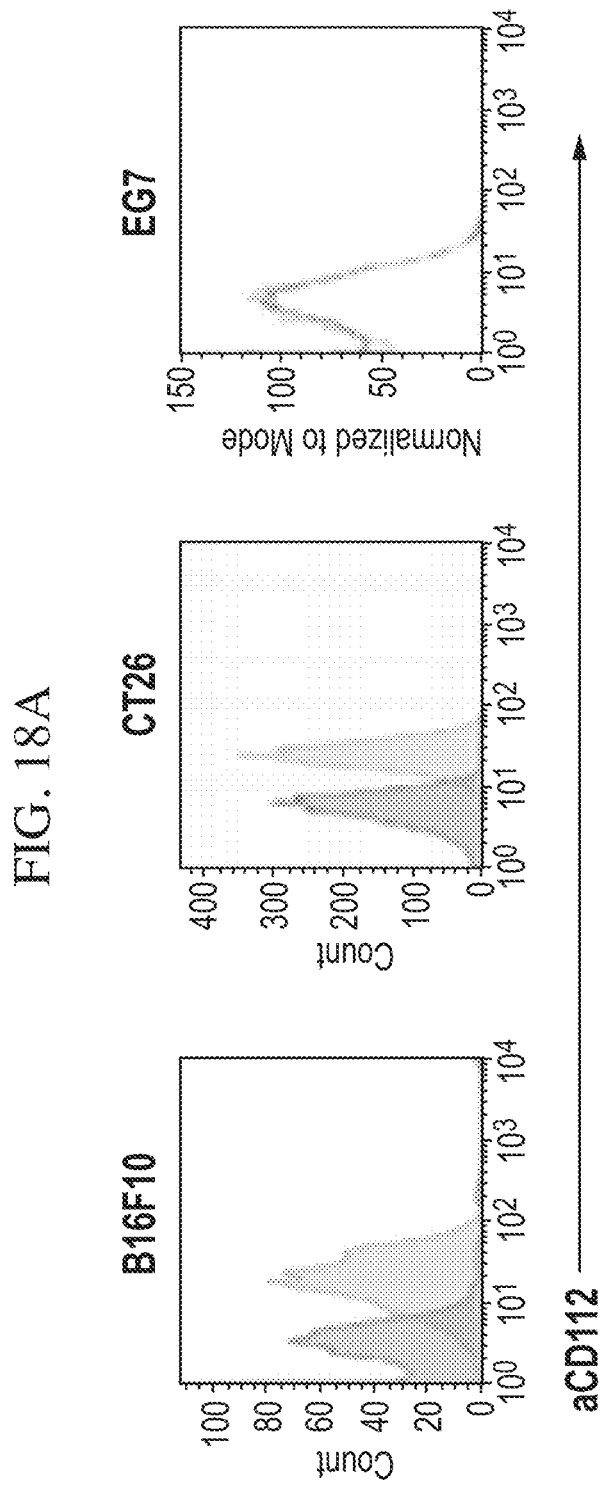
FIGS. 18A, 18B, and 18C are a series of graphs depicting that the CD112R/CD112 pathway is upregulated in mouse tumor models.
Figure 18B:
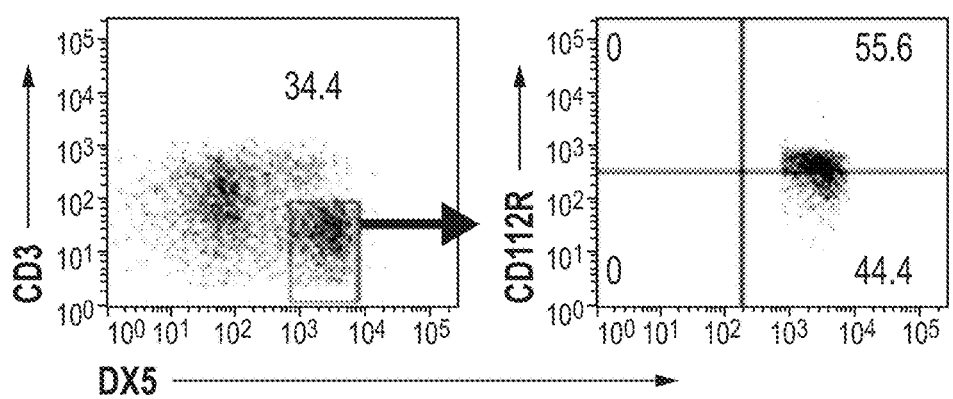
Figure 18C:
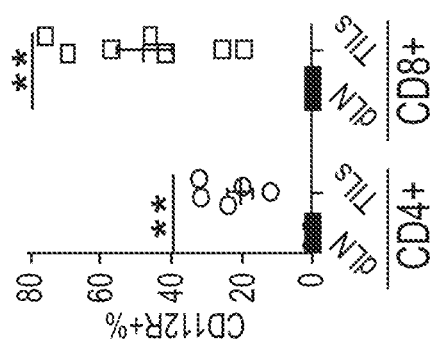
Figure 18C:
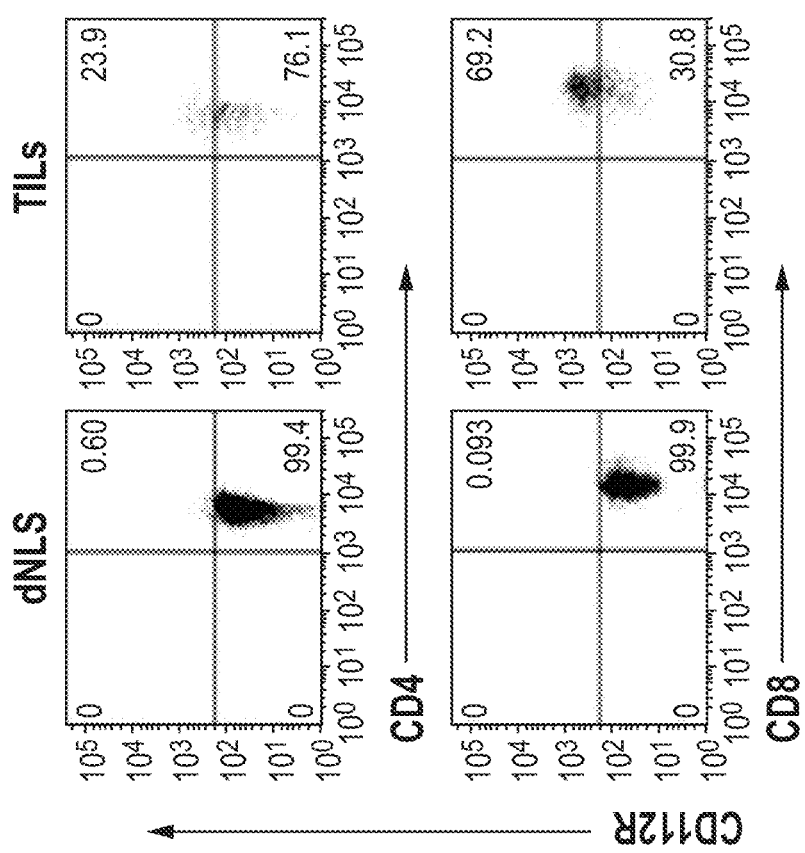

CD112 expression was assessed in several commonly used mouse tumor cell lines Similar to human CD112 expression in cancer, adherent cell lines B16F10 and CT26 consistently expressed CD112, while lymphoma cell line EG7 (EL4-OVA) was CD112-negative (FIG. 18A). CD112R expression on mouse TILs was also examined. A significant portion of NK cells (>50%) at cancer sites were CD112R-positive (FIG. 18B). Although very few T cells in draining lymph nodes (dLNs) expressed CD112R (<2%), a large percentage of T cells upregulated CD112R, including both CD4+ (~20%) and CD8+ T cell (~50%) subsets (FIG. 18C). Without intending to be bound by theory, all these data suggest a possible role of the CD112R pathway at cancer sites.

CD112R is Co-Expressed with Other Immune Checkpoints on Mouse TILs.

Figure 19A:
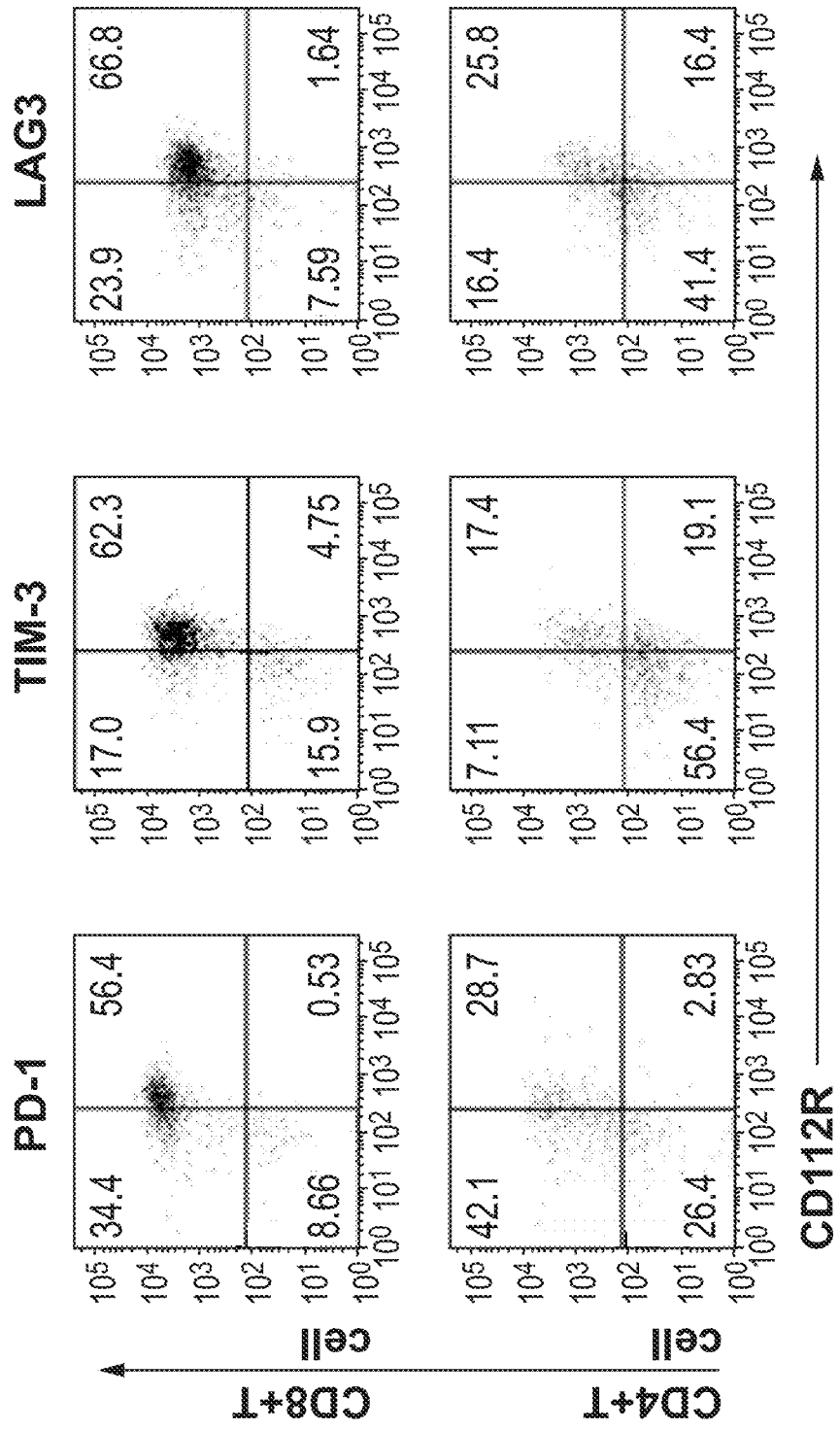
FIG. 19A: is a series of graphs depicting that CD112R is co-expressed with other known immune checkpoints on TILs. TILs from mouse tumor tissues were stained for CD3, CD4 and CD8. The co-expression of CD112R with other immune checkpoints (as indicated) on different T cell subsets was shown.
Figure 19B:
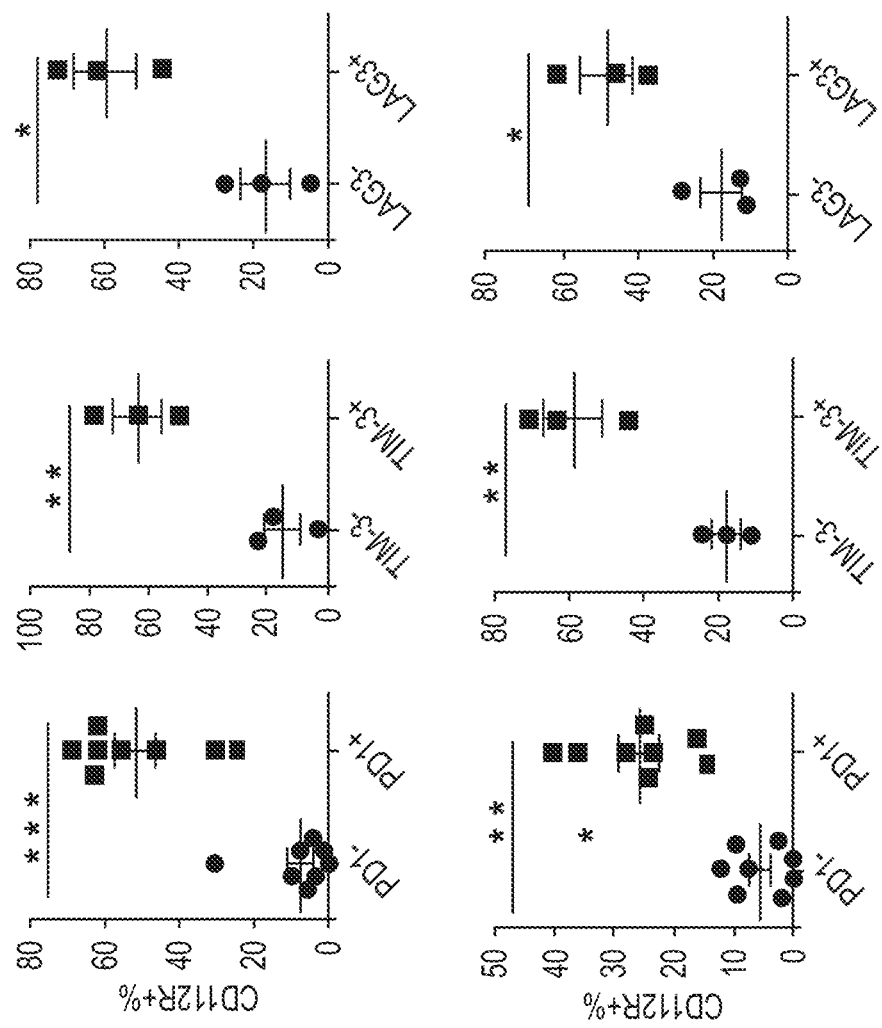
FIG. 19B: is a series of graphs depicting the percentage of CD112R-expressing cells in each population from FIG. 19A.

To further characterize these CD112R+ T cells at cancer sites, TILs were examined for the expression of CD112R along with other known immune checkpoints including PD-1, TIM-3, and LAG3. CD112R was co-expressed with PD-1, TIM-3, and LAG3 on both CD8+ and CD4+TILs (FIG. 19). Without intending to be bound by theory, the co-expression of CD112R with other immune checkpoints suggests a possible role of CD112R in TIL exhaustion, and justifies a combinatorial approach for cancer immunotherapy by targeting CD112R together with other immune checkpoints.

Blockade of CD112R Signaling Improves Anticancer Immunity in a Melanoma Lung Metastasis Mouse Model.

Figure 20:
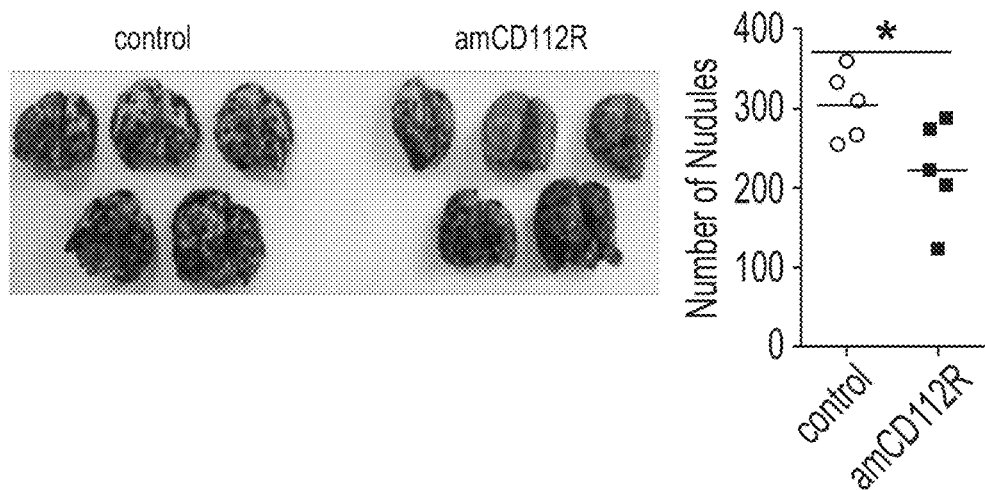
FIG. 20 is an illustration and a graph depicting that CD112R blockade improves anticancer immunity in a lung metastasis mouse model. B6 mice were intravenously (iv) injected with B16F10 melanoma cells to induce lung metastasis. Mice were treated with control or mCD112R blocking mAb for total three times (day 1, 4, 7). Lungs were collected 20 days after tumor challenge and the nodules were counted.

Because CD112R was upregulated on TILs, studies were run to examine whether targeting CD112R promoted anticancer immunity in vivo. B16F10 melanoma was selected to evaluate the possible anticancer effect of CD112R blockade, based on the fact that B16F10 is: a) NK cell-sensitive; and b) CD112-positive (FIG. 18A). When B16F10 melanoma was injected intravenously (iv) into B6 mice to induce lung metastasis, administration of mCD112R blocking mAb inhibited B16F10 tumor metastasis (FIG. 20). Without intending to be bound by theory, these results suggest an indispensable role of the CD112R/CD112 interaction in tumor immunity.

Example 20. The Effect of CD112R Blockade on Trastuzumab-Triggered ADCC by Human NK Cells CD112R Blockade Improves the Anticancer Effect Triggered by Herceptin in Human Breast Cancer.

CD112R is expressed on NK cells, and could be a functional inhibitor for NK cell activities. Trastuzumab is a humanized mAb targeting the human epidermal growth factor receptor 2 (HER2; also known as HER-2/neu), a transmembrane receptor tyrosine kinase that is overexpressed in about one-fourth of women with breast cancer. Antibody-dependent cellular cytotoxicity (ADCC) mediated by NK cells is one of the major mechanisms that contribute to the antitumor activity of trastuzumab.

Figure 21A:
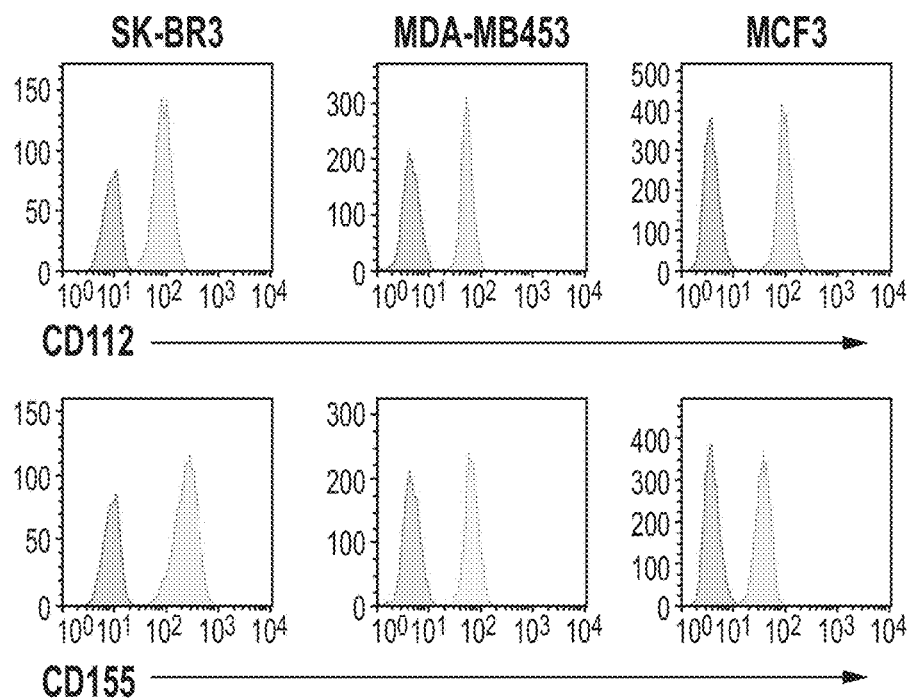
FIGS. 21A, 21B, and 21C are a series of graphs depicting CD112R blockade, alone or together with TIGIT blockade, increases Herceptin-mediated ADCC by human NK cells.
Figure 21B:
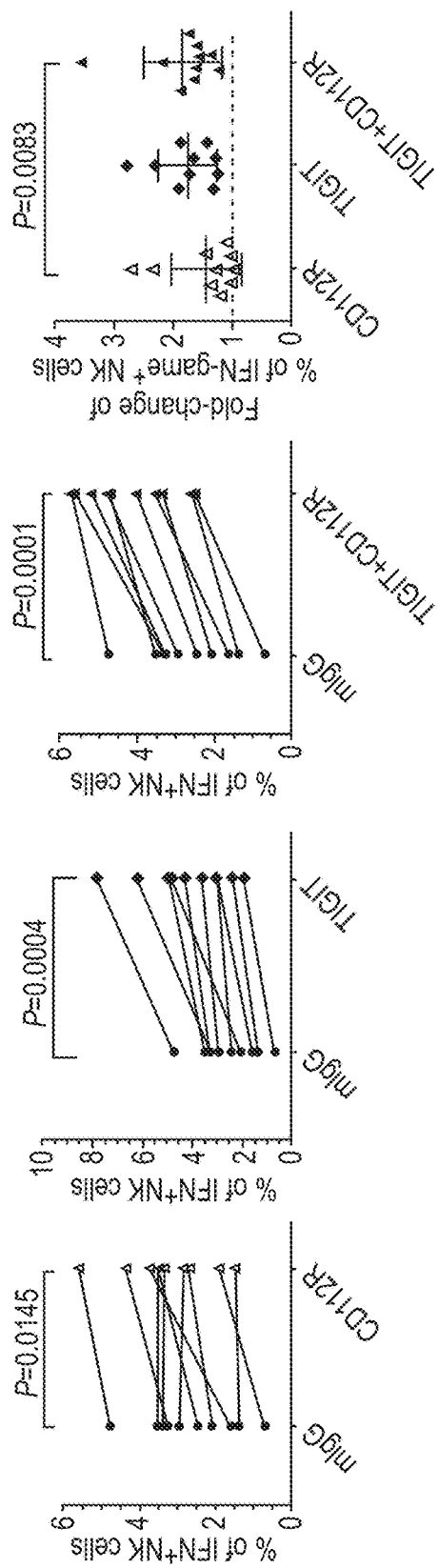
Figure 21C:
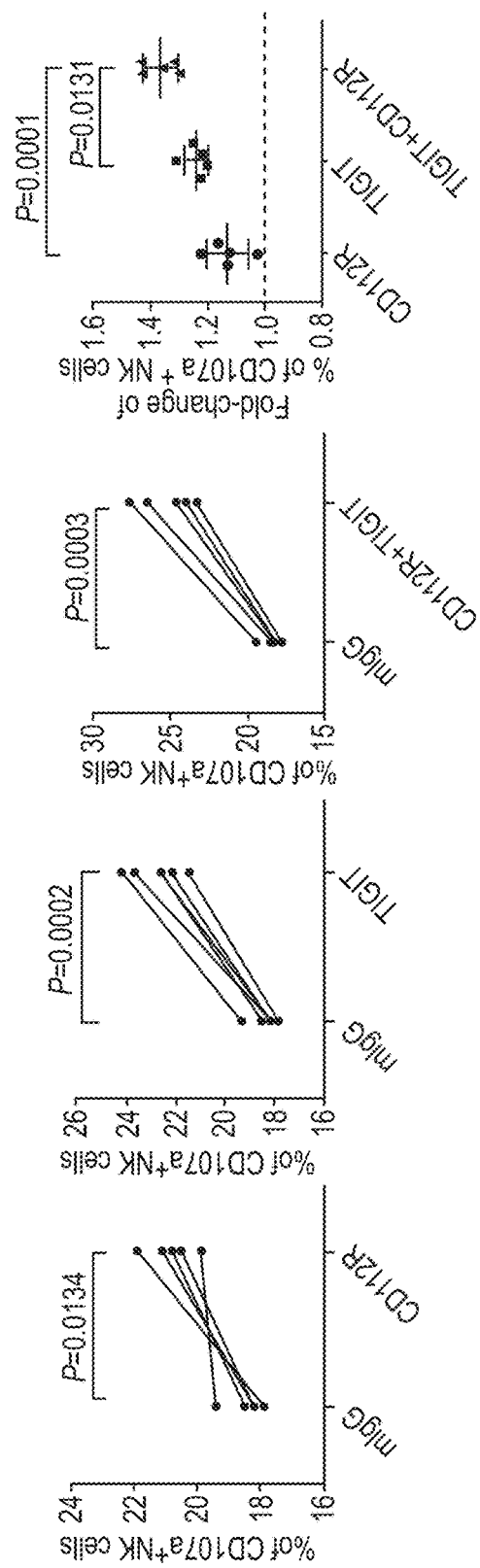

Human breast cancer cells expressed high levels of PVR-like ligand CD112 and CD155 (FIG. 21A). Therefore, studies were run to examine whether CD112R blockade can promote NK cell-mediated antibody-dependent cell-mediated cytotoxicity (ADCC). Human NK cells were cultured with SK-BR3 cells, a human breast cancer cell line expressing HER2; Trastuzumab (0.01 ug/ml) and blocking mAb against CD112R or control mouse IgG. CD112R blockade alone resulted in significant increases in the percentages of IFN-γ positive NK cells comparing with those of NK cells in the control (FIG. 21B). Similarly, the percentage of CD107a-positive NK cells was significantly increased upon CD112R blockade (FIG. 21C). Inclusion of TIGIT blocking mAb further enhanced NK cell activities (FIG. 21B, 1C). Thus, without intending to be bound by theory, these results suggest that CD112R blockade can promote NK cell activities against Trastuzumab-coated breast cancer.

Example 21. Epitope Mapping of Human Anti-CD112R 2H6 Antibody by Hydrogen Deuterium Exchange Mass Spectrometry The interacting areas between human CD112R and anti-CD112R mAb 2H6 were determined by Hydrogen Deuterium Exchange Mass Spectrometry (HDX-MS) analysis. HDX-MS examines the exchange of deuterium with hydrogen into the amide backbone of the protein. The exchange rate is influenced by the hydrogen's exposure to solvent. Comparison of the exchange levels in the antigen when the antibody is bound can identify regions of the protein where the antibody binds.

Figure 22:
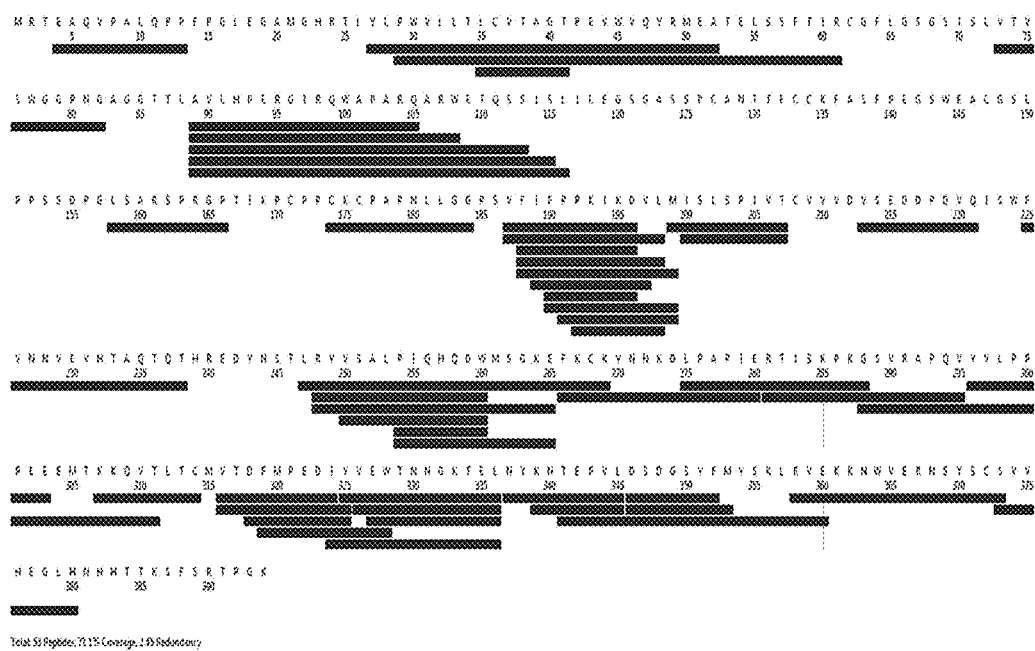
FIG. 22 is an illustration depicting epitope mapping of the interacting areas between human CD112R and the anti-CD112R antibody referred to herein as 2H6 using Hydrogen Deuterium Exchange Mass Spectrometry (HDX-MS). HXMS data analysis was performed by PLGS for peptide list identifications and DynamX 3.0 (manually verified) for isotope assignments and uptake export. 53 unique CD112R peptide sequences, which cover 71% of the entire sequence of CD112R protein as part of the CD112R-mFc protein (SEQ ID NO: 52), were identified as indicated in FIG. 22.

The studies presented herein used the CD112R-mFc protein having the following amino acid sequence, shown in FIG. 22:

(SEQ ID NO: 52)
MRTEAQVPALQPPEPGLEGAMGHRTLVLPWVLLTLCVTAGTPEVWVQVRM
EATELSSFTIRCGFLGSGSISLVTVSWGGPNGAGGTTLAVLHPERGIRQW
APARQARWETQSSISLILEGSGASSPCANTTFCCKFASFPEGSWEACGSL
PPSSDPGLSARSPRGPTIKPCPPCKCPAPNLLGGPSVFIFPPKIKDVLMI
SLSPIVTCVVVDVSEDDPDVQISWFVNNVEVHTAQTQTHREDYNSTLRVV
SALPIQHQDWMSGKEFKCKVNNKDLPAPIERTISKPKGSVRAPQVYVLPP
PEEEMTKKQVTLTCMVTDFMPEDIYVEWTNNGKTELNYKNTEPVLDSDGS
YFMYSKLRVEKKNWVERNSYSCSVVHEGLHNHHTTKSFSRTPGK

Figure 23:
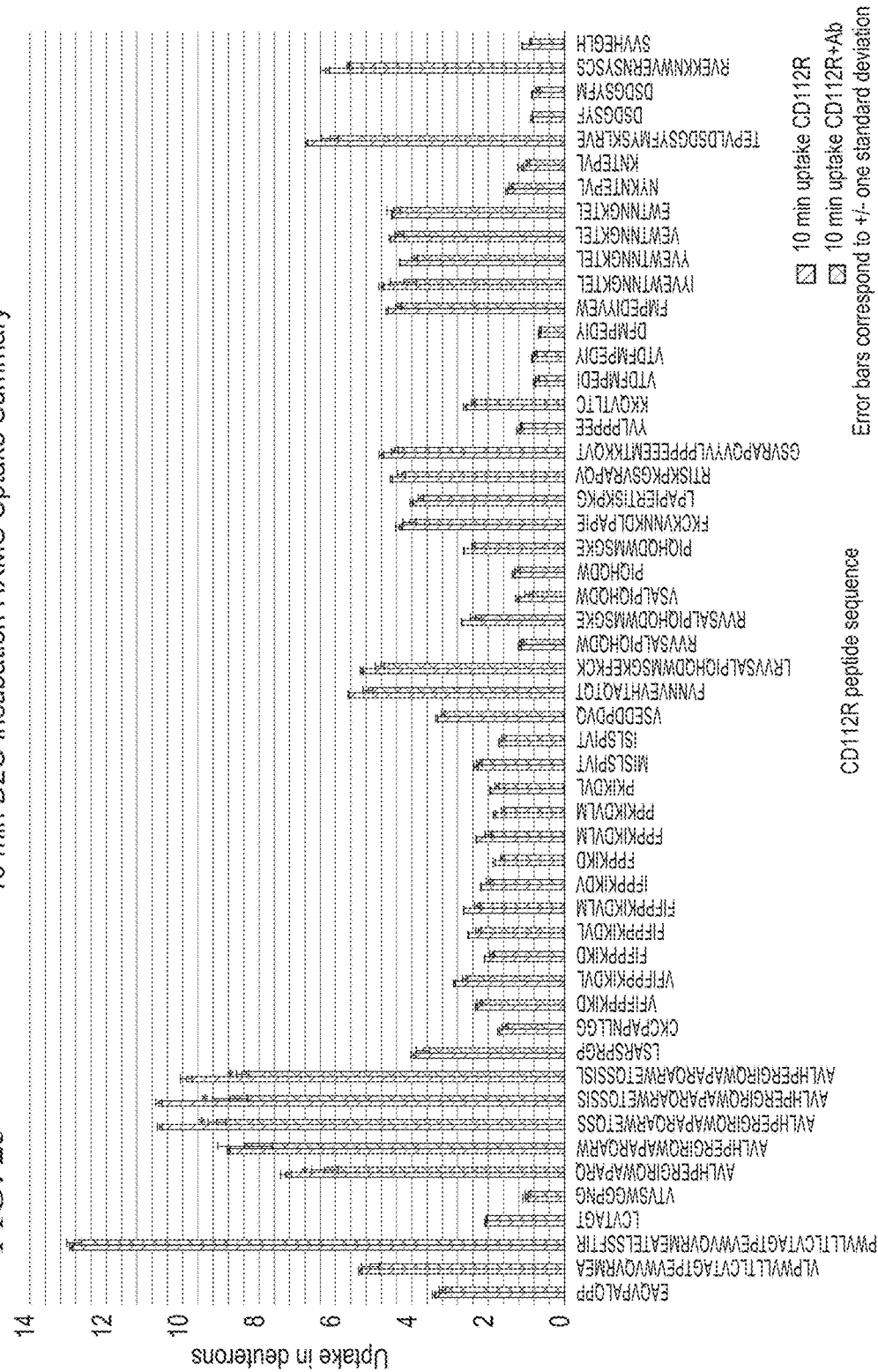
FIG. 23 is a graph depicting HXMS update summary after 10 minutes of $D_2O$ incubation. Peptides listed from left to right are identified by SEQ ID NOs: 70-122, respectively.
Figure 24:
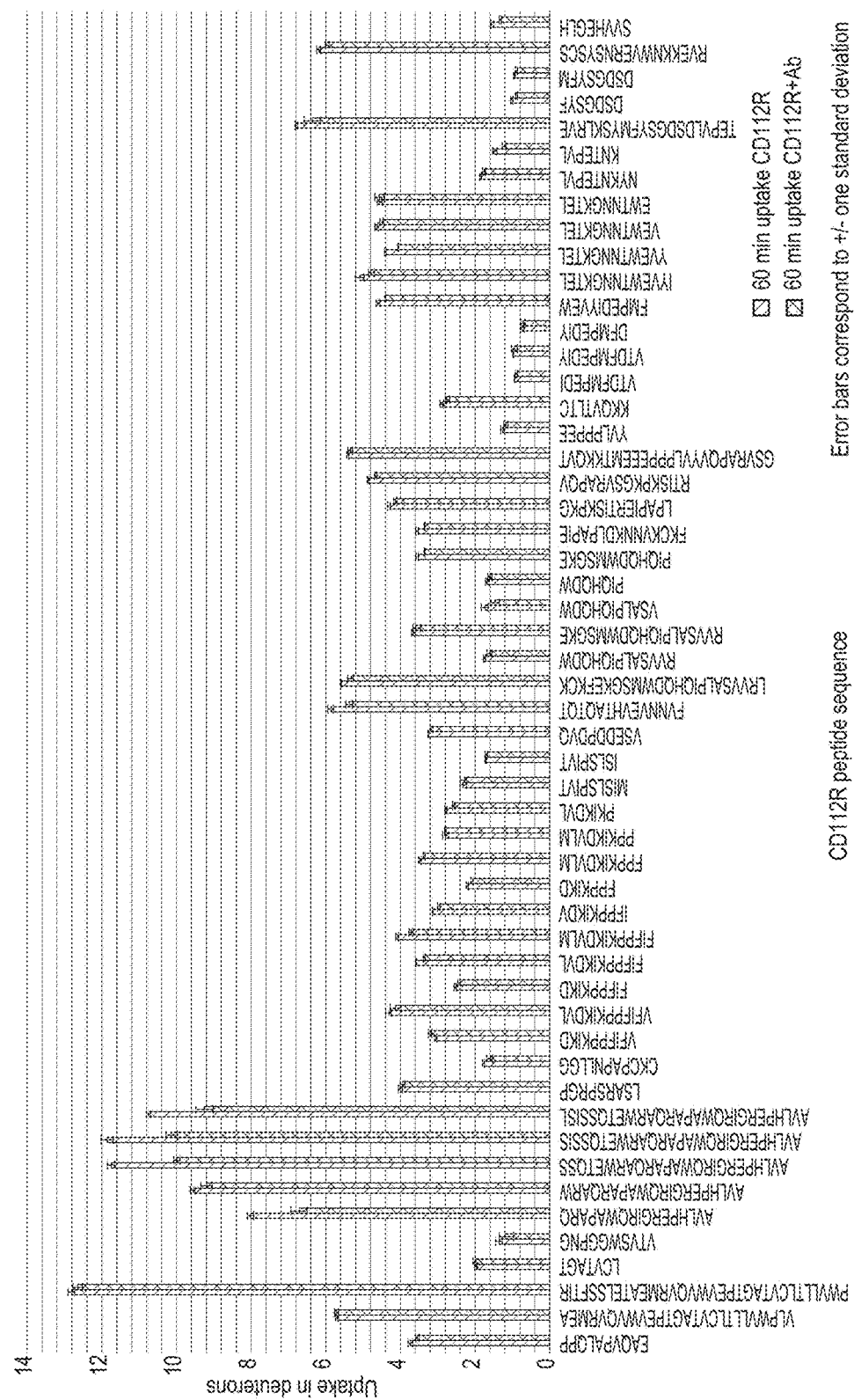
FIG. 24 is a graph depicting HXMS update summary after 60 minutes of $D_2O$ incubation. Peptides listed from left to right are identified by SEQ ID NOs: 70-122, respectively.

CD112R-mFc protein (at ~5.4504) was pre-incubated with 2H6 mAb (~13 µM) at 10 degree for 1 hr to result in an approximate 2.4 to 1 (antibody to protein) ratio to maximize the amount of CD112R protein bound to 2H6 mAb. 10 µL of protein and mAb mixture was incubated with 40 uL $D_2O$ at 10 degrees for 10 min or 60 min, and was quenched with ice cold 50 µL quench buffer (100 mM potassium phosphate dibasic HCl, pH 2.4). 10 µl CD112R protein alone (i.e., SEQ ID NO: 45) was treated at the same condition as the control. All incubations provide 80% $D_2O$ during the labeling step. HXMS data analysis was performed by PLGS for peptide list identifications and DynamX 3.0 (manually verified) for isotope assignments and uptake export. 53 unique CD112R peptide sequences, which cover 71% of the entire sequence of CD112R protein (FIG. 22), were identified. As illustrated in FIGS. 23 and 24, there is a distinct region of protection in the CD112R+Ab dataset around the peptide regions covering the sequence AVLHPERGIRQWAPARQ (SEQ ID NO: 53). This pattern is repeated in the several peptides identified in this region. This data indicate that the potential epitope bound by 2H6 mAb exists in this narrow region of amino acids.

Other Embodiments

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

What is claimed is:

1. An isolated antibody or antigen binding fragment thereof that binds CD112R, wherein the isolated antibody or antigen binding fragment thereof comprises a heavy chain CDR1 including SEQ ID NO: 6, a heavy chain CDR2 including SEQ ID NO: 7, a heavy chain CDR3 including SEQ ID NO: 8, a light chain CDR1 including SEQ ID NO: 9, a light chain CDR2 including SEQ ID NO: 10, and a light chain CDR3 including SEQ ID NO: 11.

2. A method of treating cancer in a subject in need thereof, comprising administering to said subject an effective amount of the isolated antibody of claim 1.

3. The isolated antibody or antigen fragment of claim 1, wherein the antibody or antigen binding fragment thereof binds an epitope on human CD112R comprising the amino acid sequence AVLHPERGIRQWAPARQ (SEQ ID NO: 53).

4. An isolated antibody or antigen binding fragment thereof that binds CD112R, wherein the isolated antibody or antigen binding fragment thereof comprises a heavy chain including SEQ ID NO: 5, and a light chain including SEQ ID NO: 3.

5. The isolated antibody or antigen fragment of claim 4, wherein the antibody or antigen binding fragment thereof binds an epitope on human CD112R comprising the amino acid sequence AVLHPERGIRQWAPARQ (SEQ ID NO: 53).

6. A method of treating cancer in a subject in need thereof, comprising administering to said subject an effective amount of the isolated antibody of claim 4.

* * * * *